(12) United States Patent
Blumberg et al.

(10) Patent No.: US 9,072,788 B2
(45) Date of Patent: Jul. 7, 2015

(54) PRODRUGS OF NH-ACIDIC COMPOUNDS: ESTER, CARBONATE, CARBAMATE AND PHOSPHONATE DERIVATIVES

(71) Applicant: Alkermes Pharma Ireland Limited, Dublin (IE)

(72) Inventors: Laura Cook Blumberg, Lincoln, MA (US); Julius F. Remenar, Framingham, MA (US); Orn Almarsson, Shrewsbury, MA (US); Tarek A. Zeidan, Watertown, MA (US)

(73) Assignee: Alkermes Pharma Ireland Limited, Dublin (IE)

( * ) Notice: Subject to any disclaimer, the term of this patent is extended or adjusted under 35 U.S.C. 154(b) by 0 days.

(21) Appl. No.: 14/034,918

(22) Filed: Sep. 24, 2013

(65) Prior Publication Data

US 2014/0094472 A1    Apr. 3, 2014

Related U.S. Application Data

(63) Continuation of application No. 13/168,497, filed on Jun. 24, 2011, now Pat. No. 8,592,427.

(60) Provisional application No. 61/358,348, filed on Jun. 24, 2010.

(51) Int. Cl.
*A61K 31/496* (2006.01)
*A61K 47/48* (2006.01)
*C07D 215/227* (2006.01)

(52) U.S. Cl.
CPC ......... *A61K 47/48061* (2013.01); *A61K 31/496* (2013.01); *C07D 215/227* (2013.01)

(58) Field of Classification Search
USPC ................. 514/336, 365; 548/146; 546/268.1
See application file for complete search history.

(56) References Cited

U.S. PATENT DOCUMENTS

| | | |
|---|---|---|
| 5,679,677 A | 10/1997 | Pill et al. |
| 6,258,825 B1 | 7/2001 | Ozaki et al. |
| 2003/0207868 A1 | 11/2003 | Yu et al. |
| 2006/0264457 A1 | 11/2006 | Devasthale et al. |
| 2007/0197628 A1 | 8/2007 | Chackalamannil et al. |
| 2007/0232594 A1 | 10/2007 | Yokoyama et al. |
| 2008/0200454 A1 | 8/2008 | Ameriks et al. |
| 2008/0207659 A1 | 8/2008 | Chakraborti et al. |
| 2008/0275069 A1 | 11/2008 | Mizutani et al. |
| 2009/0325944 A1 | 12/2009 | Walker et al. |
| 2009/0325987 A1 | 12/2009 | Muthuppalniappan et al. |
| 2010/0093698 A1 | 4/2010 | Bahmanyar et al. |
| 2010/0152168 A1 | 6/2010 | Arndt et al. |
| 2013/0204004 A1* | 8/2013 | Zeller et al. ............ 546/314 |

FOREIGN PATENT DOCUMENTS

| | | |
|---|---|---|
| EP | 1221443 A1 | 7/2002 |
| GB | 1146798 A | 3/1969 |
| JP | 2-191256 | 7/1990 |
| JP | 2006-316052 | 11/2006 |
| WO | 92/06089 A1 | 4/1992 |
| WO | 93/18027 A1 | 9/1993 |
| WO | 94/00113 A2 | 1/1994 |
| WO | 95/09842 A1 | 4/1995 |
| WO | 96/28424 A1 | 9/1996 |
| WO | 01/90103 | 6/2001 |
| WO | 03/080047 A1 | 10/2003 |
| WO | 2004/037819 | 5/2004 |
| WO | 2004/037819 A1 | 5/2004 |
| WO | 2006/112666 A1 | 10/2006 |
| WO | 2007/035348 A2 | 3/2007 |

OTHER PUBLICATIONS

Zeller et al. CAS: 155: 589132, 2011.*
Guarino, V.R., et al., "Chapter III: Prodrugs of Amides, Imides and Other NH-Acidic Compounds in Prodrugs: Challenges and Rewards Part I," Springer, New York, pp. 833-877 (2007).
Zhang, X., et al., "CN3-o-toluyl-fiuorouracil inhibits human hepatocellular carcinoma cell growth via sustained release of 5-FU," Cancer Chemother Pharmacal, 66(1): 11-19 (2009).
Kurimoto, A., et al., "Pro drugs of 9-Benzyl-8-hydroxy-2-(2-hydroxyethylthio )adenine: Potent Interferon Inducing Agents in Monkeys," Chern. Pharm. Bull., 52(4): 466-469 (2004).
Broch, S., et al., "First Synthesis of 3,6'- and 3,7'-Biquinoline Derivatives," Synthesis, 2008(13): 2039-2044 (2008).
Guchhait, R. B., et al., "Acetyl Coenzyme a Carboxylase System of *Escherichia coli* : Site of Carboxylation of Biotin and Enzymatic Reactivity of 1'-N-(Ureido)-Carboxybiotin Derivatives," J. Bioi. Chem., 249: 6646-6656 (1974).

* cited by examiner

*Primary Examiner* — Rei-Tsang Shiao
(74) *Attorney, Agent, or Firm* — Elmore Patent Law Group, P.C.; Carolyn S. Elmore; Roy P. Issac

(57) ABSTRACT

The invention provides a method of sustained delivery of a lactam, imide, amide, sulfonamide, carbamate or urea containing parent drug by administering to a patient an effective amount of a prodrug compound of the invention wherein upon administration to the patient, release of the parent drug from the prodrug is sustained release. Prodrug compounds suitable for use in the methods of the invention are labile conjugates of parent drugs that are derivatized through carbonyl linked prodrug moieties. The prodrug compounds of the invention can be used to treat any condition for which the lactam, imide, amide, sulfonamide, carbamate or urea containing parent drug is useful as a treatment.

12 Claims, 1 Drawing Sheet

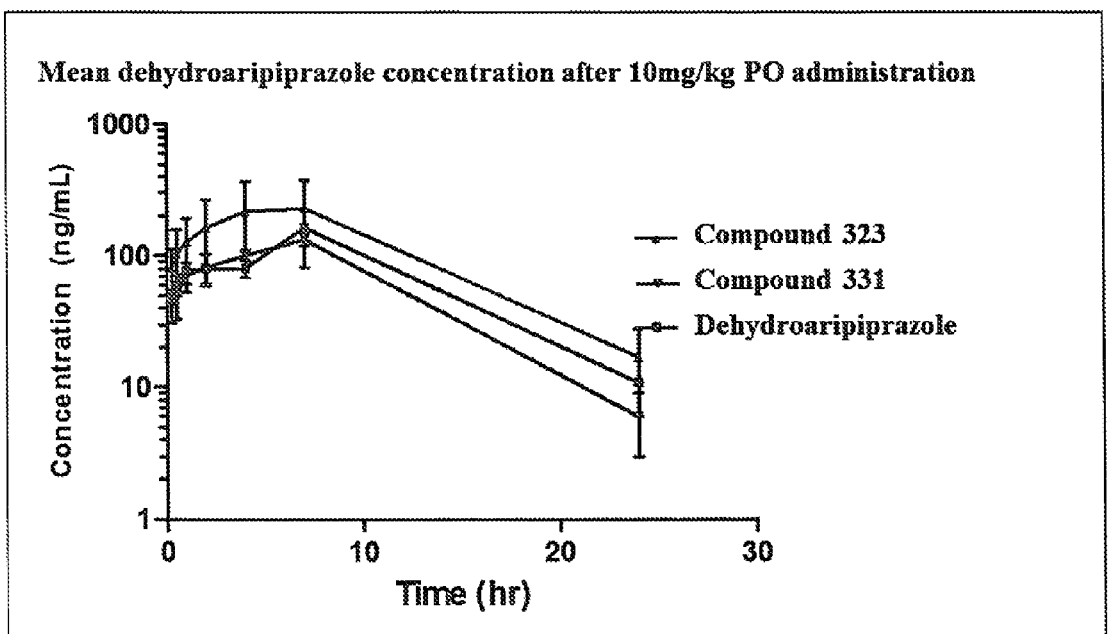

PRODRUGS OF NH-ACIDIC COMPOUNDS: ESTER, CARBONATE, CARBAMATE AND PHOSPHONATE DERIVATIVES

RELATED APPLICATIONS

This application is a continuation of U.S. application Ser. No. 13/168,497, filed Jun. 24, 2011, which claims the benefit of U.S. Provisional Application No. 61/358,348, filed on Jun. 24, 2010. The entire teachings of the above applications are incorporated herein by reference.

BACKGROUND OF THE INVENTION (i) Field of the Invention

The present invention relates to prodrugs of lactam, amide, imide, sulfonamide, carbamate, urea, benzamide, and acylaniline containing pharmacophores.

(ii) Background of the Invention

Drug delivery systems are often critical for the safe and effective administration of a biologically active agent. Perhaps the importance of these systems is best realized when patient compliance and consistent dosing are taken under consideration. For instance, reducing the dosing requirement for a drug from four-times-a-day to a single dose per day would have significant value in terms of ensuring patient compliance and optimizing therapy.

Optimization of a drug's bioavailability has many potential benefits. For patient convenience and enhanced compliance it is generally recognized that less frequent dosing is desirable. By extending the period through which the drug is released, a longer duration of action per dose is expected. This will then lead to an overall improvement of dosing parameters such as taking a drug once a day where it has previously required four doses per day or dosing once a week or even less frequently when daily dosing was previously required. Many drugs are presently dosed once per day, but not all of these drugs have pharmacokinetic properties that are suitable for dosing intervals of exactly twenty-four hours. Extending the period through which these drugs are released would also be beneficial.

One of the fundamental considerations in drug therapy involves the relationship between blood levels and therapeutic activity. For most drugs, it is of primary importance that serum levels remain between a minimally effective concentration and a potentially toxic level. In pharmacokinetic terms, the peaks and troughs of a drug's blood levels ideally fit well within the therapeutic window of serum concentrations. For certain therapeutic agents, this window is so narrow that dosage formulation becomes critical.

In an attempt to address the need for improved bioavailability, several drug release modulation technologies have been developed. For example, poorly soluble 5,5 diphenylimidazolidine-2,4-diones have been derivatized into phosphate ester prodrugs to improve solubility. (Stella et al., U.S. Pat. No. 4,260,769, 1981). Enteric coatings have been used as a protector of pharmaceuticals in the stomach and microencapsulating active agents using proteinaceous microspheres, liposomes or polysaccharides have been effective in abating enzymatic degradation of the active agent. Enzyme inhibiting adjuvants have also been used to prevent enzymatic degradation.

A wide range of pharmaceutical formulations provide sustained release through microencapsulation of the active agent in amides of dicarboxylic acids, modified amino acids or thermally condensed amino acids. Slow release rendering additives can also be intermixed with a large array of active agents in tablet formulations.

While microencapsulation and enteric coating technologies impart enhanced stability and time-release properties to active agent substances these technologies suffer from several shortcomings. Incorporation of the active agent is often dependent on diffusion into the microencapsulating matrix, which may not be quantitative and may complicate dosage reproducibility. In addition, encapsulated drugs rely on diffusion out of the matrix or degradation of the matrix, or both, which is highly dependent on the chemical properties and water solubility of the active agent. Conversely, water-soluble microspheres swell by an infinite degree and, unfortunately, may release the active agent in bursts with limited active agent available for sustained release. Furthermore, in some technologies, control of the degradation process required for active agent release is unreliable. For example, because an enterically coated active agent depends on pH to release the active agent and pH and residence time varies, the release rate is difficult to control.

Several implantable drug delivery systems have utilized polypeptide attachment to drugs. Additionally, other large polymeric carriers incorporating drugs into their matrices are used as implants for the gradual release of drug. Yet another technology combines the advantages of covalent drug attachment with liposome formation where the active ingredient is attached to highly ordered lipid films.

However there is still a need for an active agent delivery system that is able to deliver certain active agents which have been heretofore not formulated or difficult to formulate in a sustained release formulation for release over a sustained period of time and which is convenient for patient dosing.

There is a generally recognized need for sustained delivery of drugs that reduces the daily dosing requirement and allows for controlled and sustained release of the parent drug and also avoids irregularities of release and cumbersome formulations encountered with typical dissolution controlled sustained release methods.

SUMMARY OF THE INVENTION

The present invention accomplishes this by extending the period during which a lactam, amide, imide, sulfonamide, carbamate, urea, benzamide, acylaniline, and cyclic amide containing parent drug is released and absorbed after administration to the patient and providing a longer duration of action per dose than the parent drug itself. In one embodiment, the compounds suitable for use in the methods of the invention are derivatives of lactam-, amide-, imide-, sulfonamide-, carbamate-, urea-, benzamide-, acylaniline-, and cyclic amide-containing parent drugs that are substituted at the amide nitrogen or oxygen atom with prodrug moieties. Preferably, the prodrug moieties are hydrophobic and reduce the polarity and solubility of the parent drug under physiological conditions.

In one embodiment, the invention provides a prodrug compound of Formula I, II or III:

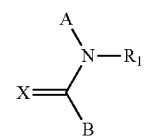

Formula I

3

-continued

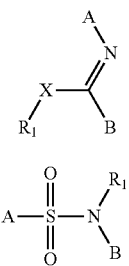

Formula II

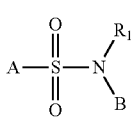

Formula III or its geometric isomers, enantiomers, diastereomers, racemates, pharmaceutically acceptable salts and solvates thereof;
wherein A and B together with the —N(C═X)— or —(SO$_2$)N— to which they are attached forms a parent drug;
X is —S— or —O—;
R$_1$ is selected from C(O)OR$_{20}$, C(O)R$_{20}$, —C(O)NR$_{20}$R$_{21}$, —PO$_3$MY, —P(O)$_2$(OR$_{20}$)M and —P(O)(OR$_{20}$)(OR$_{21}$);
  wherein each R$_{20}$ and R$_{21}$ is independently selected from hydrogen, aliphatic, substituted aliphatic, aryl or substituted aryl;
  Y and M are the same or different and each is a monovalent cation; or M and Y together is a divalent cation.

The invention further provides a method for sustained delivery of a parent drug by the administration of a conjugate of the parent drug with a labile moiety, wherein the conjugate is represented by Formula I.

BRIEF DESCRIPTION OF THE DRAWING

The foregoing and other objects, features and advantages of the invention will be apparent from the following more particular description of preferred embodiments of the invention, as illustrated in the accompanying drawing in which like reference characters refer to the same parts throughout the different views. The drawing is not necessarily to scale, emphasis instead being placed upon illustrating the principles of the invention.

The FIGURE: Plasma concentration of dehydroaripiprazole after PO administration of (10 mg/Kg) compound 323, 331 and dehydroaripiprazole to rats.

DETAILED DESCRIPTION OF THE INVENTION

In one embodiment, the invention provides a prodrug compound of Formula I, II or III:

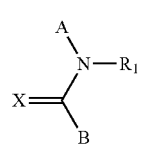

Formula I

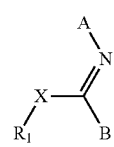

Formula II

4

-continued

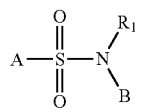

Formula III or its geometric isomers, enantiomers, diastereomers, racemates, pharmaceutically acceptable salts and solvates thereof;
wherein A and B together with the —N(C═X)— to which they are attached forms a parent drug;
X is —S— or —O—;
R$_1$ is selected from C(O)OR$_{20}$, C(O)R$_{20}$, —C(O)NR$_{20}$R$_{21}$, —PO$_3$MY, —P(O)$_2$(OR$_{20}$)M and —P(O)(OR$_{20}$)(OR$_{21}$);
  wherein each R$_{20}$ and R$_{21}$ is independently selected from hydrogen, aliphatic, substituted aliphatic, aryl or substituted aryl;
  Y and M are the same or different and each is a monovalent cation; or M and Y together is a divalent cation.

The invention further provides a method for sustained delivery of a parent drug by the administration of a conjugate of the parent drug with a labile moiety, wherein the conjugate is represented by Formula I.

In a preferred embodiment, R$_1$ is selected from —C(O)O—CH$_2$—OC(O)R$_{21}$ or —C(O)NH—CH$_2$—OC(O)R$_{21}$ or —C(O)O—CH$_2$—OC(O)N(R$_{21}$)$_2$. In a preferred embodiment, R$_1$ is selected from —C(O)O—CH(CH$_3$)—OC(O)R$_{21}$ or —C(O)NH—CH(CH$_3$)—OC(O)R$_{21}$ or —C(O)O—CH(CH$_3$)—OC(O)N(R$_{21}$)$_2$. In a preferred embodiment, R$_1$ is selected from —C(O)O—CH(C$_6$H$_5$)—OC(O)R$_{21}$ or —C(O)NH—CH(C$_6$H$_5$)—OC(O)R$_{21}$ or —C(O)O—CH(C$_6$H$_5$)—OC(O)N(R$_{21}$)$_2$. In a more preferred embodiment, R$_{21}$ is alkyl, substituted alkyl, alkenyl, or substituted alkenyl.

In a preferred embodiment, R$_1$ is selected from —C(O)OR$_{21}$ or —C(O)NHR$_{21}$ or —C(O)N(R$_{21}$)$_2$. In a more preferred embodiment, R$_{21}$ is alkyl, substituted alkyl, alkenyl, or substituted alkenyl.

In one embodiment, the compounds of the invention having Formula I, II or III are less soluble, and are preferably at least an order of magnitude less soluble, as compared to the parent drug from which they were derived. In one embodiment, the prodrugs of Formulas I has an aqueous solubility of less than about 0.5 mg/ml, preferably less than about 0.1 mg/mL, preferably less than about 0.01 mg/mL, preferably less than about 0.001 mg/mL, preferably less than about 0.0001 mg/mL and even more preferably less than about 0.00001 mg/ml when solubility is measured in a phosphate buffer (pH 7.4) at room temperature.

In a preferred embodiment, a compound of the invention provides sustained delivery of the parent drug over hours, days, weeks or months when administered, for example, orally or parenterally, to a subject. For example, the compounds can provide sustained delivery of the parent drug for at least 8, 12, 24, 36 or 48 hours or at least 4, 7, 15, 30, 60, 75 or 90 days or longer. Without being bound by a theory, it is believed that the compounds of the invention form an insoluble depot upon parenteral administration, for example subcutaneous, intramuscular or intraperitoneal injection. In one embodiment a prodrug of the invention may further comprise a sustained release delivery system for providing additional protection of the prodrug from enzymatic or chemical degradation.

In another embodiment, the invention provides a method for sustained delivery of a parent lactam, amide, imide, sulfonamide, carbamate, urea, benzamide, or acylaniline containing drug to a subject in need thereof. Each of these groups comprises an amidic N—H group. The method comprises administering to the subject an effective amount of a prodrug formed by substituting on the NH group a labile, hydrophobic prodrug moiety wherein the prodrug has reduced solubility under physiological conditions compared to the parent drug and provides for longer sustained therapeutic levels of the parent drug following administration than observed levels following administration of the parent drug. In a preferred embodiment, the amidic N—H group has a pKa of about 5 to about 22, preferably about 5 to about 21, and preferably about 5 to about 20.

In a preferred embodiment, $R_1$ is selected from Tables 1-5.

TABLE 1

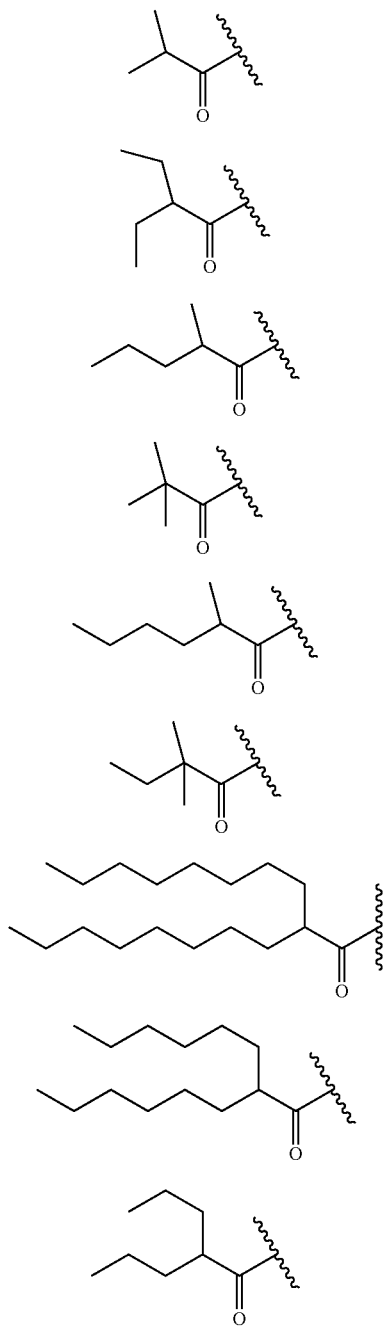

TABLE 1-continued

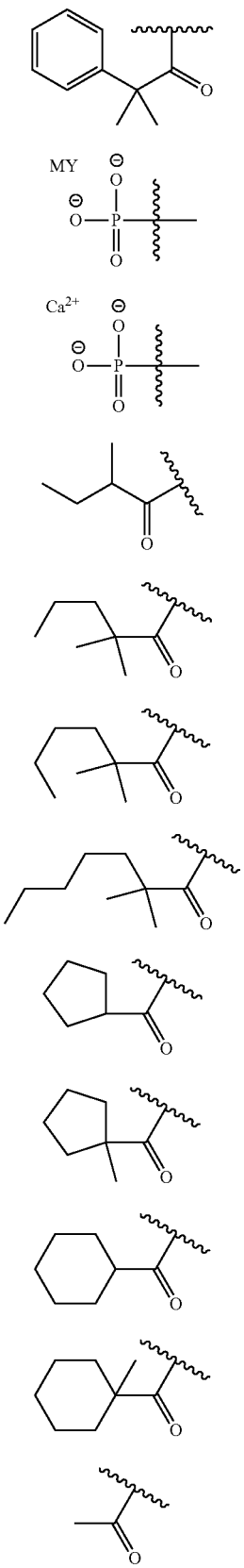

TABLE 1-continued

TABLE 1-continued
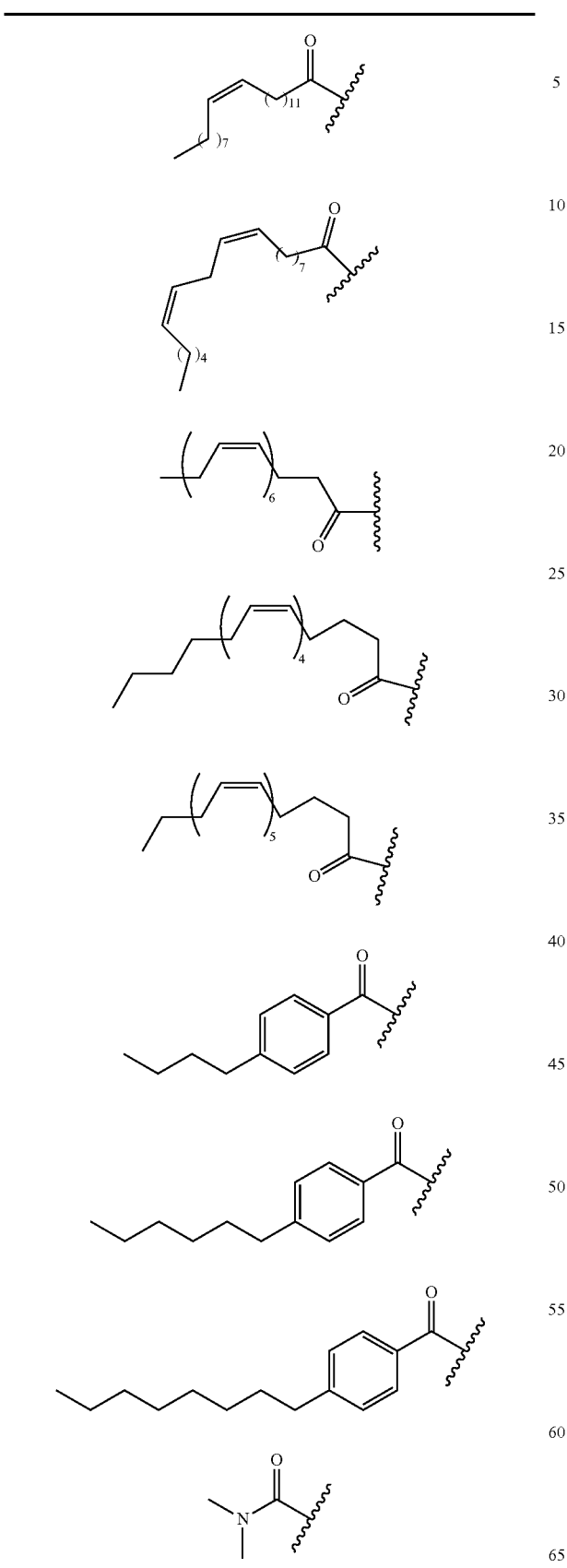
TABLE 1-continued
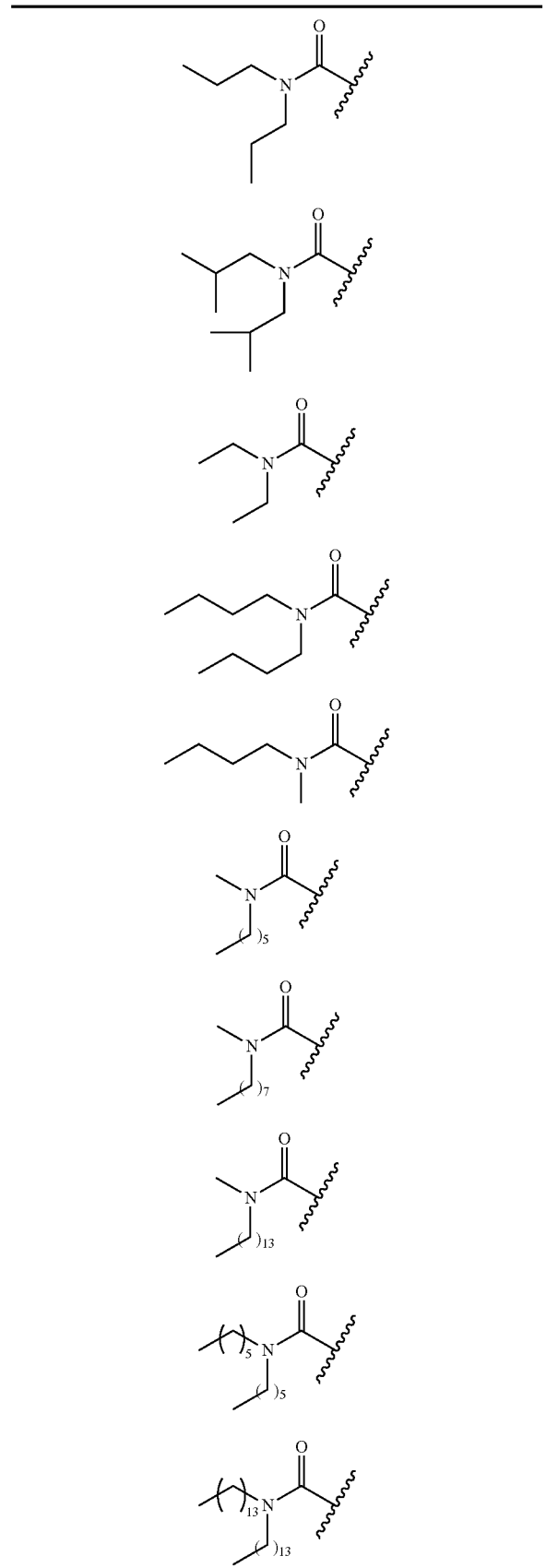

TABLE 1-continued
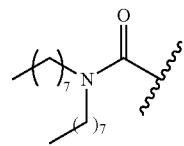
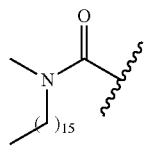
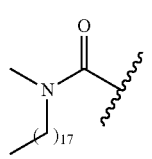
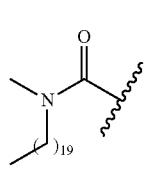
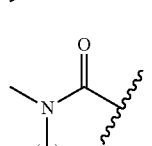
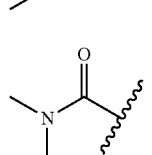
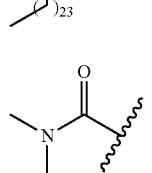
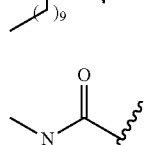
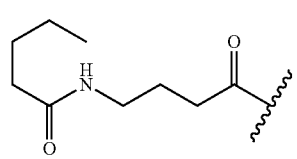 [SMILES: *C(=O)CCCNC(=O)CCCC]
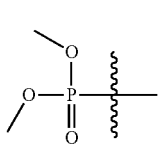
TABLE 1-continued
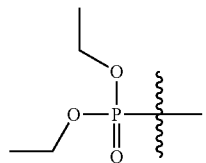 [SMILES: *P(=O)(OCC)OCC]
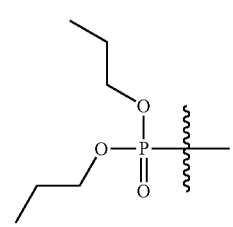 [SMILES: *P(=O)(OCCC)OCCC]
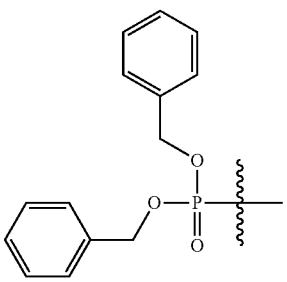 [SMILES: *P(=O)(OCc1ccccc1)OCc1ccccc1]
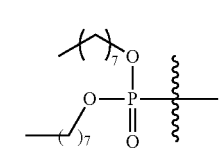
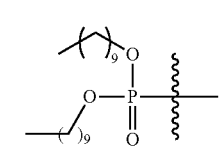
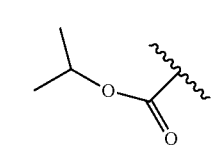 [SMILES: *C(=O)OC(C)C]
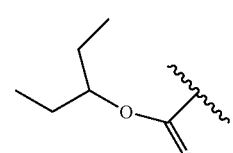
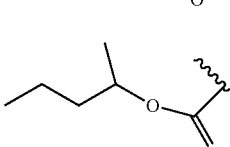
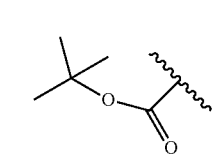 [SMILES: *C(=O)OC(C)(C)C]

TABLE 1-continued
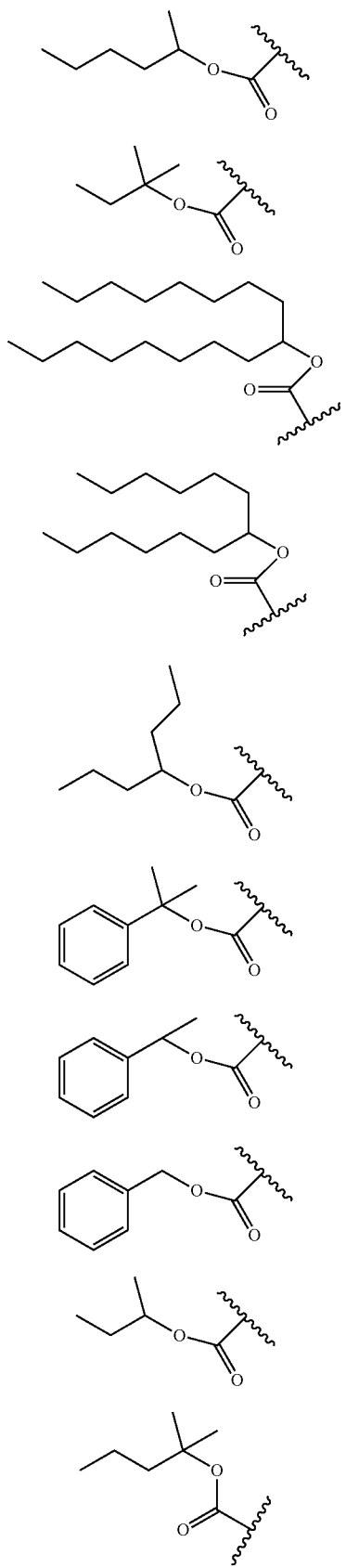
TABLE 1-continued
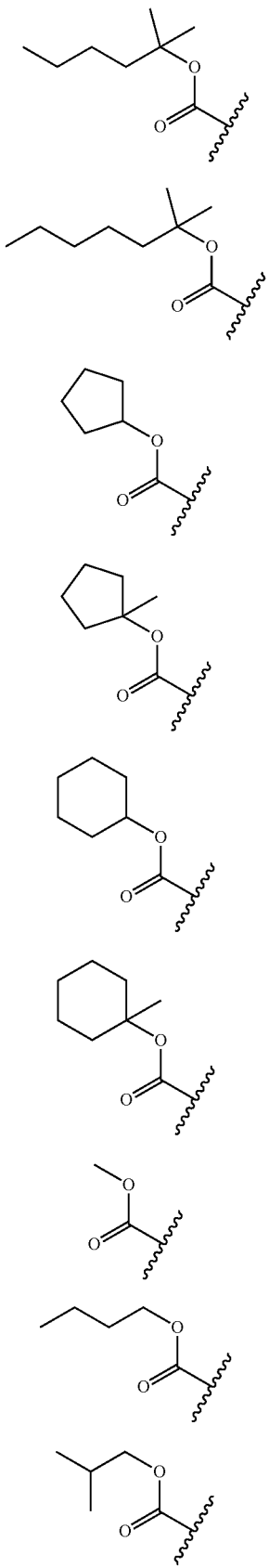

TABLE 1-continued
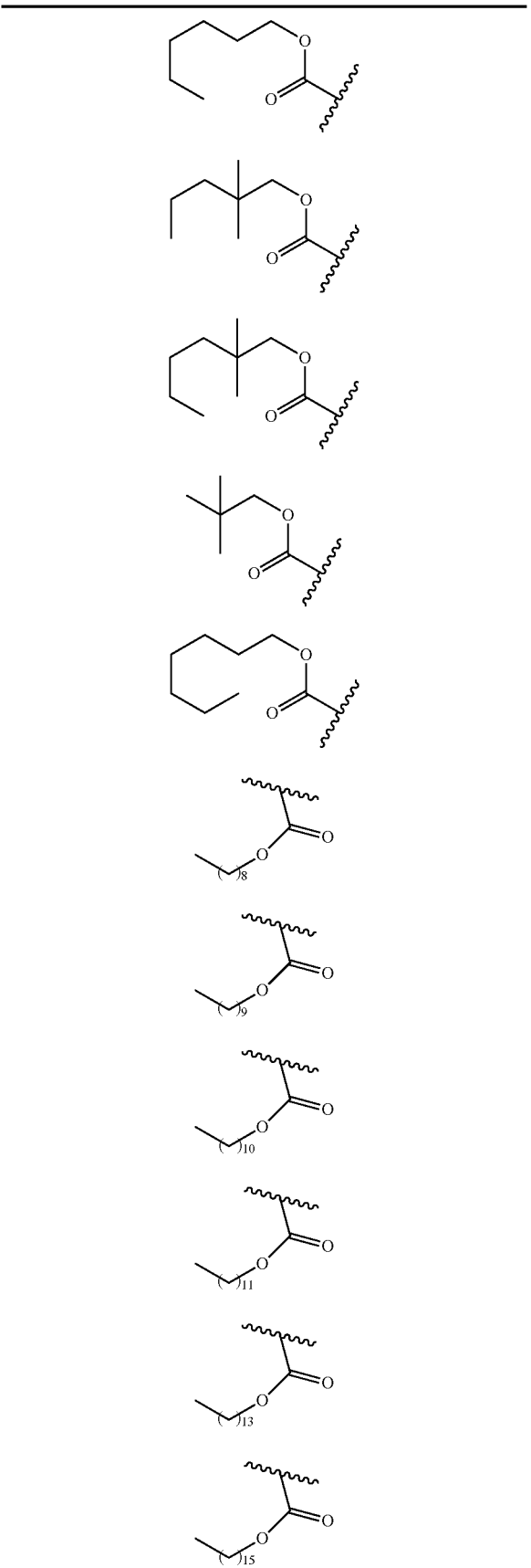
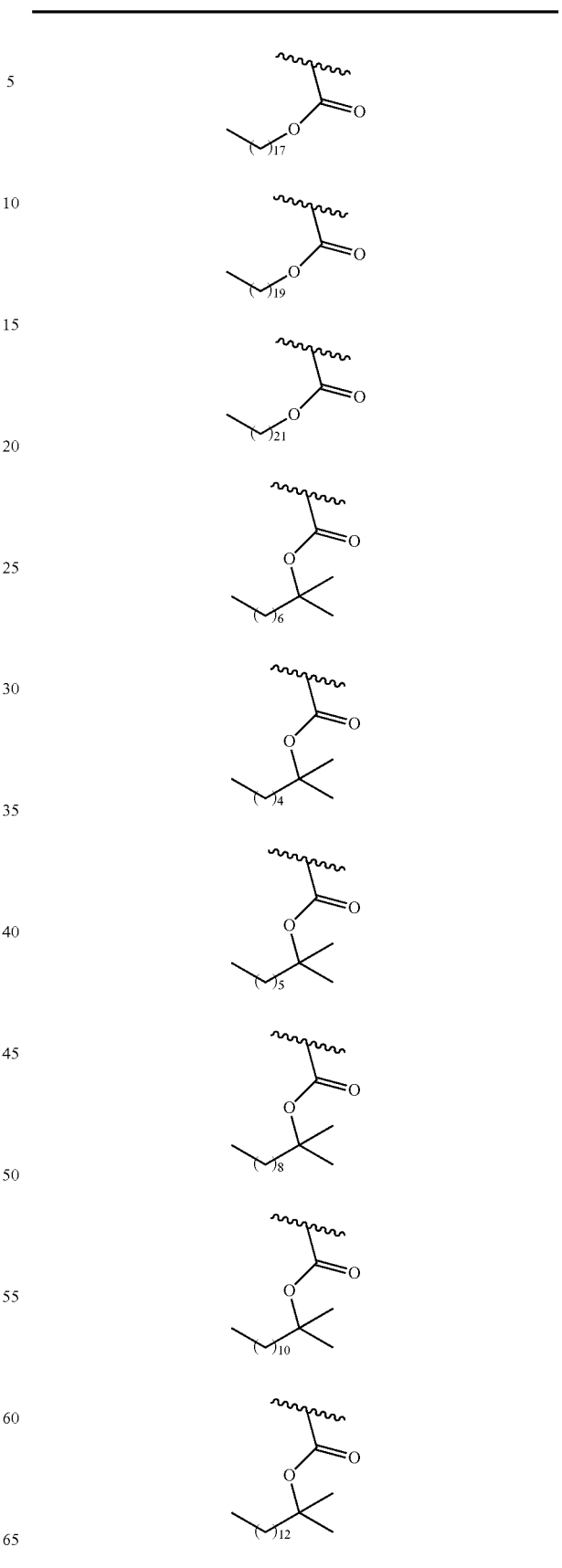

TABLE 1-continued
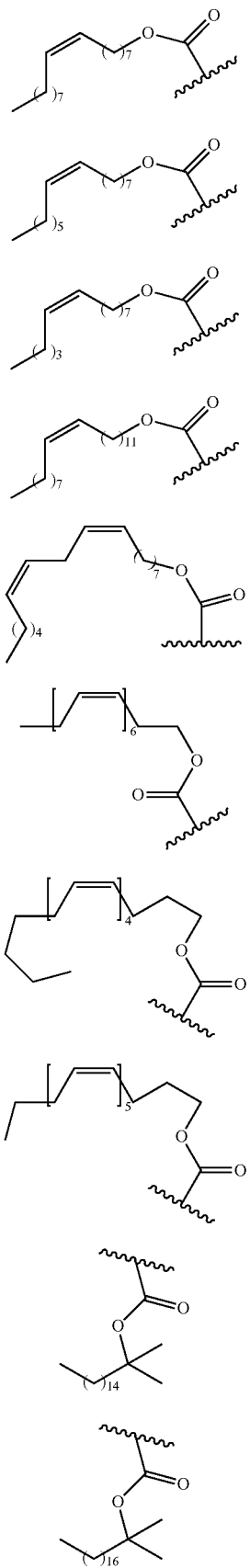
TABLE 1-continued
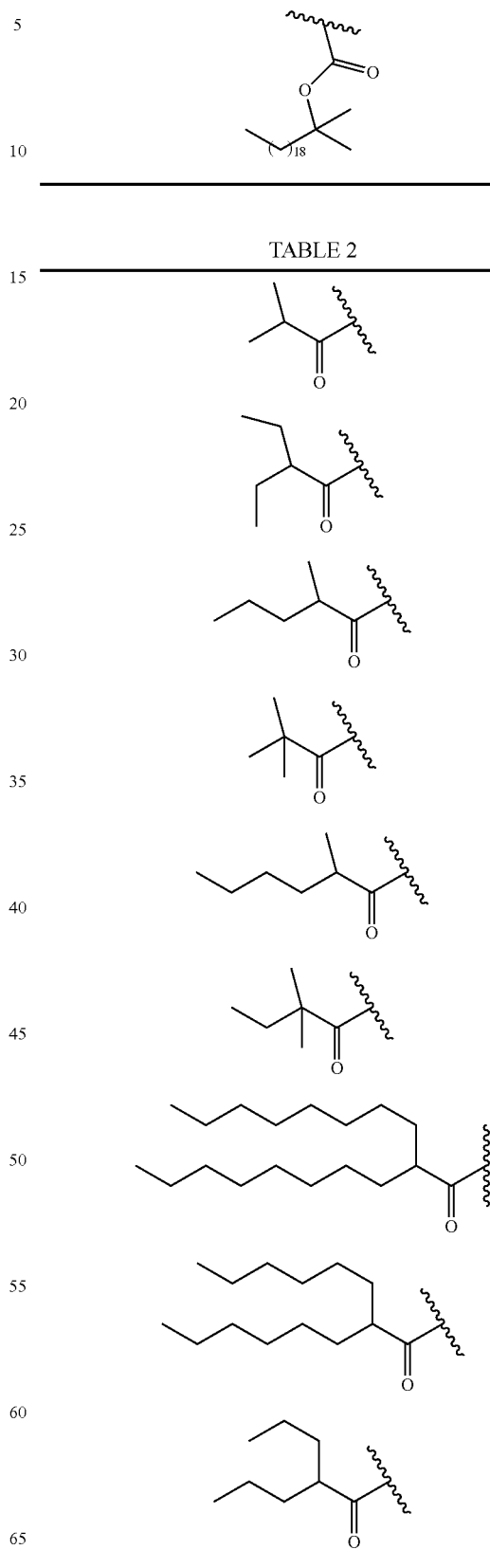
TABLE 2

TABLE 2-continued
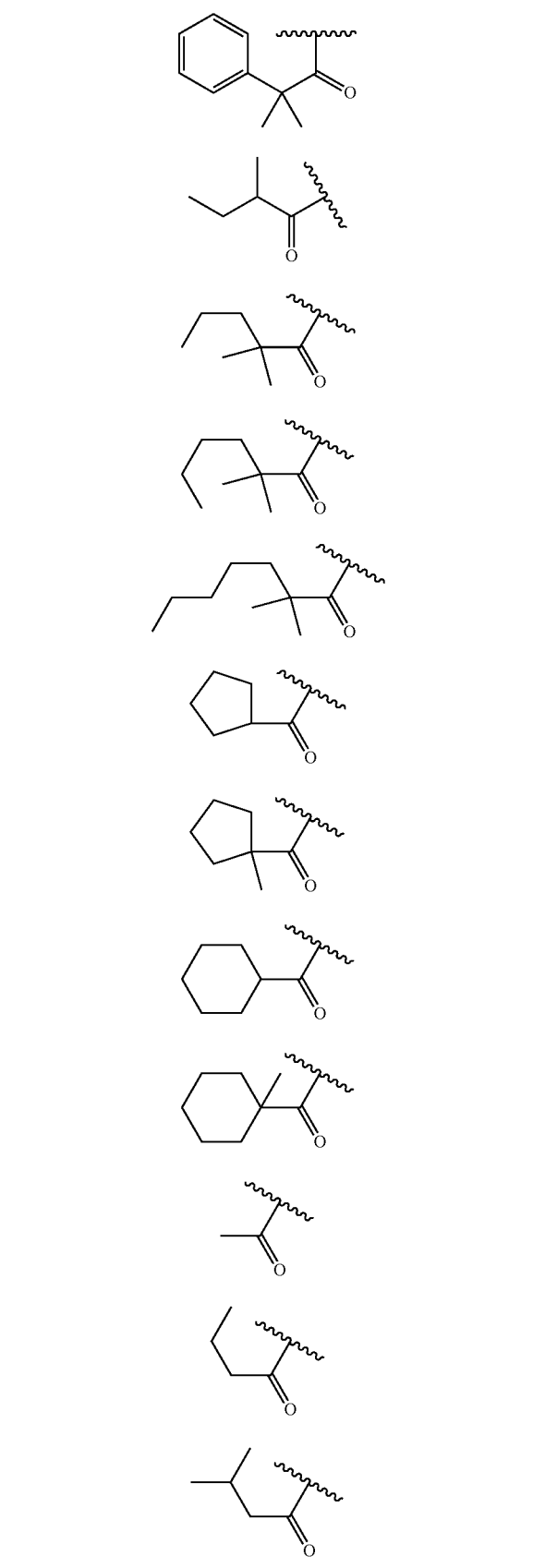
TABLE 2-continued
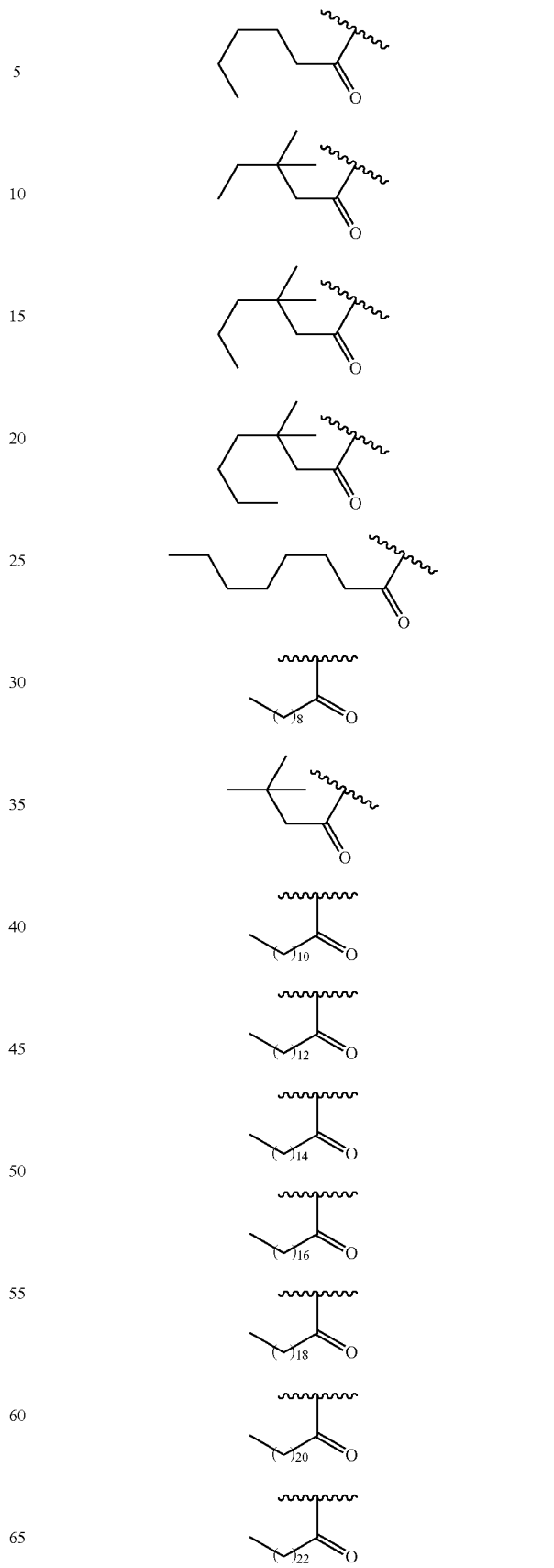

TABLE 2-continued
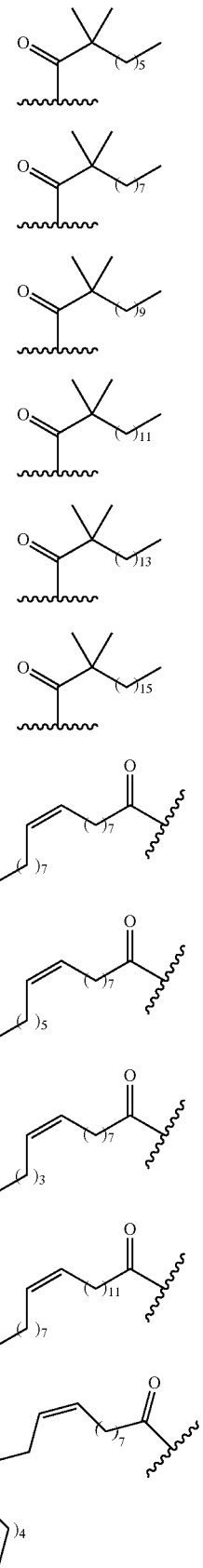
TABLE 2-continued
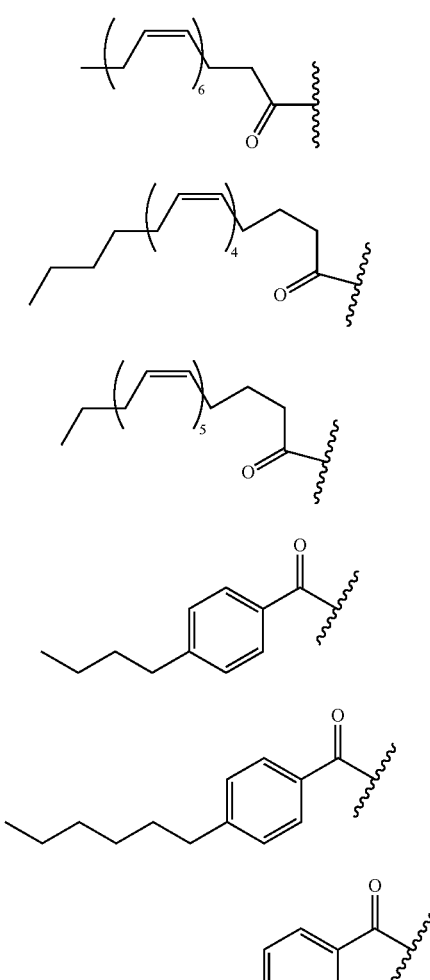
TABLE 3
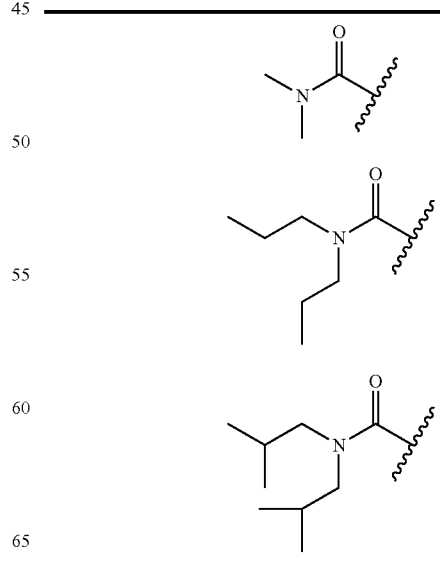

TABLE 3-continued
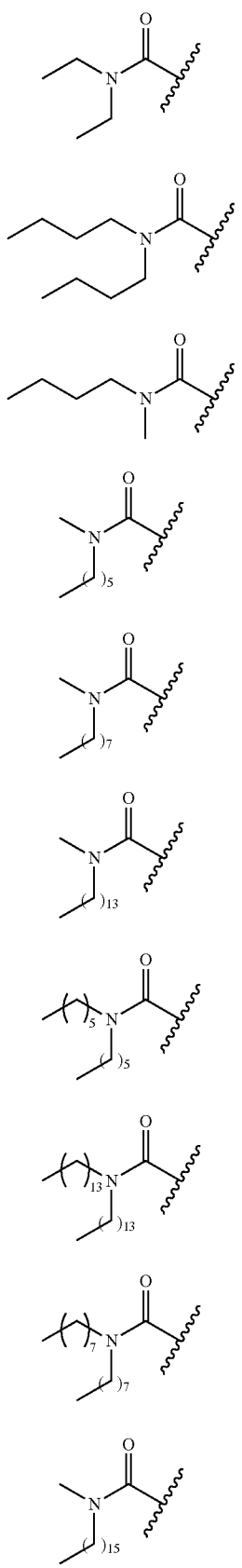
TABLE 3-continued
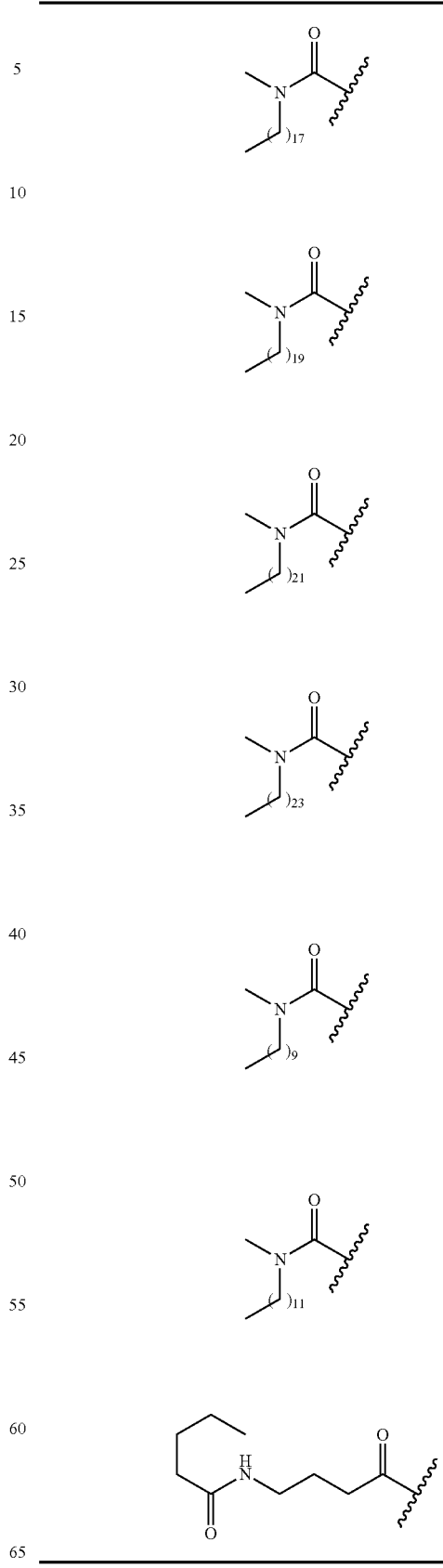

TABLE 4
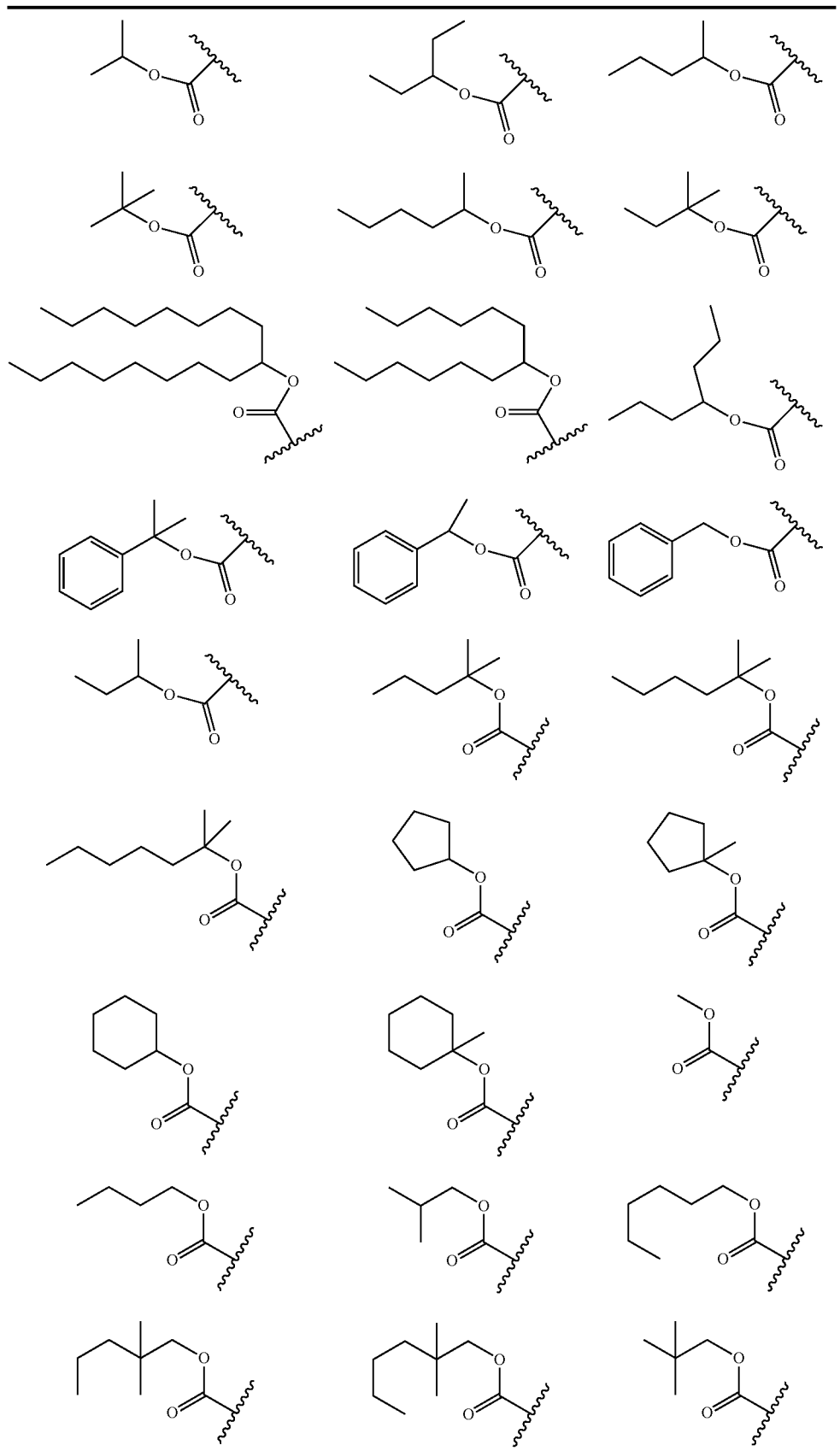

TABLE 4-continued
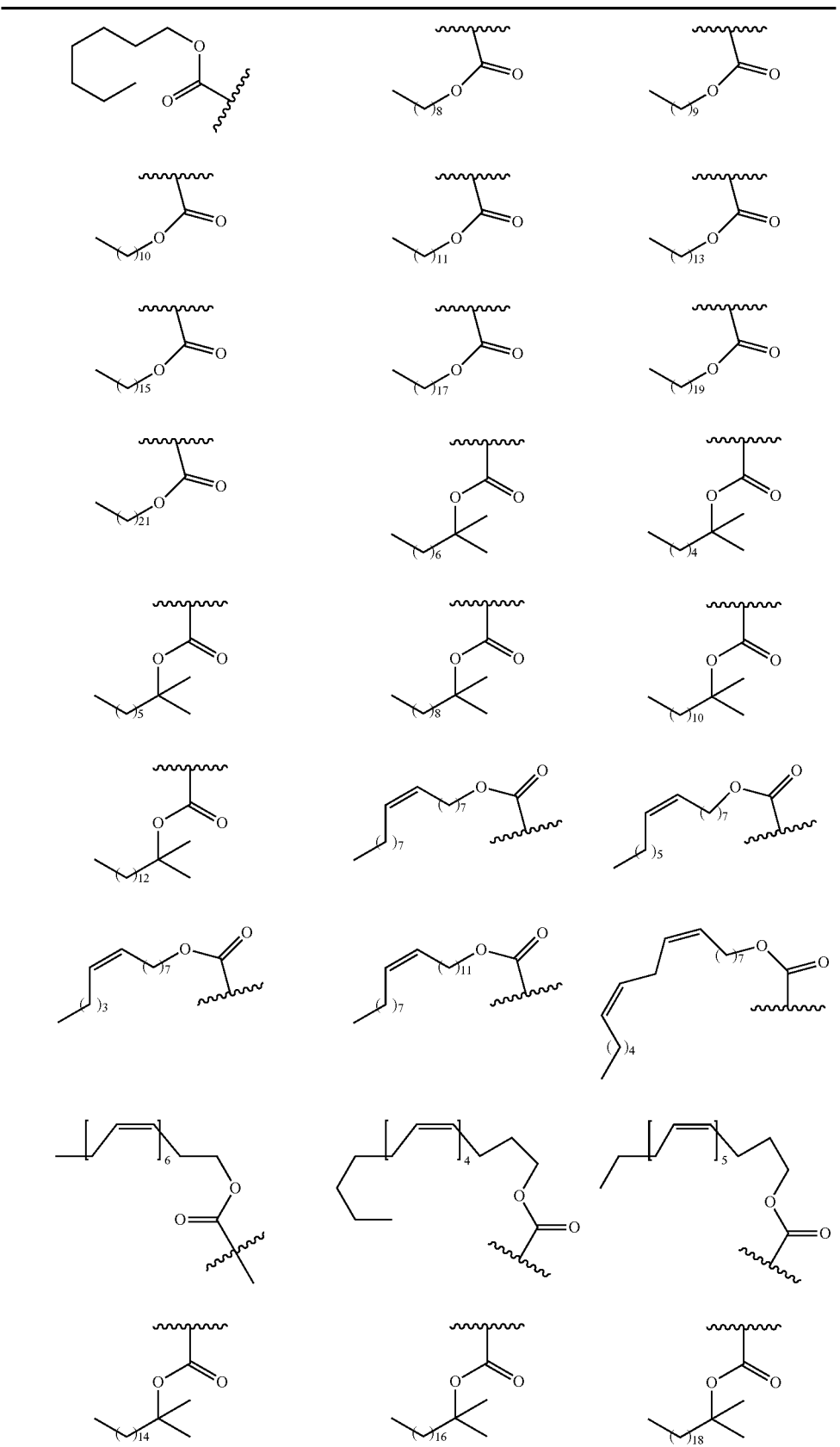

TABLE 4-continued
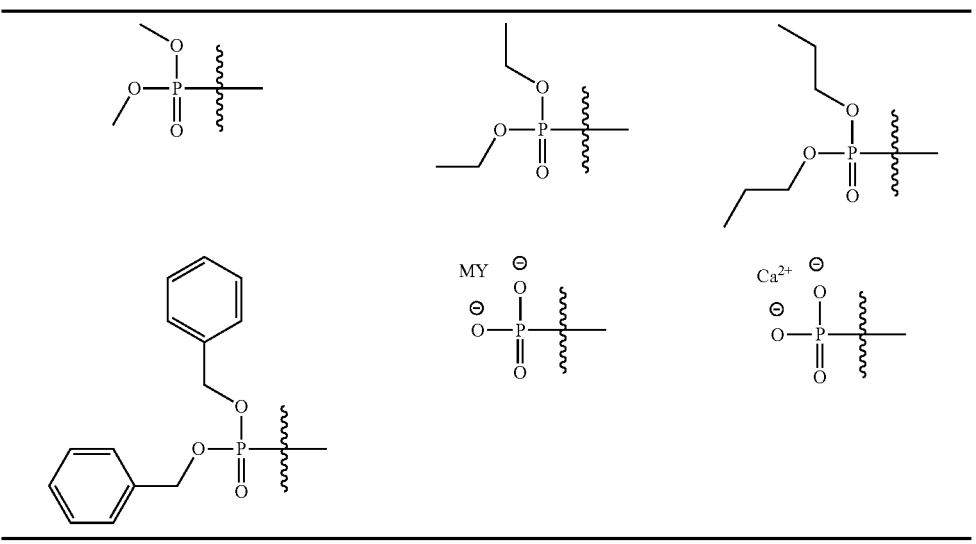
TABLE 5
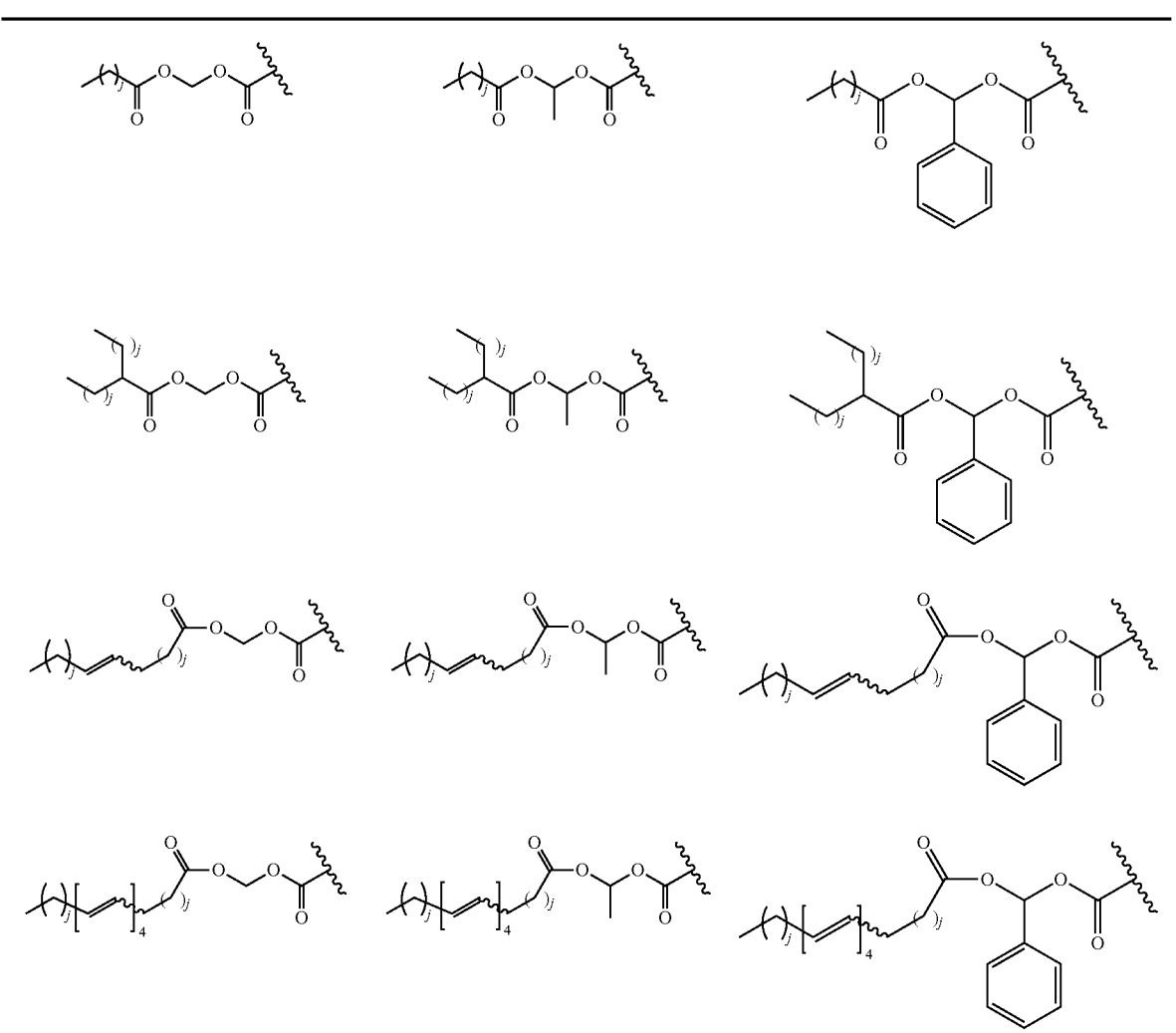

TABLE 5-continued

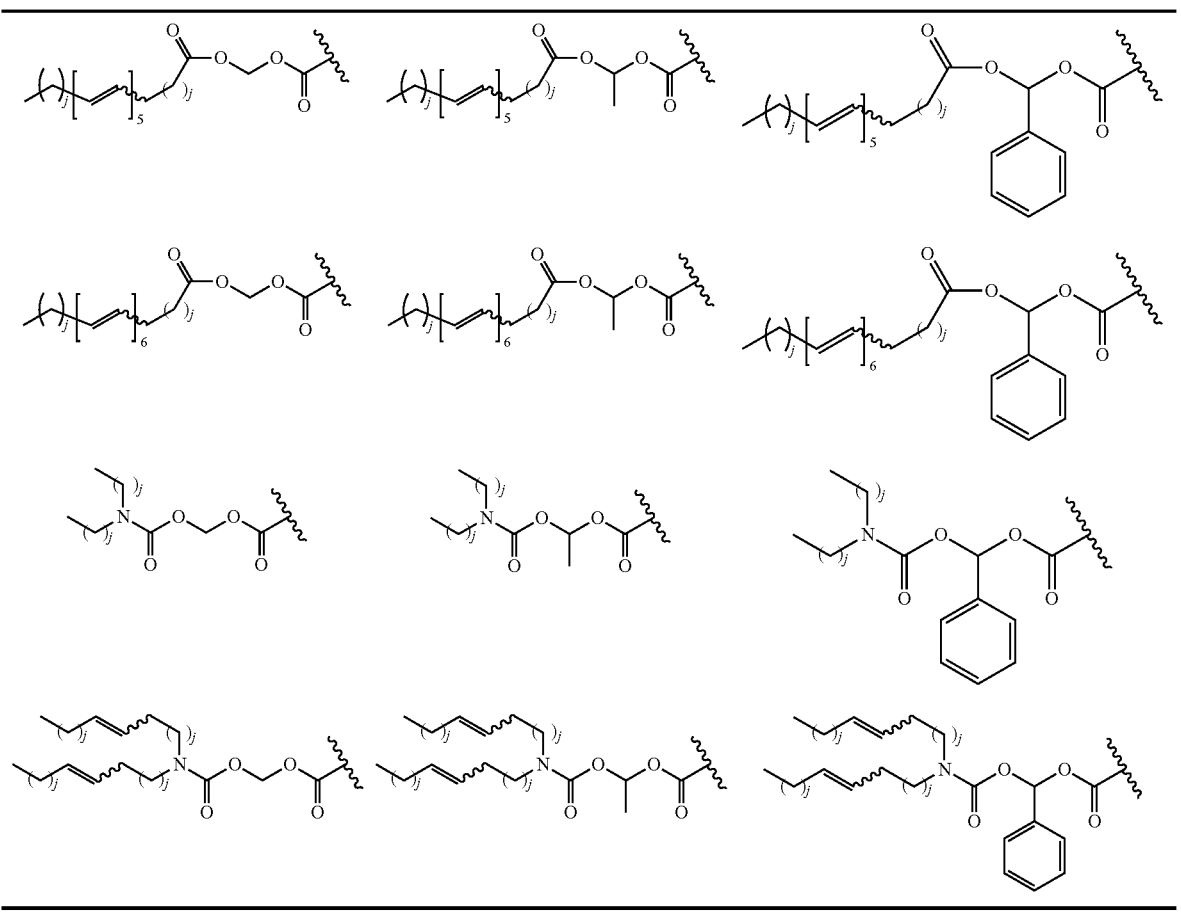

Wherein each j is independently 0, 1, 2, 3, 4, 5, 6, 7, 8, 9, 10, 11, 12, 13, 14, 15, 16, 17, 18, 19, 20, 21, 22, 23, 24, 25, 26, or 27.

Prodrugs of Lactam, Cyclic Urea, Imide, Carbamate Containing Pharmacophores

In one embodiment, compounds of the present invention are represented by Formula IV and V as illustrated below, or its geometric isomers, enantiomers, diastereomers, racemates, pharmaceutically acceptable salts co-crystals and solvates thereof:

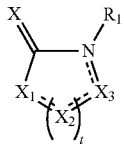

Formula IV

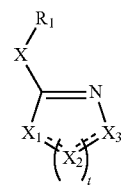

Formula V wherein ═══ represents a single or double bond;
X and $R_1$ are as defined above;

Each $X_1$, $X_2$, and $X_3$ is independently selected from absent, —S—, —O—, —S(O)—, —S(O)$_2$—, —N(R$_{10}$)—, —C(O)—, —C(OR$_{10}$)(R$_{11}$)—, —[C(R$_{10}$)(R$_{11}$)]$_v$—, —C(R$_{10}$)(R$_{11}$)═C(R$_{10}$)(R$_{11}$)—; wherein v is 0, 1, 2, 3, 4, 5, 6, 7, 8, 9 or 10;

wherein each $R_{10}$ and $R_{11}$ is independently absent, hydrogen, halogen, aliphatic, substituted aliphatic, aryl or substituted aryl; alternatively two $R_{10}$ and $R_{11}$ together with the atoms to which they are attached may form an additional optionally substituted, 3, 4, 5, 6 or 7 membered ring; and t is 0, 1, 2 or 3.

In one embodiment, compounds of the present invention are represented by Formula VI or VII as illustrated below, and the geometric isomers, enantiomers, diastereomers, racemates, pharmaceutically acceptable salts and solvates thereof:

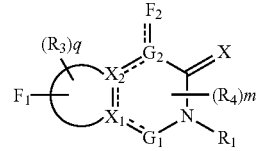

Formula VI

Formula VII

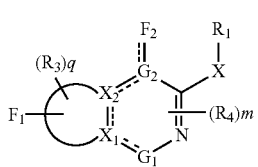

wherein ━━━━ represents a single or double bond;

X, $X_1$, $X_2$ and $R_1$ are as defined above;

semicircle represents an optionally substituted cycloalkyl, cycloalkenyl, heterocyclyl or aryl containing one, two or three rings;

each $F_1$ and $F_2$ is independently selected from absent and $R_5$-A-$Cy_1$-B-D-;

wherein, A is selected from absent, optionally substituted alkyl, optionally substituted alkenyl, optionally substituted alkynyl, —S—, —O—, —S(O)—, —S(O)$_2$—, —S[C($R_{30}$)($R_{31}$)]—$_u$, —S(O)[C($R_{30}$)($R_{31}$)]$_u$—, —S(O)$_2$[C($R_{30}$)($R_{31}$)]$_u$—, —O[C($R_{30}$)($R_{31}$)]$_u$—, —N($R_{30}$)—, —N($R_{30}$)[C($R_{31}$)($R_{32}$)]$_u$—, —[C($R_{30}$)($R_{31}$)]$_u$—, —C(O)[C($R_{30}$)($R_{31}$)]$_u$—;

wherein each u is independently 1, 2, 3, 4, 5, 6 or 7;

$Cy_1$ is absent or an optionally substituted cycloalkyl, optionally substituted cycloalkenyl, optionally substituted heterocyclyl, optionally substituted aryl or optionally substituted heteroaryl;

B is absent, or a linker;

D is selected from absent, —O—, —NR$_{33}$, —C($R_{34}$)($R_{35}$)—, —S—, —S(O)—, —S(O)$_2$—, —C(O)—;

Each $G_1$ and $G_2$ is independently selected from absent, —S—, —O—, —S(O)—, —S(O)$_2$—, —SC($R_{40}$)($R_{41}$)—, —S(O)C($R_{40}$)($R_{41}$)—, —S(O)$_2$C($R_{40}$)($R_{41}$)—, —C(O)—, —C(O$R_{40}$)($R_{41}$)—, —OC($R_{40}$)($R_{41}$)—, —N($R_{40}$)—, —C($R_{40}$)=C($R_{41}$)—, —N($R_{40}$)—C($R_{41}$)($R_{42}$)—, —[C($R_{40}$)($R_{41}$)]$_u$—;

Each $R_3$, $R_4$, $R_5$, $R_{30}$, $R_{31}$, $R_{32}$ $R_{33}$, $R_{34}$, $R_{35}$, $R_{40}$, $R_{41}$, and $R_{42}$ is independently selected from absent, hydrogen, halogen, —O$R_{10}$, —S$R_{10}$, —N$R_{10}R_{11}$—, —C(O)$R_{10}$, optionally substituted aliphatic, optionally substituted aryl or optionally substituted heterocyclyl;

Alternatively, two $R_3$ groups together or two $R_4$ groups together or one $R_3$ group with one $R_4$ group together forms an optionally substituted ring;

m and q are independently selected from 0, 1, and 2.

In a preferred embodiment, $G_2$ is selected from —N— or —C($R_{10}$)—.

In a preferred embodiment, the $R_5$ moiety is an aryl or heteroaryl group selected from:

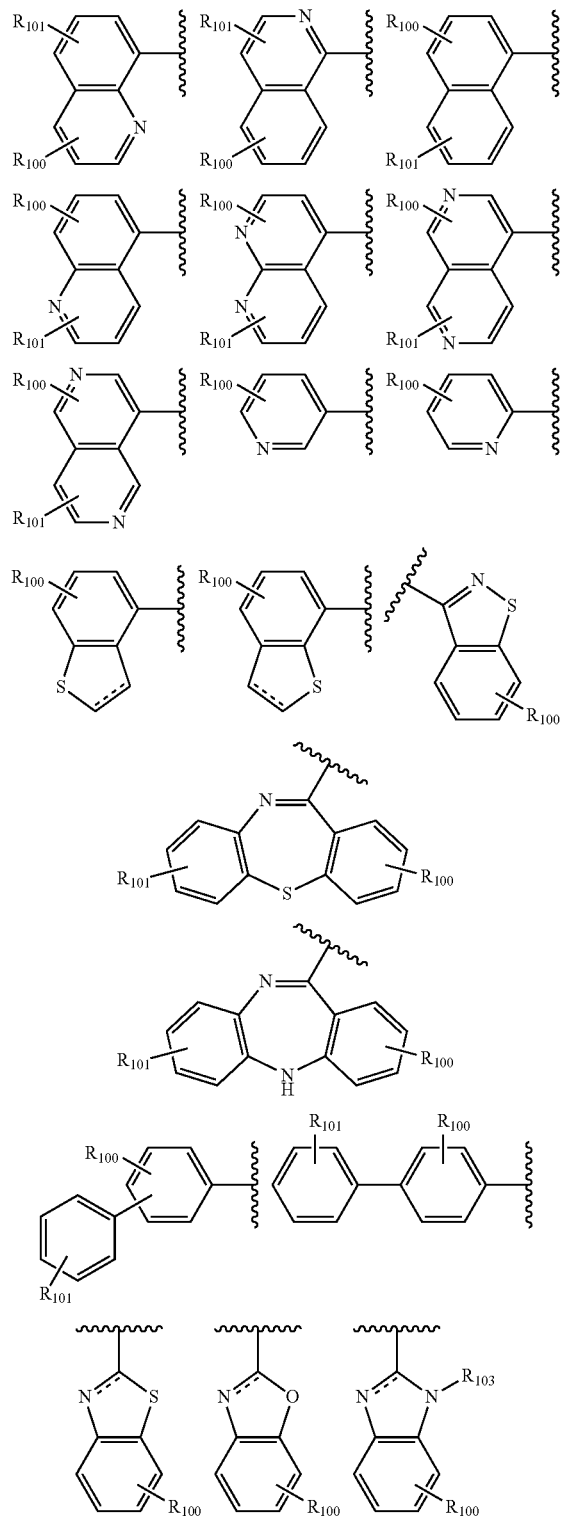

wherein $R_{100}$ $R_{101}$, and $R_{103}$ are independently selected from hydrogen, halogen, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ alkylamino and optionally substituted $C_1$-$C_8$ aryl.

In a preferred embodiment, Cy$_1$ is selected from:

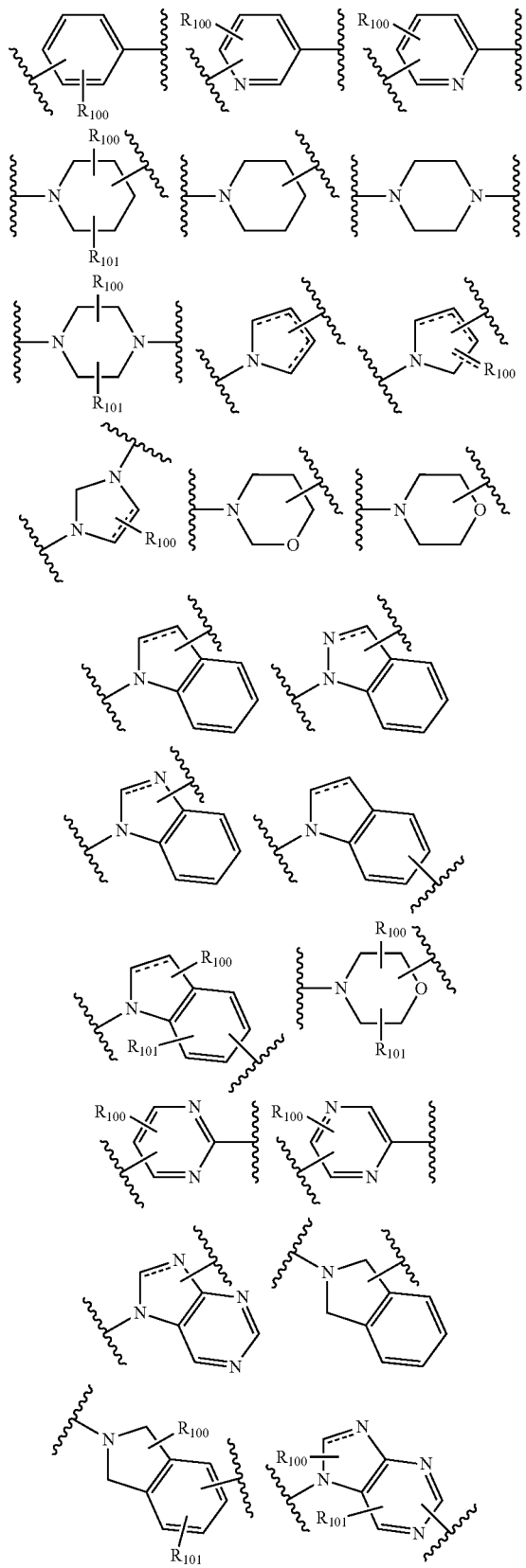

In a preferred embodiment, the bivalent B is a direct bond, a straight chain C$_1$-C$_{10}$ alkyl, C$_1$-C$_{10}$ alkenyl, C$_1$-C$_{10}$ alkynyl, C$_1$-C$_{10}$ alkoxy, alkoxyC$_1$-C$_{10}$alkoxy, C$_1$-C$_{10}$ alkylamino, alkoxyC$_1$-C$_{10}$alkylamino, C$_1$-C$_{10}$ alkylcarbonylamino, C$_1$-C$_{10}$ alkylaminocarbonyl, aryloxyC$_1$-C$_{10}$alkoxy, aryloxyC$_1$-C$_{10}$alkylamino, aryloxyC$_1$-C$_{10}$alkylamino carbonyl, C$_1$-C$_{10}$-alkylaminoalkylaminocarbonyl, C$_1$-C$_{10}$ alkyl(N-alkyl)aminoalkyl-aminocarbonyl, alkylaminoalkylamino, alkylcarbonylaminoalkylamino, alkyl(N-alkyl)aminoalkylamino, (N-alkyl)alkylcarbonylaminoalkylamino, alkylaminoalkyl, alkylaminoalkylaminoalkyl, alkylpiperazinoalkyl, piperazinoalkyl, alkylpiperazino, alkenylaryloxyC1-C10alkoxy, alkenylarylaminoC$_1$-C$_{10}$alkoxy, alkenylarylalkylaminoC$_1$-C$_{10}$alkoxy, alkenylaryloxyC$_1$-C$_{10}$alkylamino, alkenylaryloxyC$_1$-C$_{10}$alkylaminocarbonyl, piperazinoalkylaryl, heteroarylC$_1$-C$_{10}$alkyl, heteroarylC$_2$-C$_{10}$alkenyl, heteroarylC$_2$-C$_{10}$alkynyl, heteroarylC$_1$-C$_{10}$alkylamino, heteroarylC$_1$-C$_{10}$alkoxy, heteroaryloxyC$_1$-C$_{10}$alkyl, heteroaryloxyC$_2$-C$_{10}$alkenyl, heteroaryloxyC$_2$-C$_{10}$alkynyl, heteroaryloxyC$_1$-C$_{10}$alkylamino and heteroaryloxyC$_1$-C$_{10}$alkoxy.

In one embodiment, compounds of the present invention are represented by Formula VIII or VIIIA as illustrated below, or its geometric isomers, enantiomers, diastereomers, racemates, pharmaceutically acceptable salts and solvates thereof:

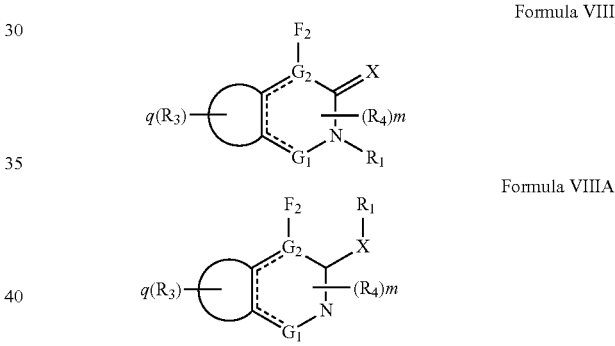

Formula VIII

Formula VIIIA wherein R$_1$, R$_3$, R$_4$, G$_1$, G$_2$, X, F$_2$, m and q are as defined above.

In a more preferred embodiment, compounds of the present invention are represented by Formula IX or X as illustrated below, or its geometric isomers, enantiomers, diastereomers, racemates, pharmaceutically acceptable salts and solvates thereof:

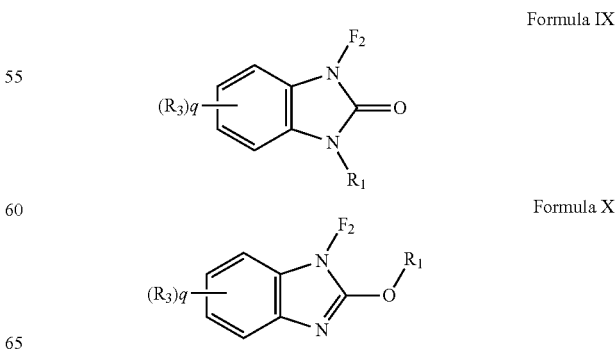

Formula IX

Formula X wherein R$_1$, R$_3$, F$_2$, and q are as defined above.

In a preferred embodiment a compound is selected from Table IX-X. A more preferred embodiment is a compound from Table IX-X wherein $R_1$ is selected from Tables 1-4.

TABLE IX-X

| No | Structure |
|---|---|
| 1 | 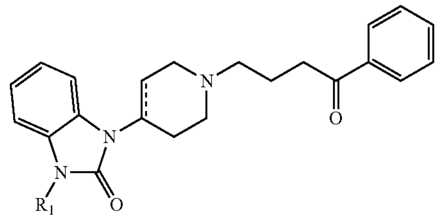 |
| 2 | 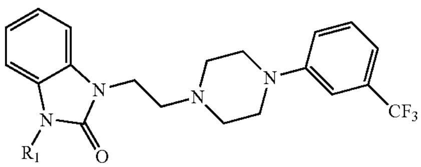 |
| 3 | 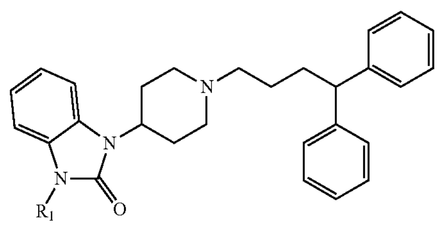 |
| 4 | 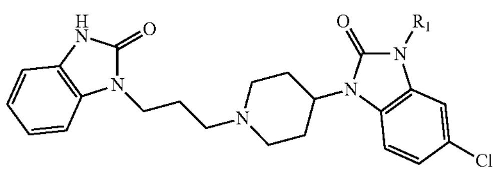 |
| 5 | 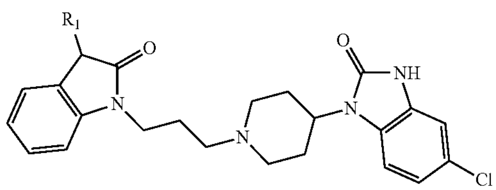 |
| 6 | 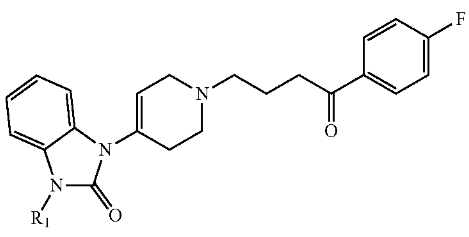 |
| 7 | 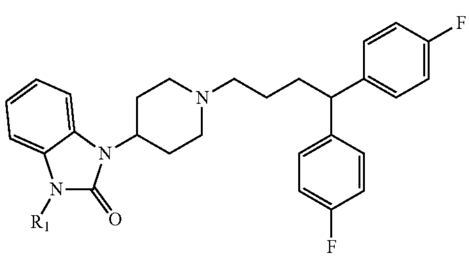 |

TABLE IX-X-continued

| No | Structure |
|---|---|
| 8 | 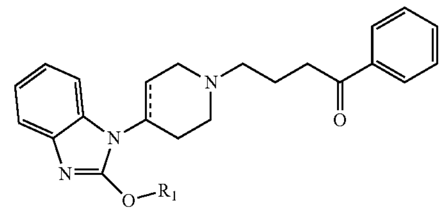 |
| 9 | 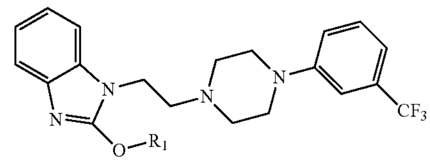 |
| 10 | 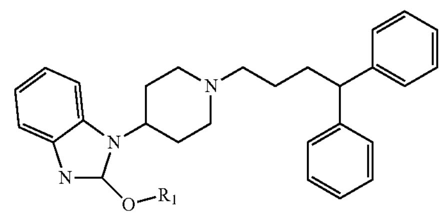 |
| 11 | 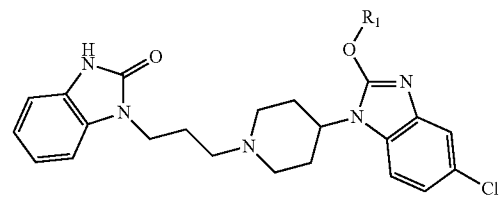 |
| 12 | 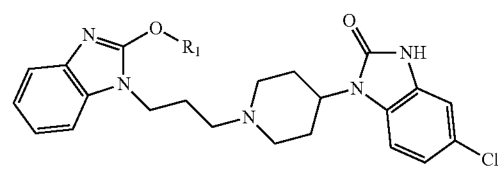 |
| 13 | 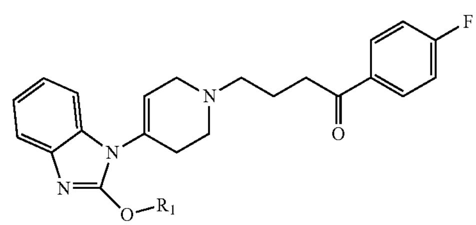 |
| 14 | 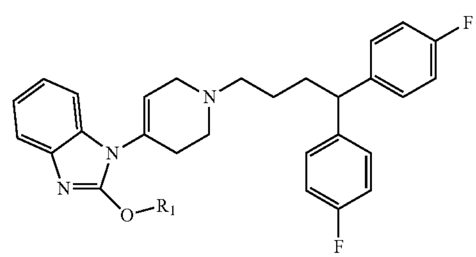 |

In a more preferred embodiment, prodrugs of domperidone are disclosed. (Formula 4 and 11 from Table IX-X). A more preferred embodiment is a compound of Formula 4 from Table IX-X, wherein $R_1$ is selected from Table 1. In a more preferred embodiment, a compound of Formula 4 from Table IX-X, wherein $R_1$ is selected from Tables 2-4 is disclosed.

In a more preferred embodiment, prodrugs of droperidol are disclosed. (Formula 6 and 13, from Table IX-X). In a more preferred embodiment, a compound of Formula 6 from Table IX-X wherein $R_1$ is selected from Table 1 is disclosed. A more preferred embodiment is a compound of Formula 6 from Table IX-X wherein $R_1$ is selected from Tables 2-4.

In a more preferred embodiment, prodrugs of pimozide are disclosed. (Formula 7 and 14 from Table IX-X). In a more preferred embodiment, a compound of Formula 7 from Table IX-X wherein $R_1$ is selected from Table 1 is disclosed. In a more preferred embodiment, a compound of Formula 7 from Table IX-X wherein $R_1$ is selected from Tables 2-4 is disclosed.

In another embodiment, compounds of the present invention are represented by Formula XI or XII as illustrated below, or its geometric isomers, enantiomers, diastereomers, racemates, pharmaceutically acceptable salts and solvates thereof:

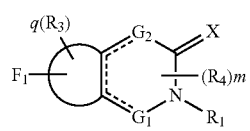

Formula XI

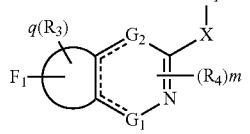

Formula XII wherein $R_1$, $R_3$, $R_4$, X, $F_1$, $G_1$, $G_2$, m and q are as defined above.

In another embodiment, compounds of the present invention are represented by Formula XIA or XIIA as illustrated below, or its geometric isomers, enantiomers, diastereomers, racemates, pharmaceutically acceptable salts and solvates thereof:

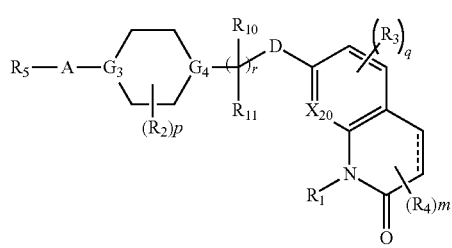

Formula XIA

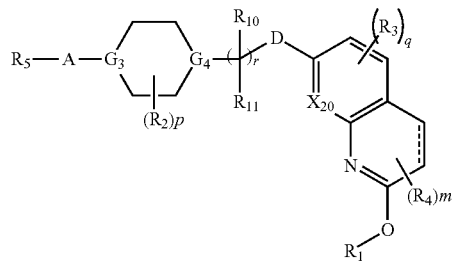

Formula XIIA wherein $R_1$, $R_3$, $R_4$, $R_5$, $R_{10}$, $R_{11}$, A, D, m, and q are as defined above;

$R_2$ is selected from absent, hydrogen, halogen, —$OR_{10}$, —$SR_{10}$, —$NR_{10}R_{11}$—, optionally substituted aliphatic, optionally substituted aryl or aryl or optionally substituted heterocyclyl;

r is 0, 1, 2, 3, 4, 5, 6, 7, 8, 9, 10 or 11;

each $G_3$ and $G_4$ is independently selected from —N—, —$C(R_{10})$—$[C(R_{10})(R_{11})]_a$—, wherein a is 0, 1 or 2;

$X_{20}$ is —$C(R_{10})$— or —N—; and p is selected 0, 1, 2 or 3.

In another embodiment, compounds of the present invention are represented by Formula XIB or XIIB as illustrated below, or its geometric isomers, enantiomers, diastereomers, racemates, pharmaceutically acceptable salts and solvates thereof:

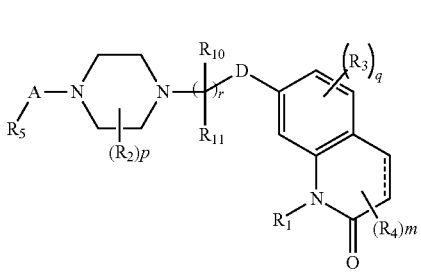

Formula XIB

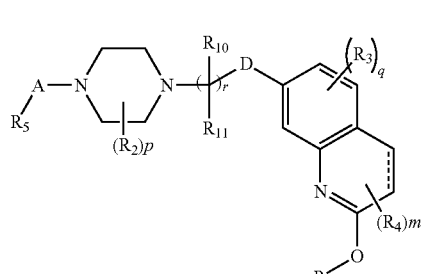

Formula XIIB wherein $R_1$, $R_2$, $R_3$, $R_4$, $R_5$, $R_{10}$, $R_{11}$, A, D, m, p and q are as defined above.

In another embodiment, compounds of the present invention are represented by Formula XIC or XIIC as illustrated below, or its geometric isomers, enantiomers, diastereomers, racemates, pharmaceutically acceptable salts and solvates thereof:

Formula XIC

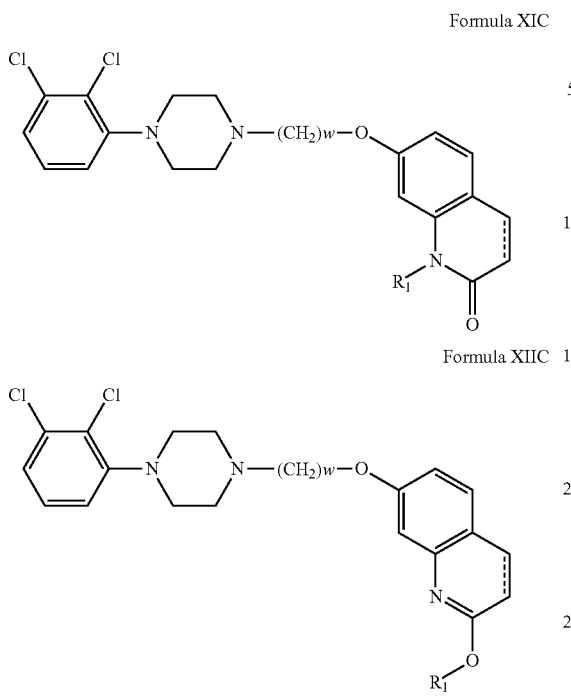

Formula XIIC

Formula XIE

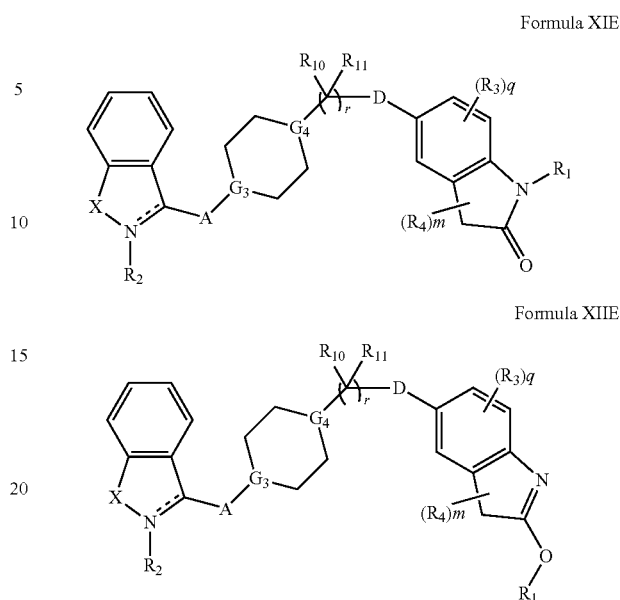

Formula XIIE wherein, X, $R_1$, $R_2$, $R_3$, $R_4$, A, D, $G_3$, $G_4$, m, q, r, $R_{10}$ and $R_{11}$ are as defined above.

In another embodiment, compounds of the present invention are represented by Formula XIF or XIIF as illustrated below, or its geometric isomers, enantiomers, diastereomers, racemates, pharmaceutically acceptable salts and solvates thereof:

wherein $R_1$, is as defined above; and w is 1, 2, 3, 4, 5, 6, 7, 8, 9, 10 or 11.

In another embodiment, compounds of the present invention are represented by Formula XID or XIID as illustrated below, or its geometric isomers, enantiomers, diastereomers, racemates, pharmaceutically acceptable salts and solvates thereof:

Formula XID

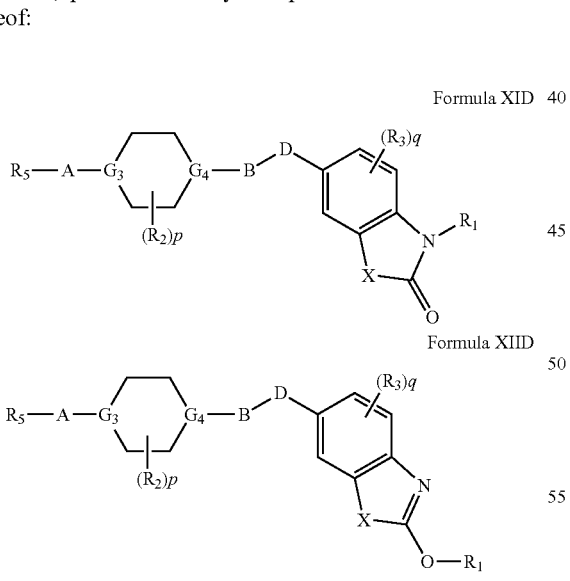

Formula XIID

Formula XIF

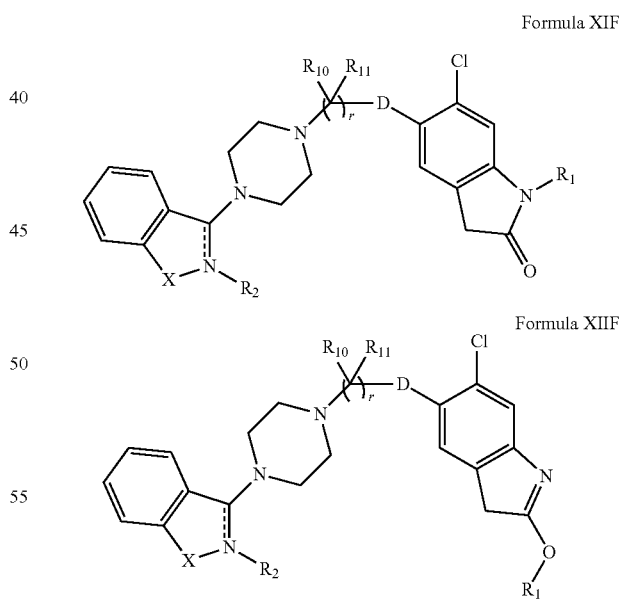

Formula XIIF wherein, $X_1$, $R_1$, $R_2$, $R_3$, $R_5$, A, B, D, $G_3$, $G_4$, p, q, $R_{10}$ and $R_{11}$ are as defined above.

In another embodiment, compounds of the present invention are represented by Formula XIE or XIIE as illustrated below, or its geometric isomers, enantiomers, diastereomers, racemates, pharmaceutically acceptable salts and solvates thereof:

wherein, X, $R_1$, $R_2$, D, r, $R_{10}$ and $R_{11}$ are as defined above.

In another embodiment, compounds of the present invention are represented by Formula XIG or XIIG as illustrated below, or its geometric isomers, enantiomers, diastereomers, racemates, pharmaceutically acceptable salts and solvates thereof:

Formula XIG

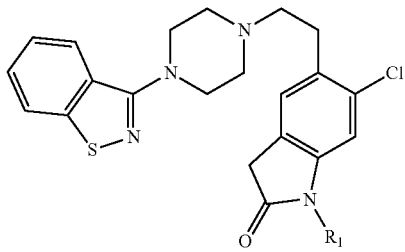

Formula XIIG

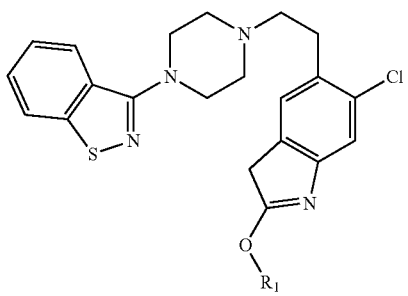

wherein R₁, is as defined above.

In another embodiment, compounds of the present invention are represented by Formula XIH or XIIIH as illustrated below, or its geometric isomers, enantiomers, diastereomers, racemates, pharmaceutically acceptable salts and solvates thereof:

Formula XIH

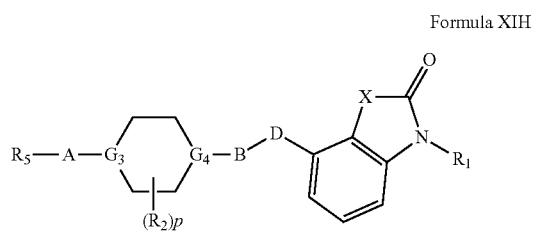

Formula XIIIH

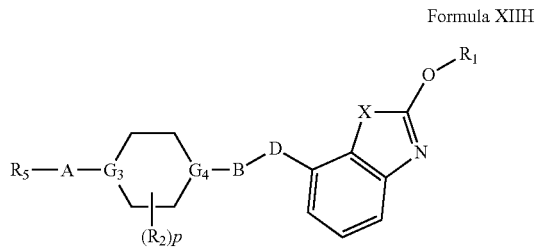

wherein, X, $R_1$, $R_2$, $R_5$, A, D, $G_3$, $G_4$ and p, are as defined above.

In another embodiment, compounds of the present invention are represented by Formula XI-I or XII-I as illustrated below, or its geometric isomers, enantiomers, diastereomers, racemates, pharmaceutically acceptable salts and solvates thereof:

Formula XI-I

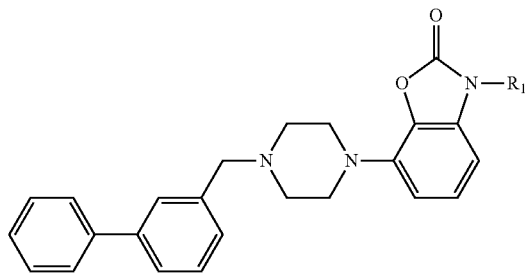

Formula XII-I

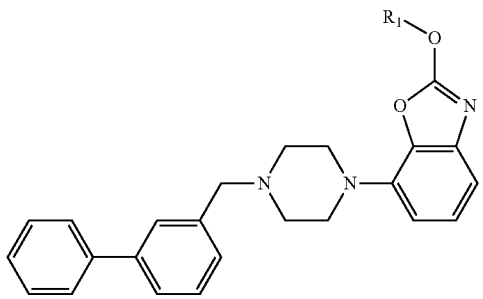

wherein R₁, is as defined above.

In another embodiment, compounds of the present invention are represented by Formula XIJ or XIIJ as illustrated below, or its geometric isomers, enantiomers, diastereomers, racemates, pharmaceutically acceptable salts and solvates thereof:

Formula XIJ

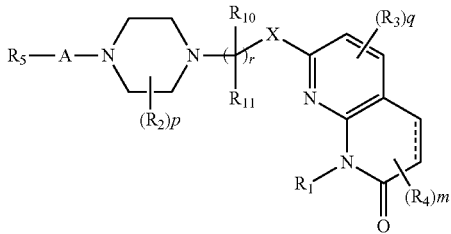

Formula XIIJ

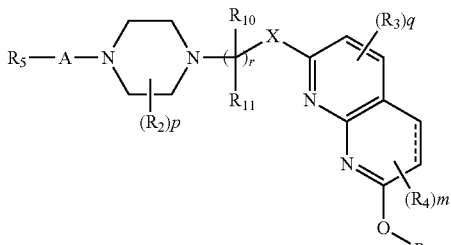

wherein, X, $R_1$, $R_2$, $R_3$, $R_4$, $R_5$, A, D, $G_3$, $G_4$, p, $R_{10}$ and $R_{11}$ are as defined above.

In another embodiment, compounds of the present invention are represented by Formula XIK or XIIK as illustrated below, or its geometric isomers, enantiomers, diastereomers, racemates, pharmaceutically acceptable salts and solvates thereof:

Formula XIK
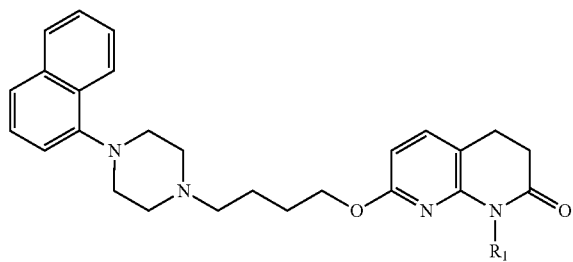
Formula XIIK
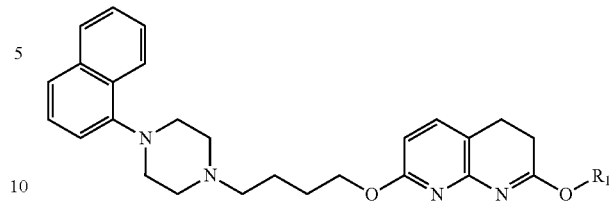
wherein $R_1$, is as defined above.
In a preferred embodiment a compound is selected from Table XI-XII. A more preferred embodiment is a compound from Table XI-XII, wherein $R_1$ is selected from Table 1-4.
TABLE XI-XII
XI-1
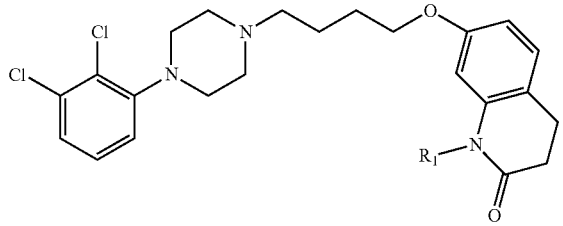
XII-1
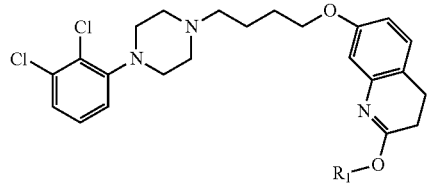
XI-2
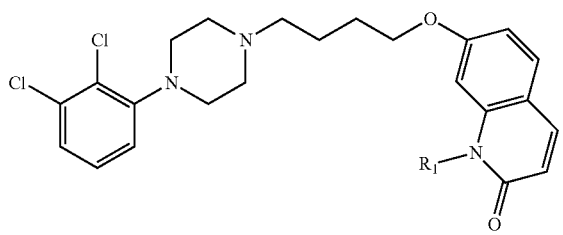
XII-2
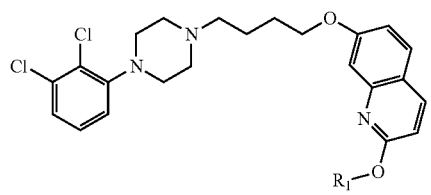
XI-3
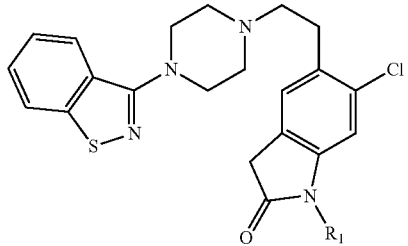
XII-3
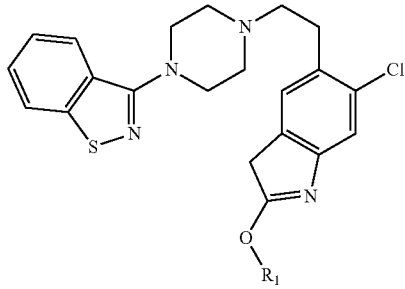
XI-4
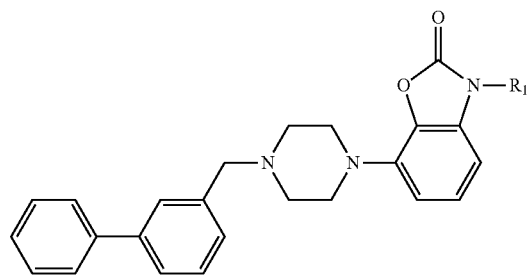
XII-4
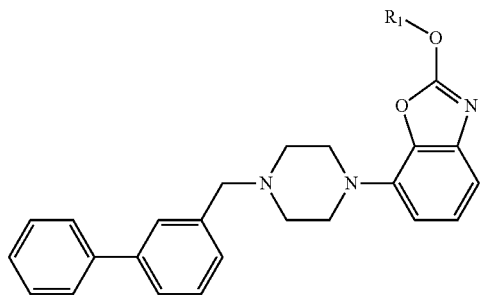

TABLE XI-XII-continued

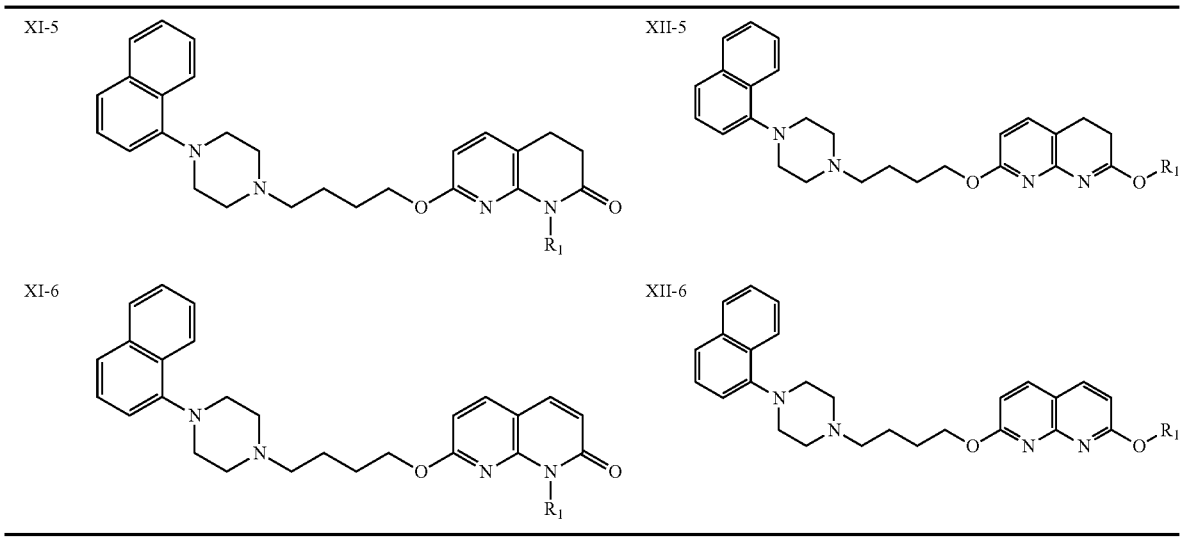

In a more preferred embodiment, prodrugs of aripiprazole are disclosed. (Formula 1 and 7 from Table XI-XII). In a more preferred embodiment, a compound of Formula 1 wherein $R_1$ is selected from Table 1 is disclosed. In a more preferred embodiment, a compound of Formula 1 wherein $R_1$ is selected from Tables 2-4 is disclosed.

In a more preferred embodiment, prodrugs of dehydroaripiprazole are disclosed. (Formula 2 and 8 from Table XI-XII). In a more preferred embodiment, a compound of Formula 2 wherein $R_1$ is selected from Table 1 is disclosed. In a more preferred embodiment, a compound of Formula 2 wherein $R_1$ is selected from tables 2-4 is disclosed.

In a more preferred embodiment, prodrugs of ziprasidone are disclosed. (Formula 3 and 9 from Table XI-XII). In a more preferred embodiment, a compound of Formula 3 wherein $R_1$ is selected from Table 1 is disclosed. In a more preferred embodiment, a compound of Formula 3 wherein $R_1$ is selected from Tables 2-4 is disclosed.

In a more preferred embodiment, prodrugs of bifeprunox are disclosed. (Formula 4 and 11 from Table XI-XII). In a more preferred embodiment, a compound of Formula 4 wherein $R_1$ is selected from Table 1 is disclosed. In a more preferred embodiment, a compound of Formula 4 wherein $R_1$ is selected from tables 2-4 is disclosed.

Representative compounds according to the invention are those selected from the Tables A-F below and the geometric isomers, enantiomers, diastereomers, racemates, pharmaceutically acceptable salts and solvates thereof:

TABLE A

| No. | Structure |
| --- | --- |
| 1. | 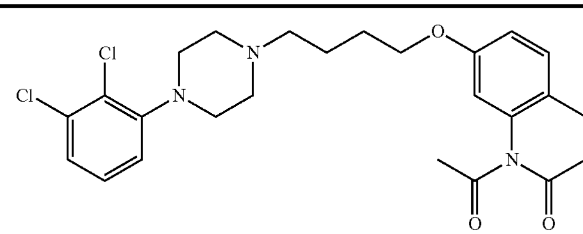 |
| 2. | 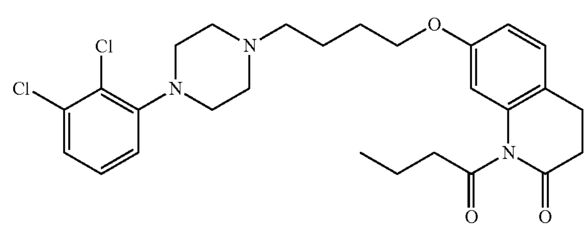 [SMILES: CCCC(=O)N1C(=O)CCc2ccc(OCCCCN3CCN(c4cccc(Cl)c4Cl)CC3)cc21] |

TABLE A-continued
| No. | Structure |
|---|---|
| 3. | 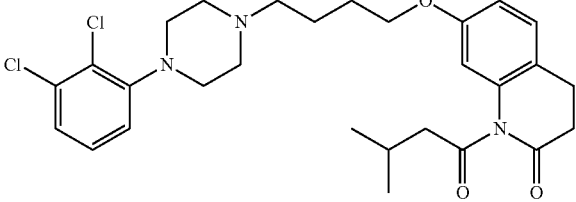 |
| 4. | 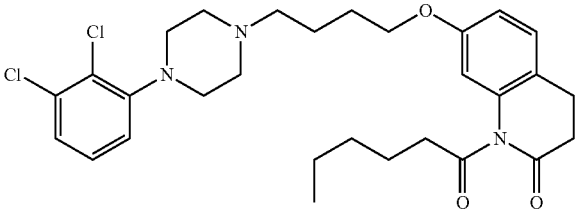 [SMILES: CCCCCC(=O)N1C(=O)CCc2ccc(OCCCCN3CCN(c4cccc(Cl)c4Cl)CC3)cc21] |
| 5. | 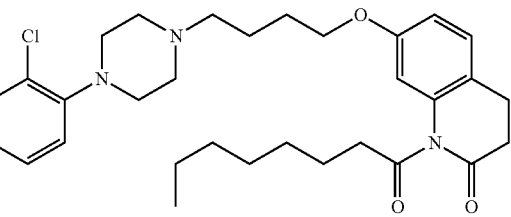 |
| 6. | 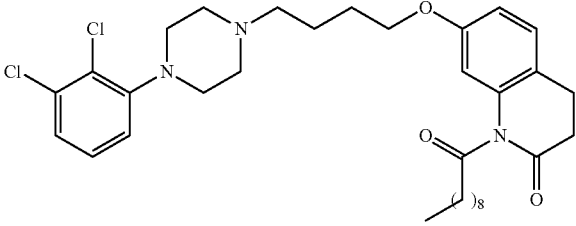 |
| 7. | 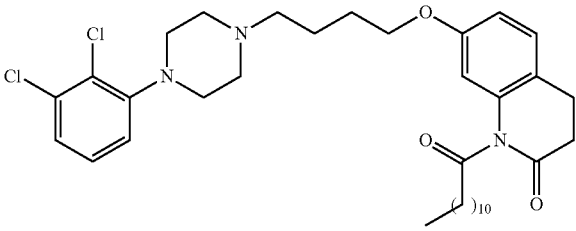 |
| 8. | 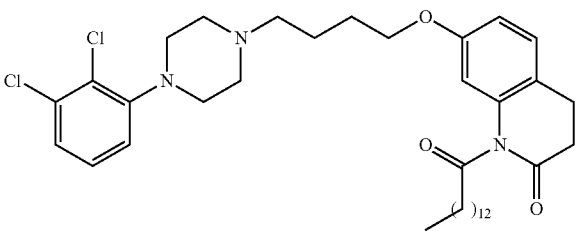 |

TABLE A-continued

| No. | Structure |
| --- | --- |
| 9. | 2,3-dichlorophenyl-piperazine-(CH$_2$)$_4$-O-(3,4-dihydroquinolin-2(1H)-one) N-acyl with (CH$_2$)$_{13}$CH$_3$ |
| 10. | 2,3-dichlorophenyl-piperazine-(CH$_2$)$_4$-O-(3,4-dihydroquinolin-2(1H)-one) N-acyl with (CH$_2$)$_{14}$CH$_3$ |
| 11. | 2,3-dichlorophenyl-piperazine-(CH$_2$)$_4$-O-(3,4-dihydroquinolin-2(1H)-one) N-acyl with (CH$_2$)$_{16}$CH$_3$ |
| 12. | 2,3-dichlorophenyl-piperazine-(CH$_2$)$_4$-O-(3,4-dihydroquinolin-2(1H)-one) N-acyl with (CH$_2$)$_{18}$CH$_3$ |
| 13. | 2,3-dichlorophenyl-piperazine-(CH$_2$)$_4$-O-(3,4-dihydroquinolin-2(1H)-one) N-acyl with (CH$_2$)$_{20}$CH$_3$ |
| 14. | 2,3-dichlorophenyl-piperazine-(CH$_2$)$_4$-O-(3,4-dihydroquinolin-2(1H)-one) N-acyl with (CH$_2$)$_{22}$CH$_3$ |

TABLE A-continued
| No. | Structure |
|---|---|
| 15. | 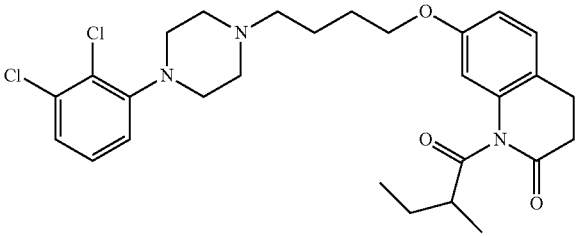 [SMILES: CCC(C)C(=O)N1C(=O)CCc2ccc(OCCCCN3CCN(c4cccc(Cl)c4Cl)CC3)cc21] |
| 16. | 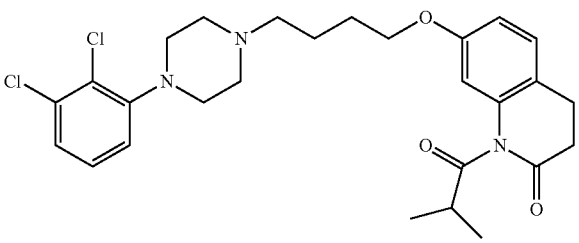 [SMILES: CC(C)C(=O)N1C(=O)CCc2ccc(OCCCCN3CCN(c4cccc(Cl)c4Cl)CC3)cc21] |
| 17. | 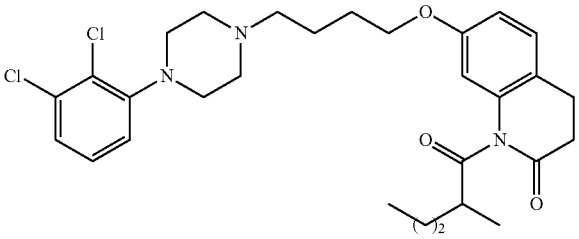 |
| 18. | 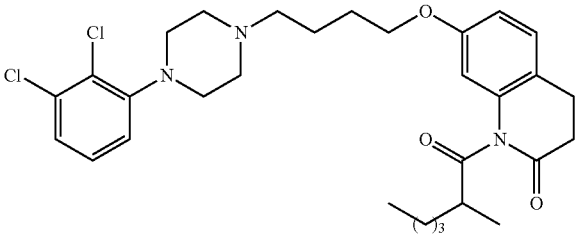 |
| 19. | 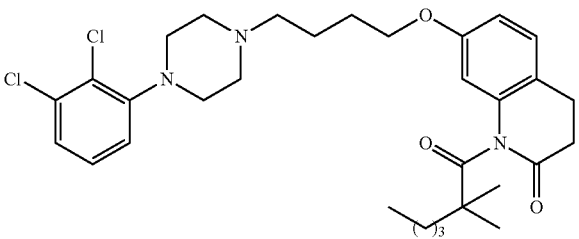 |
| 20. | 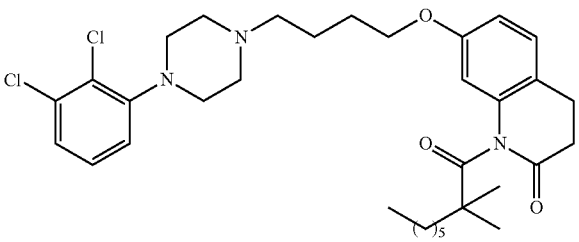 |

TABLE A-continued
| No. | Structure |
|---|---|
| 21. | 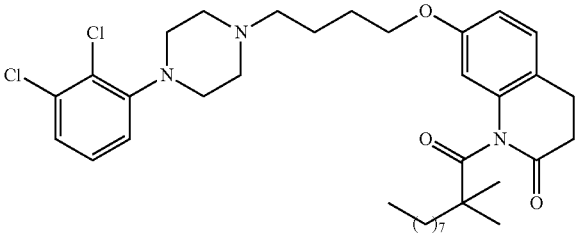 |
| 22. | 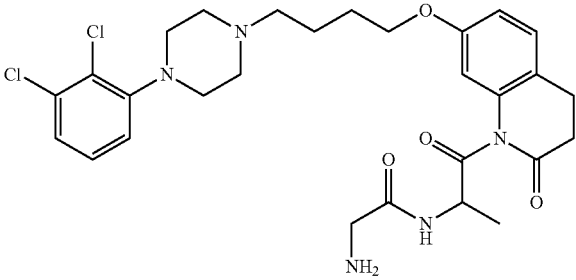 [SMILES: CC(NC(=O)CN)C(=O)N1C(=O)CCc2ccc(OCCCCN3CCN(c4cccc(Cl)c4Cl)CC3)cc21] |
| 23. | 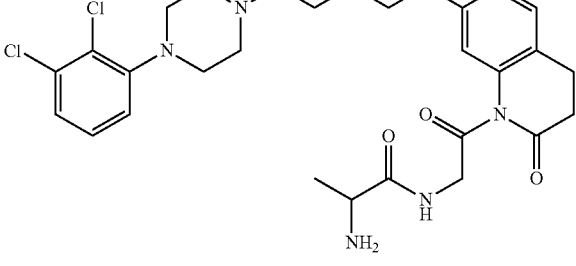 |
| 24. | 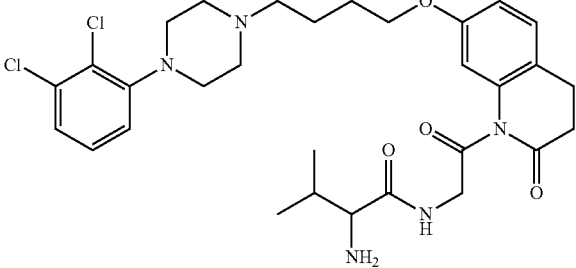 |
| 25. | 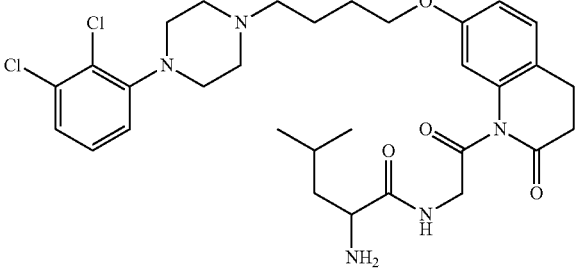 |

TABLE A-continued
| No. | Structure |
|-----|-----------|
| 26. | 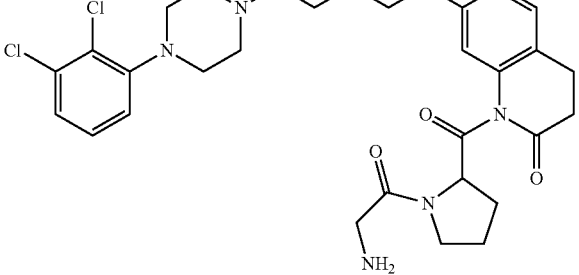 |
| 27. | 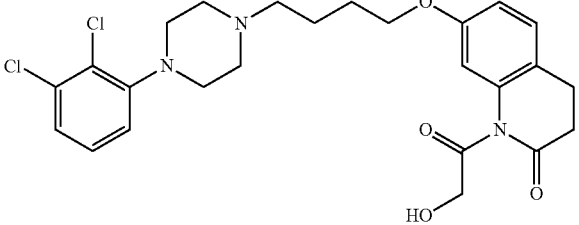 |
| 28. | 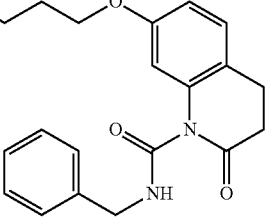 |
| 29. | 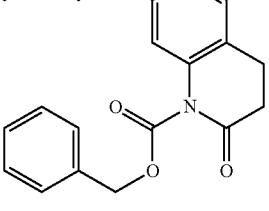 |
| 30. | 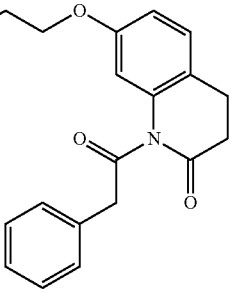 |

TABLE A-continued
| No. | Structure |
|---|---|
| 31. | 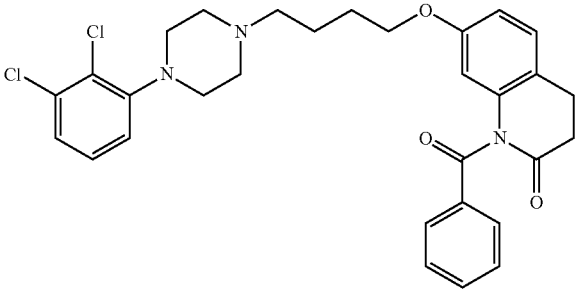 [SMILES: O=C1CCc2ccc(OCCCCN3CCN(c4cccc(Cl)c4Cl)CC3)cc2N1C(=O)c1ccccc1] |
| 32. | 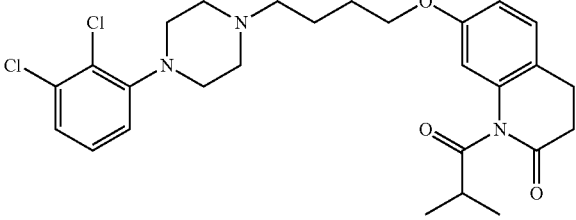 |
| 33. | 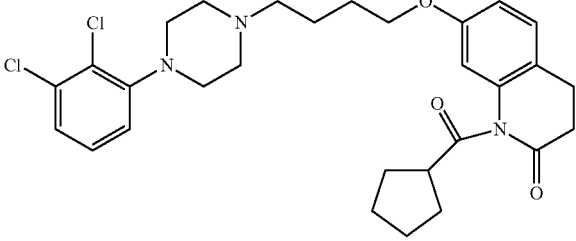 |
| 34. | 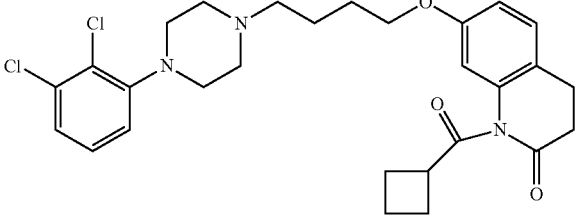 |
| 35. | 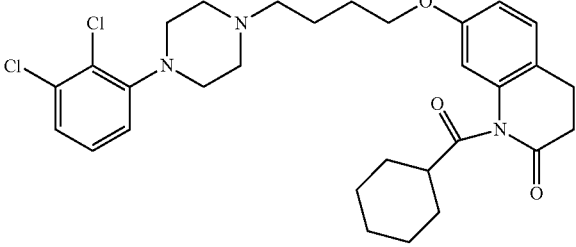 |
| 36. | 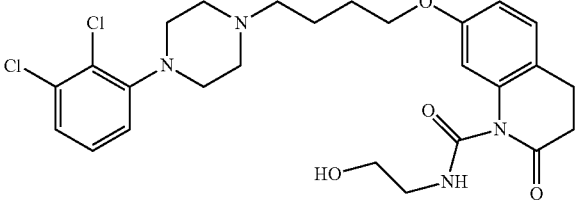 |

TABLE A-continued

| No. | Structure |
|---|---|
| 37. | 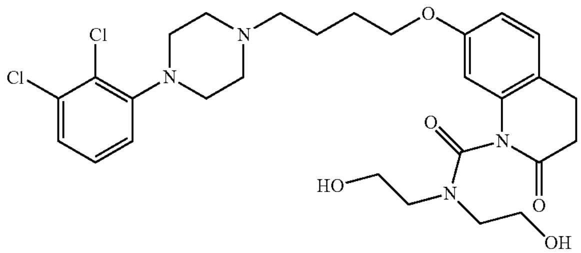 [SMILES: O=C1CCc2ccc(OCCCCN3CCN(c4cccc(Cl)c4Cl)CC3)cc2N1C(=O)N(CCO)CCO] |
| 38. | 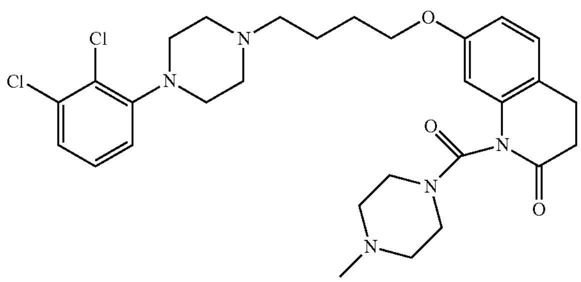 [SMILES: CN1CCN(C(=O)N2C(=O)CCc3ccc(OCCCCN4CCN(c5cccc(Cl)c5Cl)CC4)cc32)CC1] |
| 39. | 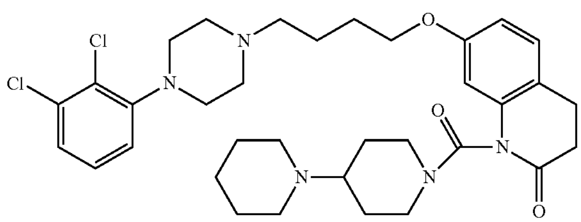 [SMILES: O=C1CCc2ccc(OCCCCN3CCN(c4cccc(Cl)c4Cl)CC3)cc2N1C(=O)N1CCC(N2CCCCC2)CC1] |
| 40. | 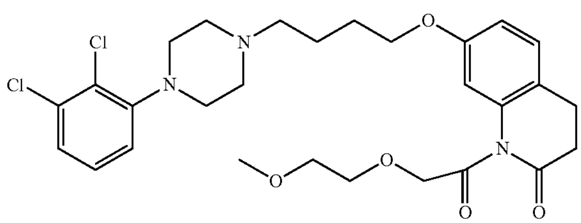 [SMILES: COCCOCC(=O)N1C(=O)CCc2ccc(OCCCCN3CCN(c4cccc(Cl)c4Cl)CC3)cc21] |
| 41. | 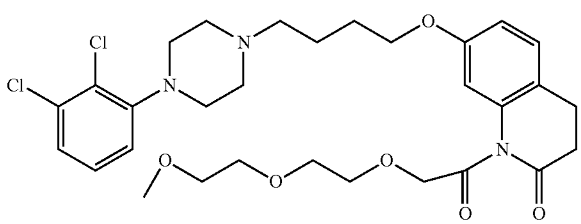 [SMILES: COCCOCCOCC(=O)N1C(=O)CCc2ccc(OCCCCN3CCN(c4cccc(Cl)c4Cl)CC3)cc21] |
| 42. | 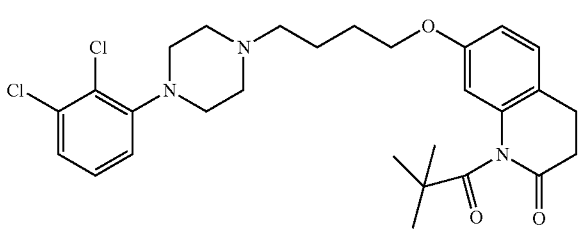 |

TABLE A-continued

| No. | Structure |
|---|---|
| 43. | 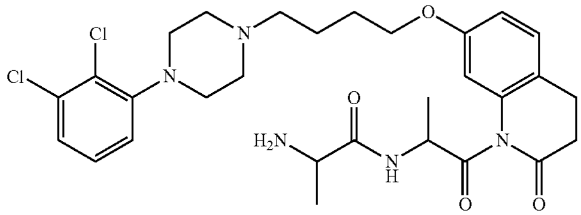 |
| 44. | 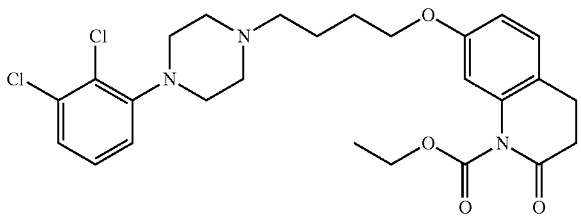 [SMILES: CCOC(=O)N1C(=O)CCc2ccc(OCCCCN3CCN(c4cccc(Cl)c4Cl)CC3)cc21] |
| 45. | 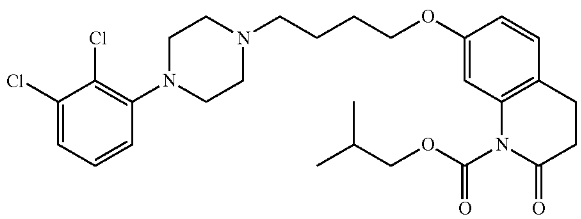 [SMILES: CC(C)COC(=O)N1C(=O)CCc2ccc(OCCCCN3CCN(c4cccc(Cl)c4Cl)CC3)cc21] |
| 46. | 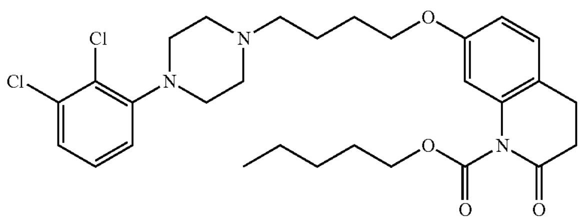 [SMILES: CCCCCOC(=O)N1C(=O)CCc2ccc(OCCCCN3CCN(c4cccc(Cl)c4Cl)CC3)cc21] |
| 47. | 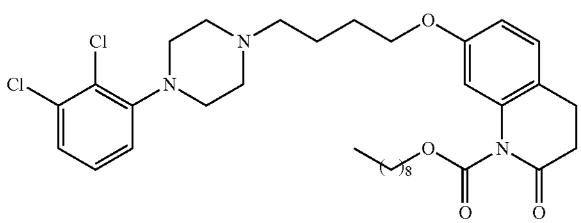 |
| 48. | 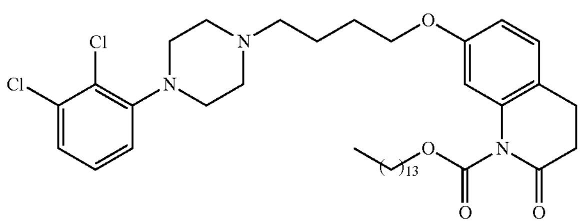 |
| 49. | 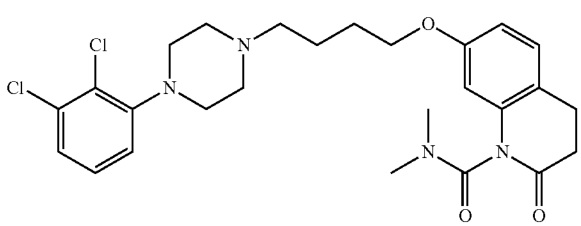 [SMILES: CN(C)C(=O)N1C(=O)CCc2ccc(OCCCCN3CCN(c4cccc(Cl)c4Cl)CC3)cc21] |

TABLE A-continued
| No. | Structure |
|---|---|
| 50. | 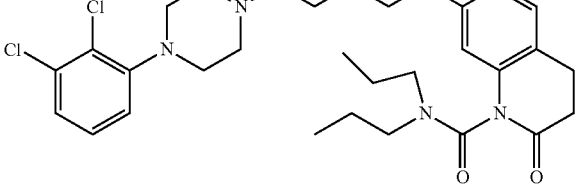 |
| 51. | 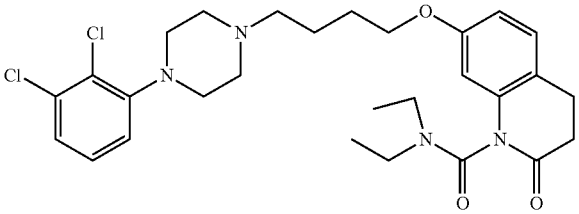 [SMILES: CCN(CC)C(=O)N1C(=O)CCc2ccc(OCCCCN3CCN(c4cccc(Cl)c4Cl)CC3)cc21] |
| 52. | 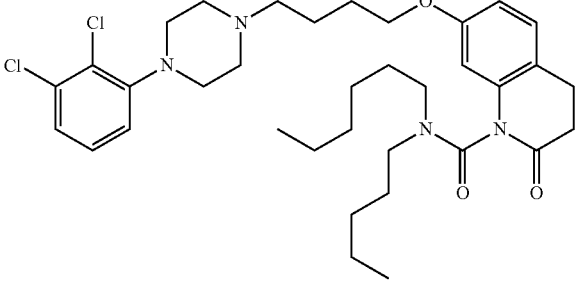 |
| 53. | 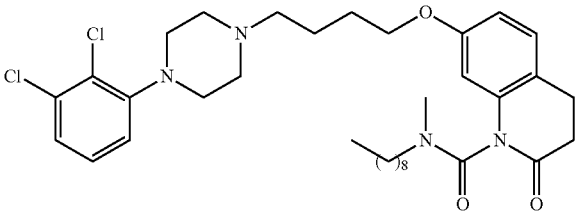 |
| 54. | 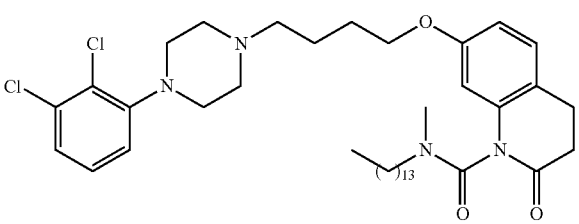 |
| 55. | 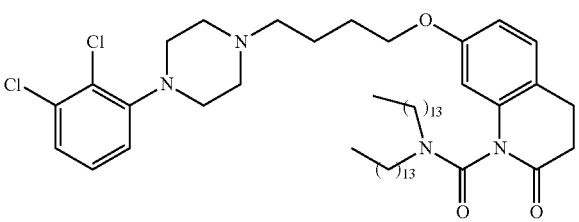 |

TABLE A-continued

| No. | Structure |
|---|---|
| 56. | 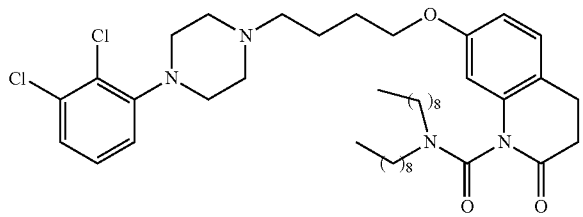 |
| 57. | 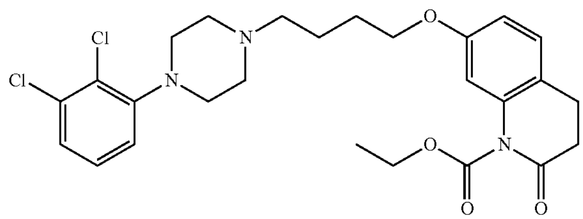 [SMILES: CCOC(=O)N1C(=O)CCc2ccc(OCCCCN3CCN(c4cccc(Cl)c4Cl)CC3)cc21] |
| 58. | 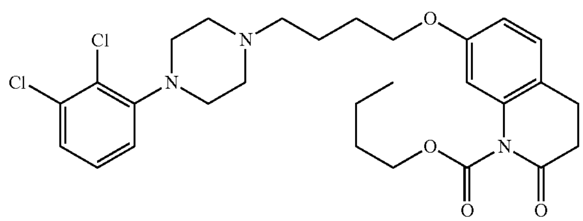 [SMILES: CCCCOC(=O)N1C(=O)CCc2ccc(OCCCCN3CCN(c4cccc(Cl)c4Cl)CC3)cc21] |
| 59. | 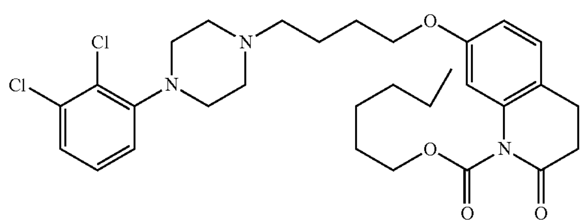 [SMILES: CCCCCCOC(=O)N1C(=O)CCc2ccc(OCCCCN3CCN(c4cccc(Cl)c4Cl)CC3)cc21] |
| 60. | 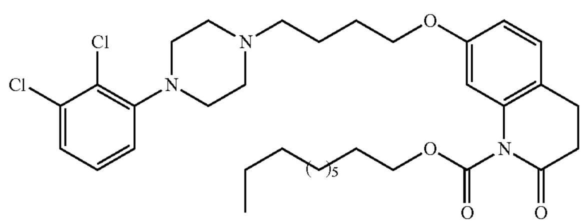 |
| 61. | 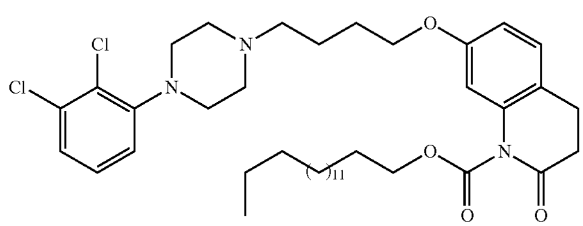 |
| 62. | 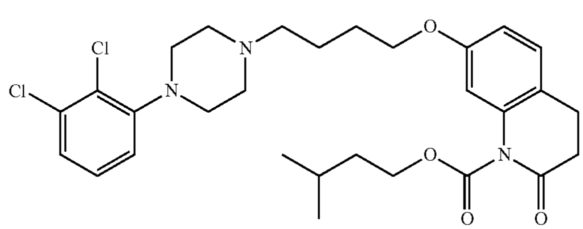 [SMILES: CC(C)CCOC(=O)N1C(=O)CCc2ccc(OCCCCN3CCN(c4cccc(Cl)c4Cl)CC3)cc21] |

TABLE A-continued
| No. | Structure |
|---|---|
| 63. | 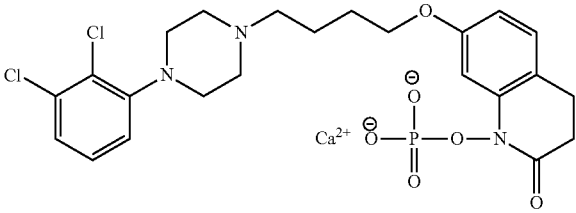 [SMILES: O=C1CCc2ccc(OCCCCN3CCN(c4cccc(Cl)c4Cl)CC3)cc2N1OP(=O)([O-])[O-] ; [Ca+2]] |
| 64. | 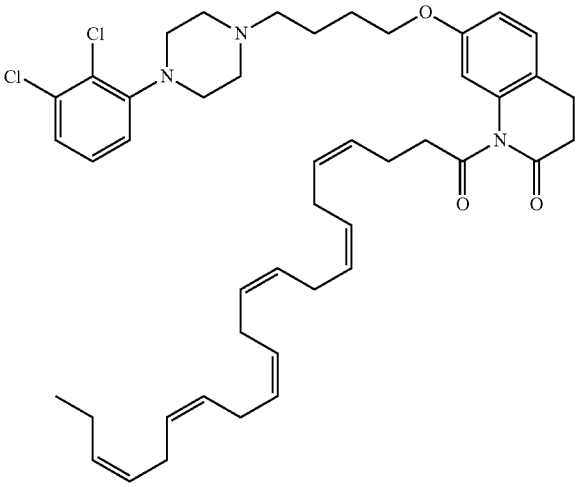 [SMILES: CC/C=C\C/C=C\C/C=C\C/C=C\C/C=C\C/C=C\CCC(=O)N1C(=O)CCc2ccc(OCCCCN3CCN(c4cccc(Cl)c4Cl)CC3)cc21] |
| 65. | 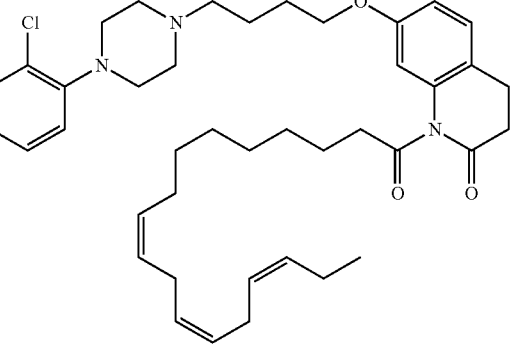 |
| 66. | 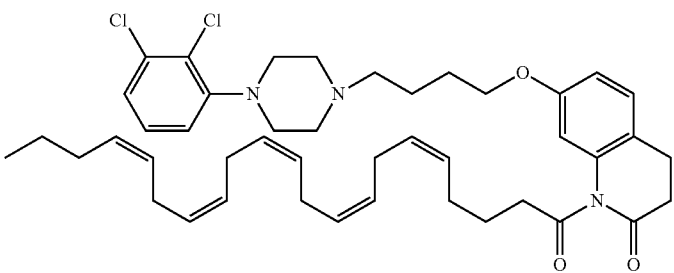 [SMILES: CCC/C=C\C/C=C\C/C=C\C/C=C\C/C=C\CCCC(=O)N1C(=O)CCc2ccc(OCCCCN3CCN(c4cccc(Cl)c4Cl)CC3)cc21] |

TABLE A-continued
| No. | Structure |
|---|---|
| 67. | 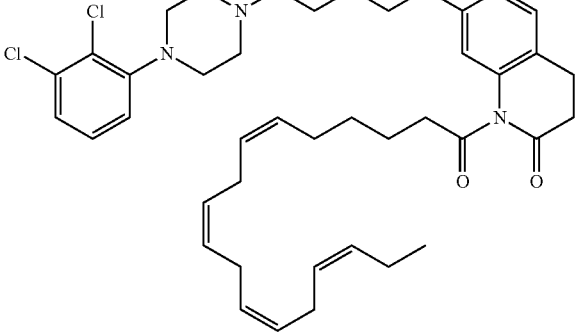 |
| 68. | 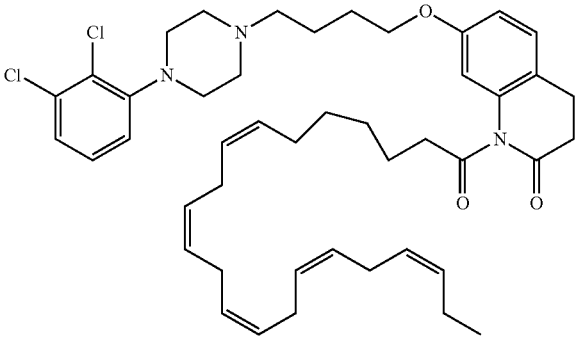 [SMILES: CC/C=C\C/C=C\C/C=C\C/C=C\C/C=C\CCCCCC(=O)N1C(=O)CCc2ccc(OCCCCN3CCN(c4cccc(Cl)c4Cl)CC3)cc21] |
| 69. | 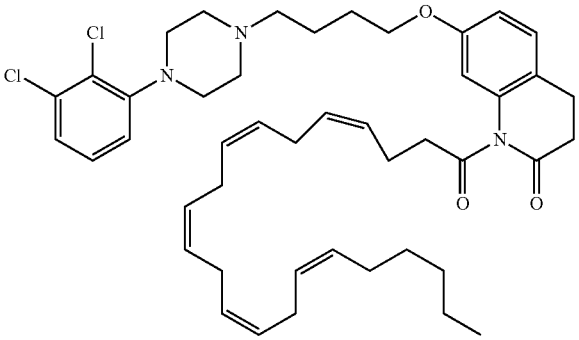 [SMILES: CCCCC/C=C\C/C=C\C/C=C\C/C=C\C/C=C\CCC(=O)N1C(=O)CCc2ccc(OCCCCN3CCN(c4cccc(Cl)c4Cl)CC3)cc21] |
| 70. | 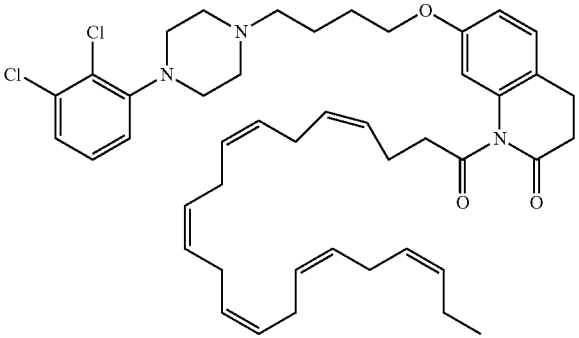 [SMILES: CC/C=C\C/C=C\C/C=C\C/C=C\C/C=C\C/C=C\CCC(=O)N1C(=O)CCc2ccc(OCCCCN3CCN(c4cccc(Cl)c4Cl)CC3)cc21] |

TABLE A-continued
| No. | Structure |
|---|---|
| 71. | 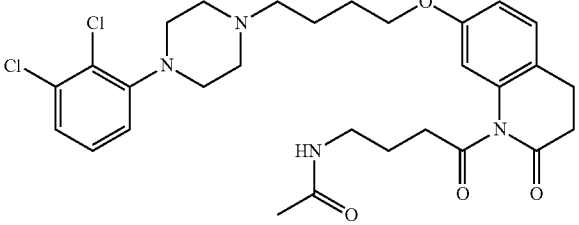 |
| 72. | 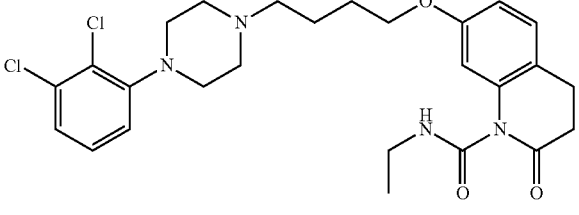 |
| 73. | 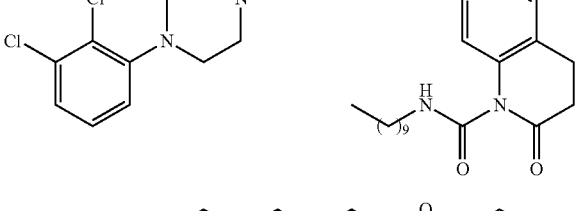 |
| 74. | 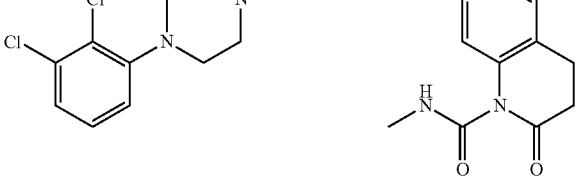 |
| 75. | 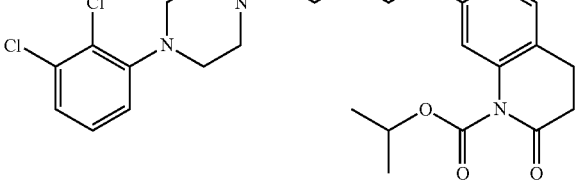 |
| 76. | 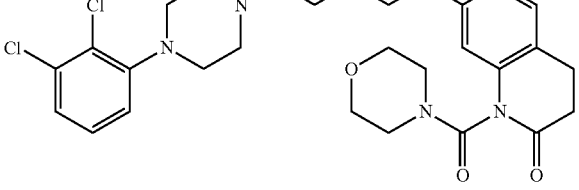 |
| 77. | 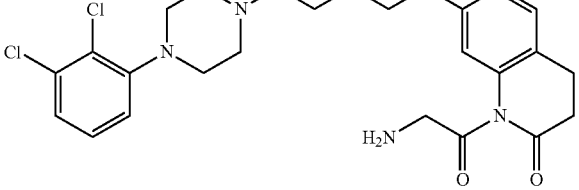 |

//

TABLE A-continued

| No. | Structure |
|---|---|
| 78. | 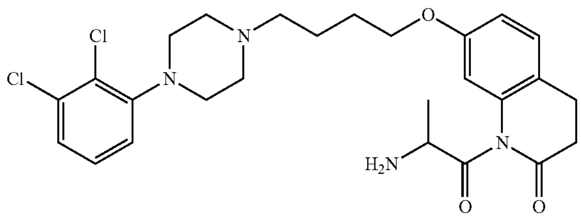 [SMILES: CC(N)C(=O)N1C(=O)CCc2ccc(OCCCCN3CCN(c4cccc(Cl)c4Cl)CC3)cc21] |
| 79. | 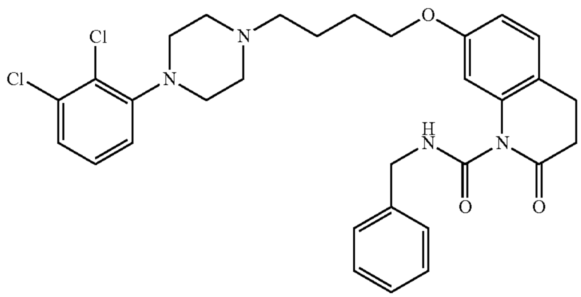 [SMILES: O=C1CCc2ccc(OCCCCN3CCN(c4cccc(Cl)c4Cl)CC3)cc2N1C(=O)NCc1ccccc1] |
| 80. | 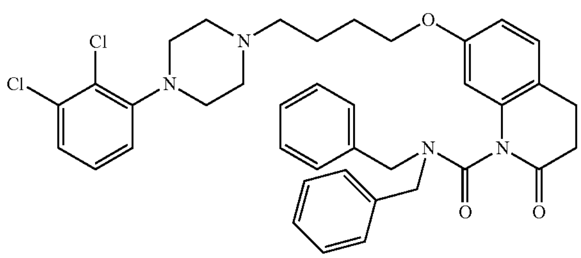 [SMILES: O=C1CCc2ccc(OCCCCN3CCN(c4cccc(Cl)c4Cl)CC3)cc2N1C(=O)N(Cc1ccccc1)Cc1ccccc1] |
| 81. | 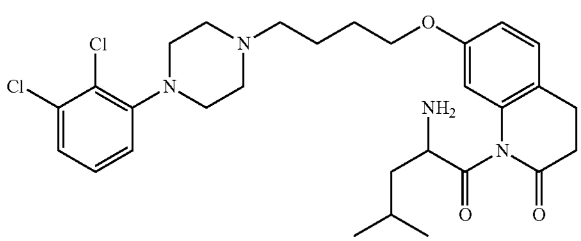 [SMILES: CC(C)CC(N)C(=O)N1C(=O)CCc2ccc(OCCCCN3CCN(c4cccc(Cl)c4Cl)CC3)cc21] |
| 82. | 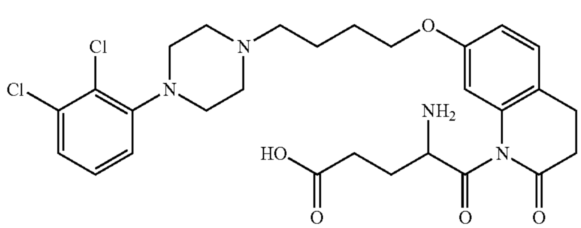 |
| 83. | 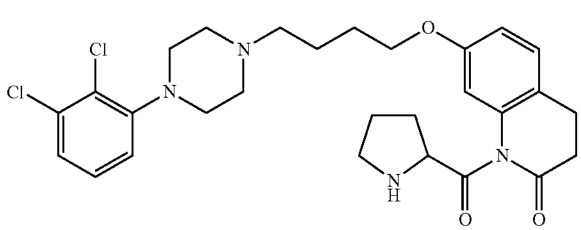 [SMILES: O=C1CCc2ccc(OCCCCN3CCN(c4cccc(Cl)c4Cl)CC3)cc2N1C(=O)C1CCCN1] |

TABLE A-continued
| No. | Structure |
|---|---|
| 84. | 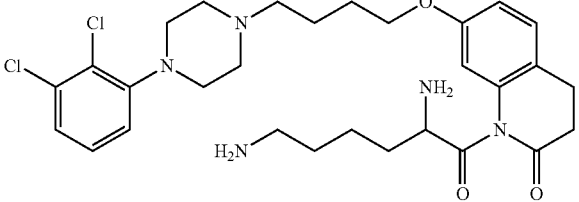 |
| 85. | 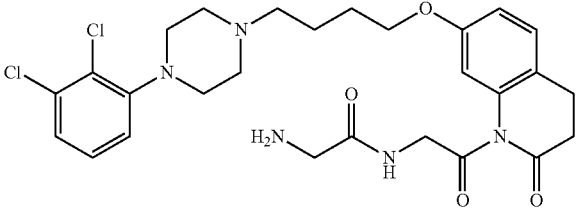 [SMILES: NCC(=O)NCC(=O)N1C(=O)CCc2ccc(OCCCCN3CCN(c4cccc(Cl)c4Cl)CC3)cc21] |
| 86. | 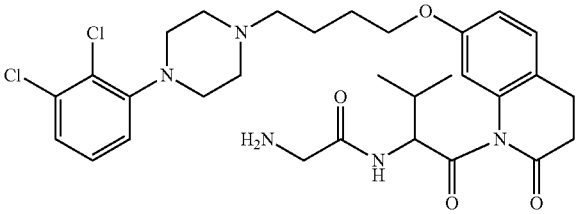 [SMILES: CC(C)C(NC(=O)CN)C(=O)N1C(=O)CCc2ccc(OCCCCN3CCN(c4cccc(Cl)c4Cl)CC3)cc21] |
| 87. | 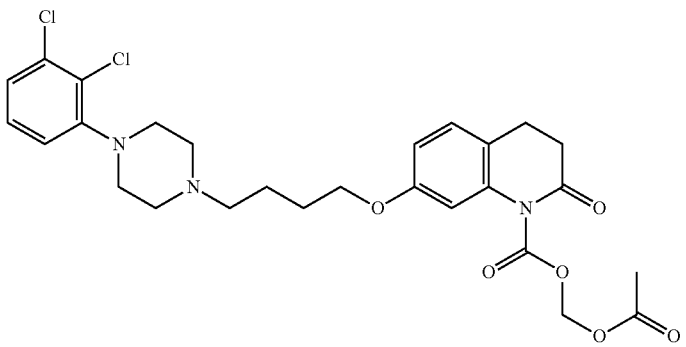 [SMILES: CC(=O)OCOC(=O)N1C(=O)CCc2ccc(OCCCCN3CCN(c4cccc(Cl)c4Cl)CC3)cc21] |
| 88. | 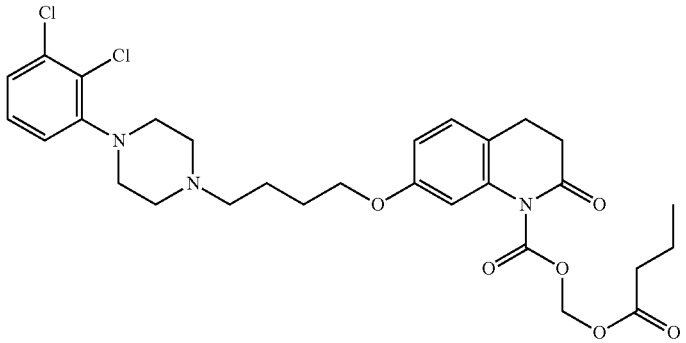 [SMILES: CCCC(=O)OCOC(=O)N1C(=O)CCc2ccc(OCCCCN3CCN(c4cccc(Cl)c4Cl)CC3)cc21] |

TABLE A-continued

| No. | Structure |
|---|---|
| 89. | (structure) |
| 90. | (structure) |
| 91. | (structure) |

TABLE B

| No. | Structure |
|---|---|
| 100. | (structure) |

TABLE B-continued
| No. | Structure |
|---|---|
| 101. | 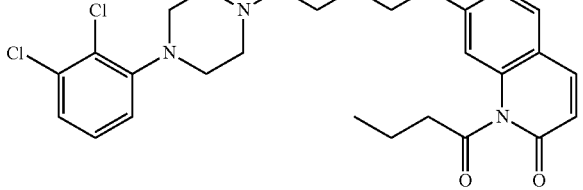 |
| 102. | 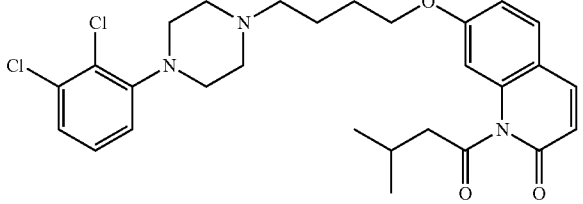 |
| 103. | 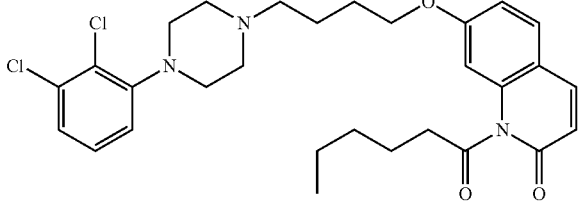 |
| 104. | 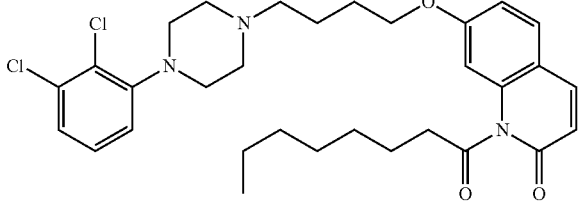 |
| 105. | 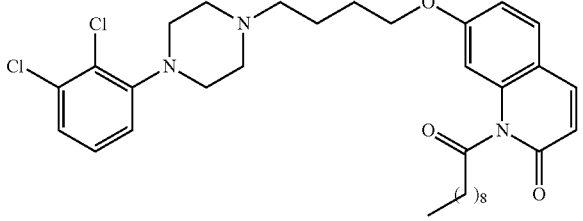 |
| 106. | 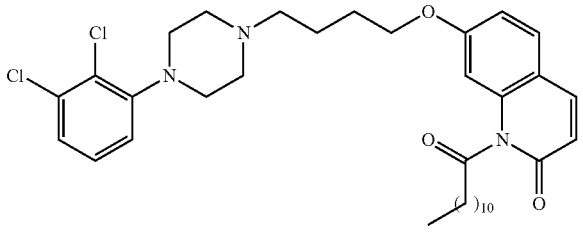 |
| 107. | 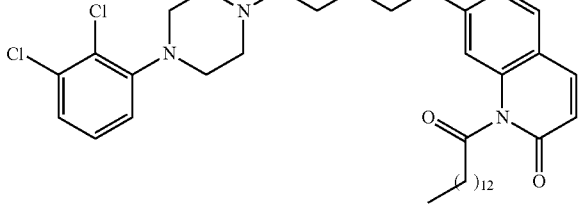 |

TABLE B-continued

| No. | Structure |
|-----|-----------|
| 108. | [2,3-dichlorophenyl-piperazine-(CH₂)₄-O-quinolin-2(1H)-one N-acyl with (CH₂)₁₃ chain] |
| 109. | [2,3-dichlorophenyl-piperazine-(CH₂)₄-O-quinolin-2(1H)-one N-acyl with (CH₂)₁₄ chain] |
| 110. | [2,3-dichlorophenyl-piperazine-(CH₂)₄-O-quinolin-2(1H)-one N-acyl with (CH₂)₁₆ chain] |
| 111. | [2,3-dichlorophenyl-piperazine-(CH₂)₄-O-quinolin-2(1H)-one N-acyl with (CH₂)₁₈ chain] |
| 112. | [2,3-dichlorophenyl-piperazine-(CH₂)₄-O-quinolin-2(1H)-one N-acyl with (CH₂)₂₀ chain] |
| 113. | [2,3-dichlorophenyl-piperazine-(CH₂)₄-O-quinolin-2(1H)-one N-acyl with (CH₂)₂₂ chain] |

TABLE B-continued
| No. | Structure |
|---|---|
| 114. | 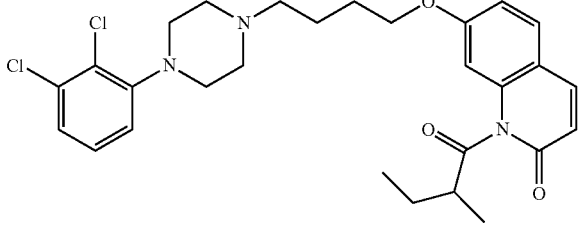 |
| 115. | 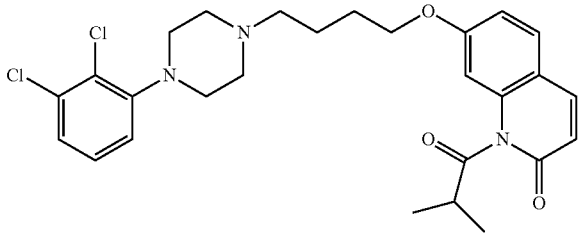 [SMILES: CC(C)C(=O)n1c(=O)ccc2ccc(OCCCCN3CCN(c4cccc(Cl)c4Cl)CC3)cc21] |
| 116. | 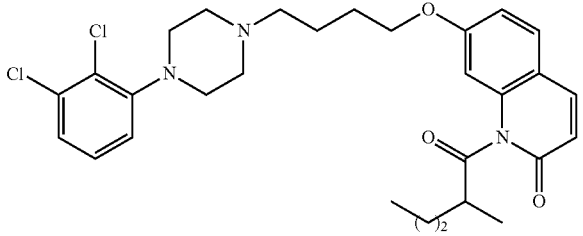 |
| 117. | 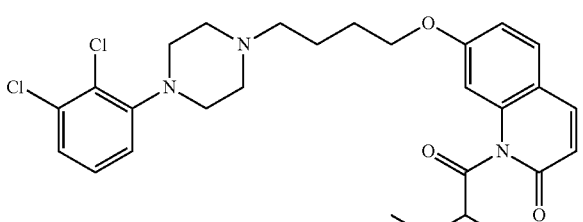 |
| 118. | 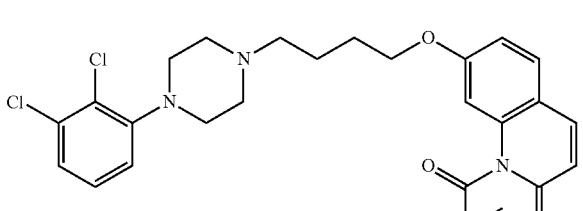 |
| 119. | 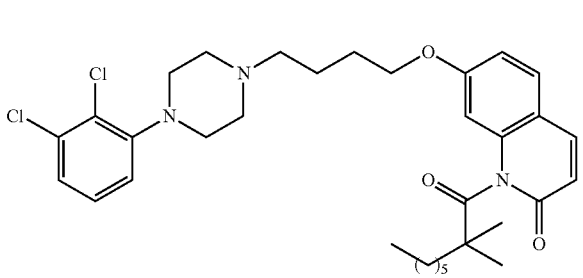 |

TABLE B-continued
| No. | Structure |
|---|---|
| 120. | 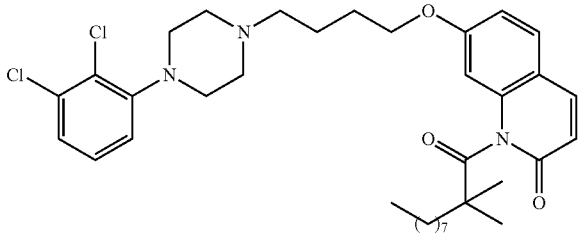 |
| 121. | 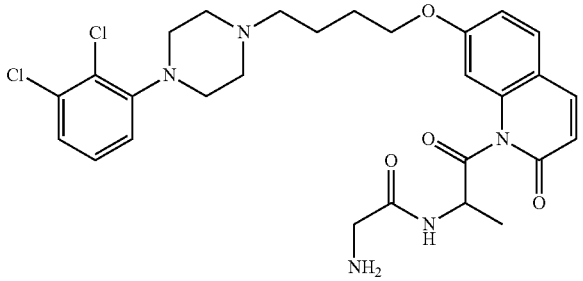 [SMILES: CC(NC(=O)CN)C(=O)n1c(=O)ccc2ccc(OCCCCN3CCN(c4cccc(Cl)c4Cl)CC3)cc21] |
| 122. | 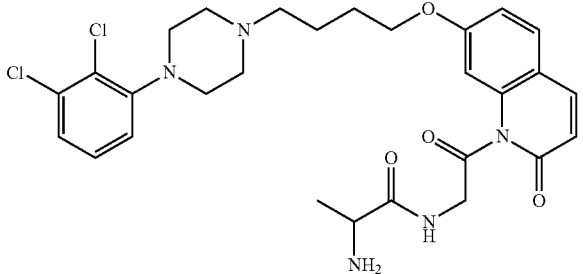 [SMILES: CC(N)C(=O)NCC(=O)n1c(=O)ccc2ccc(OCCCCN3CCN(c4cccc(Cl)c4Cl)CC3)cc21] |
| 123. | 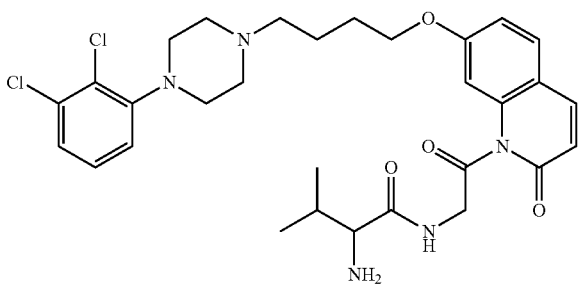 [SMILES: CC(C)C(N)C(=O)NCC(=O)n1c(=O)ccc2ccc(OCCCCN3CCN(c4cccc(Cl)c4Cl)CC3)cc21] |
| 124. | 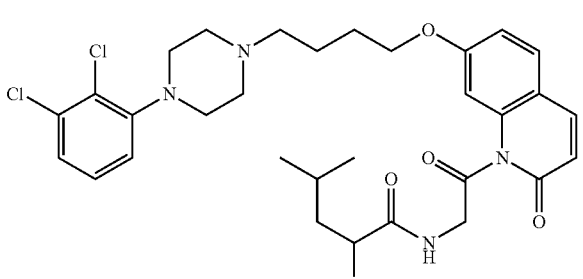 |

TABLE B-continued
| No. | Structure |
|---|---|
| 125. | 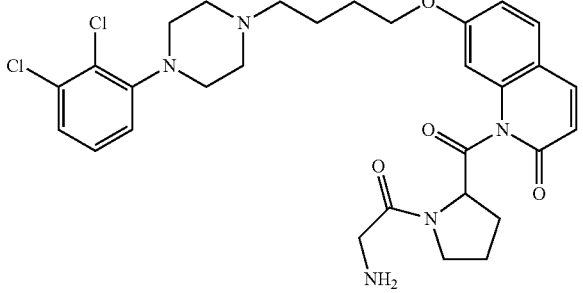 |
| 126. | 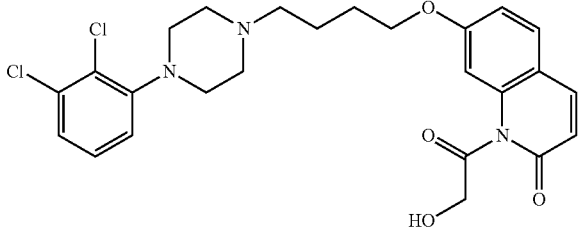 [SMILES: O=C(CO)n1c(=O)ccc2ccc(OCCCCN3CCN(c4cccc(Cl)c4Cl)CC3)cc21] |
| 127. | 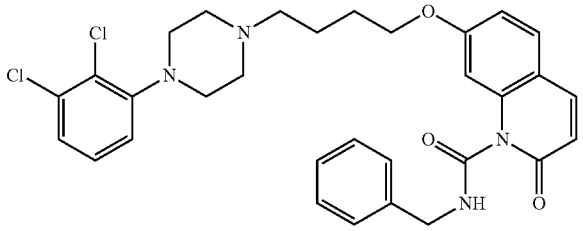 [SMILES: O=C(OCc1ccccc1)n1c(=O)ccc2ccc(OCCCCN3CCN(c4cccc(Cl)c4Cl)CC3)cc21] |
| 128. | 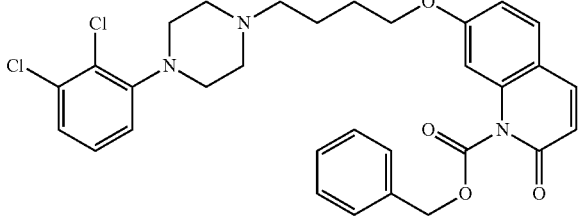 |
| 129. | 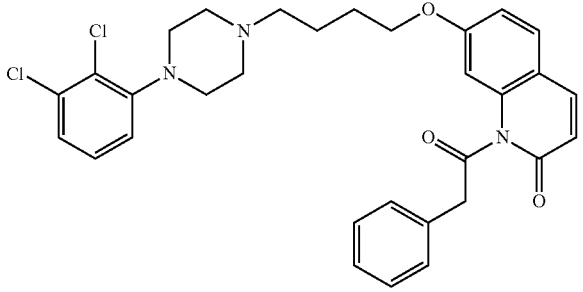 [SMILES: O=C(Cc1ccccc1)n1c(=O)ccc2ccc(OCCCCN3CCN(c4cccc(Cl)c4Cl)CC3)cc21] |

TABLE B-continued
| No. | Structure |
|---|---|
| 130. | 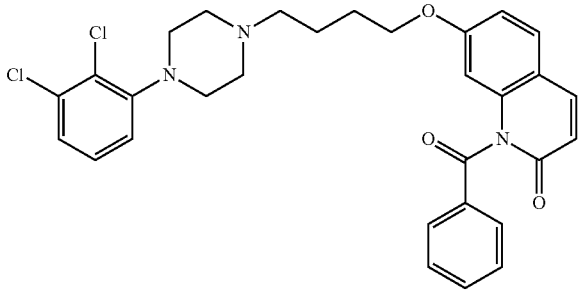 [SMILES: O=C(c1ccccc1)n1c(=O)ccc2ccc(OCCCCN3CCN(c4cccc(Cl)c4Cl)CC3)cc21] |
| 131. | 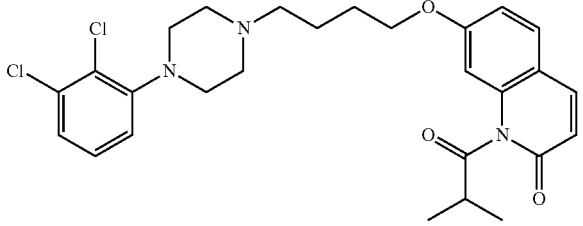 |
| 132. | 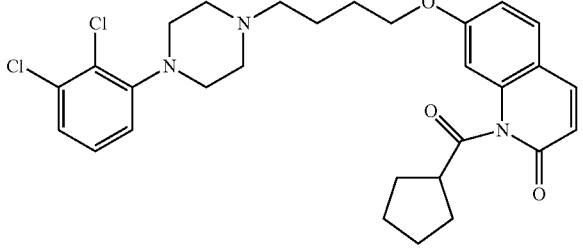 |
| 133. | 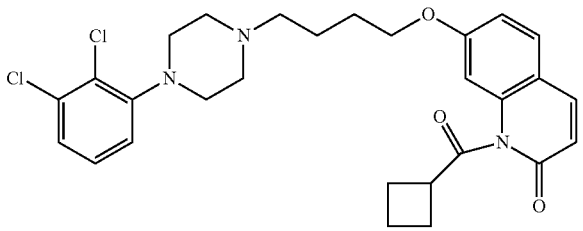 [SMILES: O=C(C1CCC1)n1c(=O)ccc2ccc(OCCCCN3CCN(c4cccc(Cl)c4Cl)CC3)cc21] |
| 134. | 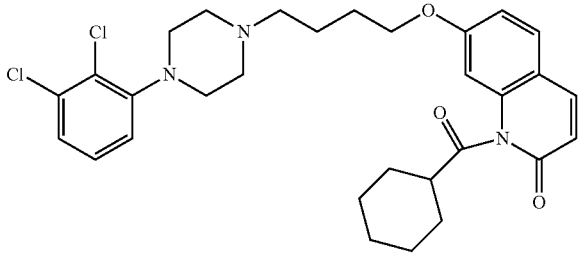 [SMILES: O=C(C1CCCCC1)n1c(=O)ccc2ccc(OCCCCN3CCN(c4cccc(Cl)c4Cl)CC3)cc21] |
| 135. | 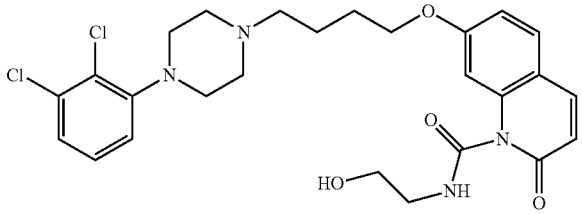 [SMILES: O=C(NCCO)n1c(=O)ccc2ccc(OCCCCN3CCN(c4cccc(Cl)c4Cl)CC3)cc21] |

TABLE B-continued
| No. | Structure |
|---|---|
| 136. | 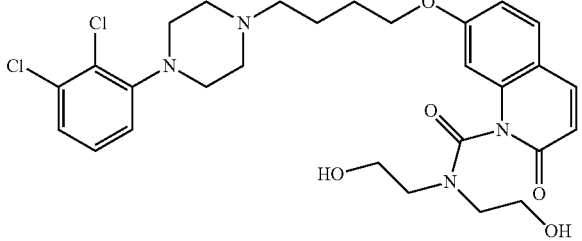 |
| 137. | 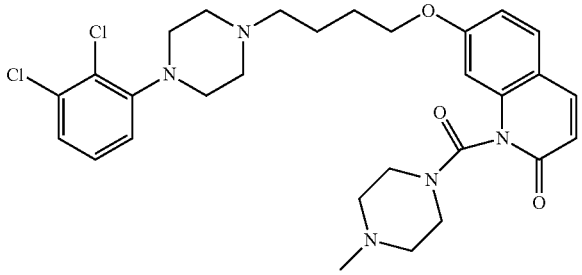 [SMILES: CN1CCN(C(=O)n2c(=O)ccc3ccc(OCCCCN4CCN(c5cccc(Cl)c5Cl)CC4)cc32)CC1] |
| 138. | 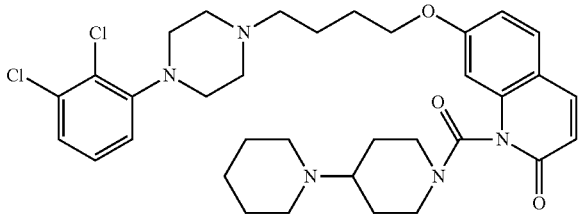 [SMILES: O=C(N1CCC(N2CCCCC2)CC1)n1c(=O)ccc2ccc(OCCCCN3CCN(c4cccc(Cl)c4Cl)CC3)cc21] |
| 139. | 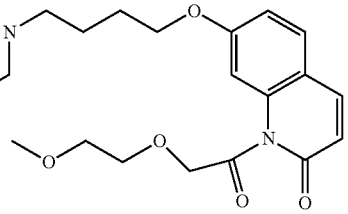 |
| 140. | 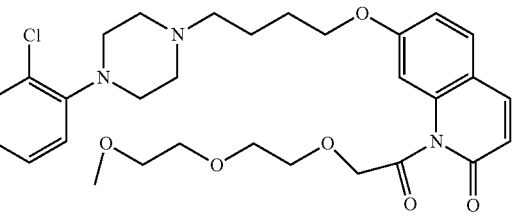 |
| 141. | 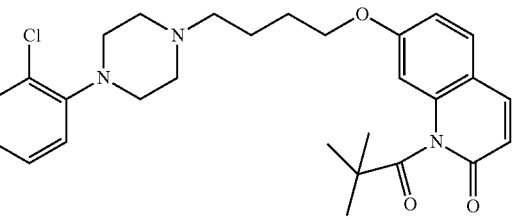 |

TABLE B-continued
| No. | Structure |
|---|---|
| 142. | 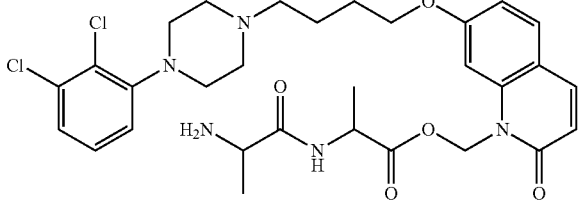 |
| 143. | 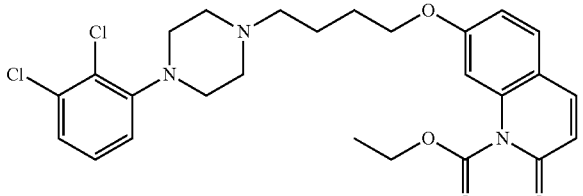 |
| 144. | 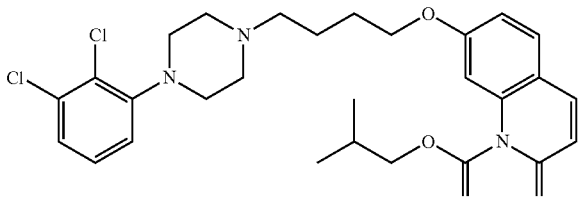 |
| 145. | 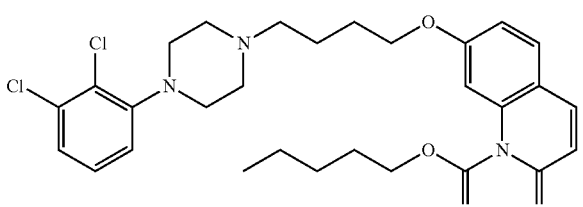 |
| 146. | 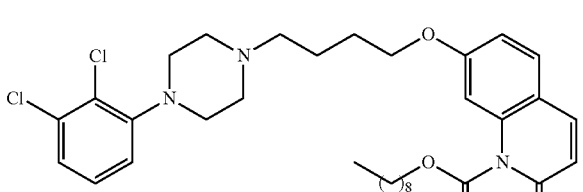 |
| 147. | 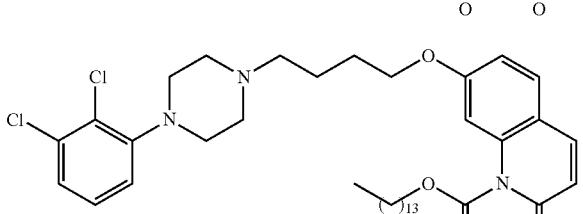 |
| 148. | 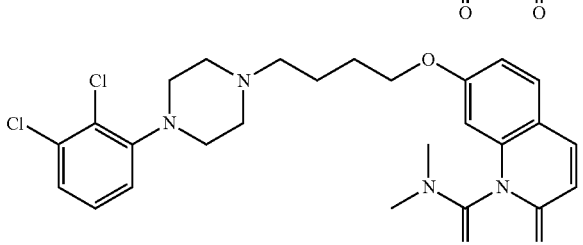 |

TABLE B-continued

| No. | Structure |
|---|---|
| 149. | 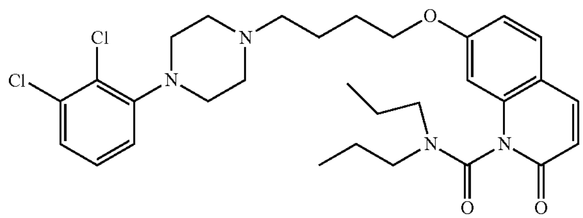 [SMILES: CCCN(CCC)C(=O)n1c(=O)ccc2ccc(OCCCCN3CCN(c4cccc(Cl)c4Cl)CC3)cc21] |
| 150. | 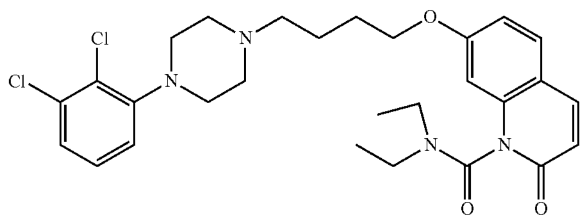 [SMILES: CCN(CC)C(=O)n1c(=O)ccc2ccc(OCCCCN3CCN(c4cccc(Cl)c4Cl)CC3)cc21] |
| 151. | 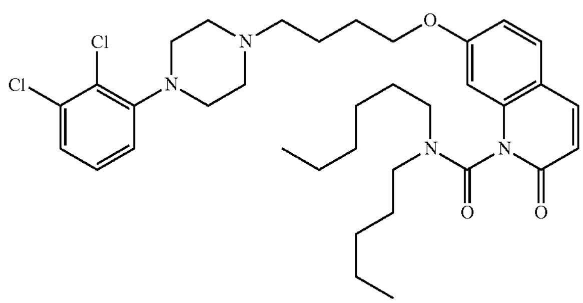 [SMILES: CCCCCCN(CCCCC)C(=O)n1c(=O)ccc2ccc(OCCCCN3CCN(c4cccc(Cl)c4Cl)CC3)cc21] |
| 152. | 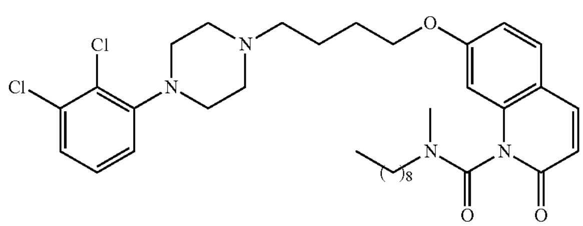 |
| 153. | 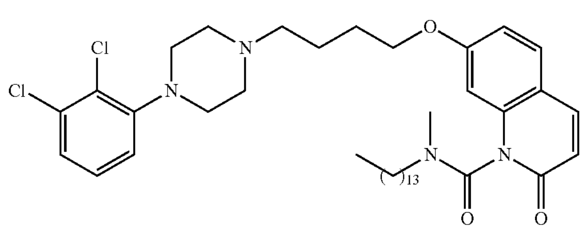 |
| 154. | 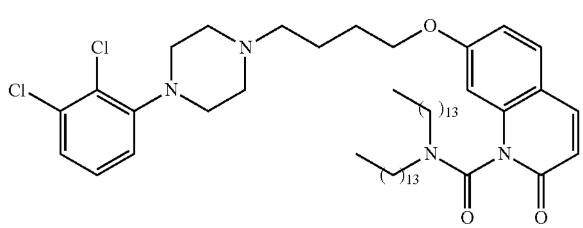 |

TABLE B-continued
| No. | Structure |
|---|---|
| 155. | 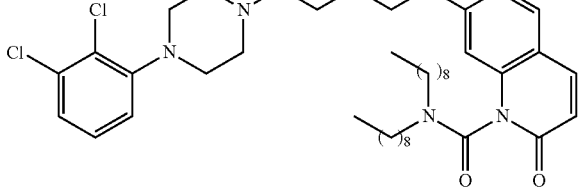 |
| 156. | 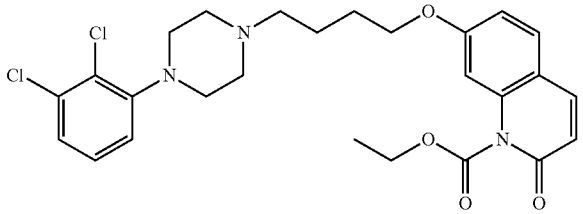 |
| 157. | 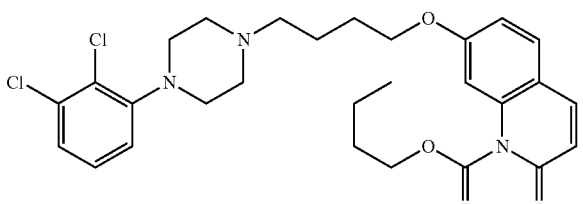 |
| 158. | 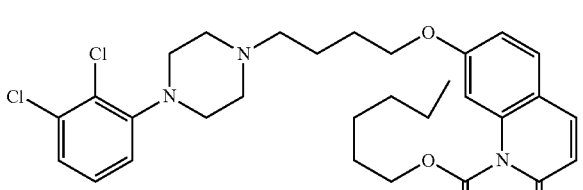 |
| 159. | 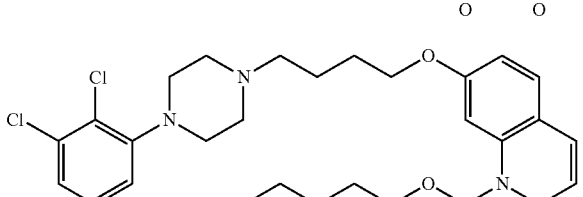 |
| 160. | 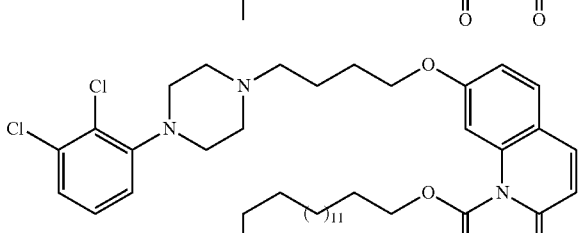 |
| 161. | 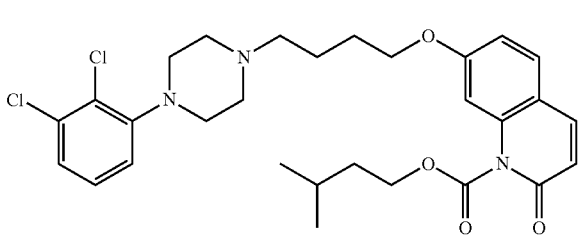 [SMILES: CC(C)CCOC(=O)n1c(=O)ccc2ccc(OCCCCN3CCN(c4cccc(Cl)c4Cl)CC3)cc21] |

TABLE B-continued
| No. | Structure |
|---|---|
| 162. | 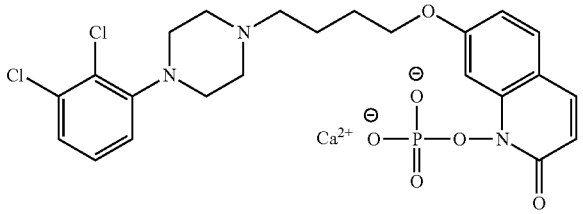 [SMILES: O=c1ccc2ccc(OCCCCN3CCN(c4cccc(Cl)c4Cl)CC3)cc2n1OP(=O)([O-])[O-] ; [Ca+2]] |
| 163. | 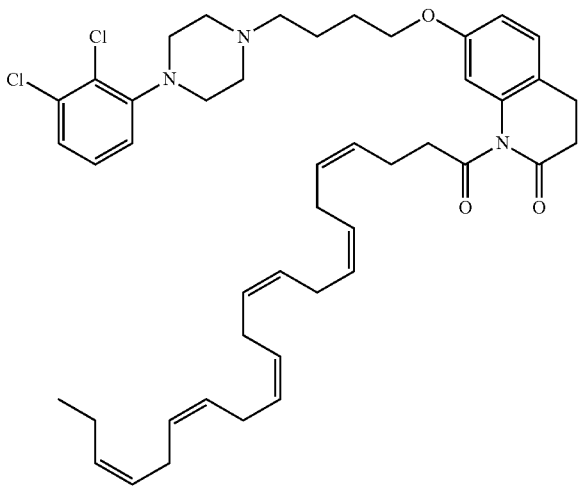 [SMILES: CC/C=C\C/C=C\C/C=C\C/C=C\C/C=C\C/C=C\CCC(=O)N1C(=O)CCc2ccc(OCCCCN3CCN(c4cccc(Cl)c4Cl)CC3)cc21] |
| 164. | 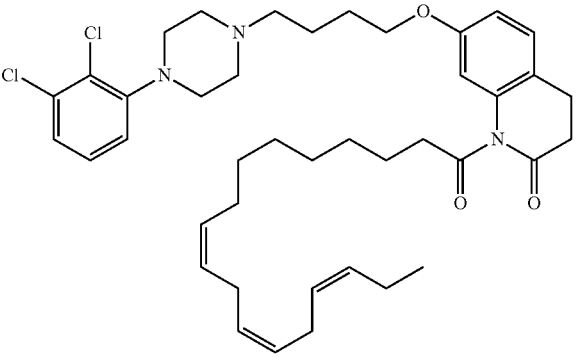 [SMILES: CC/C=C\C/C=C\C/C=C\CCCCCCCC(=O)N1C(=O)CCc2ccc(OCCCCN3CCN(c4cccc(Cl)c4Cl)CC3)cc21] |
| 165. | 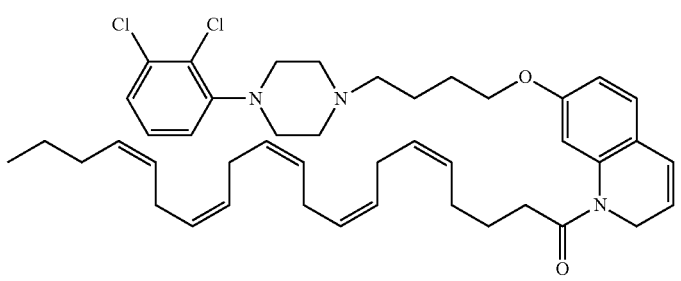 [SMILES: CCC/C=C\C/C=C\C/C=C\C/C=C\C/C=C\CCCC(=O)N1CC=Cc2ccc(OCCCCN3CCN(c4cccc(Cl)c4Cl)CC3)cc21] |

TABLE B-continued
| No. | Structure |
|---|---|
| 166. | 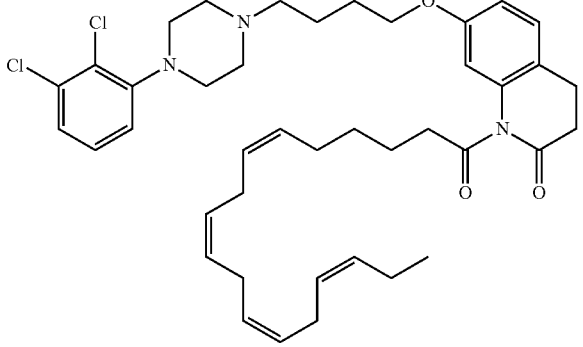 |
| 167. | 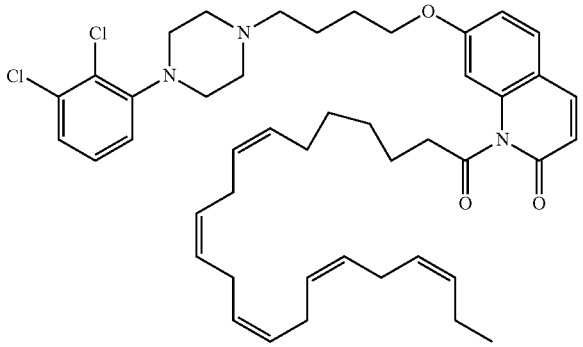 [SMILES: CC/C=C\C/C=C\C/C=C\C/C=C\C/C=C\CCCCCC(=O)n1c(=O)ccc2ccc(OCCCCN3CCN(c4cccc(Cl)c4Cl)CC3)cc21] |
| 168. | 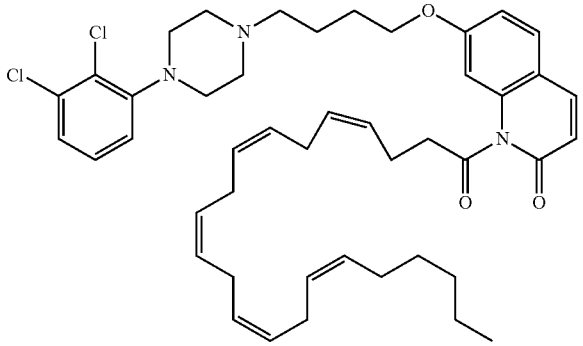 [SMILES: CCCCC/C=C\C/C=C\C/C=C\C/C=C\C/C=C\CCC(=O)n1c(=O)ccc2ccc(OCCCCN3CCN(c4cccc(Cl)c4Cl)CC3)cc21] |
| 169. | 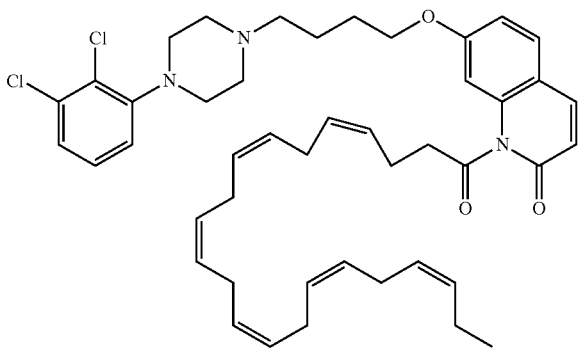 [SMILES: CC/C=C\C/C=C\C/C=C\C/C=C\C/C=C\C/C=C\CCC(=O)n1c(=O)ccc2ccc(OCCCCN3CCN(c4cccc(Cl)c4Cl)CC3)cc21] |

TABLE B-continued

| No. | Structure |
|---|---|
| 170. | 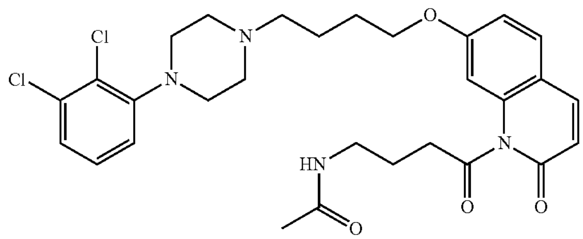 [SMILES: CC(=O)NCCCC(=O)n1c(=O)ccc2ccc(OCCCCN3CCN(c4cccc(Cl)c4Cl)CC3)cc21] |
| 171. | 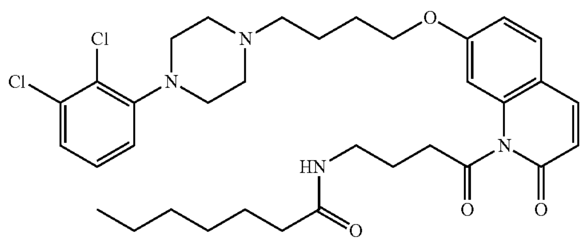 [SMILES: CCCCCCC(=O)NCCCC(=O)n1c(=O)ccc2ccc(OCCCCN3CCN(c4cccc(Cl)c4Cl)CC3)cc21] |
| 172. | 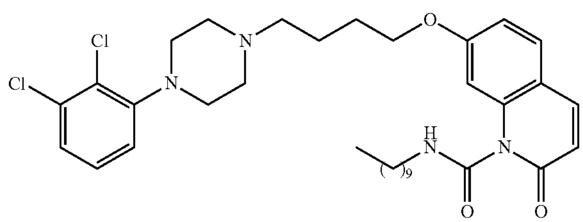 |
| 173. | 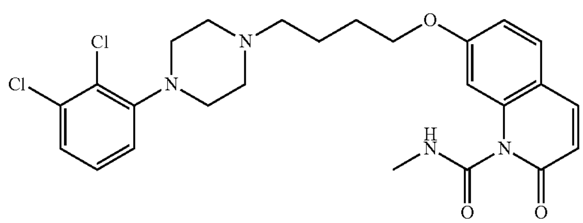 |
| 174. | 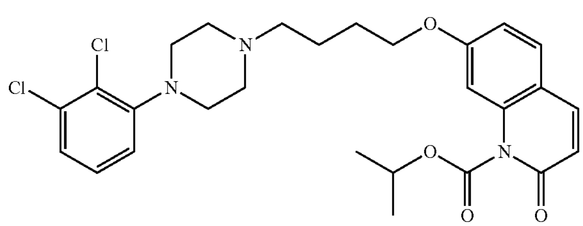 [SMILES: CC(C)OC(=O)n1c(=O)ccc2ccc(OCCCCN3CCN(c4cccc(Cl)c4Cl)CC3)cc21] |
| 175. | 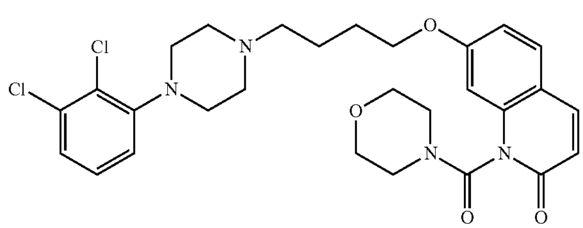 [SMILES: O=C(N1CCOCC1)n1c(=O)ccc2ccc(OCCCCN3CCN(c4cccc(Cl)c4Cl)CC3)cc21] |
| 176. | 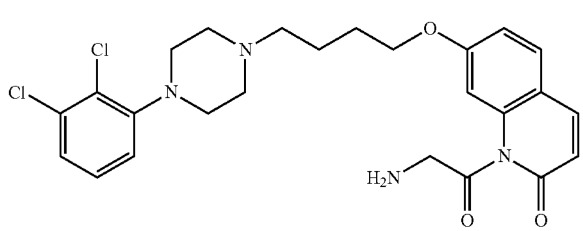 |

TABLE B-continued
| No. | Structure |
|---|---|
| 177. | 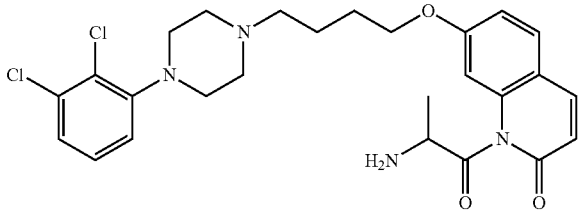 [SMILES: NCC(=O)n1c(=O)ccc2ccc(OCCCCN3CCN(c4cccc(Cl)c4Cl)CC3)cc21] |
| 178. | 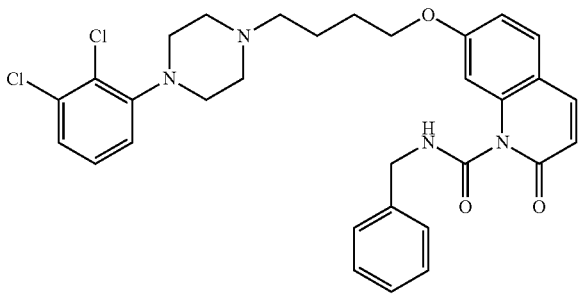 [SMILES: O=C(NCc1ccccc1)n1c(=O)ccc2ccc(OCCCCN3CCN(c4cccc(Cl)c4Cl)CC3)cc21] |
| 179. | 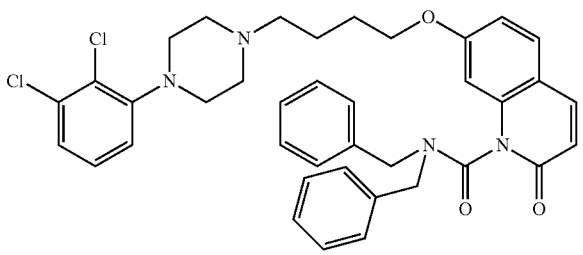 [SMILES: O=C(N(Cc1ccccc1)Cc1ccccc1)n1c(=O)ccc2ccc(OCCCCN3CCN(c4cccc(Cl)c4Cl)CC3)cc21] |
| 180. | 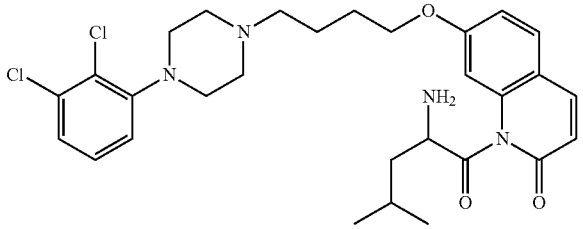 |
| 181. | 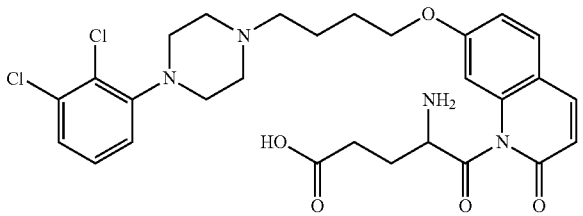 |
| 182. | 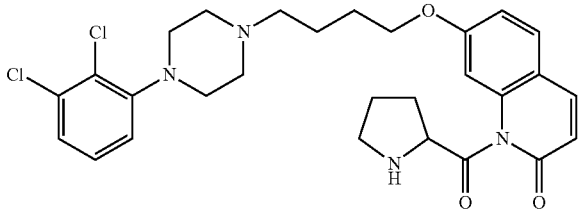 [SMILES: O=C(C1CCCN1)n1c(=O)ccc2ccc(OCCCCN3CCN(c4cccc(Cl)c4Cl)CC3)cc21] |

TABLE B-continued
| No. | Structure |
|---|---|
| 183. | 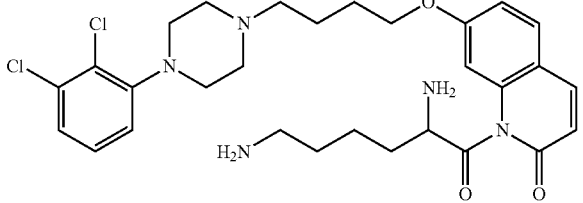 |
| 184. | 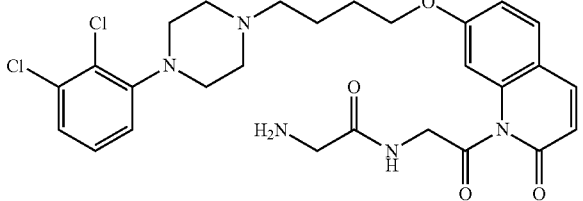 |
| 185. | 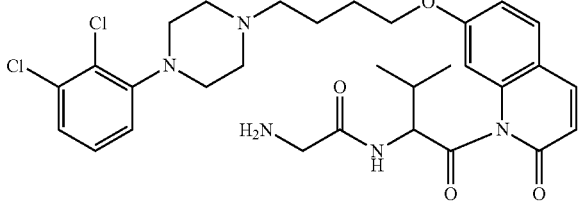 |
TABLE C
| No. | Structure |
|---|---|
| 200. | 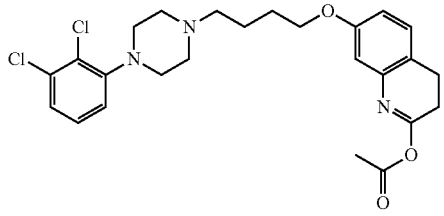 [SMILES: CC(=O)OC1=Nc2cc(OCCCCN3CCN(c4cccc(Cl)c4Cl)CC3)ccc2CC1] |
| 201. | 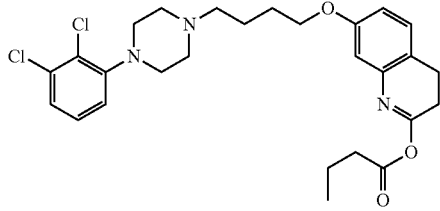 [SMILES: CCCC(=O)OC1=Nc2cc(OCCCCN3CCN(c4cccc(Cl)c4Cl)CC3)ccc2CC1] |
| 202. | 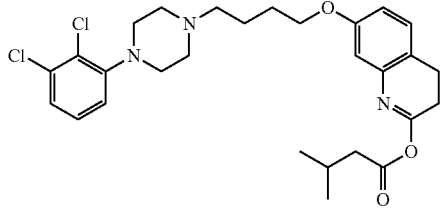 [SMILES: CC(C)CC(=O)OC1=Nc2cc(OCCCCN3CCN(c4cccc(Cl)c4Cl)CC3)ccc2CC1] |
| 203. | 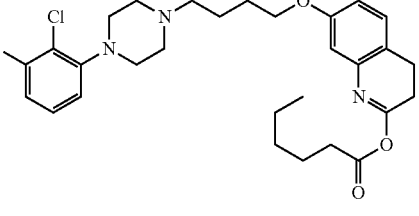 |
| 204. | 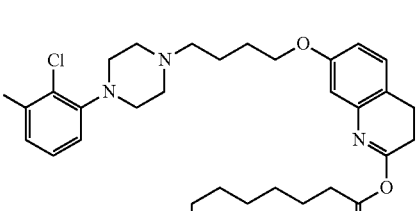 |
| 205. | 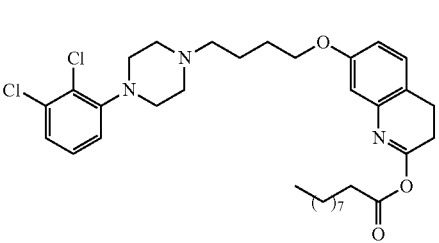 |

TABLE C-continued

| No. | Structure |
|---|---|
| 206. | 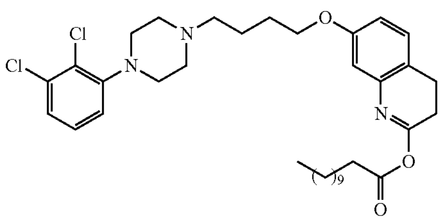 |
| 207. | 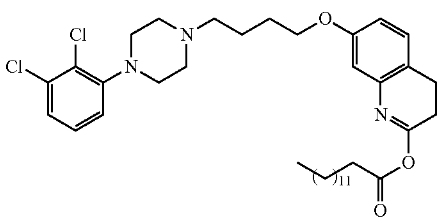 |
| 208. | 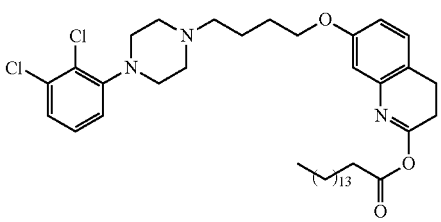 |
| 209. | 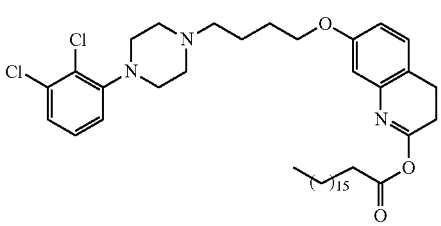 |
| 210. | 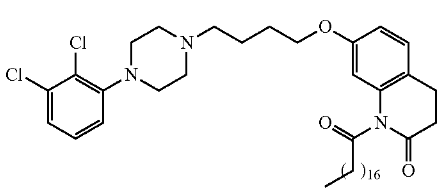 |
| 211. | 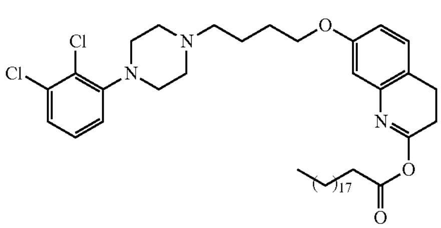 |
| 212. | 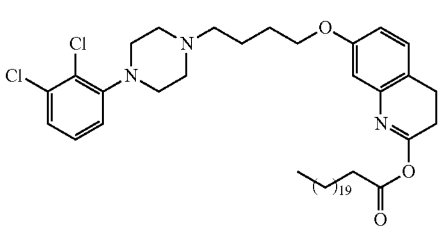 |
| 213. | |
| 214. | |
| 215. | |
| 216. | |
| 217. | |
| 218. | |
| 219. | |

TABLE C-continued
| No. | Structure |
|---|---|
| 220. | 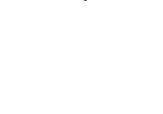 |
| 221. | 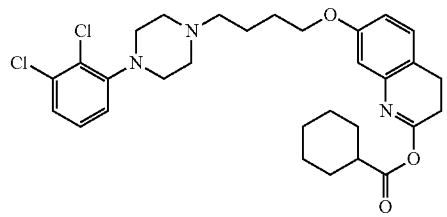 [SMILES: O=C(OC1=Nc2cc(OCCCCN3CCN(c4cccc(Cl)c4Cl)CC3)ccc2CC1)C1CCCCC1] |
| 222. | 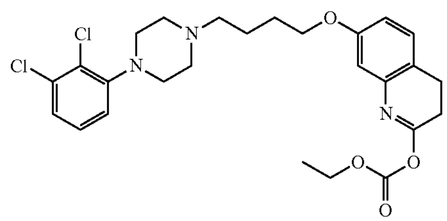 |
| 223. | 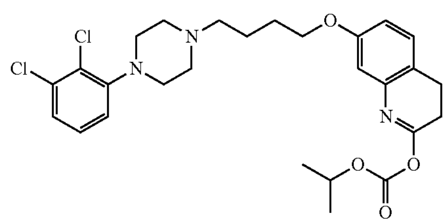 [SMILES: CC(C)OC(=O)OC1=Nc2cc(OCCCCN3CCN(c4cccc(Cl)c4Cl)CC3)ccc2CC1] |
| 224. | 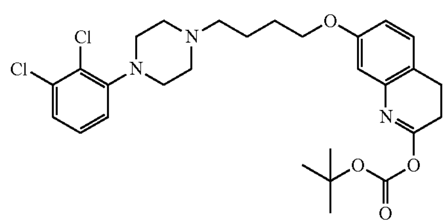 [SMILES: CC(C)(C)OC(=O)OC1=Nc2cc(OCCCCN3CCN(c4cccc(Cl)c4Cl)CC3)ccc2CC1] |
| 225. | 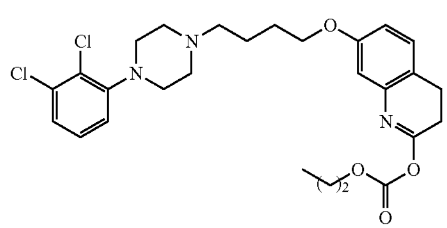 |
| 226. | 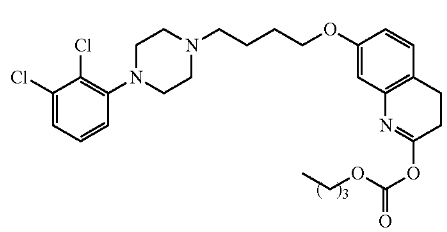 |
| 227. | |
| 228. | |
| 229. | |
| 230. | |
| 231. | |
| 232. | |
| 233. | |

TABLE C-continued
| No. | Structure |
|-----|-----------|
| 234. | 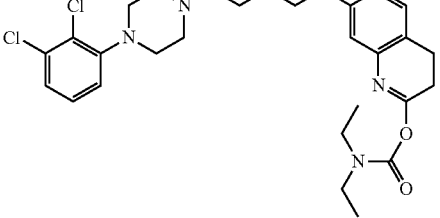 |
| 235. | 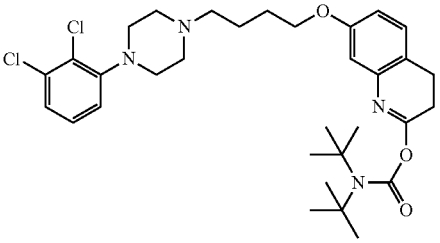 [SMILES: CC(C)(C)N(C(=O)OC1=Nc2cc(OCCCCN3CCN(c4cccc(Cl)c4Cl)CC3)ccc2CC1)C(C)(C)C] |
| 236. | 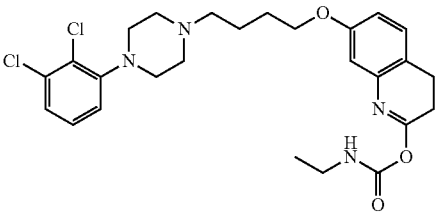 [SMILES: CC(C)NC(=O)OC1=Nc2cc(OCCCCN3CCN(c4cccc(Cl)c4Cl)CC3)ccc2CC1] |
| 237. | 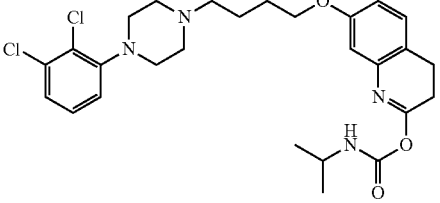 |
| 238. | 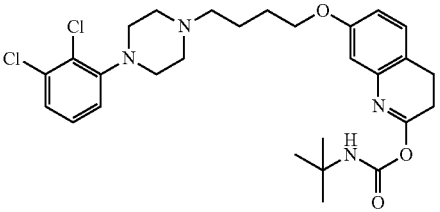 [SMILES: CC(C)(C)NC(=O)OC1=Nc2cc(OCCCCN3CCN(c4cccc(Cl)c4Cl)CC3)ccc2CC1] |
TABLE C-continued
| No. | Structure |
|-----|-----------|
| 239. | 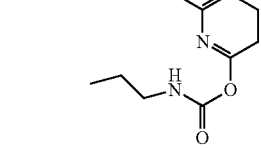 |
| 240. | 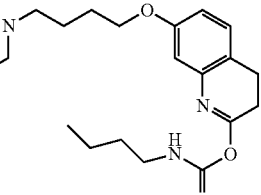 |
| 241. | 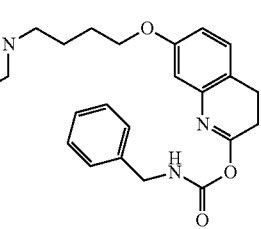 |
| 242. | 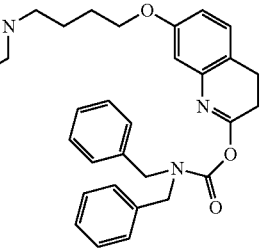 |
| 243. | 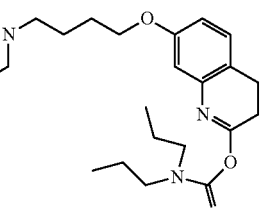 |
TABLE D
| No. | Structure |
|-----|-----------|
| 300. | 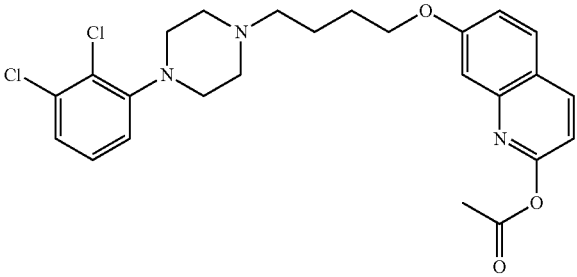 [SMILES: CC(=O)Oc1ccc2ccc(OCCCCN3CCN(c4cccc(Cl)c4Cl)CC3)cc2n1] |

TABLE D-continued
| No. | Structure |
|---|---|
| 301. | 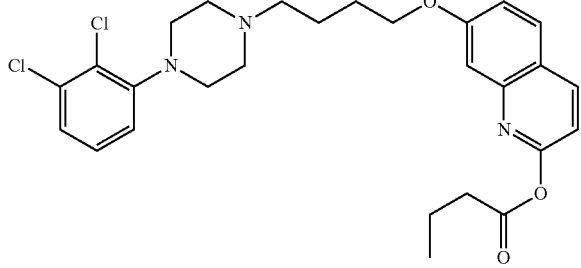 |
| 302. | 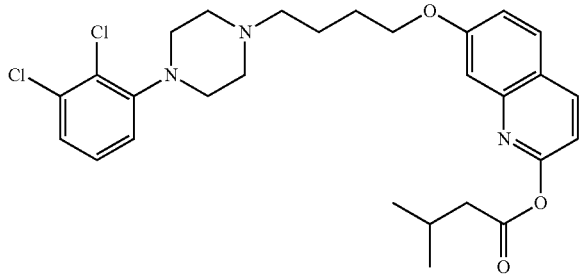 [SMILES: CC(C)CC(=O)Oc1ccc2ccc(OCCCCN3CCN(c4cccc(Cl)c4Cl)CC3)cc2n1] |
| 303. | 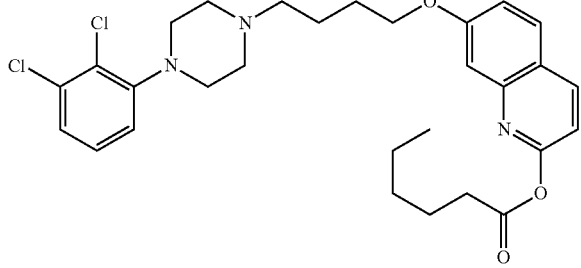 |
| 304. | 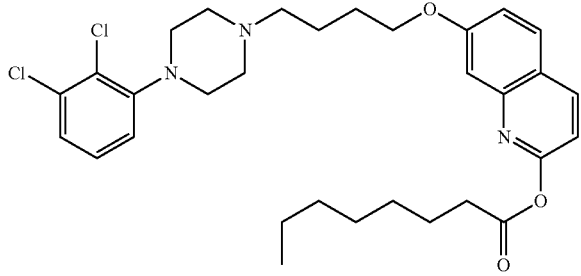 [SMILES: CCCCCCCC(=O)Oc1ccc2ccc(OCCCCN3CCN(c4cccc(Cl)c4Cl)CC3)cc2n1] |
| 305. | 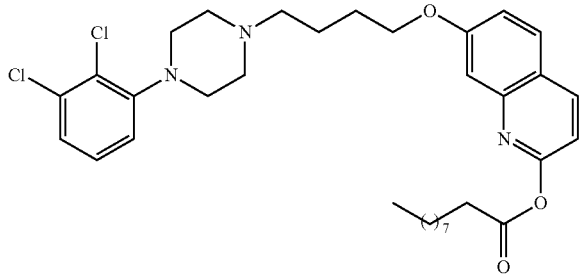 [SMILES: CCCC(=O)Oc1ccc2ccc(OCCCCN3CCN(c4cccc(Cl)c4Cl)CC3)cc2n1] |

TABLE D-continued
| No. | Structure |
|---|---|
| 306. | 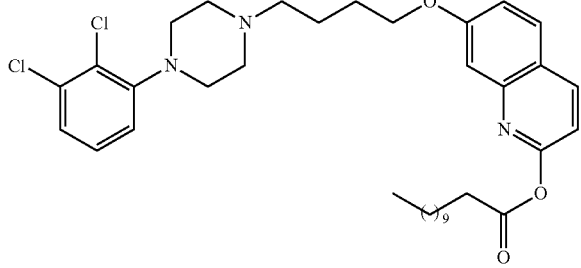 |
| 307. | 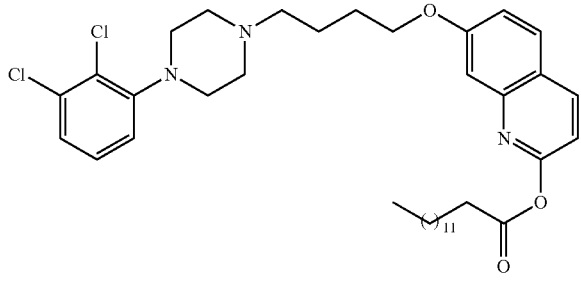 [SMILES: CCCC(=O)Oc1ccc2ccc(OCCCCN3CCN(c4cccc(Cl)c4Cl)CC3)cc2n1] |
| 308. | 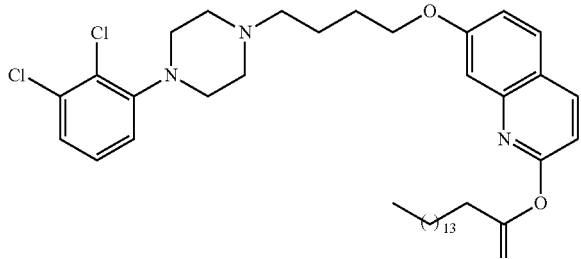 |
| 309. | 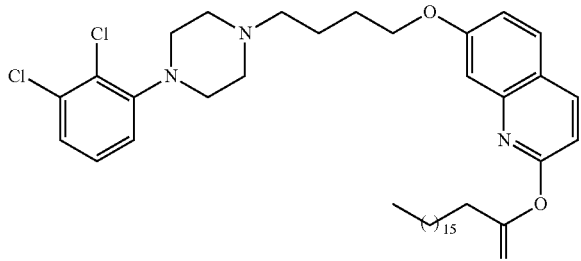 |
| 310. | 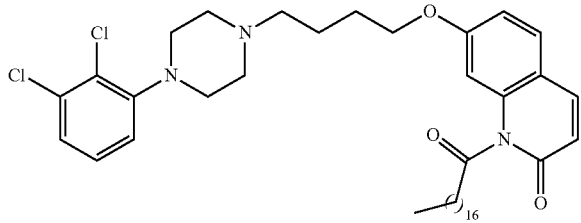 [SMILES: CCC(=O)n1c(=O)ccc2ccc(OCCCCN3CCN(c4cccc(Cl)c4Cl)CC3)cc21] |

TABLE D-continued

| No. | Structure |
|---|---|
| 311. | 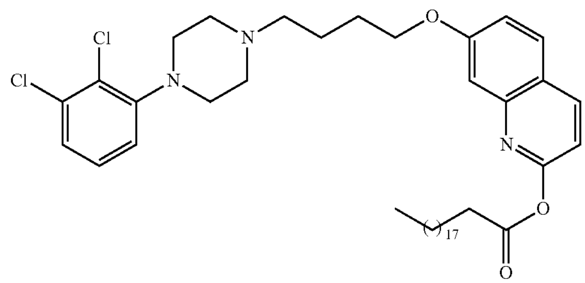 [SMILES: CCCC(=O)Oc1ccc2ccc(OCCCCN3CCN(c4cccc(Cl)c4Cl)CC3)cc2n1] |
| 312. | 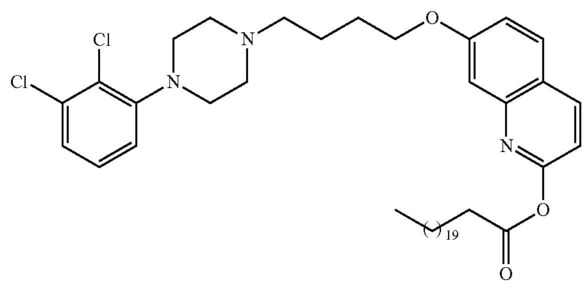 |
| 313. | 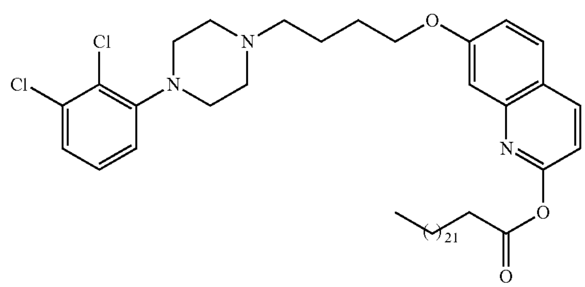 [SMILES: CCCC(=O)Oc1ccc2ccc(OCCCCN3CCN(c4cccc(Cl)c4Cl)CC3)cc2n1] |
| 314. | 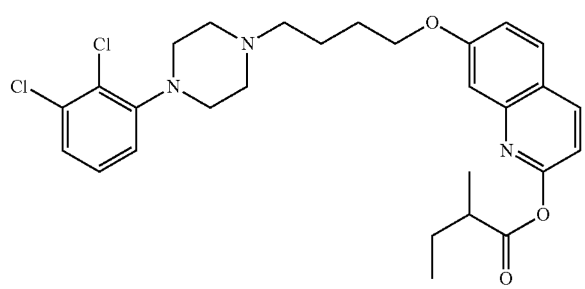 [SMILES: CCC(C)C(=O)Oc1ccc2ccc(OCCCCN3CCN(c4cccc(Cl)c4Cl)CC3)cc2n1] |
| 315. | 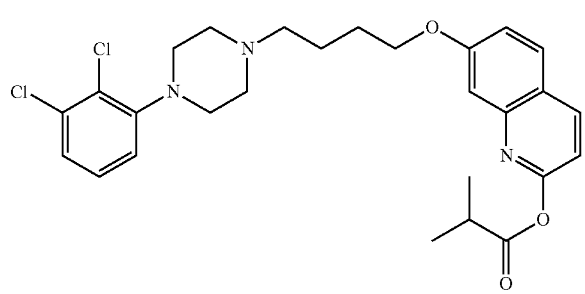 [SMILES: CC(C)C(=O)Oc1ccc2ccc(OCCCCN3CCN(c4cccc(Cl)c4Cl)CC3)cc2n1] |

TABLE D-continued
| No. | Structure |
|---|---|
| 316. | 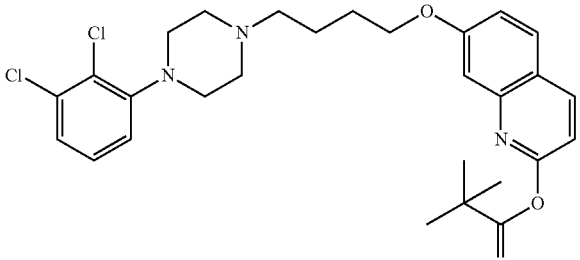 |
| 317. | 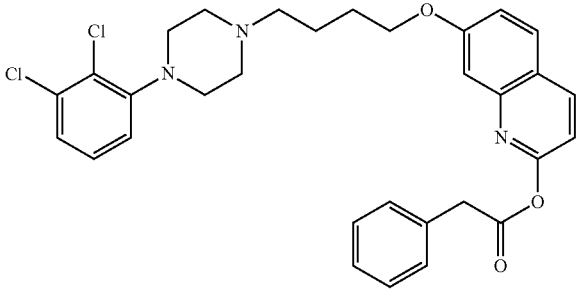 [SMILES: O=C(Cc1ccccc1)Oc1ccc2ccc(OCCCCN3CCN(c4cccc(Cl)c4Cl)CC3)cc2n1] |
| 318. | 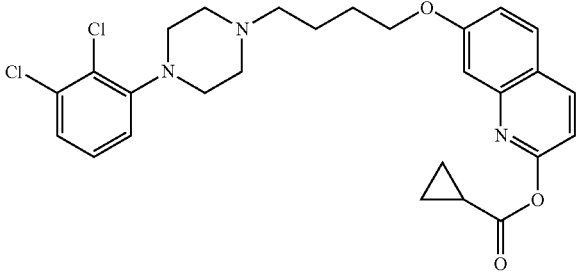 [SMILES: O=C(Oc1ccc2ccc(OCCCCN3CCN(c4cccc(Cl)c4Cl)CC3)cc2n1)C1CC1] |
| 319. | 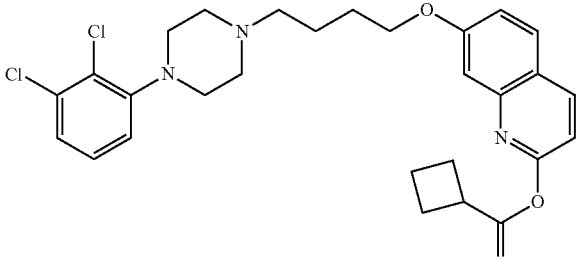 |
| 320. | 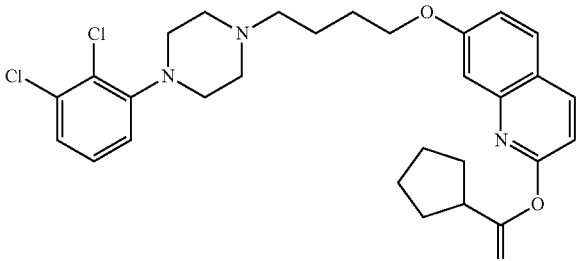 |

TABLE D-continued

| No. | Structure |
|---|---|
| 321. | 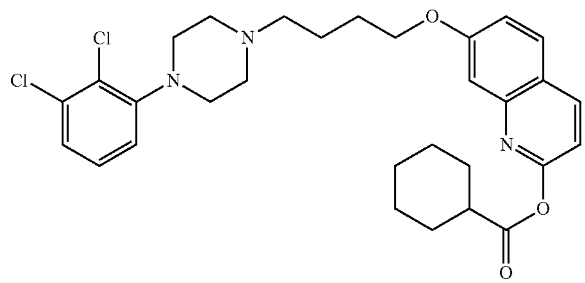 [SMILES: O=C(Oc1ccc2ccc(OCCCCN3CCN(c4cccc(Cl)c4Cl)CC3)cc2n1)C1CCCCC1] |
| 322. | |
| 322. | |
| 323. | 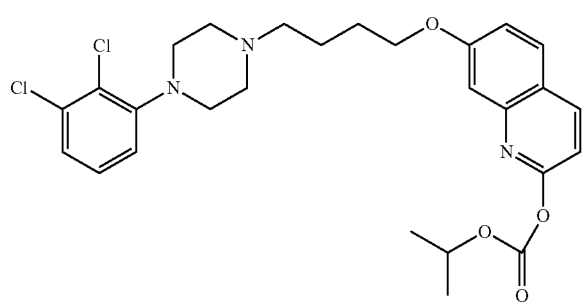 [SMILES: CC(C)OC(=O)Oc1ccc2ccc(OCCCCN3CCN(c4cccc(Cl)c4Cl)CC3)cc2n1] |
| 324. | 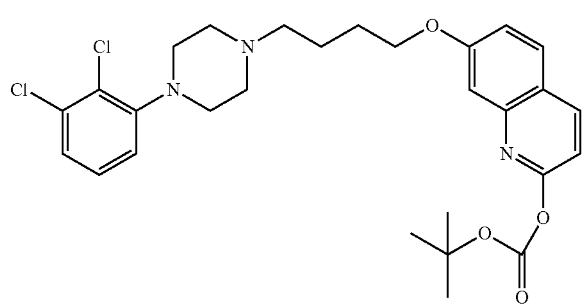 [SMILES: CC(C)(C)OC(=O)Oc1ccc2ccc(OCCCCN3CCN(c4cccc(Cl)c4Cl)CC3)cc2n1] |

TABLE D-continued

| No. | Structure |
|---|---|
| 325. | 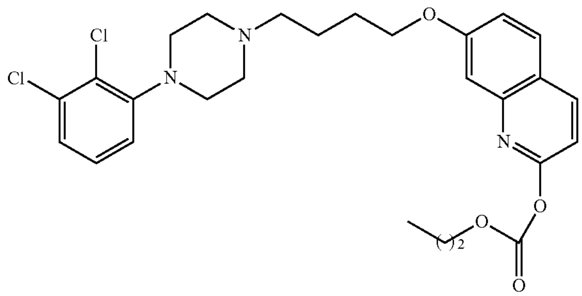 [SMILES: CCOC(=O)Oc1ccc2ccc(OCCCCN3CCN(c4cccc(Cl)c4Cl)CC3)cc2n1] |
| 326. | 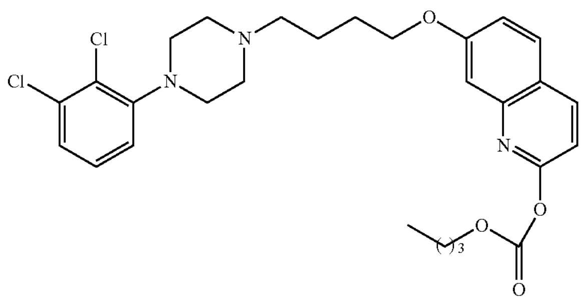 [SMILES: CCOC(=O)Oc1ccc2ccc(OCCCCN3CCN(c4cccc(Cl)c4Cl)CC3)cc2n1] |
| 327. | 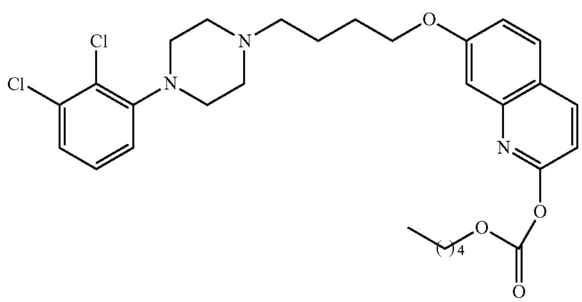 [SMILES: CCOC(=O)Oc1ccc2ccc(OCCCCN3CCN(c4cccc(Cl)c4Cl)CC3)cc2n1] |
| 328. | 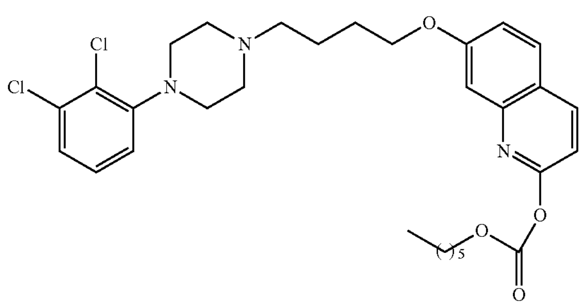 [SMILES: CCOC(=O)Oc1ccc2ccc(OCCCCN3CCN(c4cccc(Cl)c4Cl)CC3)cc2n1] |
| 329. | 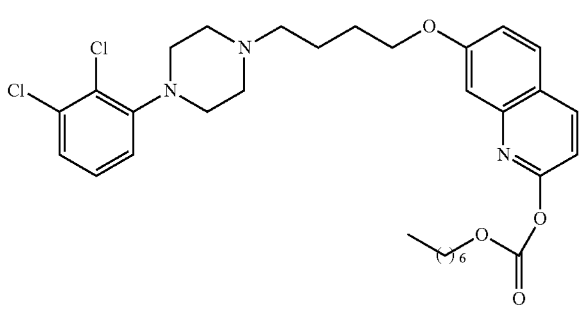 [SMILES: CCOC(=O)Oc1ccc2ccc(OCCCCN3CCN(c4cccc(Cl)c4Cl)CC3)cc2n1] |

TABLE D-continued
| No. | Structure |
|---|---|
| 330. | 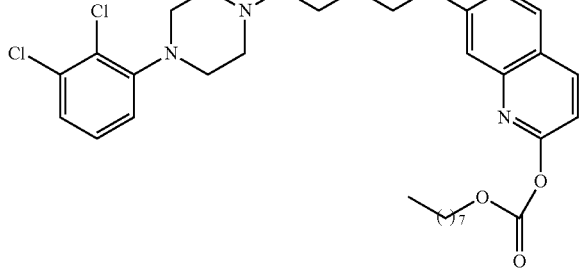 |
| 331. | 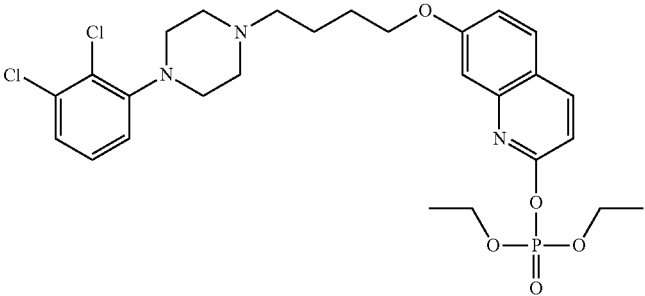 [SMILES: CCOP(=O)(OCC)Oc1ccc2ccc(OCCCCN3CCN(c4cccc(Cl)c4Cl)CC3)cc2n1] |
| 332. | 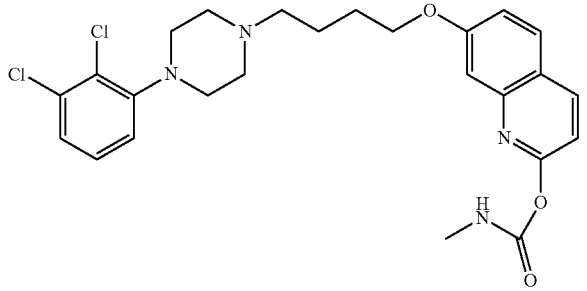 [SMILES: CNC(=O)Oc1ccc2ccc(OCCCCN3CCN(c4cccc(Cl)c4Cl)CC3)cc2n1] |
| 333. | 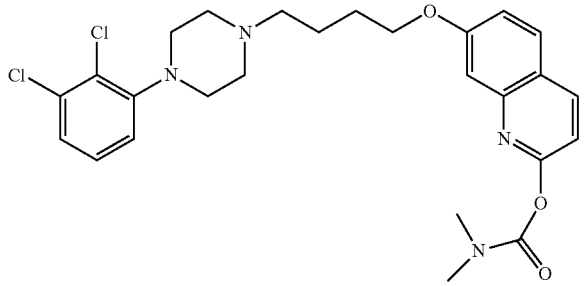 [SMILES: CN(C)C(=O)Oc1ccc2ccc(OCCCCN3CCN(c4cccc(Cl)c4Cl)CC3)cc2n1] |
| 334. | 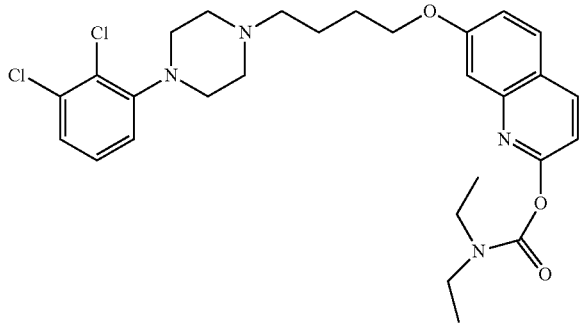 [SMILES: CCN(CC)C(=O)Oc1ccc2ccc(OCCCCN3CCN(c4cccc(Cl)c4Cl)CC3)cc2n1] |

TABLE D-continued
| No. | Structure |
|---|---|
| 335. | 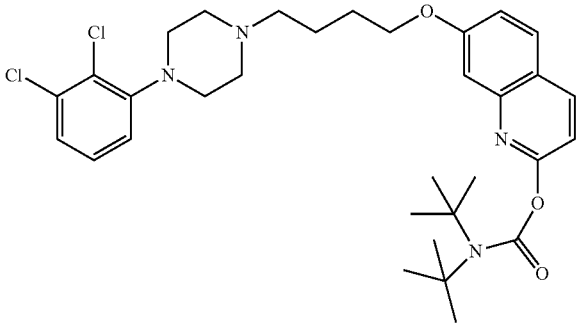 [SMILES: CC(C)(C)N(C(=O)Oc1ccc2ccc(OCCCCN3CCN(c4cccc(Cl)c4Cl)CC3)cc2n1)C(C)(C)C] |
| 336. | 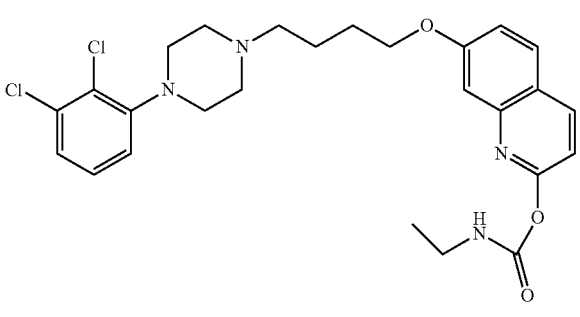 [SMILES: CCNC(=O)Oc1ccc2ccc(OCCCCN3CCN(c4cccc(Cl)c4Cl)CC3)cc2n1] |
| 337. | 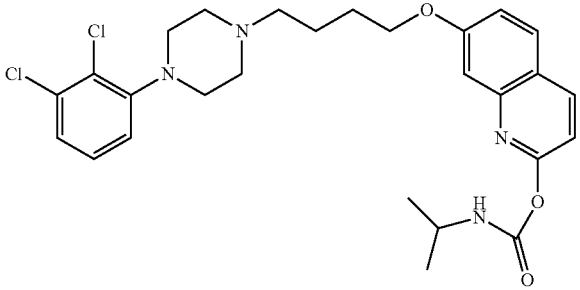 [SMILES: CC(C)NC(=O)Oc1ccc2ccc(OCCCCN3CCN(c4cccc(Cl)c4Cl)CC3)cc2n1] |
| 338. | 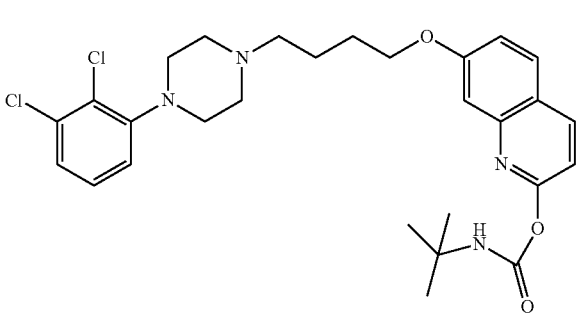 [SMILES: CC(C)(C)NC(=O)Oc1ccc2ccc(OCCCCN3CCN(c4cccc(Cl)c4Cl)CC3)cc2n1] |
| 339. | 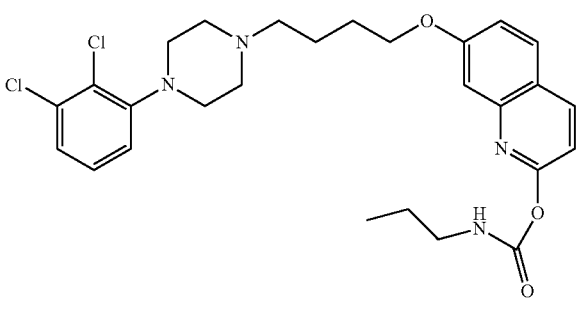 [SMILES: CCCNC(=O)Oc1ccc2ccc(OCCCCN3CCN(c4cccc(Cl)c4Cl)CC3)cc2n1] |

TABLE D-continued
| No. | Structure |
|---|---|
| 340. | 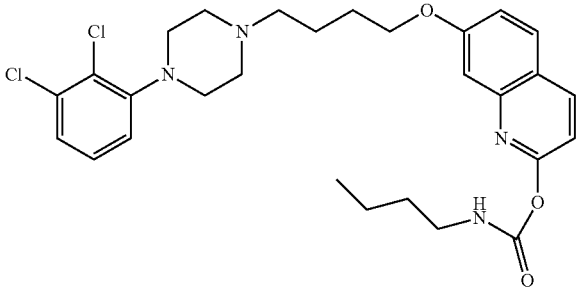 [SMILES: CCCCNC(=O)Oc1ccc2ccc(OCCCCN3CCN(c4cccc(Cl)c4Cl)CC3)cc2n1] |
| 341. | 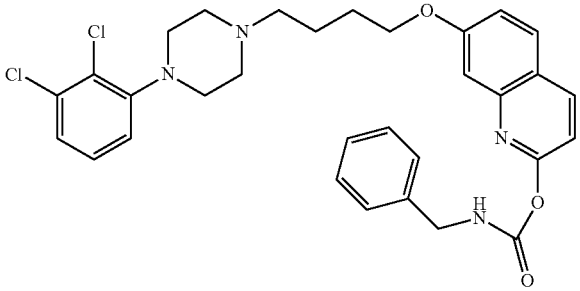 [SMILES: O=C(NCc1ccccc1)Oc1ccc2ccc(OCCCCN3CCN(c4cccc(Cl)c4Cl)CC3)cc2n1] |
| 342. | 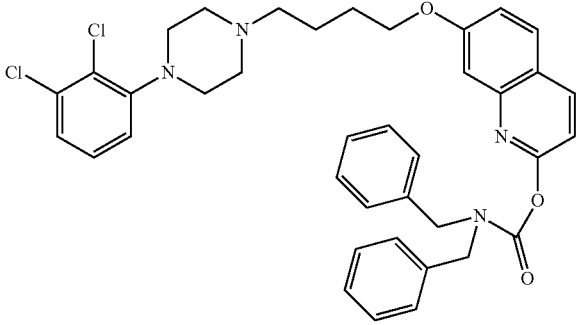 [SMILES: O=C(Oc1ccc2ccc(OCCCCN3CCN(c4cccc(Cl)c4Cl)CC3)cc2n1)N(Cc1ccccc1)Cc1ccccc1] |
| 343. | 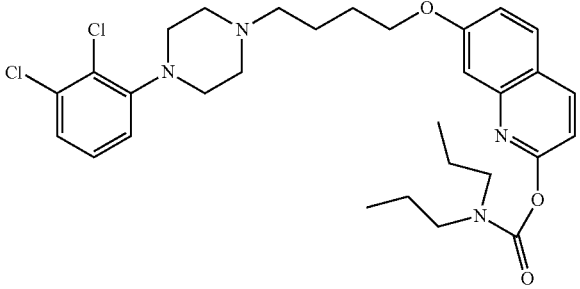 [SMILES: CCCN(CCC)C(=O)Oc1ccc2ccc(OCCCCN3CCN(c4cccc(Cl)c4Cl)CC3)cc2n1] |
| 344. | 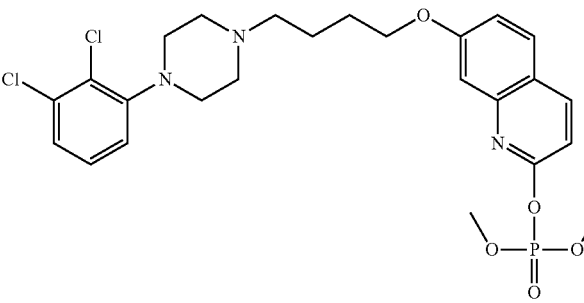 |

TABLE E
| No. | Structure |
|---|---|
| 400. | 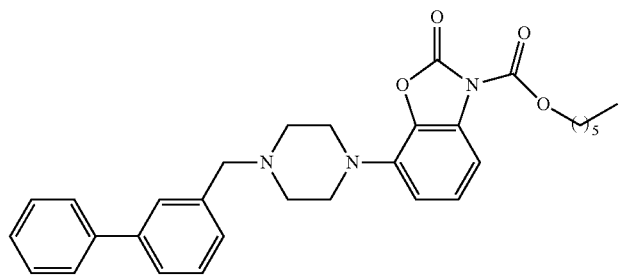 |
| 401. | 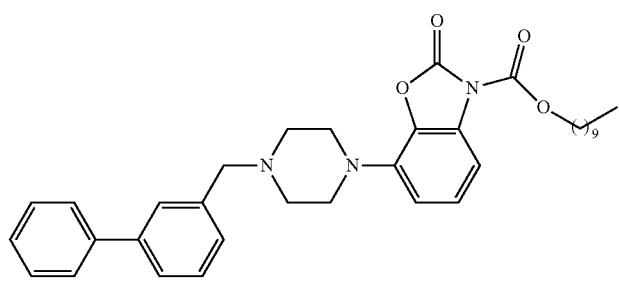 [SMILES: CCOC(=O)n1c(=O)oc2c(N3CCN(Cc4cccc(-c5ccccc5)c4)CC3)cccc21] |
| 402. | 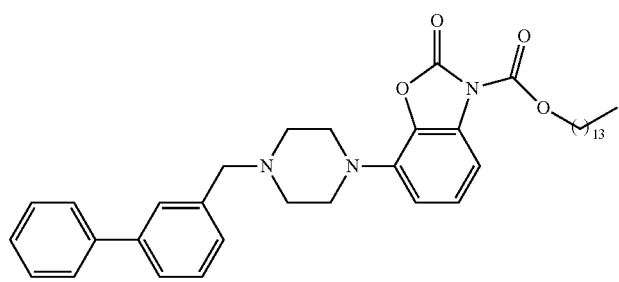 [SMILES: CCOC(=O)n1c(=O)oc2c(N3CCN(Cc4cccc(-c5ccccc5)c4)CC3)cccc21] |
| 403. | 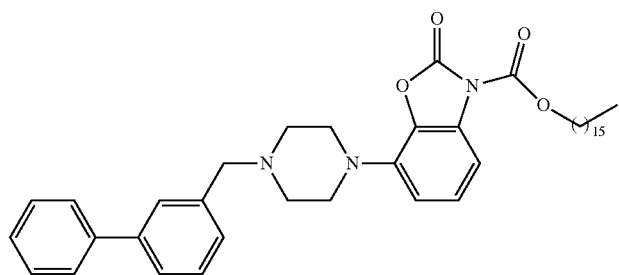 [SMILES: CCOC(=O)n1c(=O)oc2c(N3CCN(Cc4cccc(-c5ccccc5)c4)CC3)cccc21] |
| 404. | 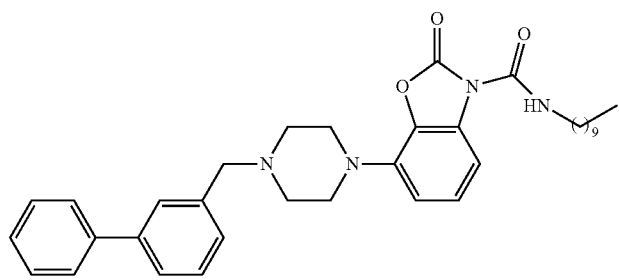 [SMILES: CCNC(=O)n1c(=O)oc2c(N3CCN(Cc4cccc(-c5ccccc5)c4)CC3)cccc21] |

TABLE E-continued
| No. | Structure |
|-----|-----------|
| 405. | 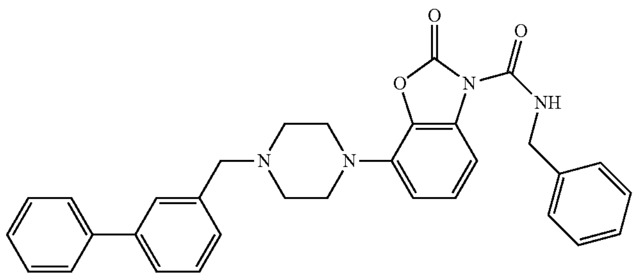 [SMILES: O=C(NCc1ccccc1)n1c(=O)oc2c(N3CCN(Cc4cccc(-c5ccccc5)c4)CC3)cccc21] |
| 406. | 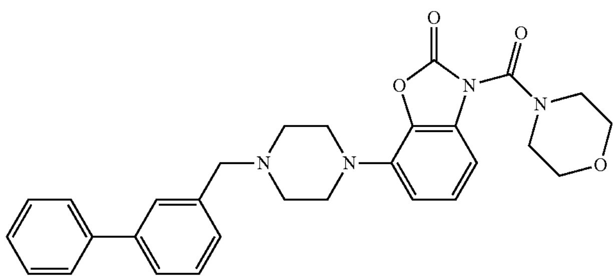 [SMILES: O=C(N1CCOCC1)n1c(=O)oc2c(N3CCN(Cc4cccc(-c5ccccc5)c4)CC3)cccc21] |
| 407. | 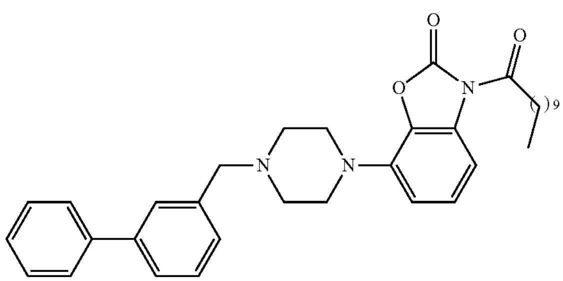 [SMILES: CCC(=O)n1c(=O)oc2c(N3CCN(Cc4cccc(-c5ccccc5)c4)CC3)cccc21] |
| 408. | 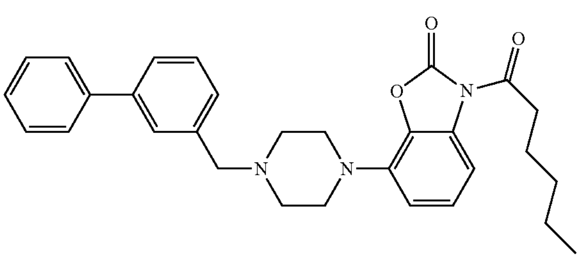 [SMILES: CCCCCC(=O)n1c(=O)oc2c(N3CCN(Cc4cccc(-c5ccccc5)c4)CC3)cccc21] |
| 409. | 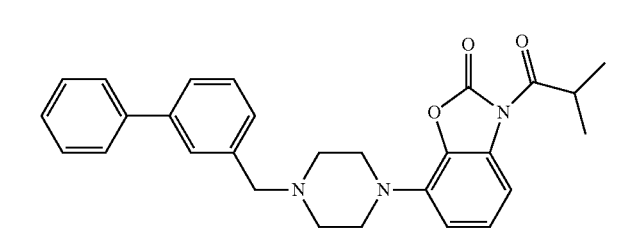 [SMILES: CC(C)C(=O)n1c(=O)oc2c(N3CCN(Cc4cccc(-c5ccccc5)c4)CC3)cccc21] |

TABLE E-continued
| No. | Structure |
|---|---|
| 410. | 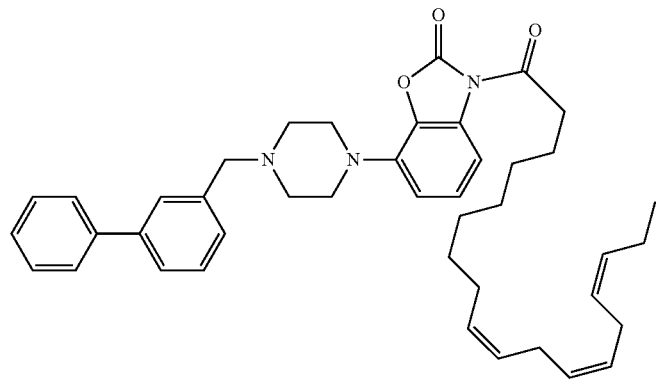 [SMILES: CC/C=C\C/C=C\C/C=C\CCCCCCCC(=O)n1c(=O)oc2c(N3CCN(Cc4cccc(-c5ccccc5)c4)CC3)cccc21] |
| 411. | 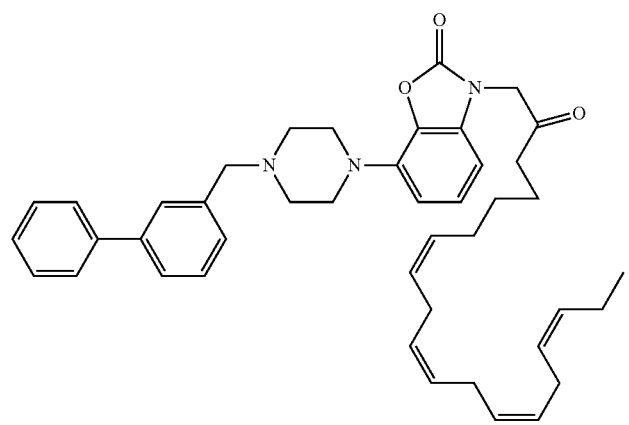 [SMILES: CC/C=C\C/C=C\C/C=C\C/C=C\CCCCC(=O)Cn1c(=O)oc2c(N3CCN(Cc4cccc(-c5ccccc5)c4)CC3)cccc21] |
| 412. | 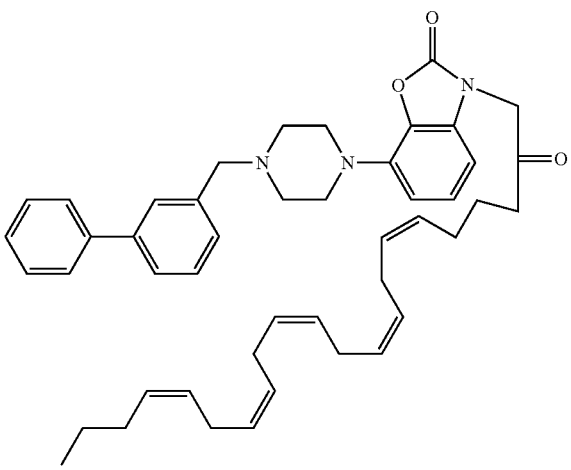 [SMILES: CCC/C=C\C/C=C\C/C=C\C/C=C\C/C=C\CCCC(=O)Cn1c(=O)oc2c(N3CCN(Cc4cccc(-c5ccccc5)c4)CC3)cccc21] |

141
TABLE E-continued
| No. | Structure |
|---|---|
| 413. | 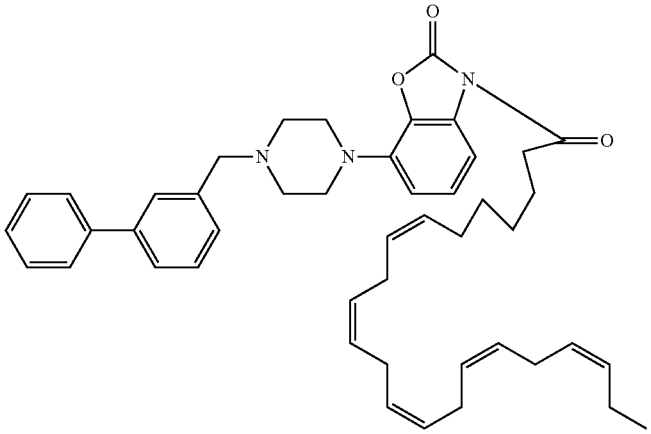 [SMILES: CC/C=C\C/C=C\C/C=C\C/C=C\C/C=C\CCCCCC(=O)n1c(=O)oc2c(N3CCN(Cc4cccc(-c5ccccc5)c4)CC3)cccc21] |
| 414. | 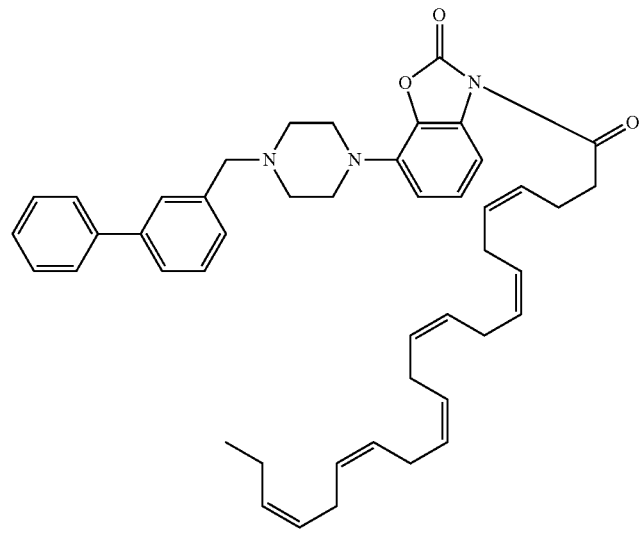 [SMILES: CC/C=C\C/C=C\C/C=C\C/C=C\C/C=C\C/C=C\CCC(=O)n1c(=O)oc2c(N3CCN(Cc4cccc(-c5ccccc5)c4)CC3)cccc21] |
| 415. | 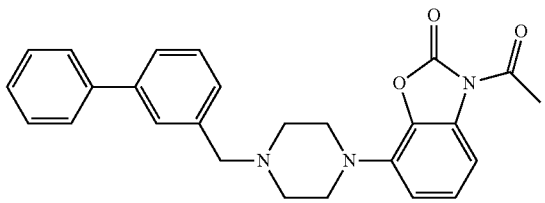 [SMILES: CC(=O)n1c(=O)oc2c(N3CCN(Cc4cccc(-c5ccccc5)c4)CC3)cccc21] |
| 416. | 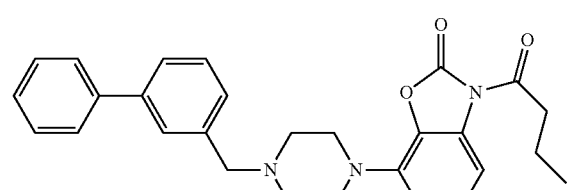 |

TABLE E-continued

| No. | Structure |
|-----|-----------|
| 417. | 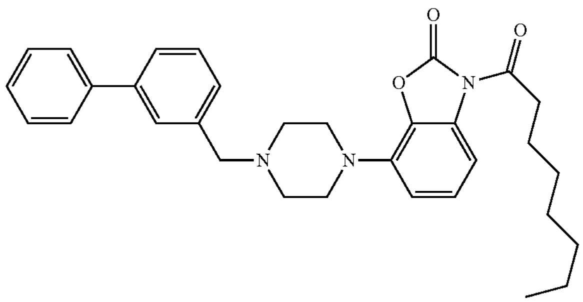 [SMILES: CCCCCCCC(=O)n1c(=O)oc2c(N3CCN(Cc4cccc(-c5ccccc5)c4)CC3)cccc21] |
| 418. | 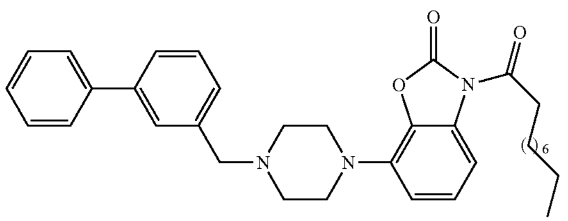 [SMILES: CCCCC(=O)n1c(=O)oc2c(N3CCN(Cc4cccc(-c5ccccc5)c4)CC3)cccc21] |
| 419. | 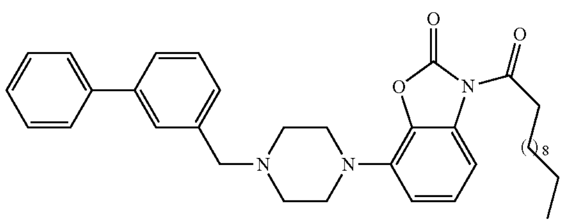 [SMILES: CCCCC(=O)n1c(=O)oc2c(N3CCN(Cc4cccc(-c5ccccc5)c4)CC3)cccc21] |
| 420. | 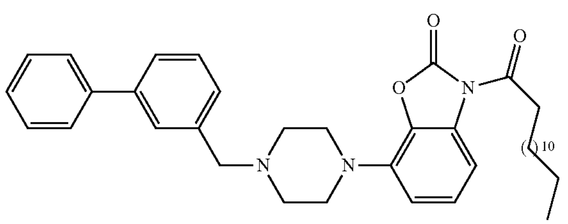 [SMILES: CCCCC(=O)n1c(=O)oc2c(N3CCN(Cc4cccc(-c5ccccc5)c4)CC3)cccc21] |
| 421. | 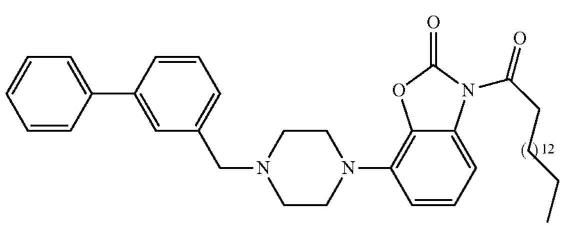 [SMILES: CCCCC(=O)n1c(=O)oc2c(N3CCN(Cc4cccc(-c5ccccc5)c4)CC3)cccc21] |
| 422. | 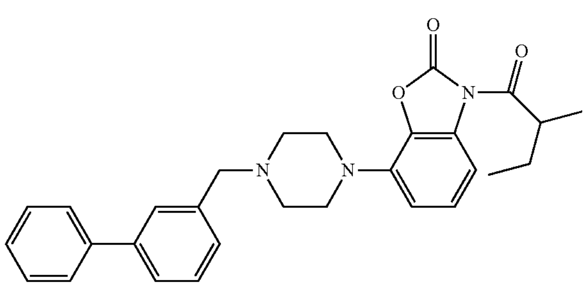 [SMILES: CCC(C)(C)C(=O)n1c(=O)oc2c(N3CCN(Cc4cccc(-c5ccccc5)c4)CC3)cccc21] |

TABLE E-continued
| No. | Structure |
|---|---|
| 423. | 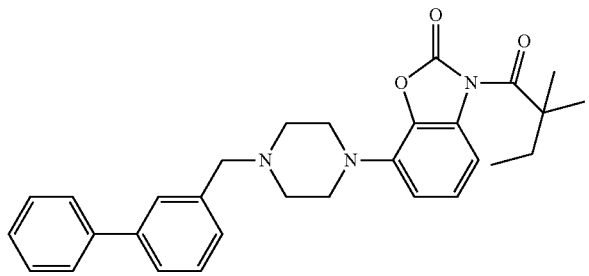 |
| 424. | 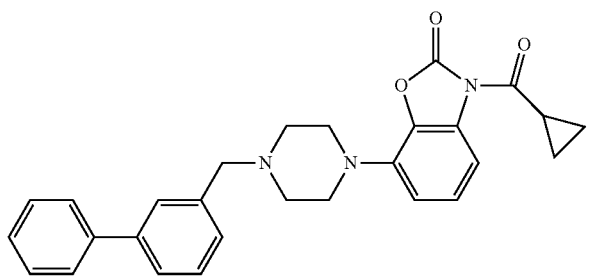 [SMILES: O=C(C1CC1)n1c(=O)oc2c(N3CCN(Cc4cccc(-c5ccccc5)c4)CC3)cccc21] |
| 425. | 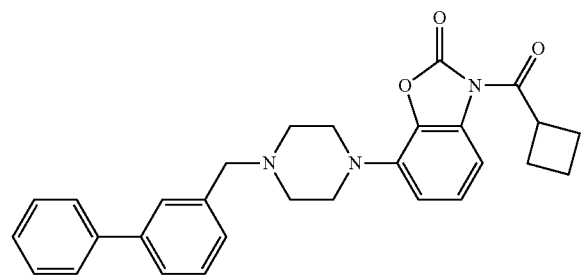 [SMILES: O=C(C1CCC1)n1c(=O)oc2c(N3CCN(Cc4cccc(-c5ccccc5)c4)CC3)cccc21] |
| 426. | 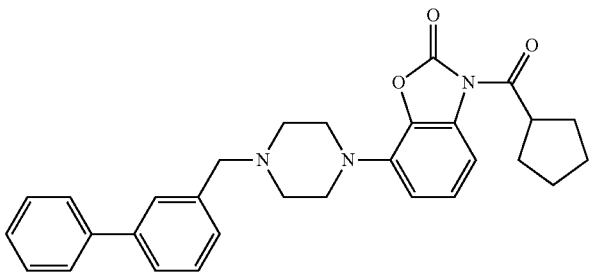 [SMILES: O=C(C1CCCC1)n1c(=O)oc2c(N3CCN(Cc4cccc(-c5ccccc5)c4)CC3)cccc21] |
| 427. | 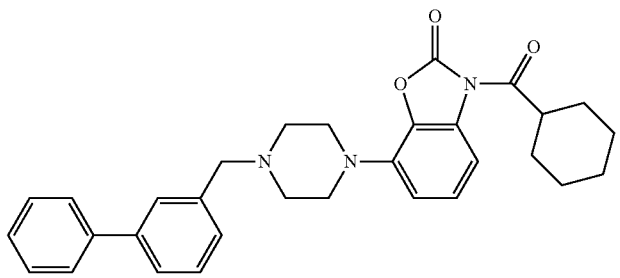 [SMILES: O=C(C1CCCCC1)n1c(=O)oc2c(N3CCN(Cc4cccc(-c5ccccc5)c4)CC3)cccc21] |

TABLE E-continued
| No. | Structure |
|---|---|
| 428. | 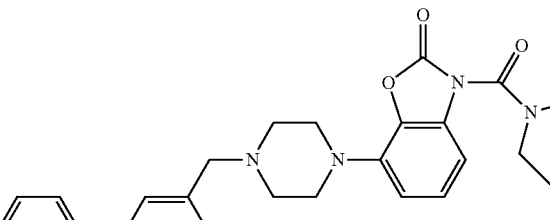 |
| 429. | 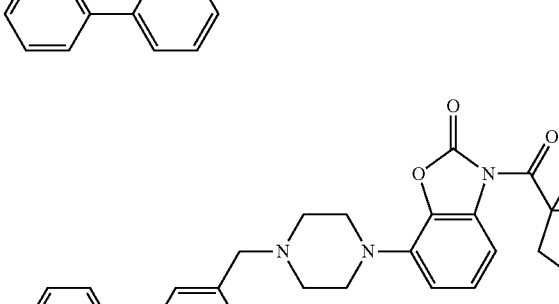 |
TABLE F
| No. | Structure |
|---|---|
| 500. | 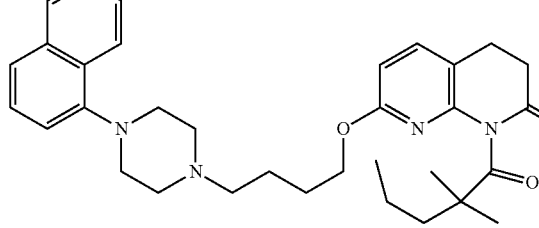 |
| 501. | 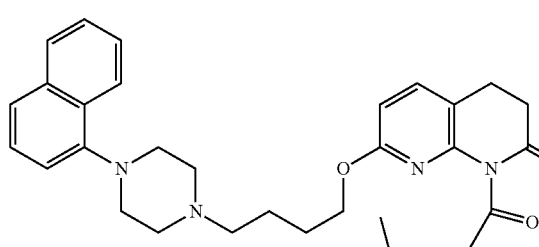 |
| 502. | 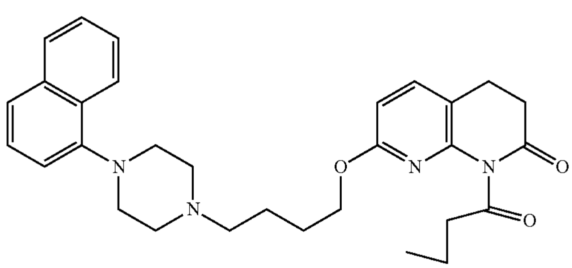 [SMILES: CCCC(=O)N1C(=O)CCc2ccc(OCCCCN3CCN(c4cccc5ccccc45)CC3)nc21] |

TABLE F-continued

| No. | Structure |
|---|---|
| 503. | 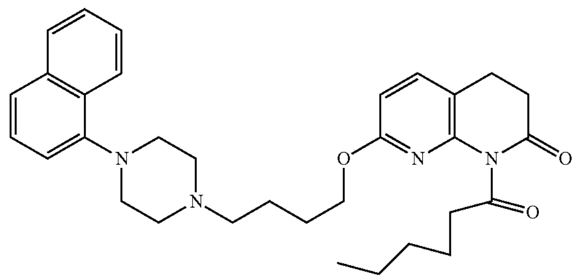 [SMILES: CCCCCC(=O)N1C(=O)CCc2ccc(OCCCCN3CCN(c4cccc5ccccc45)CC3)nc21] |
| 504. | 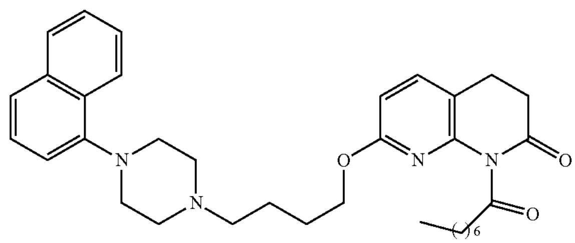 [SMILES: CCC(=O)N1C(=O)CCc2ccc(OCCCCN3CCN(c4cccc5ccccc45)CC3)nc21] |
| 505. | 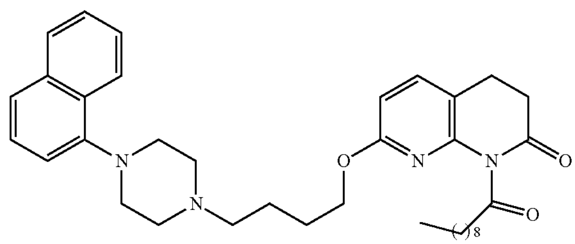 [SMILES: CCC(=O)N1C(=O)CCc2ccc(OCCCCN3CCN(c4cccc5ccccc45)CC3)nc21] |
| 506. | 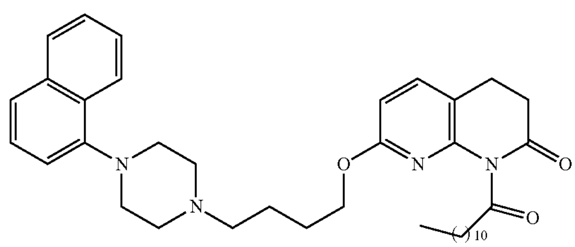 [SMILES: CCC(=O)N1C(=O)CCc2ccc(OCCCCN3CCN(c4cccc5ccccc45)CC3)nc21] |
| 507. | 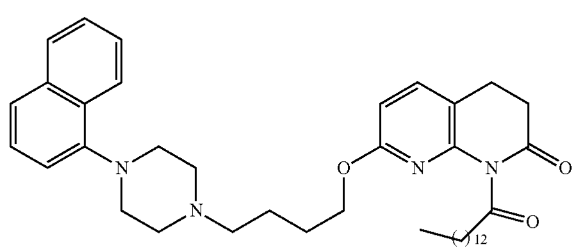 [SMILES: CCC(=O)N1C(=O)CCc2ccc(OCCCCN3CCN(c4cccc5ccccc45)CC3)nc21] |
| 508. | 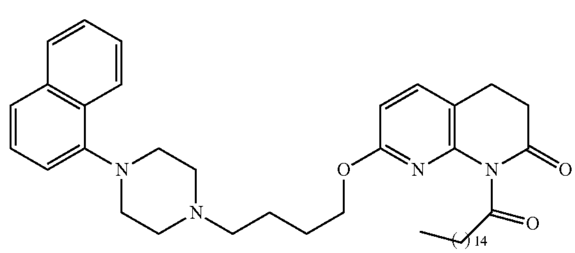 [SMILES: CCC(=O)N1C(=O)CCc2ccc(OCCCCN3CCN(c4cccc5ccccc45)CC3)nc21] |

TABLE F-continued
| No. | Structure |
|---|---|
| 509. | 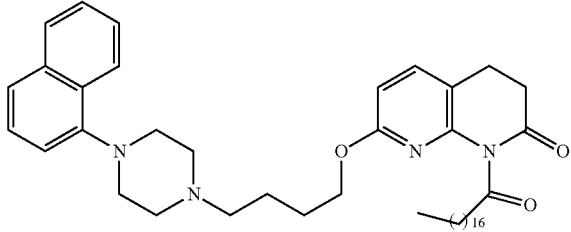 |
| 510. | 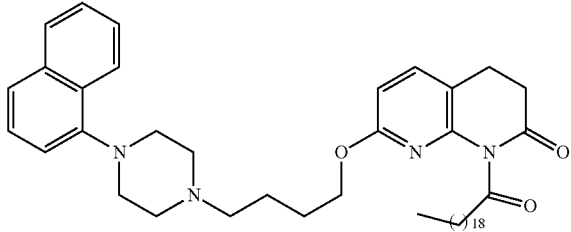 |
| 511. | 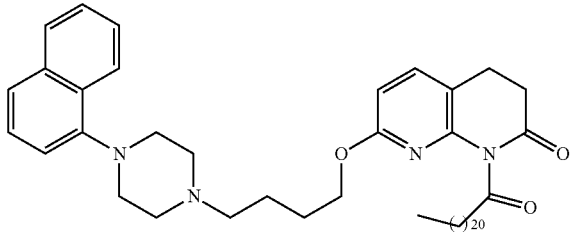 [SMILES: CCC(=O)N1C(=O)CCc2ccc(OCCCCN3CCN(c4cccc5ccccc45)CC3)nc21] |
| 512. | 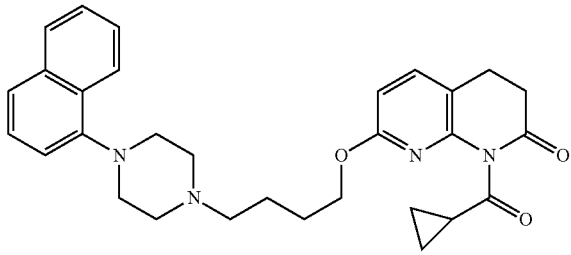 [SMILES: O=C1CCc2ccc(OCCCCN3CCN(c4cccc5ccccc45)CC3)nc2N1C(=O)C1CC1] |
| 513. | 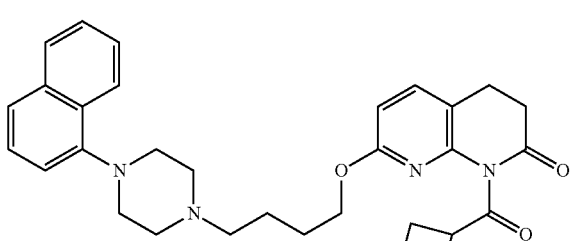 |
| 514. | 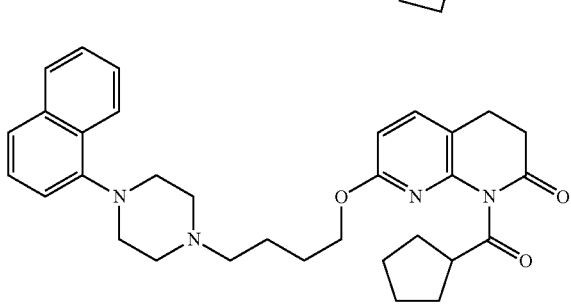 |

TABLE F-continued
| No. | Structure |
|---|---|
| 515. | 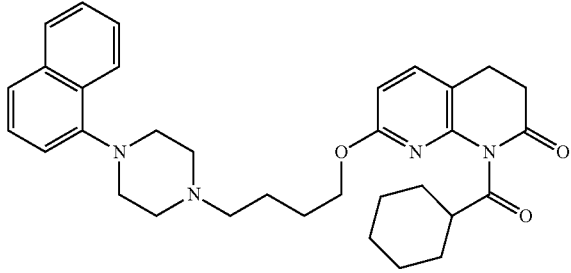 [SMILES: O=C1CCc2ccc(OCCCCN3CCN(c4cccc5ccccc45)CC3)nc2N1C(=O)C1CCCCC1] |
| 516. | 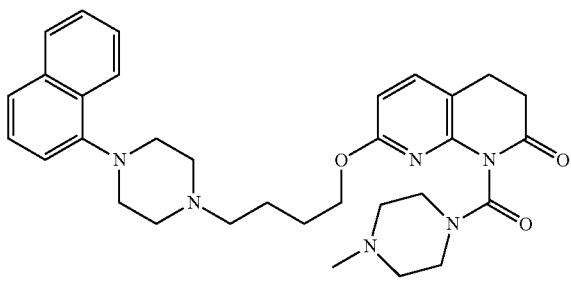 [SMILES: CN1CCN(C(=O)N2C(=O)CCc3ccc(OCCCCN4CCN(c5cccc6ccccc56)CC4)nc32)CC1] |
| 517. | 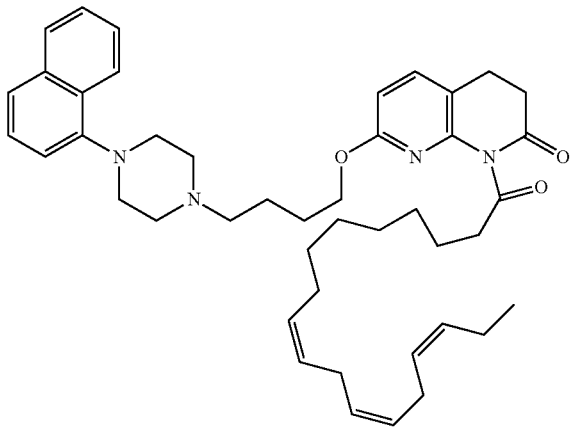 [SMILES: CC/C=C\C/C=C\C/C=C\CCCCCCCC(=O)N1C(=O)CCc2ccc(OCCCCN3CCN(c4cccc5ccccc45)CC3)nc21] |
| 518. | 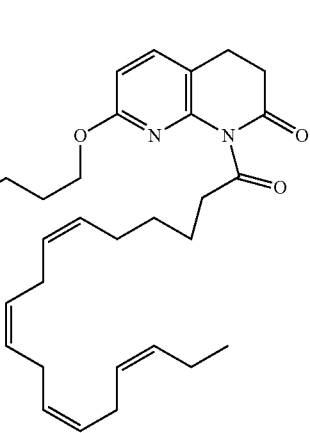 |

TABLE F-continued

| No. | Structure |
|---|---|
| 519. | 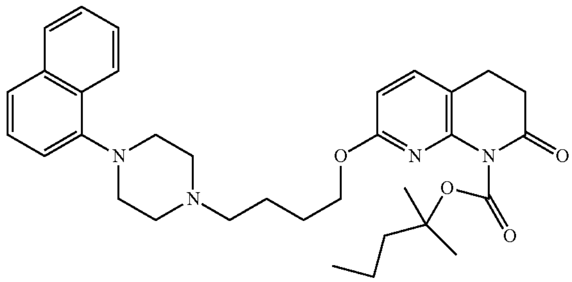 [SMILES: CCCC(C)(C)OC(=O)N1C(=O)CCc2ccc(OCCCCN3CCN(c4cccc5ccccc45)CC3)nc21] |
| 520. | 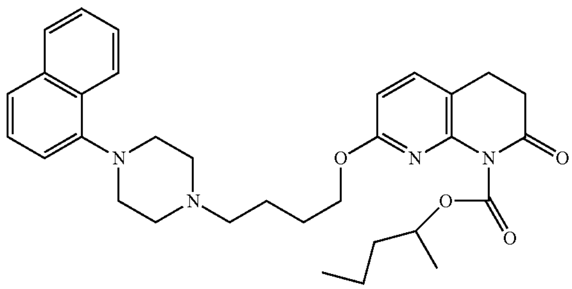 [SMILES: CCCC(C)OC(=O)N1C(=O)CCc2ccc(OCCCCN3CCN(c4cccc5ccccc45)CC3)nc21] |
| 521. | 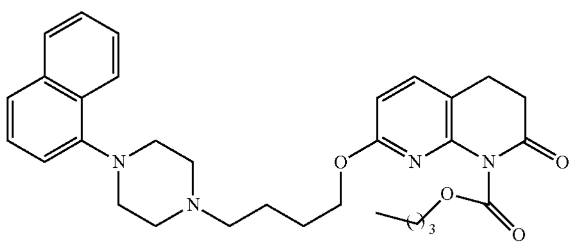 [SMILES: CCOC(=O)N1C(=O)CCc2ccc(OCCCCN3CCN(c4cccc5ccccc45)CC3)nc21] |
| 522. | 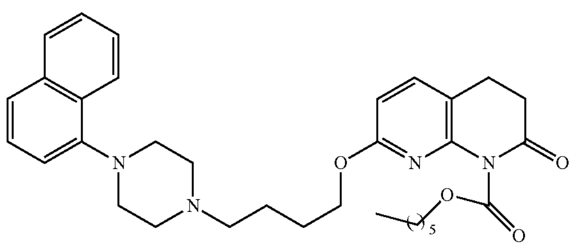 [SMILES: CCOC(=O)N1C(=O)CCc2ccc(OCCCCN3CCN(c4cccc5ccccc45)CC3)nc21] |
| 523. | 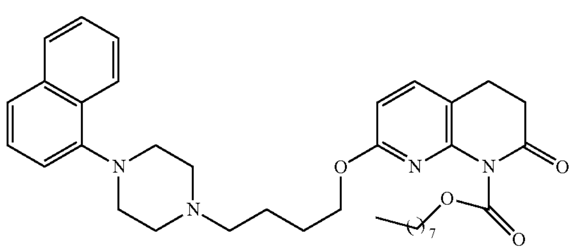 [SMILES: CCOC(=O)N1C(=O)CCc2ccc(OCCCCN3CCN(c4cccc5ccccc45)CC3)nc21] |
| 524. | 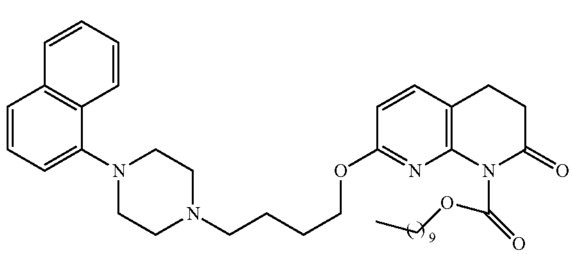 [SMILES: CCOC(=O)N1C(=O)CCc2ccc(OCCCCN3CCN(c4cccc5ccccc45)CC3)nc21] |

TABLE F-continued
| No. | Structure |
|---|---|
| 525. | 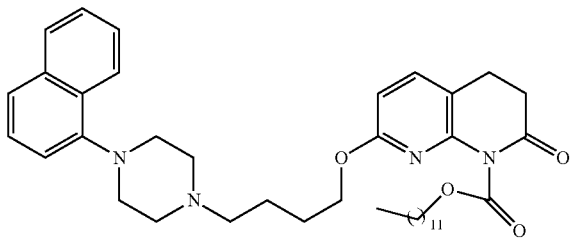 [SMILES: CCOC(=O)N1C(=O)CCc2ccc(OCCCCN3CCN(c4cccc5ccccc45)CC3)nc21] |
| 526. | 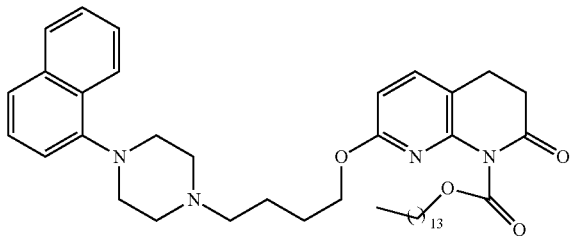 [SMILES: CCOC(=O)N1C(=O)CCc2ccc(OCCCCN3CCN(c4cccc5ccccc45)CC3)nc21] |
| 527. | 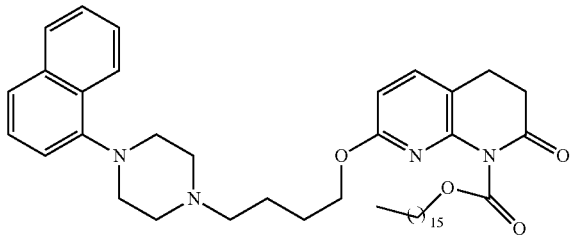 [SMILES: CCOC(=O)N1C(=O)CCc2ccc(OCCCCN3CCN(c4cccc5ccccc45)CC3)nc21] |
| 528. | 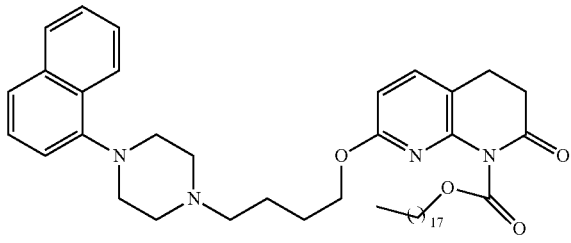 [SMILES: CCOC(=O)N1C(=O)CCc2ccc(OCCCCN3CCN(c4cccc5ccccc45)CC3)nc21] |
| 529. | 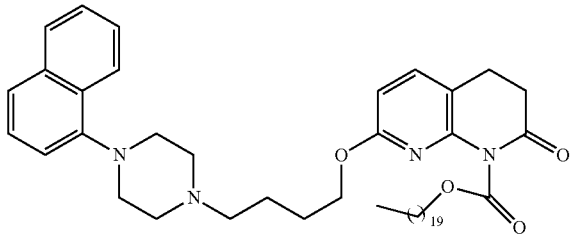 [SMILES: CCOC(=O)N1C(=O)CCc2ccc(OCCCCN3CCN(c4cccc5ccccc45)CC3)nc21] |
| 530. | 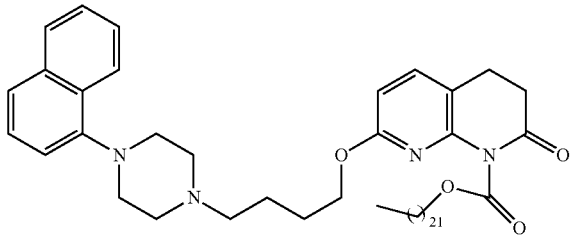 [SMILES: CCOC(=O)N1C(=O)CCc2ccc(OCCCCN3CCN(c4cccc5ccccc45)CC3)nc21] |

TABLE F-continued
| No. | Structure |
|---|---|
| 531. | 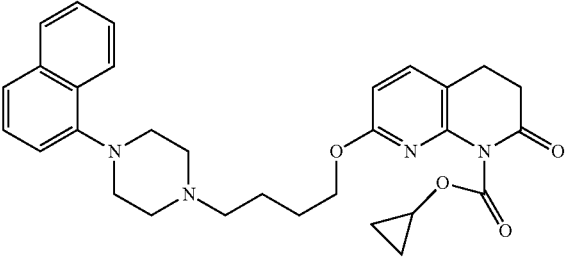 [SMILES: O=C1CCc2ccc(OCCCCN3CCN(c4cccc5ccccc45)CC3)nc2N1C(=O)OC1CC1] |
| 532. | 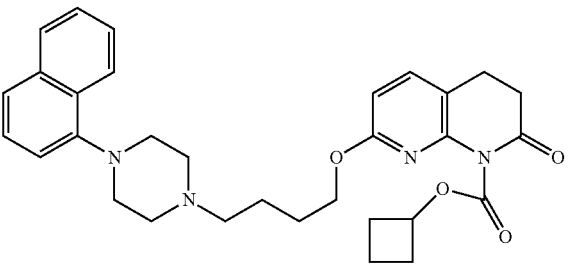 [SMILES: O=C1CCc2ccc(OCCCCN3CCN(c4cccc5ccccc45)CC3)nc2N1C(=O)OC1CCC1] |
| 533. | 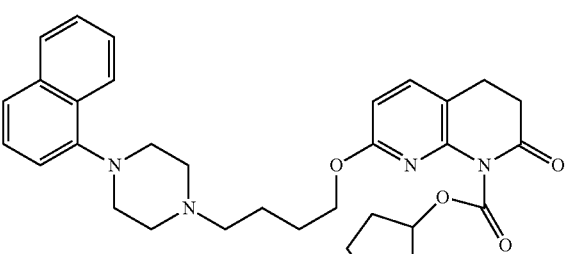 |
| 534. | 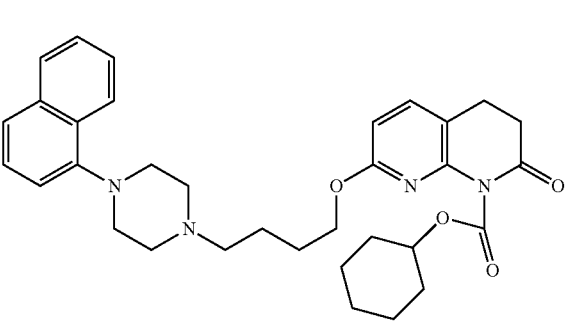 [SMILES: O=C1CCc2ccc(OCCCCN3CCN(c4cccc5ccccc45)CC3)nc2N1C(=O)OC1CCCCC1] |
| 535. | 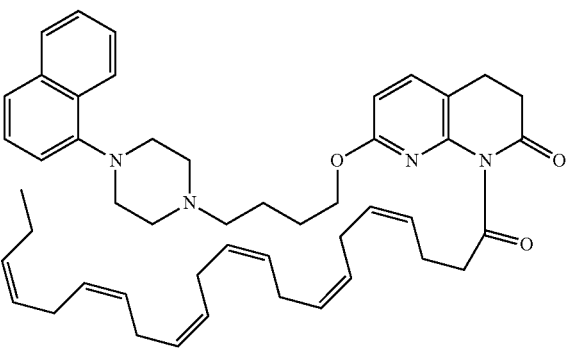 [SMILES: CC/C=C\C/C=C\C/C=C\C/C=C\C/C=C\C/C=C\CCC(=O)N1C(=O)CCc2ccc(OCCCCN3CCN(c4cccc5ccccc45)CC3)nc21] |

TABLE F-continued
| No. | Structure |
|---|---|
| 536. | 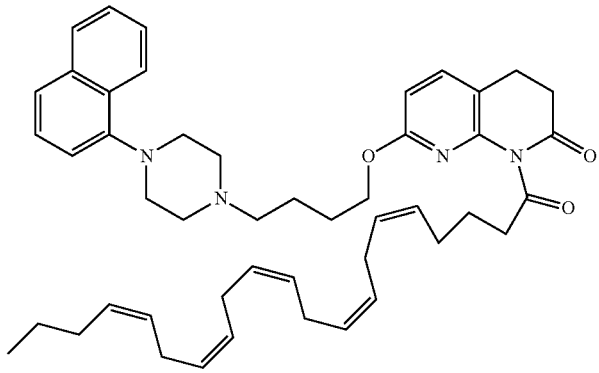 [SMILES: CCC/C=C\C/C=C\C/C=C\C/C=C\C/C=C\CCCC(=O)N1C(=O)CCc2ccc(OCCCCN3CCN(c4cccc5ccccc45)CC3)nc21] |
| 537. | 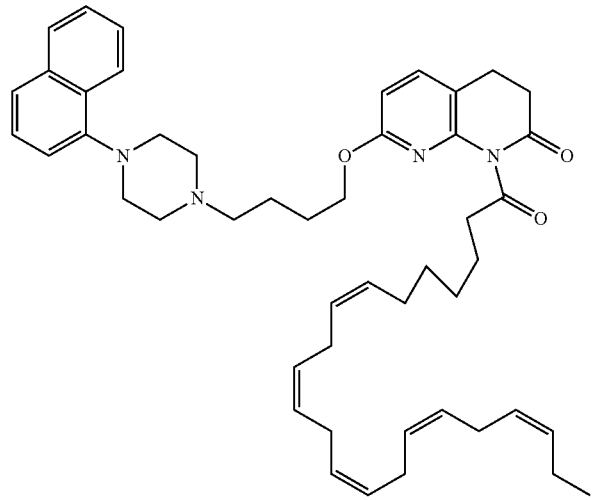 [SMILES: CC/C=C\C/C=C\C/C=C\C/C=C\C/C=C\CCCCCC(=O)N1C(=O)CCc2ccc(OCCCCN3CCN(c4cccc5ccccc45)CC3)nc21] |
In another embodiment, the invention relates to a compound of Formula LI and LII:
Formula LI
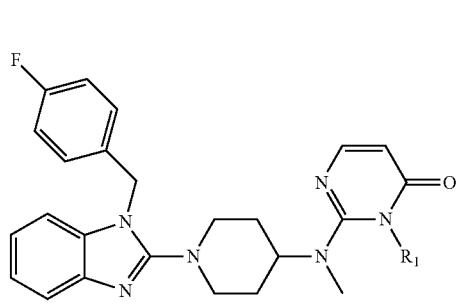
Formula LII
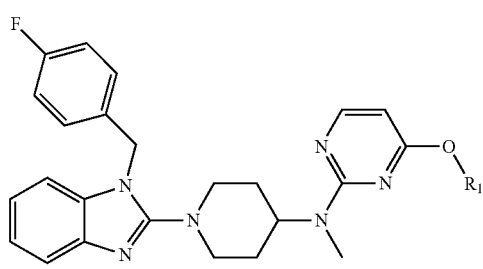
In another aspect of the invention, compounds of Formula LI and LII are selected from Table G:

TABLE G

| No. | Structure |
|---|---|
| 700. | 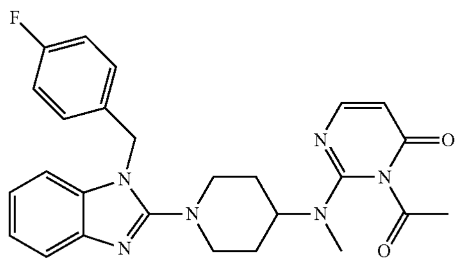 [SMILES: CC(=O)n1c(N(C)C2CCN(c3nc4ccccc4n3Cc3ccc(F)cc3)CC2)nccc1=O] |
| 701. | 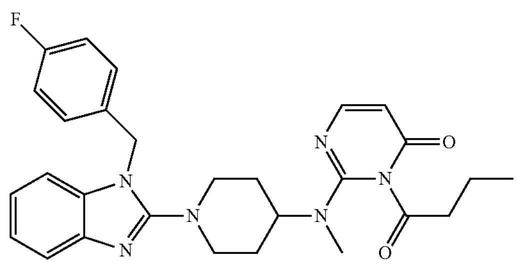 [SMILES: CCCC(=O)n1c(N(C)C2CCN(c3nc4ccccc4n3Cc3ccc(F)cc3)CC2)nccc1=O] |
| 702. | 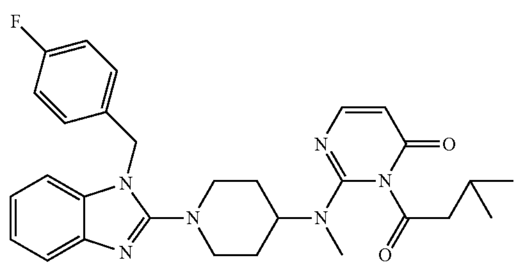 |
| 703. | 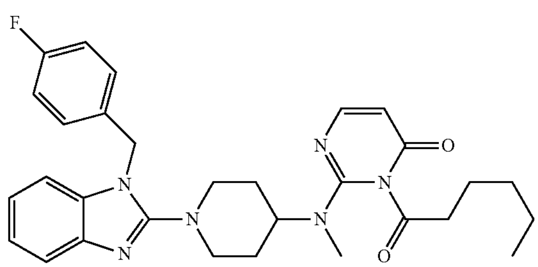 [SMILES: CCCCCC(=O)n1c(N(C)C2CCN(c3nc4ccccc4n3Cc3ccc(F)cc3)CC2)nccc1=O] |
| 704. | 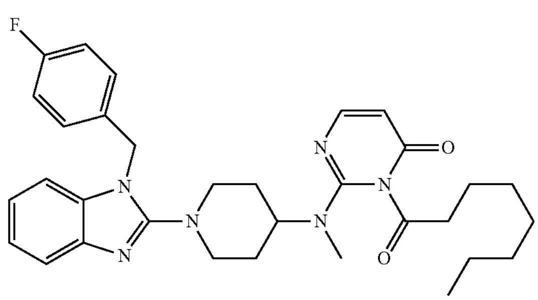 [SMILES: CCCCCCCC(=O)n1c(N(C)C2CCN(c3nc4ccccc4n3Cc3ccc(F)cc3)CC2)nccc1=O] |
| 705. | 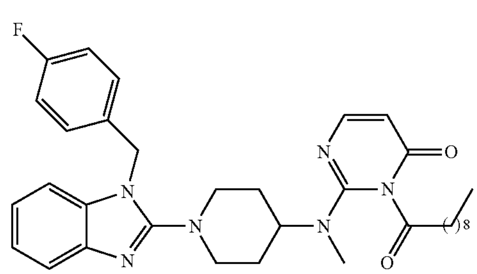 [SMILES: CCC(=O)n1c(N(C)C2CCN(c3nc4ccccc4n3Cc3ccc(F)cc3)CC2)nccc1=O] |

TABLE G-continued
| No. | Structure |
|---|---|
| 706. | 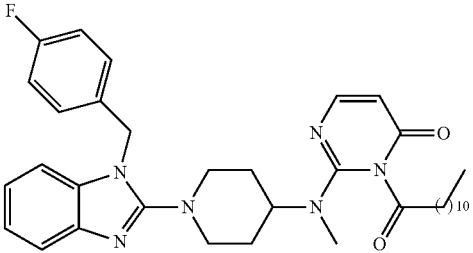 [SMILES: CCC(=O)n1c(N(C)C2CCN(c3nc4ccccc4n3Cc3ccc(F)cc3)CC2)nccc1=O] |
| 707. | 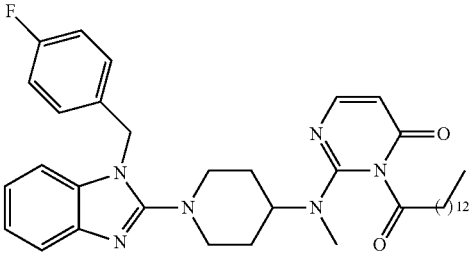 [SMILES: CCC(=O)n1c(N(C)C2CCN(c3nc4ccccc4n3Cc3ccc(F)cc3)CC2)nccc1=O] |
| 708. | 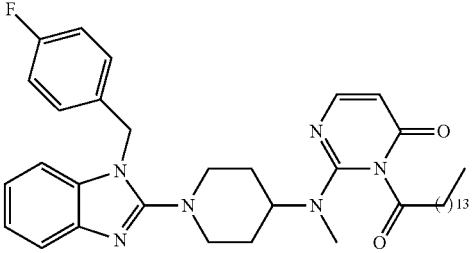 [SMILES: CCC(=O)n1c(N(C)C2CCN(c3nc4ccccc4n3Cc3ccc(F)cc3)CC2)nccc1=O] |
| 709. | 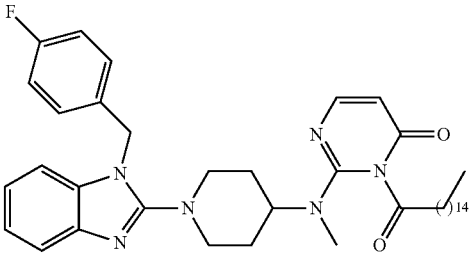 [SMILES: CCC(=O)n1c(N(C)C2CCN(c3nc4ccccc4n3Cc3ccc(F)cc3)CC2)nccc1=O] |
| 710. | 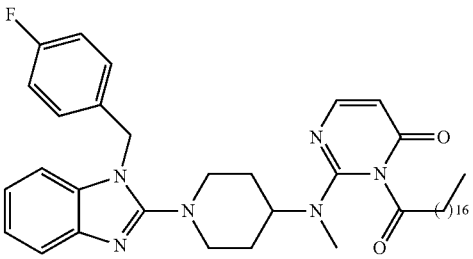 [SMILES: CCC(=O)n1c(N(C)C2CCN(c3nc4ccccc4n3Cc3ccc(F)cc3)CC2)nccc1=O] |
| 711. | 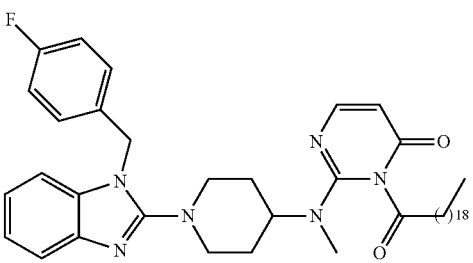 [SMILES: CCC(=O)n1c(N(C)C2CCN(c3nc4ccccc4n3Cc3ccc(F)cc3)CC2)nccc1=O] |

TABLE G-continued
| No. | Structure |
|---|---|
| 712. | 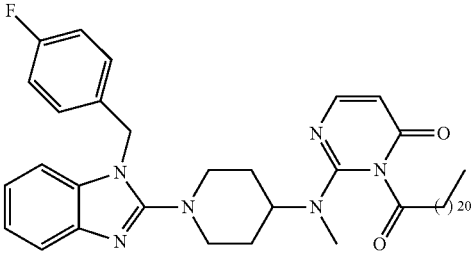 [SMILES: CCC(=O)n1c(N(C)C2CCN(c3nc4ccccc4n3Cc3ccc(F)cc3)CC2)nccc1=O] |
| 713. | 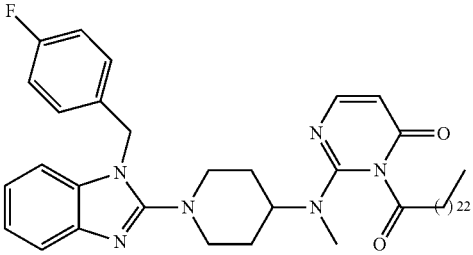 [SMILES: CCC(=O)n1c(N(C)C2CCN(c3nc4ccccc4n3Cc3ccc(F)cc3)CC2)nccc1=O] |
| 714. | 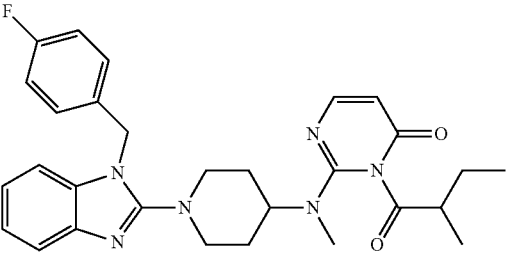 [SMILES: CCC(C)C(=O)n1c(N(C)C2CCN(c3nc4ccccc4n3Cc3ccc(F)cc3)CC2)nccc1=O] |
| 715. | 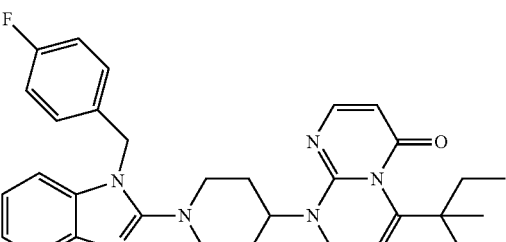 |
| 716. | 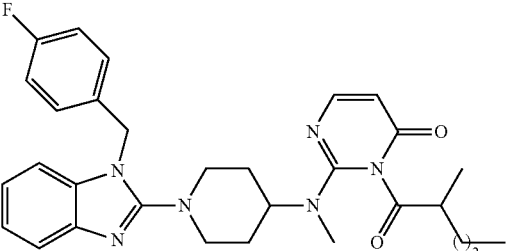 |

TABLE G-continued
| No. | Structure |
|---|---|
| 717. | 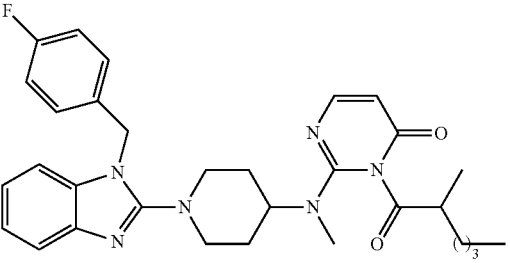 [SMILES: CCC(C)C(=O)n1c(N(C)C2CCN(c3nc4ccccc4n3Cc3ccc(F)cc3)CC2)nccc1=O] |
| 718. | 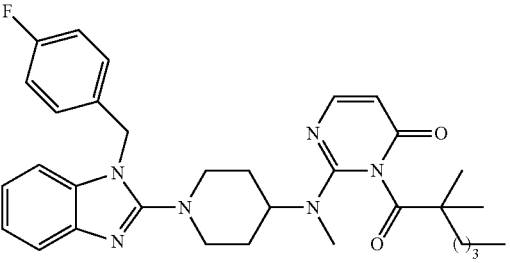 [SMILES: CCC(C)(C)C(=O)n1c(N(C)C2CCN(c3nc4ccccc4n3Cc3ccc(F)cc3)CC2)nccc1=O] |
| 719. | 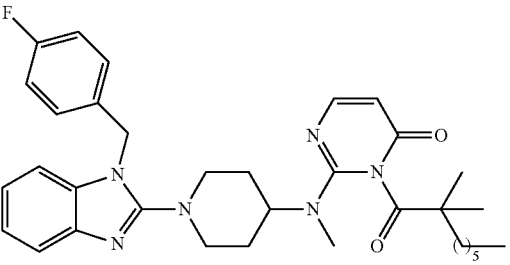 [SMILES: CCC(C)(C)C(=O)n1c(N(C)C2CCN(c3nc4ccccc4n3Cc3ccc(F)cc3)CC2)nccc1=O] |
| 720. | 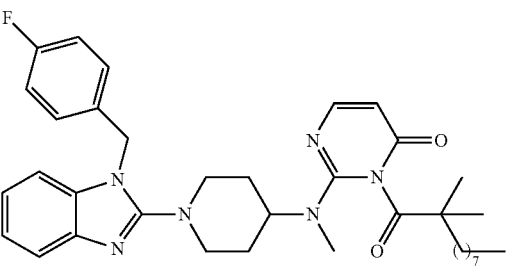 |
| 721. | 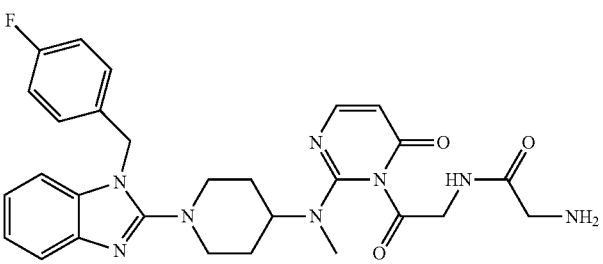 [SMILES: CN(c1nccc(=O)n1C(=O)CNC(=O)CN)C1CCN(c2nc3ccccc3n2Cc2ccc(F)cc2)CC1] |

TABLE G-continued

| No. | Structure |
|-----|-----------|
| 722. | 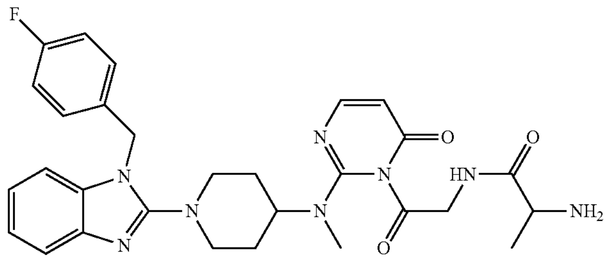 [SMILES: CC(N)C(=O)NCC(=O)n1c(N(C)C2CCN(c3nc4ccccc4n3Cc3ccc(F)cc3)CC2)nccc1=O] |
| 723. | 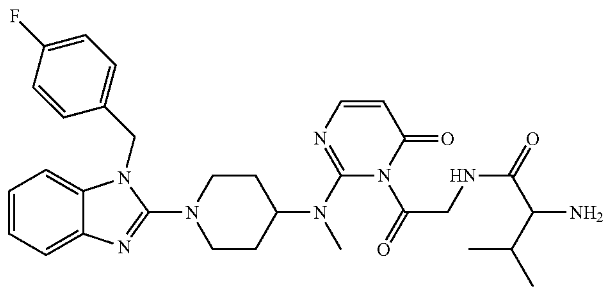 [SMILES: CC(C)C(N)C(=O)NCC(=O)n1c(N(C)C2CCN(c3nc4ccccc4n3Cc3ccc(F)cc3)CC2)nccc1=O] |
| 724. | 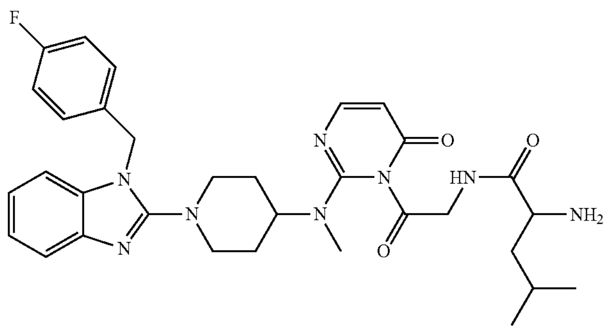 [SMILES: CC(C)CC(N)C(=O)NCC(=O)n1c(N(C)C2CCN(c3nc4ccccc4n3Cc3ccc(F)cc3)CC2)nccc1=O] |
| 725. | 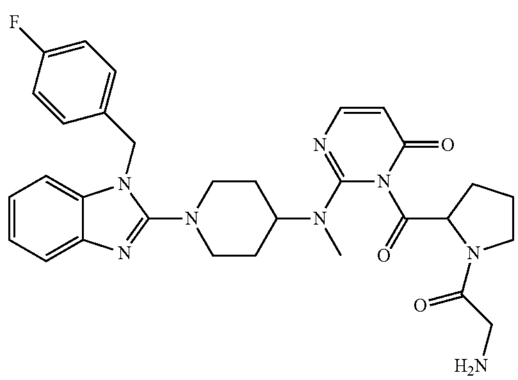 [SMILES: CN(c1nccc(=O)n1C(=O)C1CCCN1C(=O)CN)C1CCN(c2nc3ccccc3n2Cc2ccc(F)cc2)CC1] |
| 726. | 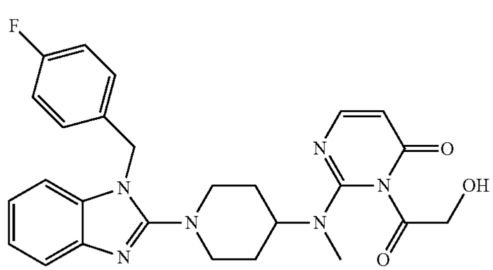 [SMILES: CN(c1nccc(=O)n1C(=O)CO)C1CCN(c2nc3ccccc3n2Cc2ccc(F)cc2)CC1] |

TABLE G-continued
| No. | Structure |
|---|---|
| 727. | 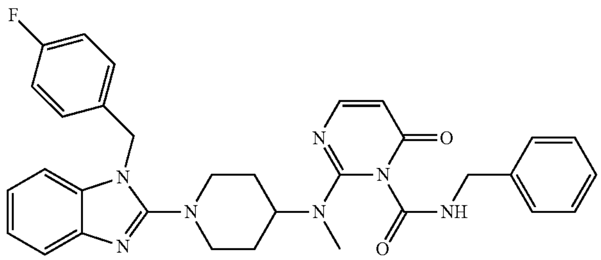 [SMILES: CN(c1nccc(=O)n1C(=O)NCc1ccccc1)C1CCN(c2nc3ccccc3n2Cc2ccc(F)cc2)CC1] |
| 728. | 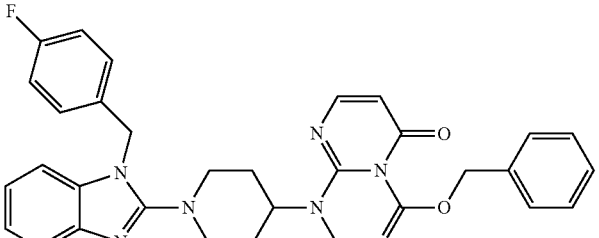 |
| 729. | 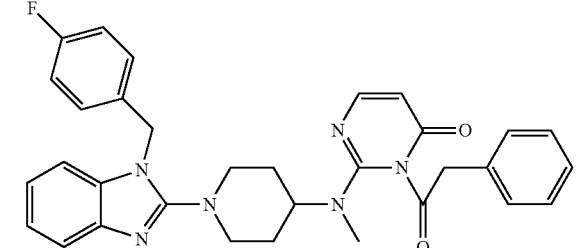 |
| 730. | 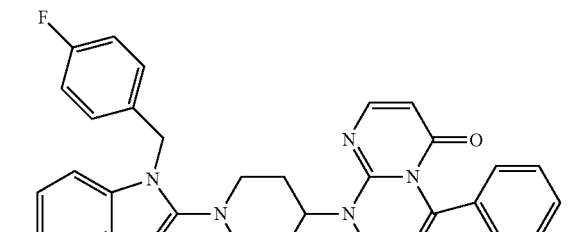 |
| 731. | 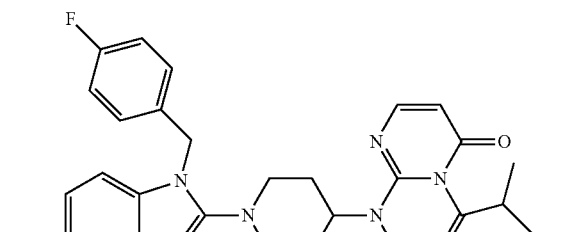 |
| 732. | 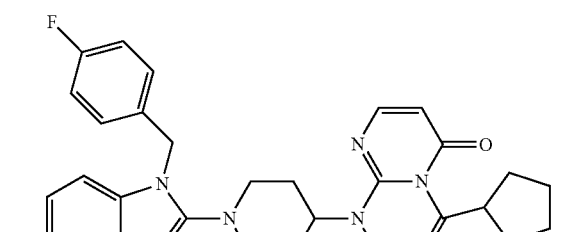 |

TABLE G-continued

| No. | Structure |
|---|---|
| 733. | 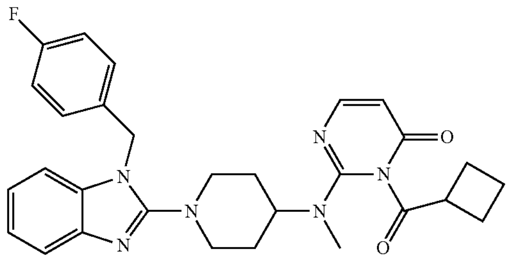 [SMILES: CN(c1nccc(=O)n1C(=O)C1CCC1)C1CCN(c2nc3ccccc3n2Cc2ccc(F)cc2)CC1] |
| 734. | 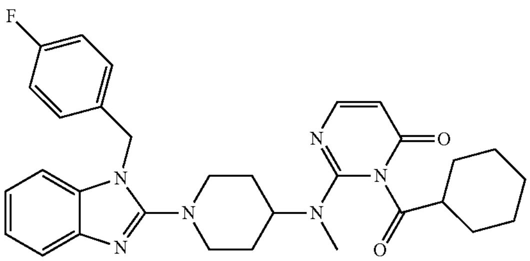 [SMILES: CN(c1nccc(=O)n1C(=O)C1CCCCC1)C1CCN(c2nc3ccccc3n2Cc2ccc(F)cc2)CC1] |
| 735. | 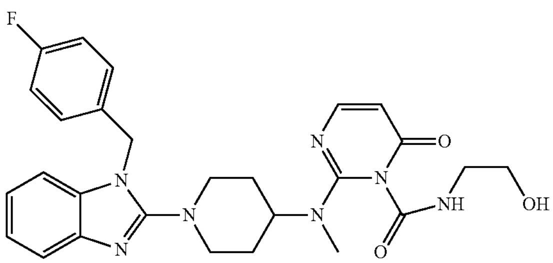 [SMILES: CN(c1nccc(=O)n1C(=O)NCCO)C1CCN(c2nc3ccccc3n2Cc2ccc(F)cc2)CC1] |
| 736. | 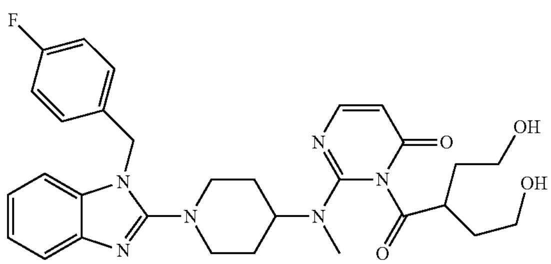 [SMILES: CN(c1nccc(=O)n1C(=O)C(CCO)CCO)C1CCN(c2nc3ccccc3n2Cc2ccc(F)cc2)CC1] |
| 737. | 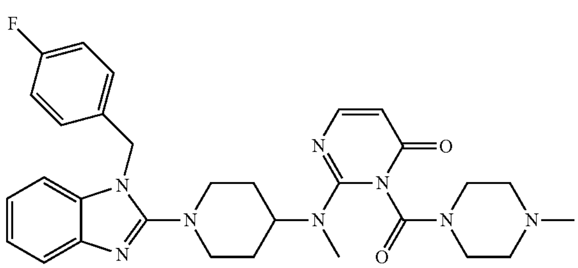 [SMILES: CN1CCN(C(=O)n2c(N(C)C3CCN(c4nc5ccccc5n4Cc4ccc(F)cc4)CC3)nccc2=O)CC1] |
| 738. | 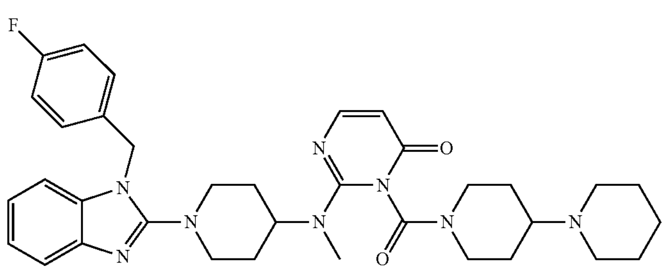 [SMILES: CN(c1nccc(=O)n1C(=O)N1CCC(N2CCCCC2)CC1)C1CCN(c2nc3ccccc3n2Cc2ccc(F)cc2)CC1] |

TABLE G-continued
| No. | Structure |
|---|---|
| 739. | 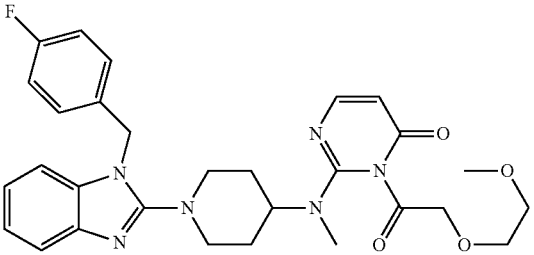 [SMILES: COCCOCC(=O)n1c(N(C)C2CCN(c3nc4ccccc4n3Cc3ccc(F)cc3)CC2)nccc1=O] |
| 740. | 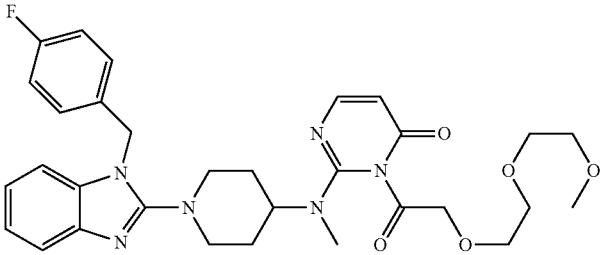 [SMILES: COCCOCCOCC(=O)n1c(N(C)C2CCN(c3nc4ccccc4n3Cc3ccc(F)cc3)CC2)nccc1=O] |
| 741. | 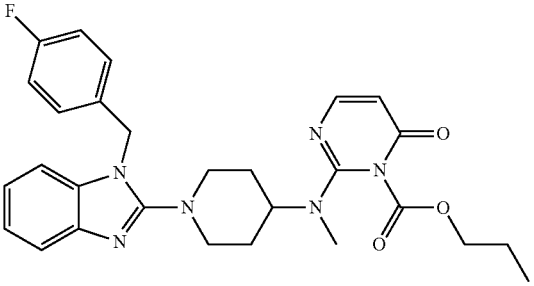 [SMILES: CCCOC(=O)n1c(N(C)C2CCN(c3nc4ccccc4n3Cc3ccc(F)cc3)CC2)nccc1=O] |
| 742. | 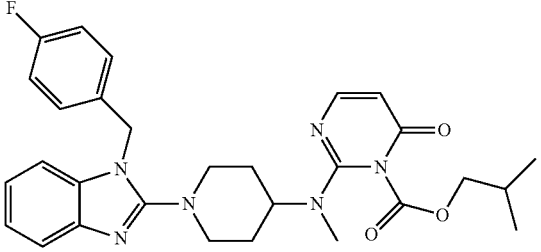 [SMILES: CC(C)COC(=O)n1c(N(C)C2CCN(c3nc4ccccc4n3Cc3ccc(F)cc3)CC2)nccc1=O] |
| 743. | 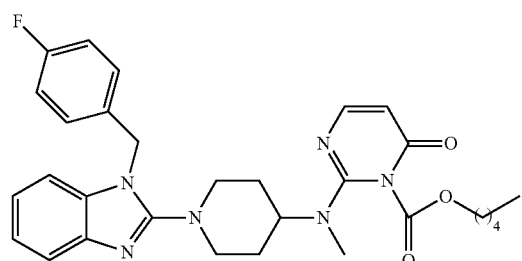 |

TABLE G-continued
| No. | Structure |
|---|---|
| 744. | 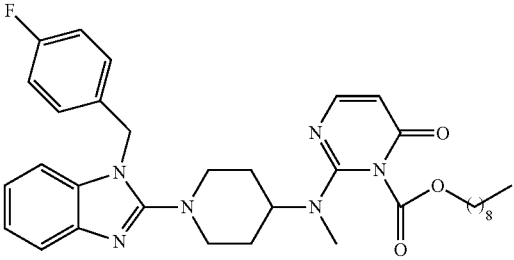 [SMILES: CCOC(=O)n1c(N(C)C2CCN(c3nc4ccccc4n3Cc3ccc(F)cc3)CC2)nccc1=O] |
| 745. | 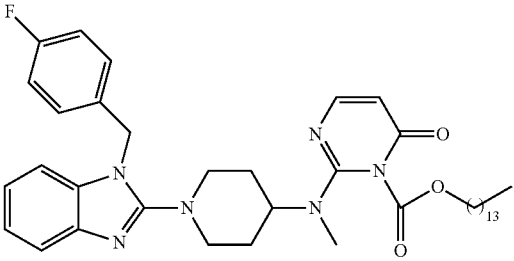 [SMILES: CCOC(=O)n1c(N(C)C2CCN(c3nc4ccccc4n3Cc3ccc(F)cc3)CC2)nccc1=O] |
| 746. | 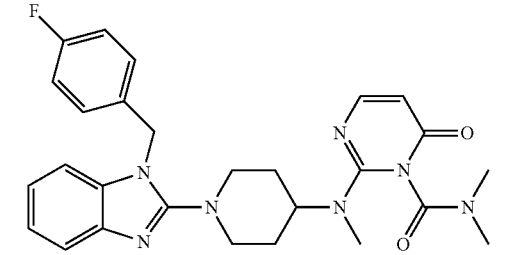 |
| 747. | 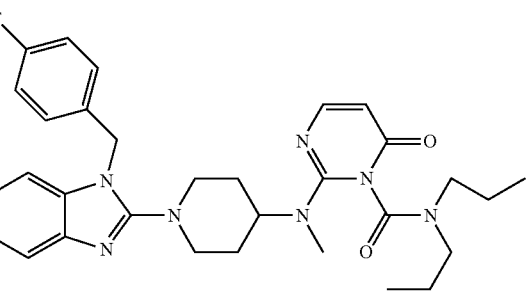 |
| 748. | 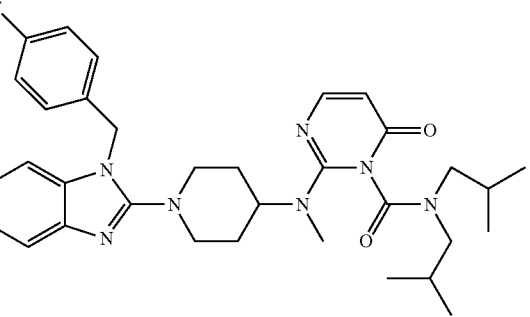 |

TABLE G-continued
| No. | Structure |
|---|---|
| 749. | 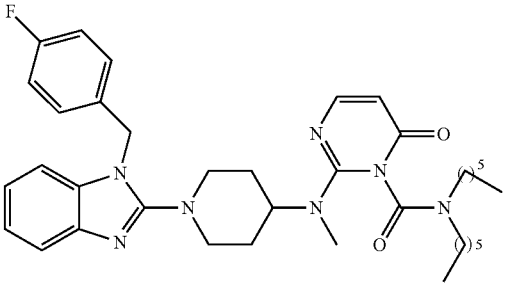 [SMILES: CCN(CC)C(=O)n1c(N(C)C2CCN(c3nc4ccccc4n3Cc3ccc(F)cc3)CC2)nccc1=O] |
| 750. | 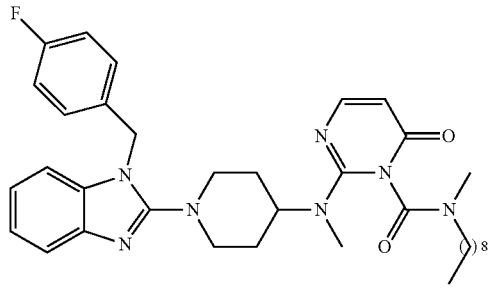 [SMILES: CCN(C)C(=O)n1c(N(C)C2CCN(c3nc4ccccc4n3Cc3ccc(F)cc3)CC2)nccc1=O] |
| 751. | 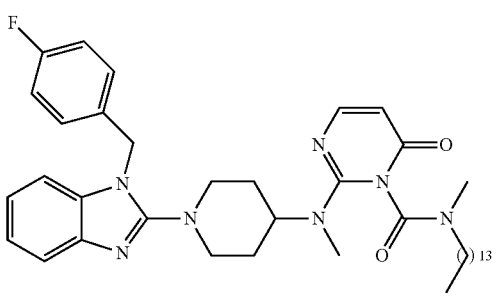 [SMILES: CCN(C)C(=O)n1c(N(C)C2CCN(c3nc4ccccc4n3Cc3ccc(F)cc3)CC2)nccc1=O] |
| 752. | 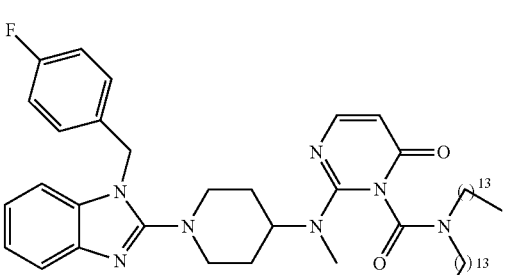 |
| 753. | 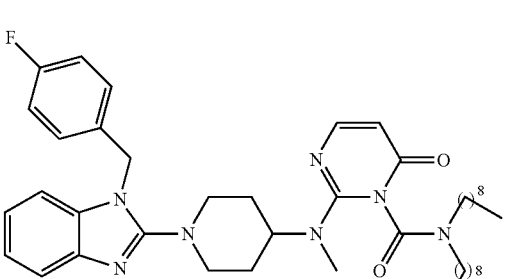 |

TABLE G-continued

| No. | Structure |
|-----|-----------|
| 754. | 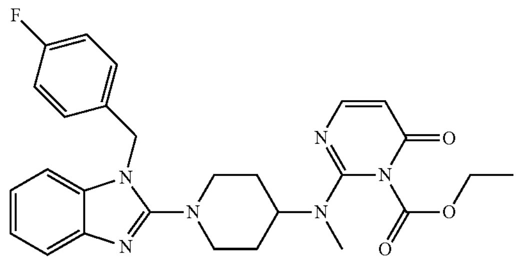 [SMILES: CCOC(=O)n1c(N(C)C2CCN(c3nc4ccccc4n3Cc3ccc(F)cc3)CC2)nccc1=O] |
| 755. | 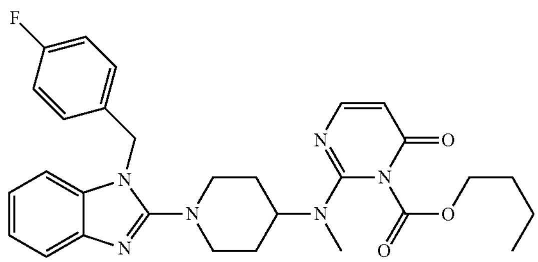 [SMILES: CCCCOC(=O)n1c(N(C)C2CCN(c3nc4ccccc4n3Cc3ccc(F)cc3)CC2)nccc1=O] |
| 756. | 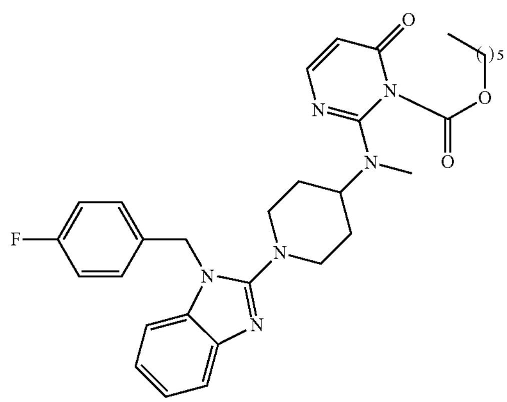 [SMILES: CCOC(=O)n1c(N(C)C2CCN(c3nc4ccccc4n3Cc3ccc(F)cc3)CC2)nccc1=O] |
| 757. | 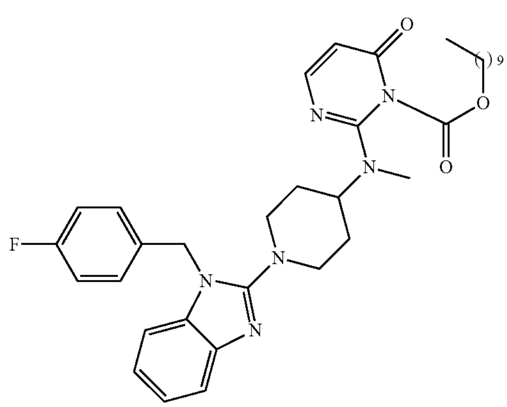 [SMILES: CCOC(=O)n1c(N(C)C2CCN(c3nc4ccccc4n3Cc3ccc(F)cc3)CC2)nccc1=O] |
| 758. | 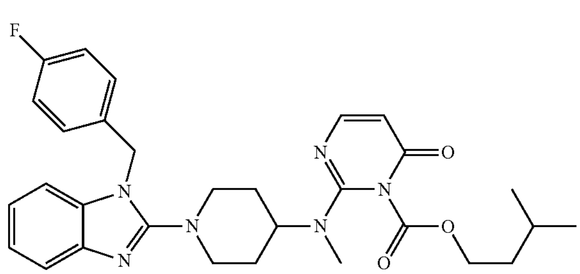 [SMILES: CC(C)CCOC(=O)n1c(N(C)C2CCN(c3nc4ccccc4n3Cc3ccc(F)cc3)CC2)nccc1=O] |

TABLE G-continued
| No. | Structure |
|---|---|
| 759. | 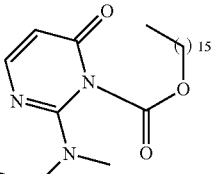 |
| 760. | 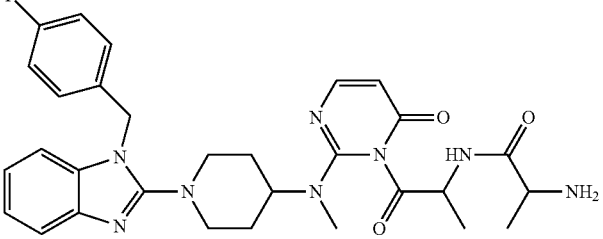 |
| 761. | 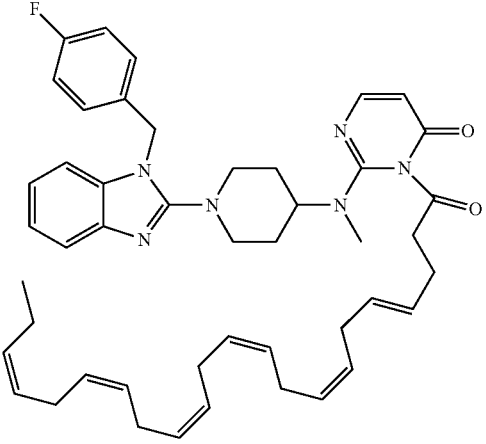 [SMILES: CC/C=C\C/C=C\C/C=C\C/C=C\C/C=C\C/C=C/CCC(=O)n1c(N(C)C2CCN(c3nc4ccccc4n3Cc3ccc(F)cc3)CC2)nccc1=O] |
| 762. | 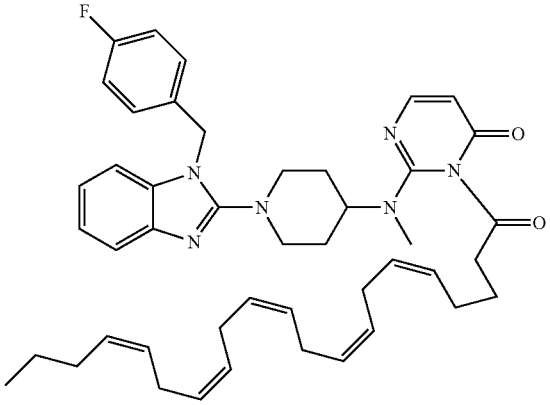 [SMILES: CCC/C=C\C/C=C\C/C=C\C/C=C\C/C=C\CCCC(=O)n1c(N(C)C2CCN(c3nc4ccccc4n3Cc3ccc(F)cc3)CC2)nccc1=O] |

TABLE G-continued
| No. | Structure |
|---|---|
| 763. | 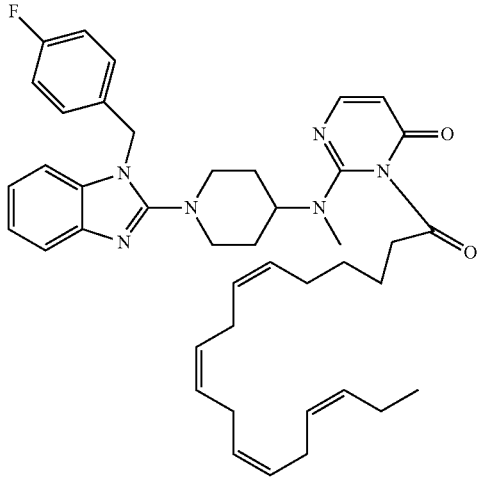 [SMILES: CC/C=C\C/C=C\C/C=C\C/C=C\CCCCC(=O)n1c(N(C)C2CCN(c3nc4ccccc4n3Cc3ccc(F)cc3)CC2)nccc1=O] |
| 764. | 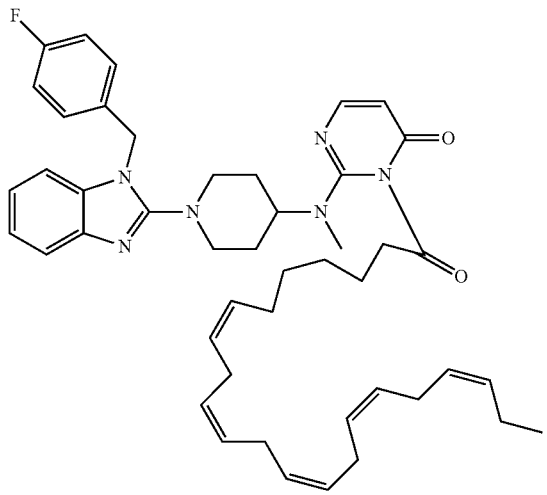 [SMILES: CC/C=C\C/C=C\C/C=C\C/C=C\C/C=C\CCCCCC(=O)n1c(N(C)C2CCN(c3nc4ccccc4n3Cc3ccc(F)cc3)CC2)nccc1=O] |
| 765. | 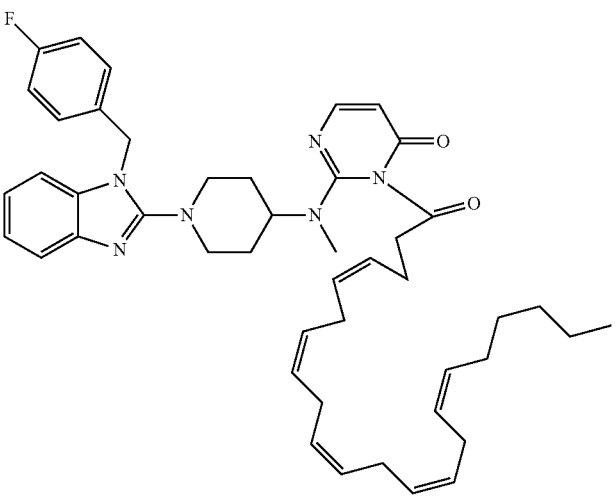 [SMILES: CCCCC/C=C\C/C=C\C/C=C\C/C=C\C/C=C\CCC(=O)n1c(N(C)C2CCN(c3nc4ccccc4n3Cc3ccc(F)cc3)CC2)nccc1=O] |

TABLE G-continued
| No. | Structure |
|---|---|
| 766. | 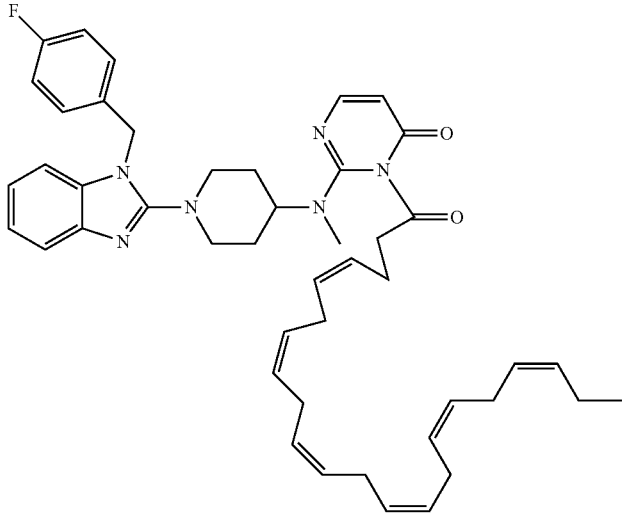 [SMILES: CC/C=C\C/C=C\C/C=C\C/C=C\C/C=C\C/C=C\CCC(=O)n1c(N(C)C2CCN(c3nc4ccccc4n3Cc3ccc(F)cc3)CC2)nccc1=O] |
| 767. | 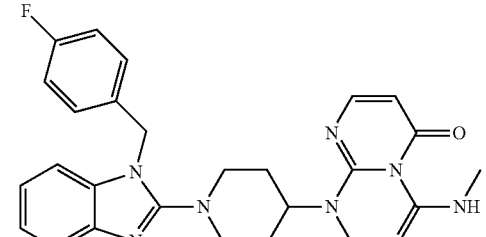 |
| 768. | 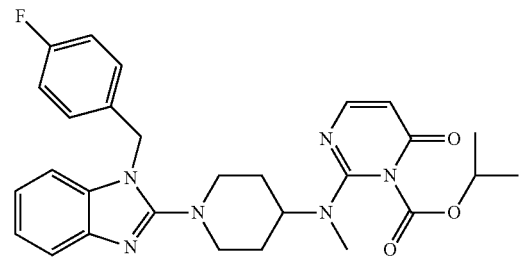 [SMILES: CC(C)OC(=O)n1c(N(C)C2CCN(c3nc4ccccc4n3Cc3ccc(F)cc3)CC2)nccc1=O] |
| 769. | 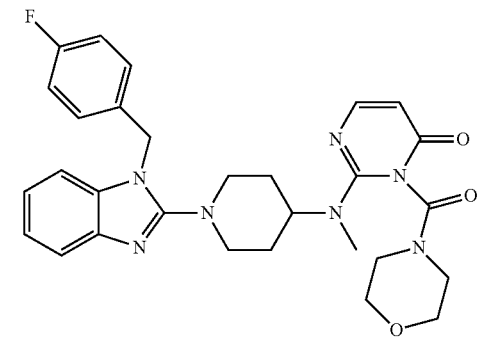 [SMILES: CN(c1nccc(=O)n1C(=O)N1CCOCC1)C1CCN(c2nc3ccccc3n2Cc2ccc(F)cc2)CC1] |

TABLE G-continued
| No. | Structure |
|---|---|
| 770. | 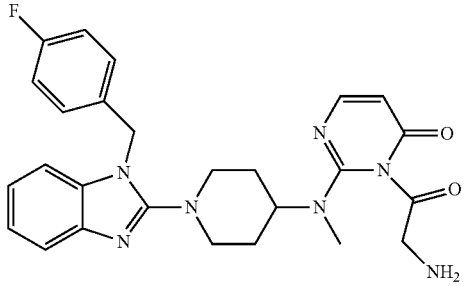 [SMILES: CN(c1nccc(=O)n1C(=O)CN)C1CCN(c2nc3ccccc3n2Cc2ccc(F)cc2)CC1] |
| 771. | 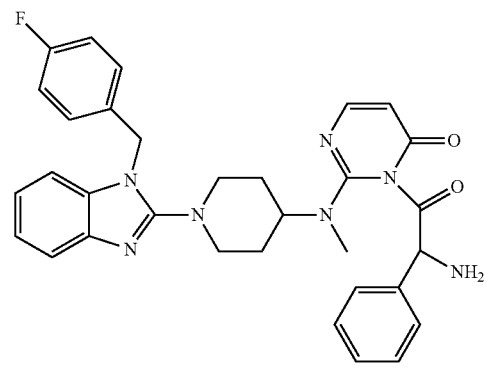 [SMILES: CN(c1nccc(=O)n1C(=O)C(N)c1ccccc1)C1CCN(c2nc3ccccc3n2Cc2ccc(F)cc2)CC1] |
| 772. | 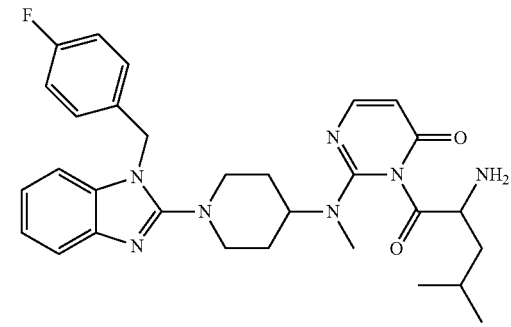 [SMILES: CC(C)CC(N)C(=O)n1c(N(C)C2CCN(c3nc4ccccc4n3Cc3ccc(F)cc3)CC2)nccc1=O] |
| 773. | 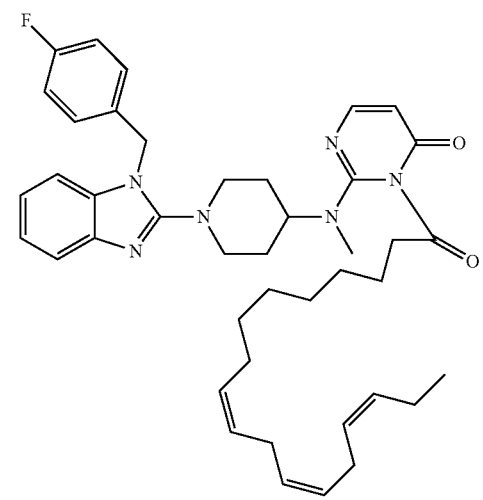 [SMILES: CC/C=C\C/C=C\C/C=C\CCCCCCCC(=O)n1c(N(C)C2CCN(c3nc4ccccc4n3Cc3ccc(F)cc3)CC2)nccc1=O] |

TABLE G-continued

| No. | Structure |
|---|---|
| 774. | 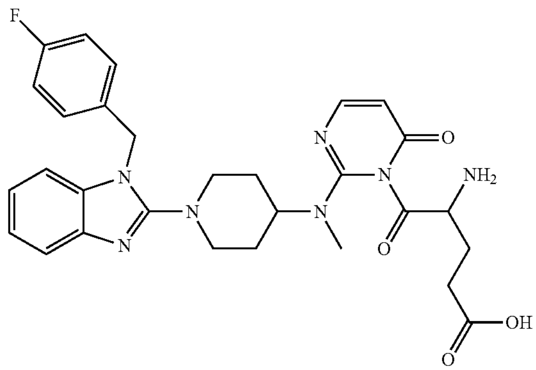 [SMILES: CN(c1nccc(=O)n1C(=O)C(N)CCC(=O)O)C1CCN(c2nc3ccccc3n2Cc2ccc(F)cc2)CC1] |
| 775. | 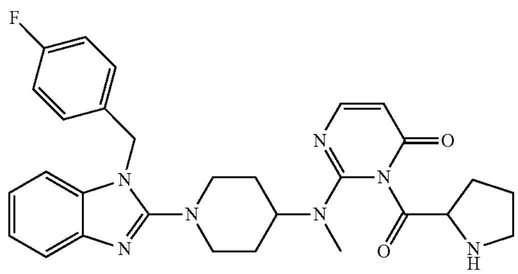 [SMILES: CN(c1nccc(=O)n1C(=O)C1CCCN1)C1CCN(c2nc3ccccc3n2Cc2ccc(F)cc2)CC1] |
| 776. | 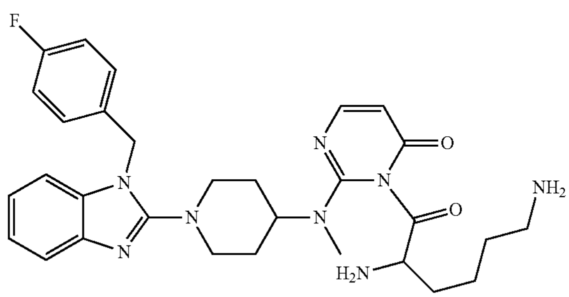 [SMILES: CN(c1nccc(=O)n1C(=O)C(N)CCCCN)C1CCN(c2nc3ccccc3n2Cc2ccc(F)cc2)CC1] |
| 777. | 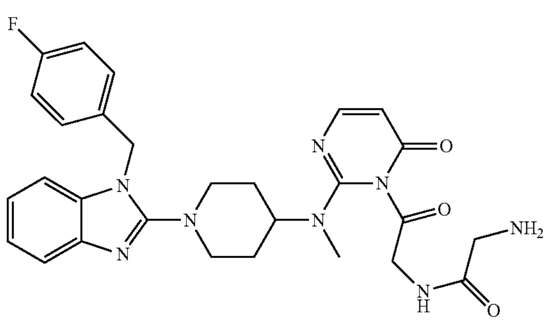 [SMILES: CN(c1nccc(=O)n1C(=O)CNC(=O)CN)C1CCN(c2nc3ccccc3n2Cc2ccc(F)cc2)CC1] |
| 778. | 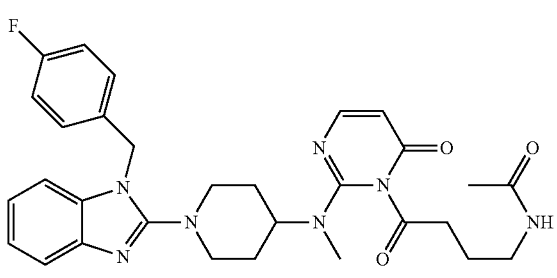 [SMILES: CC(=O)NCCCC(=O)n1c(N(C)C2CCN(c3nc4ccccc4n3Cc3ccc(F)cc3)CC2)nccc1=O] |

TABLE G-continued

| No. | Structure |
|---|---|
| 779. | 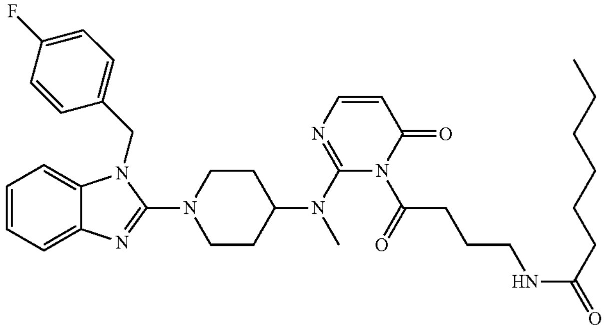 [SMILES: CCCCCCC(=O)NCCCC(=O)n1c(N(C)C2CCN(c3nc4ccccc4n3Cc3ccc(F)cc3)CC2)nccc1=O] |
| 780. | 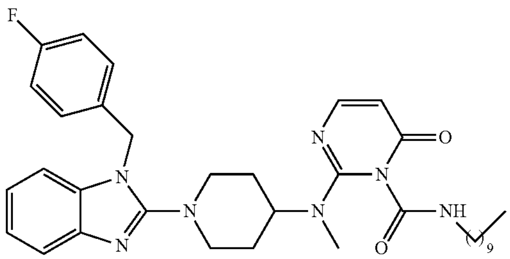 [SMILES: CCNC(=O)n1c(N(C)C2CCN(c3nc4ccccc4n3Cc3ccc(F)cc3)CC2)nccc1=O] |
| 781. | 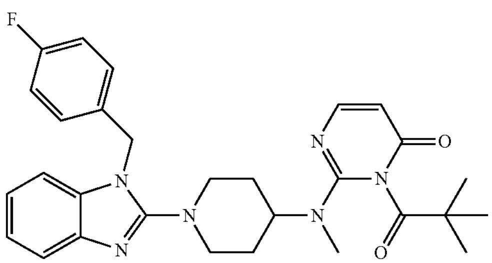 [SMILES: CN(c1nccc(=O)n1C(=O)C(C)(C)C)C1CCN(c2nc3ccccc3n2Cc2ccc(F)cc2)CC1] |

Compounds of Formula IX, X, XI, XII and in particular compounds of Tables A-E are useful for the treatment of neurological and psychiatric disorders including schizophrenia, mania, anxiety and bipolar disease. These compounds provide sustained release of parent pharmacophores by cleavage of the labile moiety, $R_1$.

In another embodiment, compounds of the present invention are represented by Formula XIII or XIV as illustrated below, or its geometric isomers, enantiomers, diastereomers, racemates, pharmaceutically acceptable salts and solvates thereof:

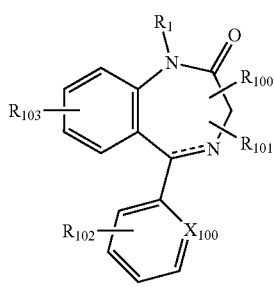

Formula XIII

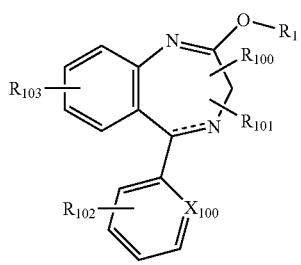

Formula XIV wherein $R_{100}$, $R_{101}$, $R_{102}$, and $R_{103}$ are independently selected from absent, hydrogen, halogen, —$OR_{10}$, —$SR_{10}$, —$NR_{10}R_{11}$—, optionally substituted aliphatic, optionally substituted aryl or aryl or optionally substituted heterocyclyl;

alternatively, two $R_{100}$, and $R_{101}$ together form an optionally substituted ring; and $X_{100}$ is —CH— or —N—.

A preferred embodiment is a compound selected from Table XIII-XIV. A more preferred embodiment is a compound from Table XIII-XIV wherein $R_1$ is selected from tables 1-4.

TABLE XIII-XIV
1 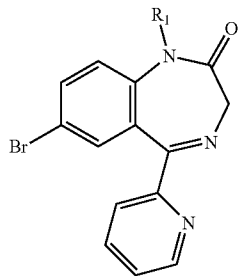
2 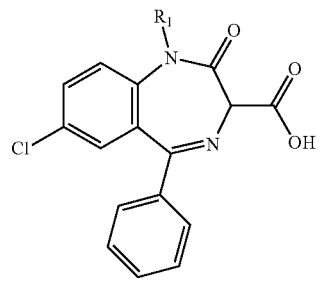
3 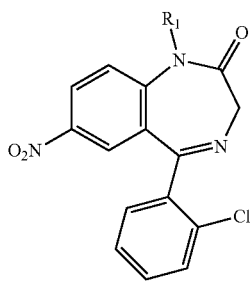
4 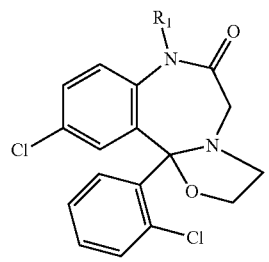
5 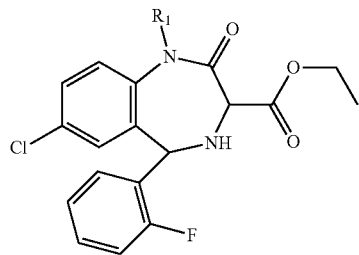
6 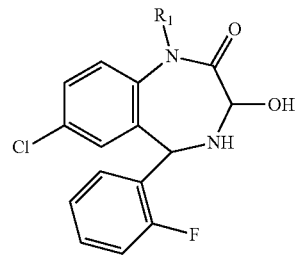
TABLE XIII-XIV-continued
7 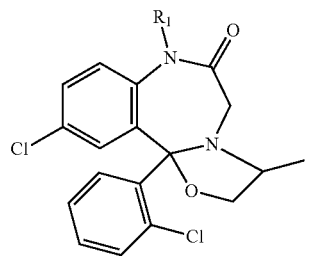
8 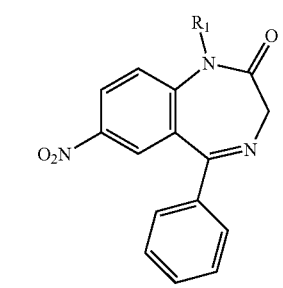
9 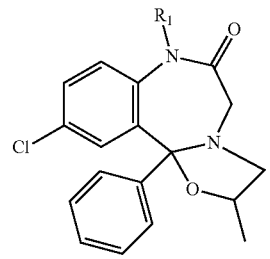
10 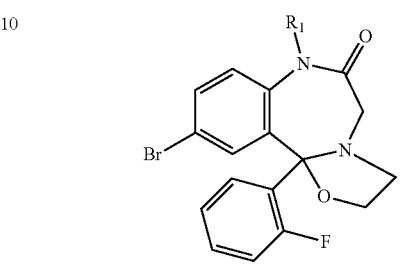
11 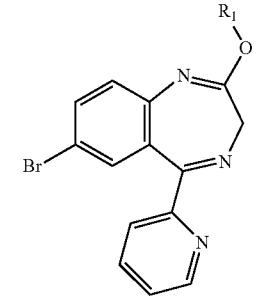

TABLE XIII-XIV-continued
12
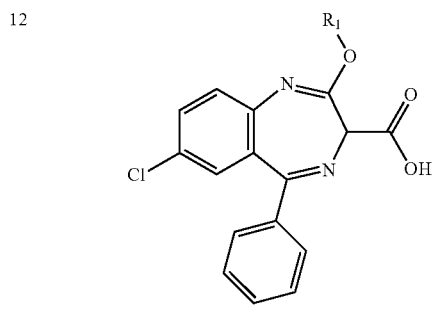
13
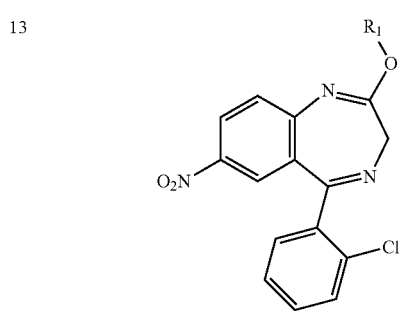
14
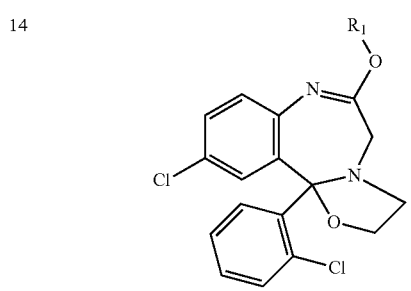
15
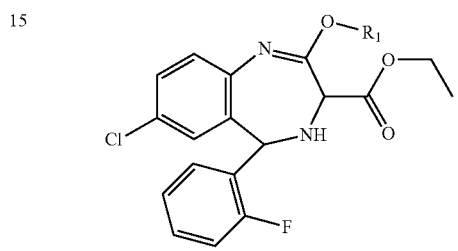
16
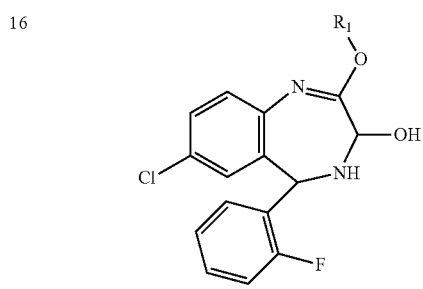
TABLE XIII-XIV-continued
17
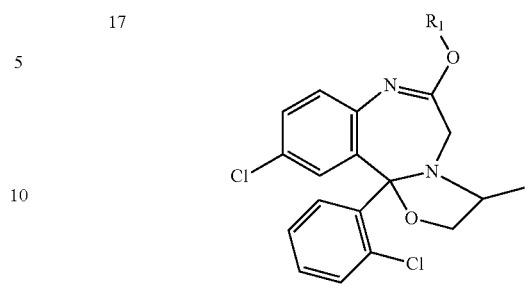
18
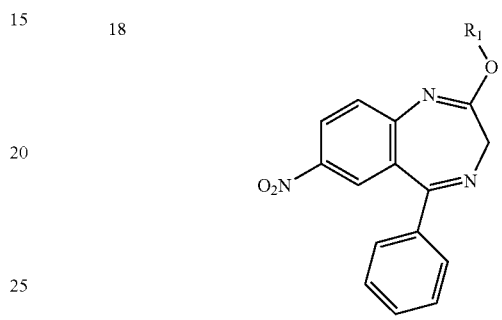
19
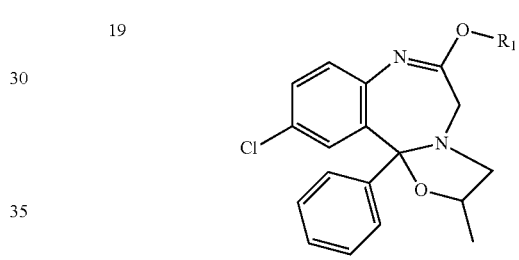
20
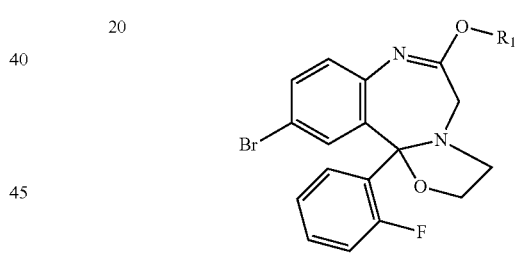
Prodrugs of Acylanilines
In another embodiment, compounds of the present invention are represented by Formula XV or XVI as illustrated below, or its geometric isomers, enantiomers, diastereomers, racemates, pharmaceutically acceptable salts and solvates thereof:
Formula XV
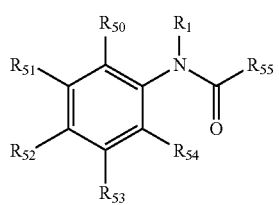

-continued

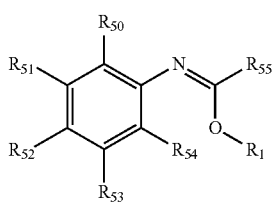

wherein $R_1$ is as defined above;

Formula XVI each $R_{50}$, $R_{51}$, $R_{52}$, $R_{53}$, $R_{54}$ and $R_{55}$ is independently selected from hydrogen, halogen, —$OR_{10}$, —$SR_{10}$, —$NR_{10}R_{11}$—, optionally substituted aliphatic, optionally substituted aryl or aryl or optionally substituted heterocyclyl;

alternatively, two or more $R_{50}$, $R_{51}$, $R_{52}$, $R_{53}$, $R_{54}$ and $R_{55}$ together form an optionally substituted ring.

A preferred embodiment is a compound selected from Table XV-XVI. A more preferred embodiment is a compound from Table XV-XVI wherein $R_1$ is selected from Tables 1-4.

TABLE XV-XVI

1 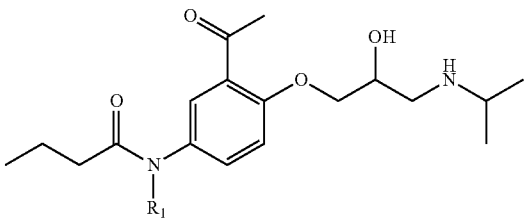

2 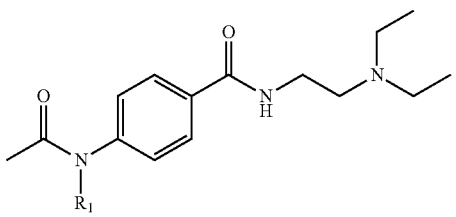

3 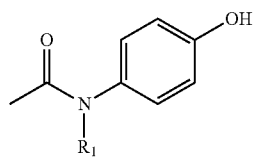

4 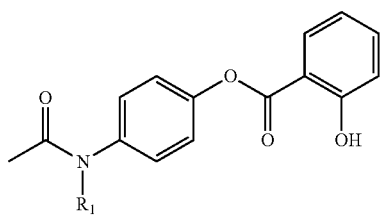

5 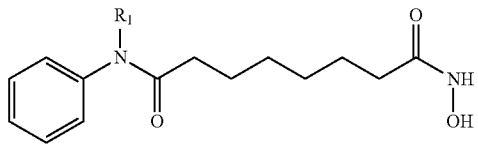

6 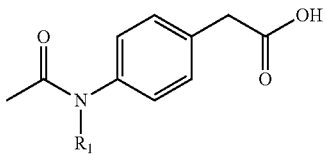

7 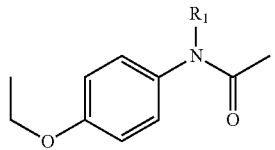

TABLE XV-XVI-continued
8 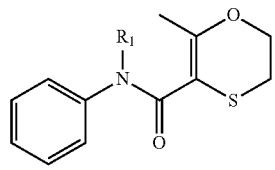
9 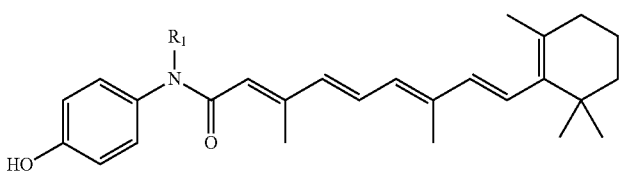
10 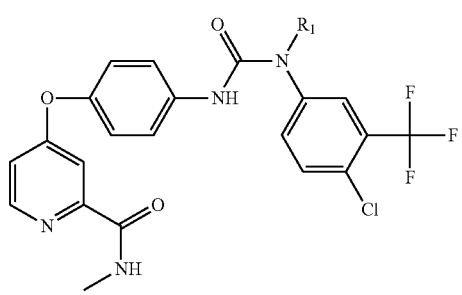
11 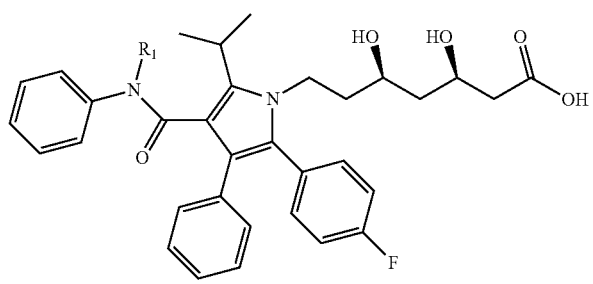
12 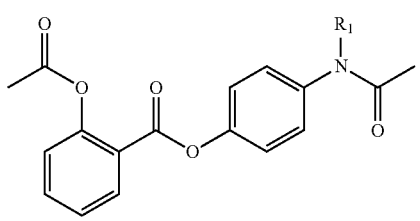
13 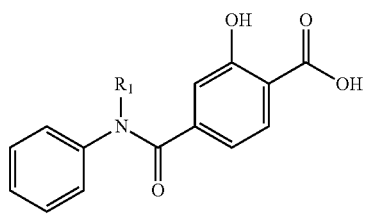
14 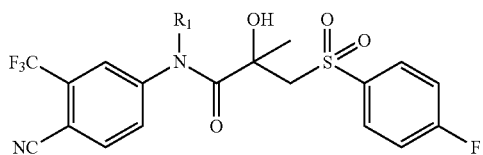

TABLE XV-XVI-continued
15 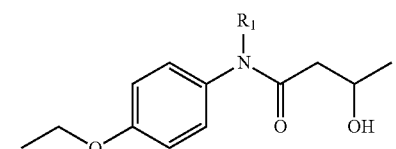
16 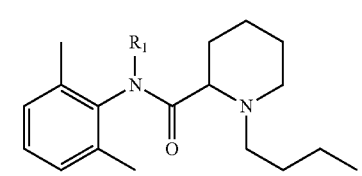
17 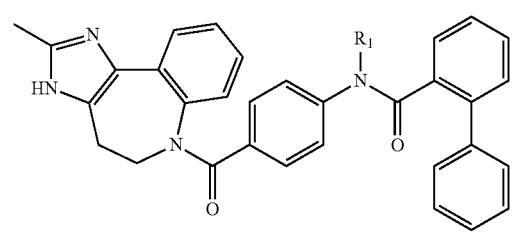
18 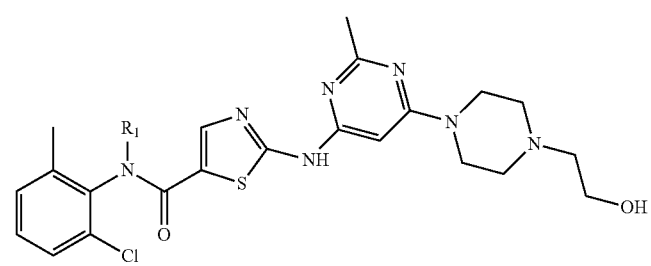
19 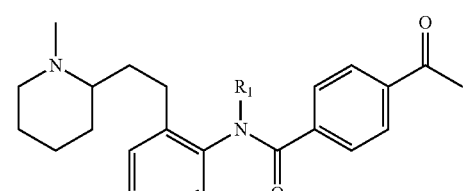
20 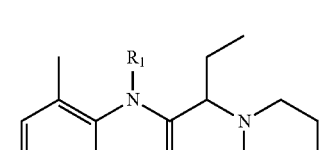
21 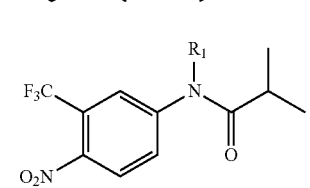
22

TABLE XV-XVI-continued
23 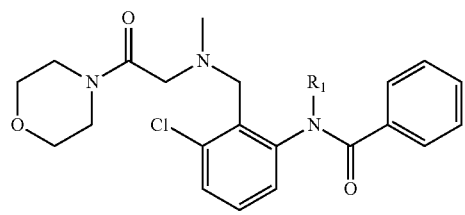
24 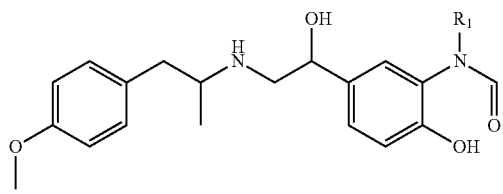
25 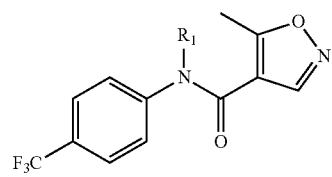
26 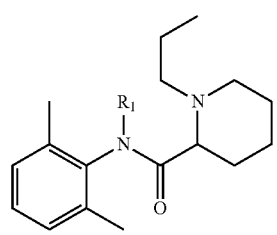
27 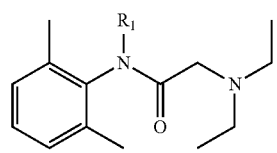
28 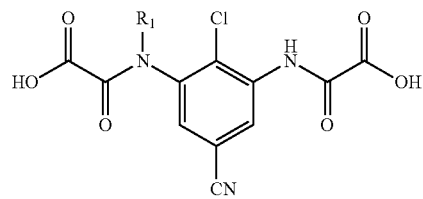
29 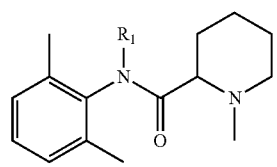

TABLE XV-XVI-continued
30
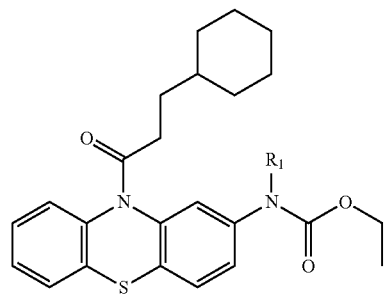
31
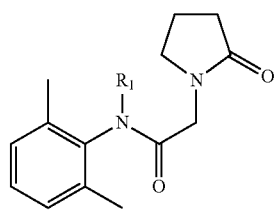
32
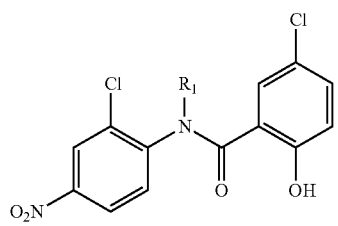
33
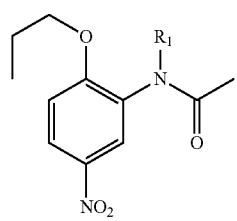
34
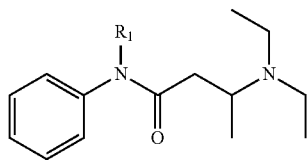
35
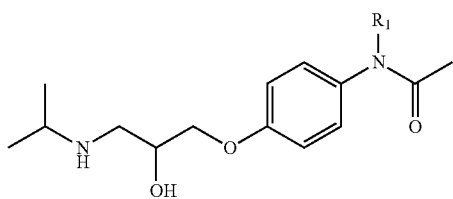
36
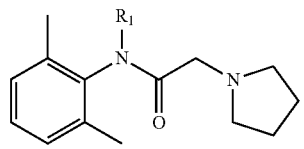

TABLE XV-XVI-continued
| 37 | 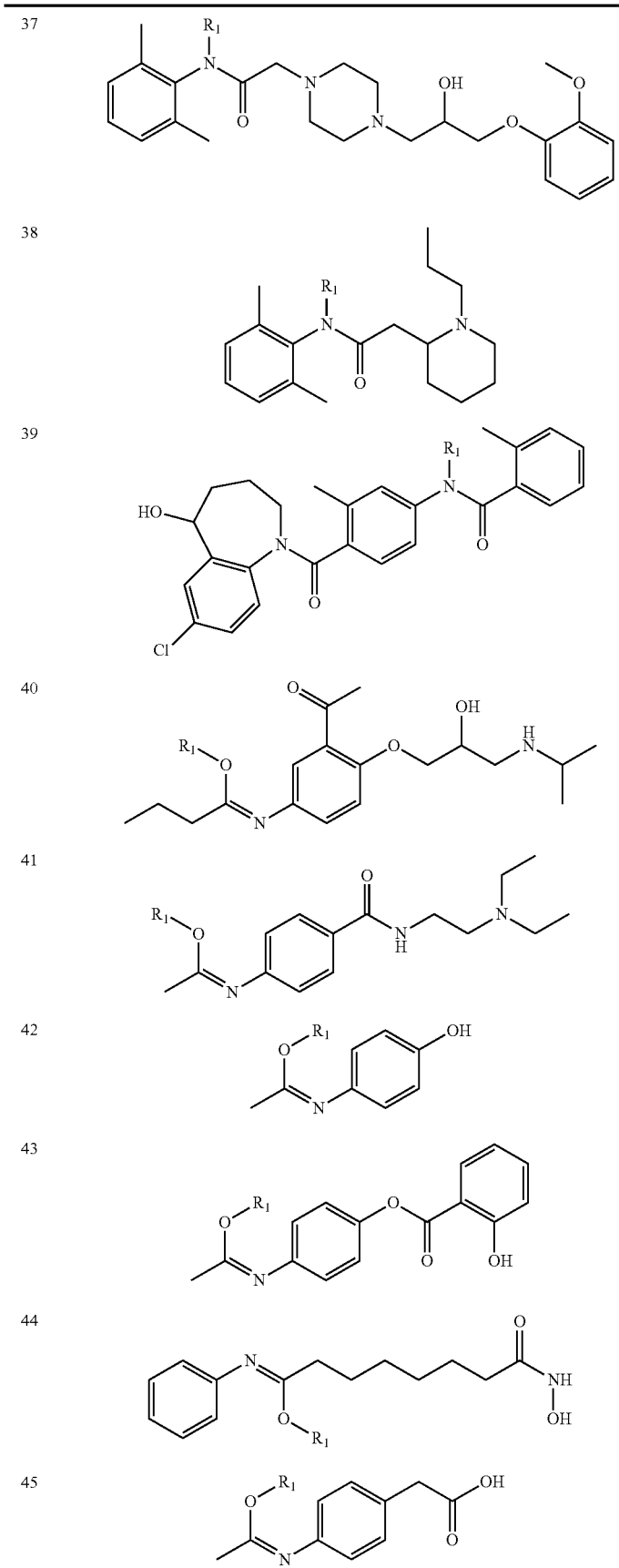 |
| --- | --- |
| 38 | |
| 39 | |
| 40 | |
| 41 | |
| 42 | |
| 43 | |
| 44 | |
| 45 | |

TABLE XV-XVI-continued
46 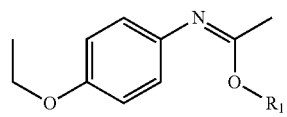
47 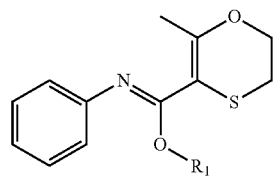
48 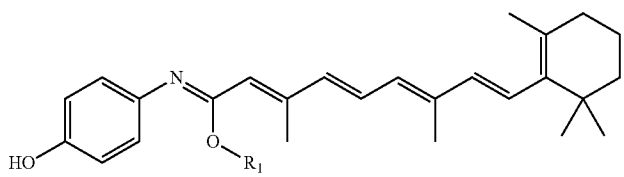
49 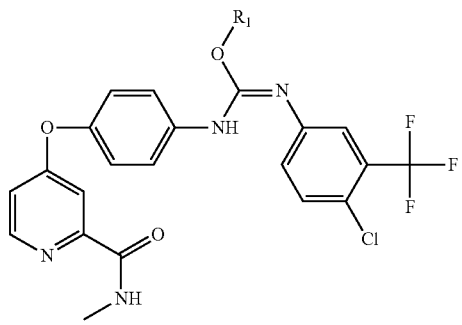
50 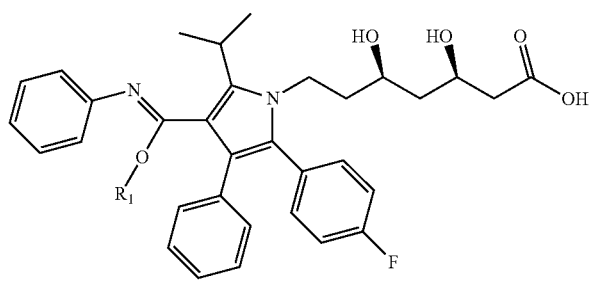
51 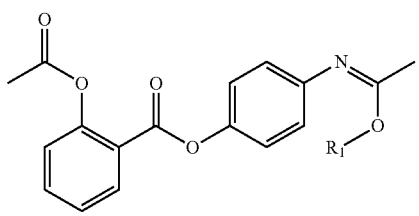
52 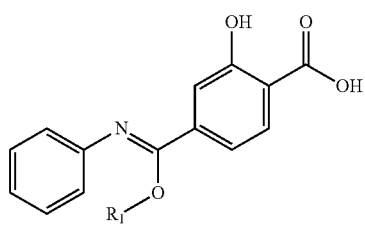

TABLE XV-XVI-continued
53 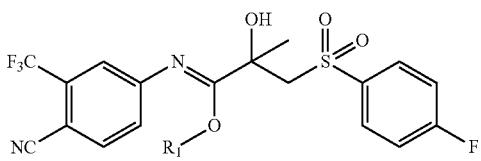
54 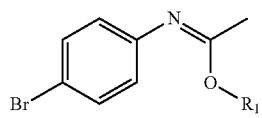
55 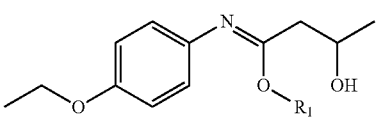
56 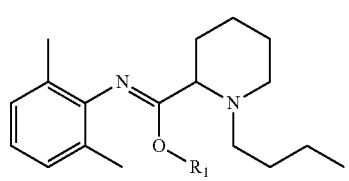
57 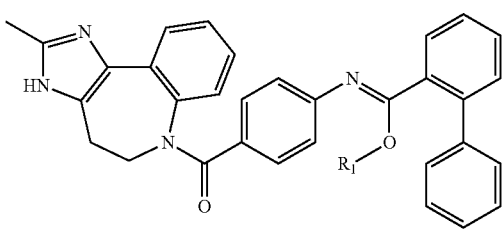
58 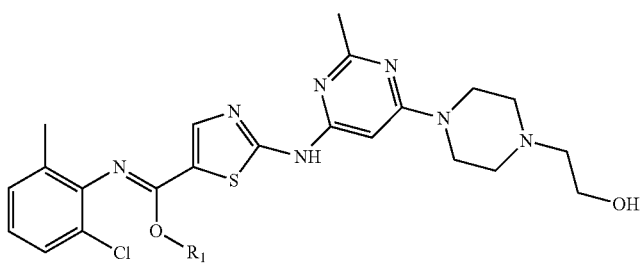
59 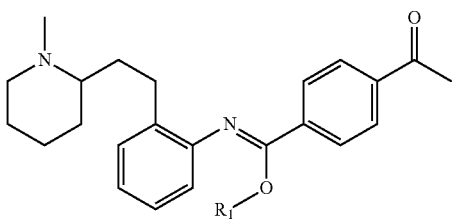
60 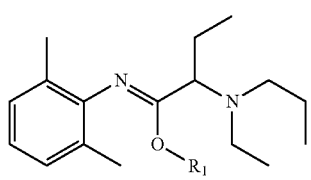

TABLE XV-XVI-continued
| | |
|---|---|
| 61 | 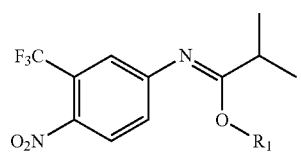 |
| 62 | 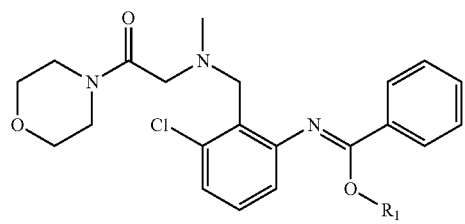 |
| 63 | 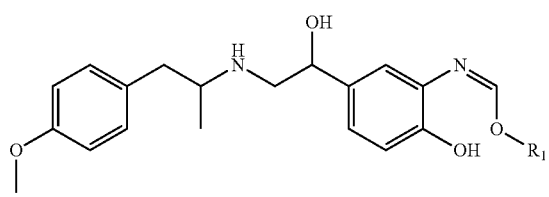 |
| 64 | 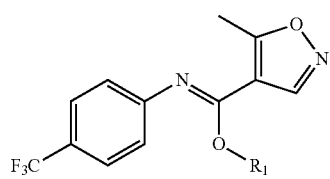 |
| 65 | 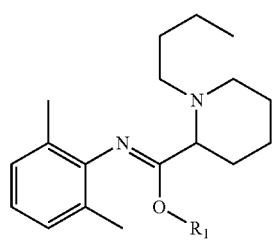 |
| 66 | 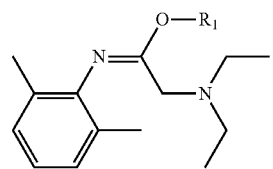 |
| 67 | 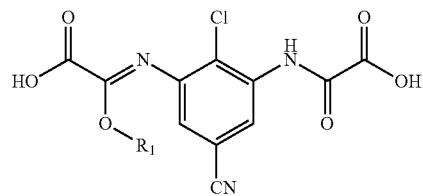 |
| 68 | 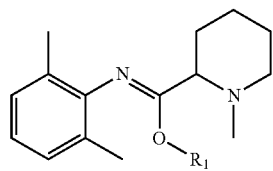 |

TABLE XV-XVI-continued
69 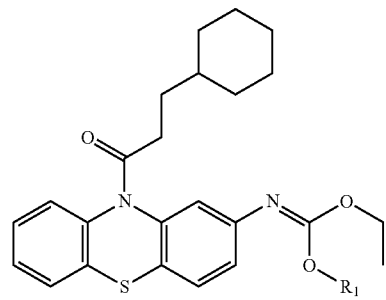
70 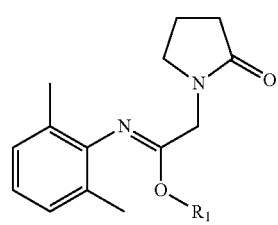
71 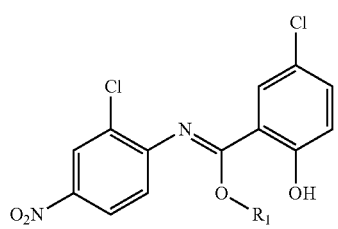
72 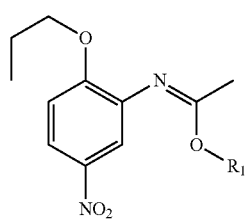
73 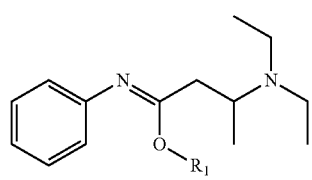
74 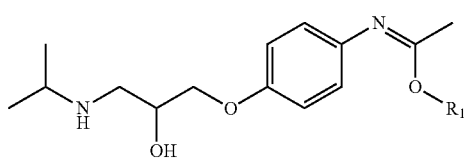
75 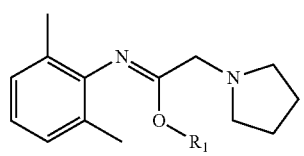

TABLE XV-XVI-continued

76

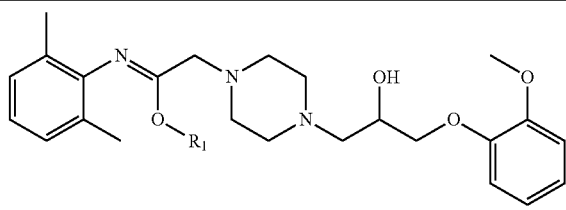

77

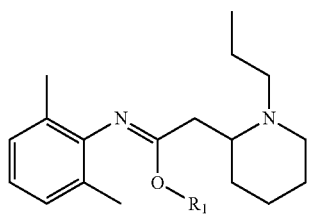

78

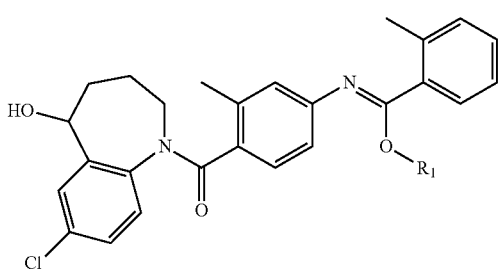

Thiazolidinones

In another embodiment, compounds of the present invention are represented by Formula XVII, XVIII or XIX as illustrated below, or its geometric isomers, enantiomers, diastereomers, racemates, pharmaceutically acceptable salts and solvates thereof:

Formula XVII

Formula XVIII

Formula XIX wherein $F_1$ and $R_1$ are as defined above.

A preferred embodiment is a compound of Formula XX, XXI or XXII as illustrated below, or its geometric isomers, enantiomers, diastereomers, racemates, pharmaceutically acceptable salts and solvates thereof:

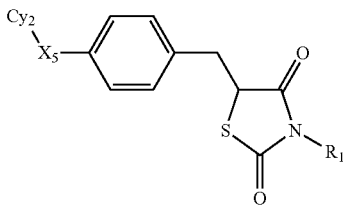

Formula XX

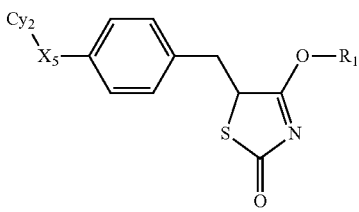

Formula XXI

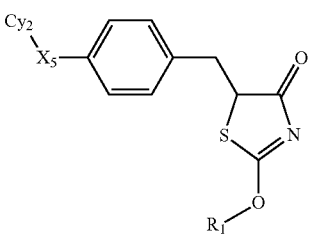

Formula XXII wherein $R_1$ is as defined above;

$Cy_2$ is an optionally substituted heterocyclic ring; and $X_5$ is selected from absent, —S—, —O—, —S(O)—, —S(O)$_2$—, —N($R_{10}$)—, —C(O)—, —C(O$R_{10}$)($R_{11}$)—, —[C $(R_{10})(R_{11})]_v$—, —O[C$(R_{10})(R_{11})]_v$—, —O[C$(R_{10})(R_{11})]_v$O—, —S[C$(R_{10})(R_{11})]_v$O—, —NR$_{12}$[C$(R_{10})(R_{11})]_v$O—, —NR$_{12}$[C$(R_{10})(R_{11})]_v$S—, —S[C$(R_{10})(R_{11})]_v$—, —C(O)[C$(R_{10})(R_{11})]_v$—, and —C$(R_{10})(R_{11})$=C$(R_{10})(R_{11})$—;
wherein v is 0, 1, 2, 3, 4, 5, 6, 7, 8, 9 or 10.

A preferred embodiment is a compound of Formula XXIV as illustrated below, or its geometric isomers, enantiomers, diastereomers, racemates, pharmaceutically acceptable salts and solvates thereof:

Formula XXIV

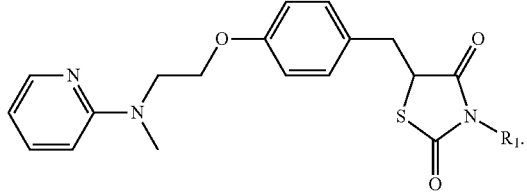

In a more preferred embodiment of Formula XXIV, $R_1$ is selected from Tables 1-4.

A preferred embodiment is a compound of Formula XXV as illustrated below, or its geometric isomers, enantiomers, diastereomers, racemates, pharmaceutically acceptable salts and solvates thereof:

Formula XXV

In a more preferred embodiment of Formula XXV, $R_1$ is selected from Tables 1-4.

A preferred embodiment is a compound of Formula XXVI as illustrated below, or its geometric isomers, enantiomers, diastereomers, racemates, pharmaceutically acceptable salts and solvates thereof:

Formula XXVI

In a more preferred embodiment of Formula XXVI, $R_1$ is selected from Tables 1-4.

A preferred embodiment is a compound of Formula XXVII as illustrated below, or its geometric isomers, enantiomers, diastereomers, racemates, pharmaceutically acceptable salts and solvates thereof:

Formula XXVII

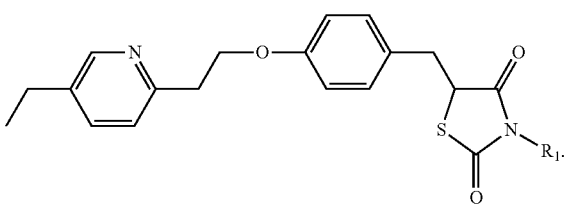

In a more preferred embodiment of Formula XXVII, $R_1$ is selected from Tables 1-4.

A preferred embodiment is a compound of Formula XXVIII as illustrated below, or its geometric isomers, enantiomers, diastereomers, racemates, pharmaceutically acceptable salts and solvates thereof:

Formula XXVIII

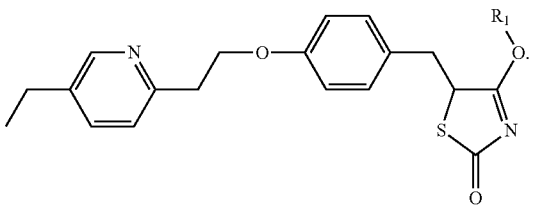

In a more preferred embodiment of Formula)(XVIII, $R_1$ is selected from tables 1-4.

A preferred embodiment is a compound of Formula XXIX as illustrated below, or its geometric isomers, enantiomers, diastereomers, racemates, pharmaceutically acceptable salts and solvates thereof:

Formula XXIX

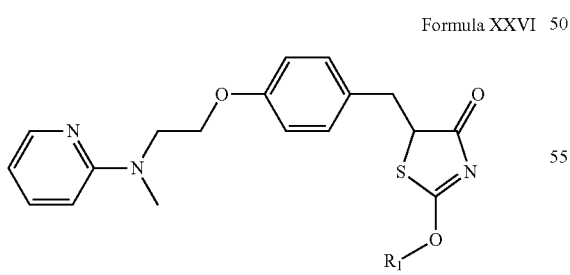

In a more preferred embodiment of Formula XXIX, $R_1$ is selected from tables 1-4.

A preferred embodiment is a compound of Formula XXX as illustrated below, or its geometric isomers, diastereomers, racemates, pharmaceutically acceptable salts and solvates thereof:

Formula XXX

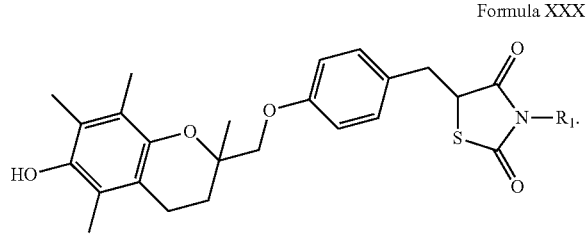

In a more preferred embodiment of Formula XXX, R₁ is selected from Table 1.

A preferred embodiment is a compound of Formula XXXI as illustrated below, or its geometric isomers, enantiomers, diastereomers, racemates, pharmaceutically acceptable salts and solvates thereof:

Formula XXXI

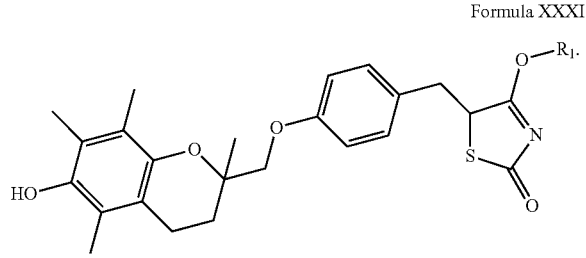

In a more preferred embodiment of Formula XXXI, R₁ is selected from Table 1.

A preferred embodiment is a compound of Formula XXXII as illustrated below, or its geometric isomers, enantiomers, diastereomers, racemates, pharmaceutically acceptable salts and solvates thereof:

Formula XXXII

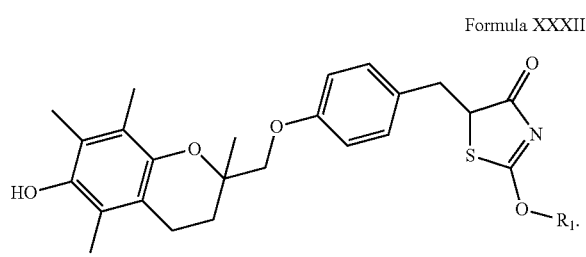

In a more preferred embodiment of Formula XXXII, R₁ is selected from Table 1.

In a preferred embodiment a compound of Formula XX-XXII is selected from table XX-XXII below, wherein R₁ is as described above. A more preferred embodiment is a compound of table XX-XXII wherein R₁ is selected from Tables 1-4.

TABLE XX-XXII

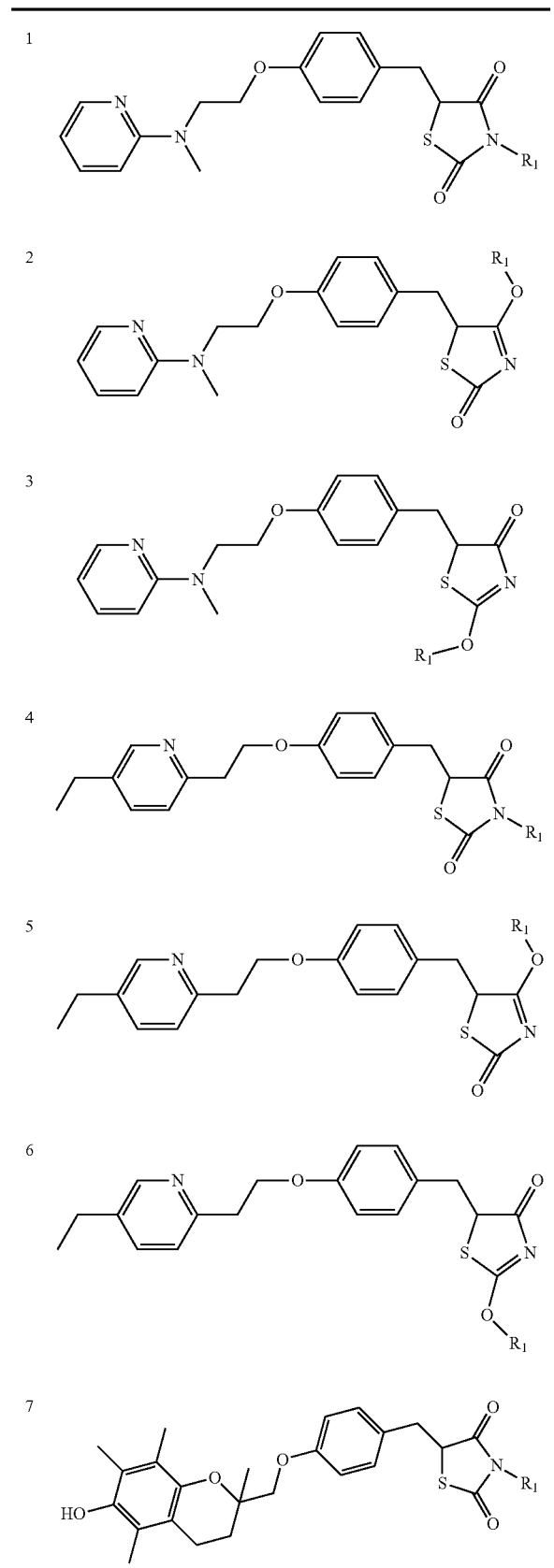

TABLE XX-XXII-continued
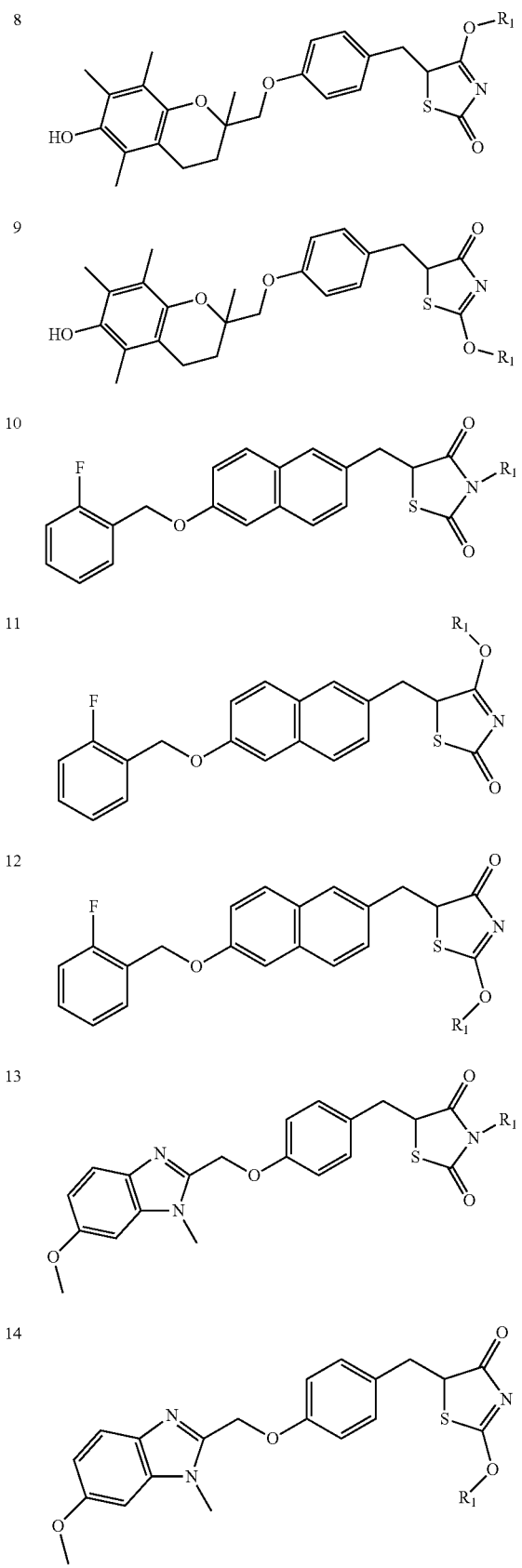
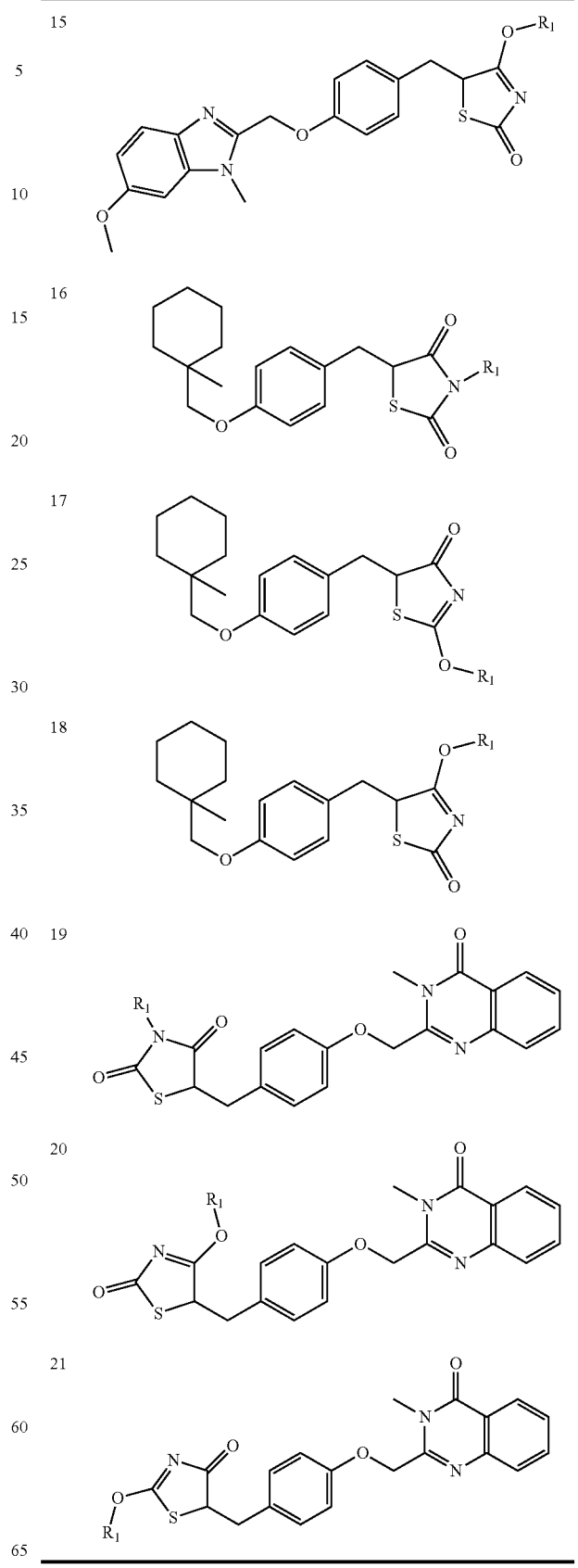

Thiazolidinedione prodrugs of Formula XVII to XXXII are useful for the treatment of type 2 diabetes mellitus. Herein provided is a method of treating type 2 diabetes mellitus by the administration of a prodrug of Formula XVII to XXXII, in particular a compound of table XX-XXII above wherein the prodrug provides sustained release of the parent drug. The parent drug results from the cleavage of the labile $R_1$ moiety.

In some embodiments, a compound of Formula XXVII is selected from table H:

TABLE H

| No. | Structure |
|---|---|
| 1000. | 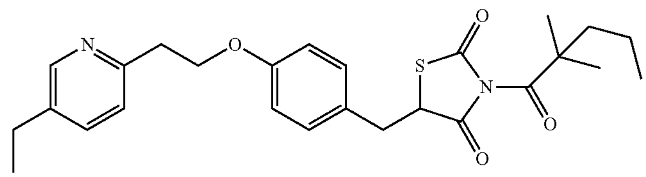 [SMILES: CCCC(C)(C)C(=O)N1C(=O)SC(Cc2ccc(OCCc3ccc(CC)cn3)cc2)C1=O] |
| 1001. | 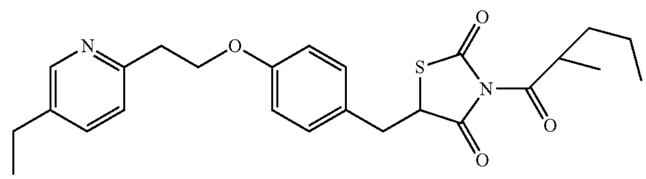 [SMILES: CCCC(C)C(=O)N1C(=O)SC(Cc2ccc(OCCc3ccc(CC)cn3)cc2)C1=O] |
| 1002. | 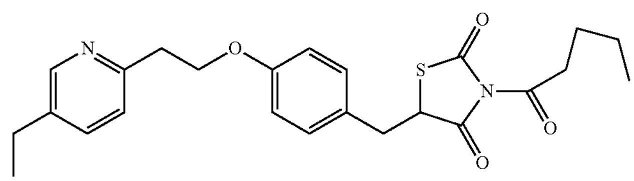 [SMILES: CCCCC(=O)N1C(=O)SC(Cc2ccc(OCCc3ccc(CC)cn3)cc2)C1=O] |
| 1003. | 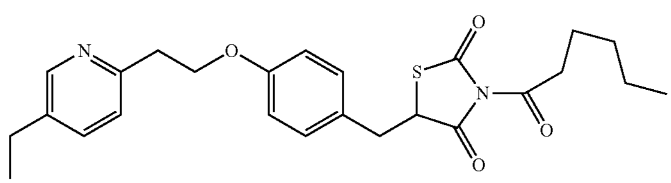 [SMILES: CCCCCC(=O)N1C(=O)SC(Cc2ccc(OCCc3ccc(CC)cn3)cc2)C1=O] |
| 1004. | 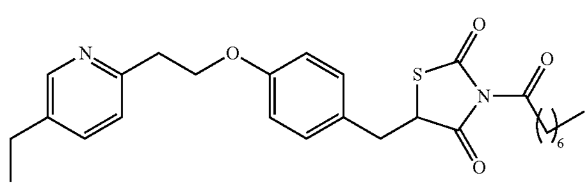 |
| 1005. | 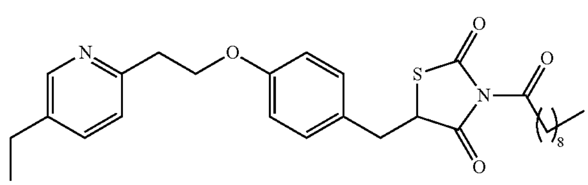 |
| 1006. | 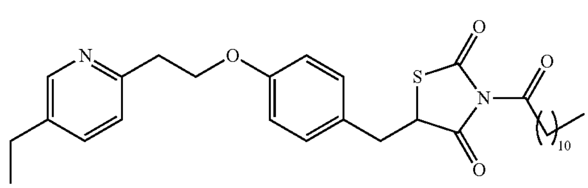 |
| 1007. | 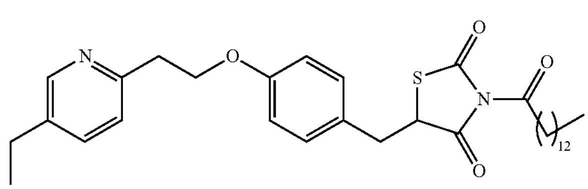 |

TABLE H-continued
| No. | Structure |
|---|---|
| 1008. | 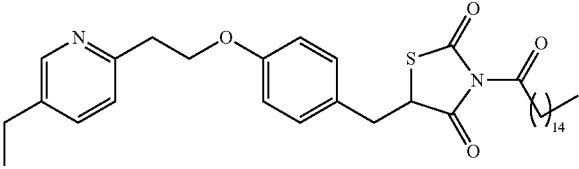 |
| 1009. | 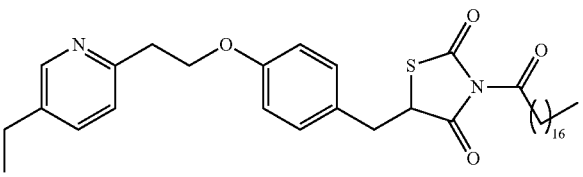 |
| 1010. | 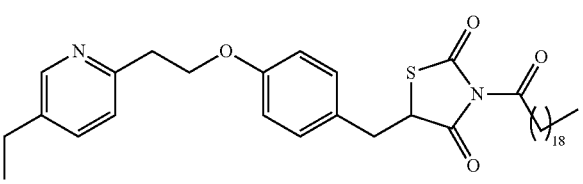 |
| 1011. | 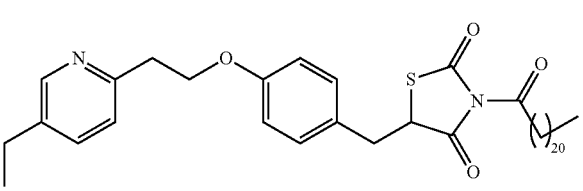 |
| 1012. | 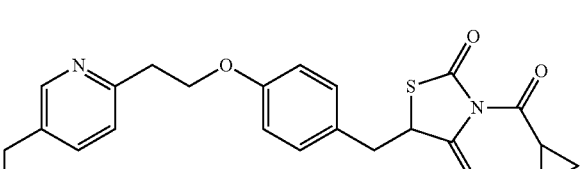 |
| 1013. | 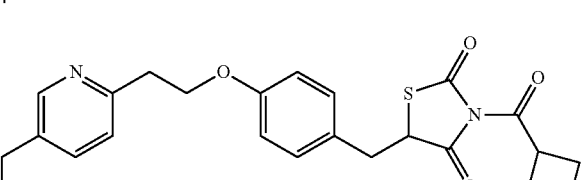 |
| 1014. | 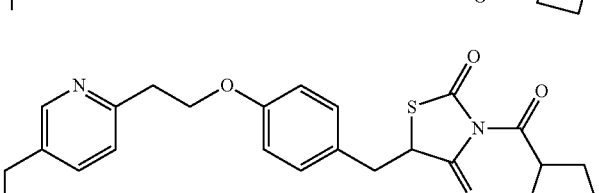 |
| 1015. | 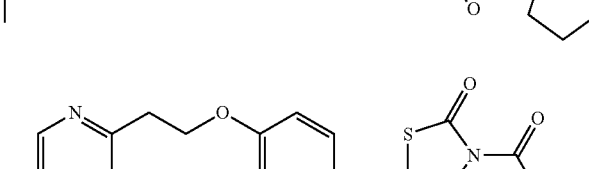 |

TABLE H-continued
| No. | Structure |
|---|---|
| 1016. | 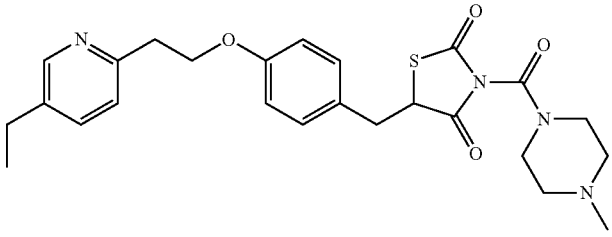 [SMILES: CCc1ccc(CCOc2ccc(CC3SC(=O)N(C(=O)N4CCN(C)CC4)C3=O)cc2)nc1] |
| 1017. | 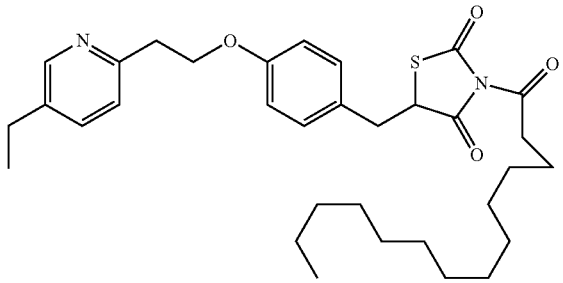 [SMILES: CCCCCCCCCCCCCC(=O)N1C(=O)SC(Cc2ccc(OCCc3ccc(CC)cn3)cc2)C1=O] |
| 1018. | 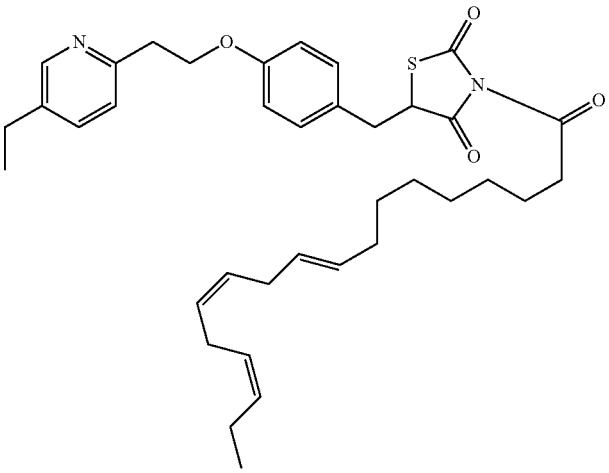 [SMILES: CC/C=C\C/C=C\C/C=C/CCCCCCCC(=O)N1C(=O)SC(Cc2ccc(OCCc3ccc(CC)cn3)cc2)C1=O] |
| 1019. | 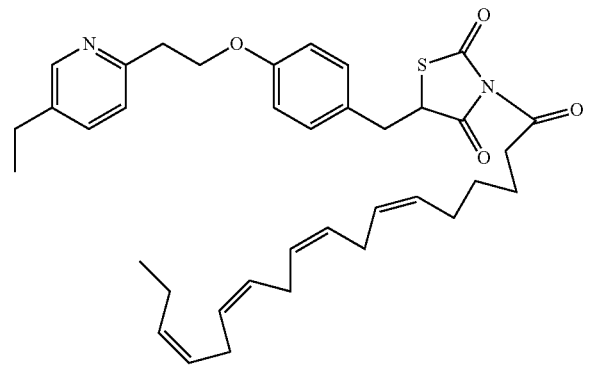 [SMILES: CC/C=C\C/C=C\C/C=C\C/C=C\CCCCC(=O)N1C(=O)SC(Cc2ccc(OCCc3ccc(CC)cn3)cc2)C1=O] |
| 1020. | 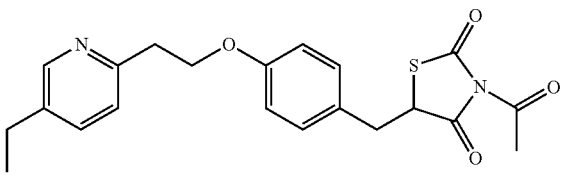 [SMILES: CCc1ccc(CCOc2ccc(CC3SC(=O)N(C(C)=O)C3=O)cc2)nc1] |

TABLE H-continued
| No. | Structure |
|---|---|
| 1021. | 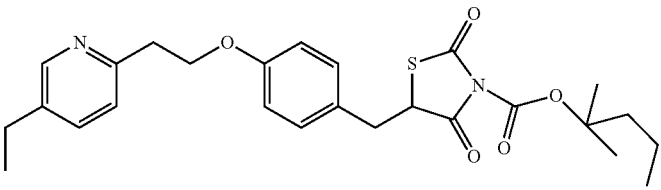 [SMILES: CCCC(C)(C)OC(=O)N1C(=O)SC(Cc2ccc(OCCc3ccc(CC)cn3)cc2)C1=O] |
| 1022. | 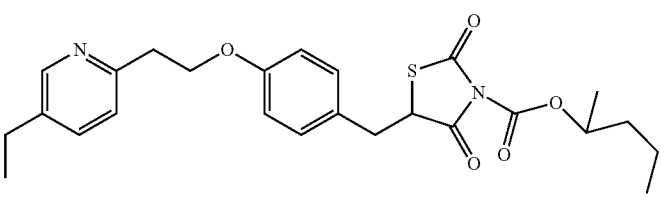 [SMILES: CCCC(C)OC(=O)N1C(=O)SC(Cc2ccc(OCCc3ccc(CC)cn3)cc2)C1=O] |
| 1023. | 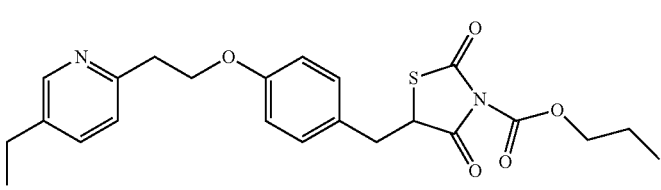 [SMILES: CCCOC(=O)N1C(=O)SC(Cc2ccc(OCCc3ccc(CC)cn3)cc2)C1=O] |
| 1024. | 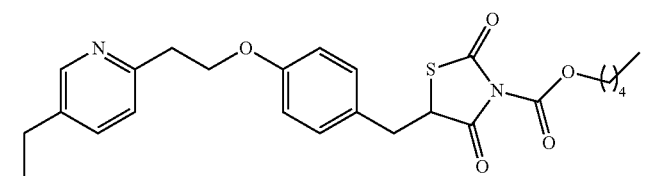 |
| 1025. | 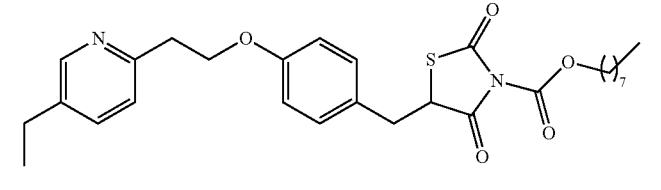 |
| 1026. | 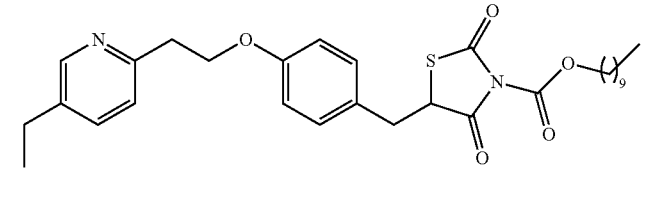 |
| 1027. | 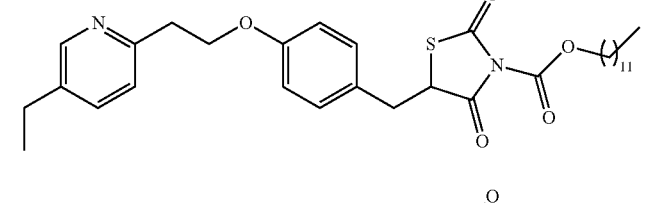 |
| 1028. | 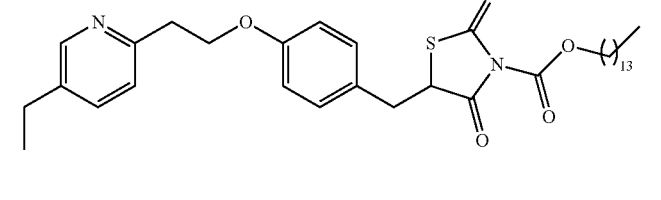 |

TABLE H-continued

| No. | Structure |
|---|---|
| 1029. | (structure with (CH₂)₁₅ chain) |
| 1030. | (structure with (CH₂)₁₇ chain) |
| 1031. | (structure with (CH₂)₁₉ chain) |
| 1032. | (structure with (CH₂)₂₁ chain) |
| 1033. | (structure with cyclopropyl group) |
| 1034. | (structure with cyclobutyl group) |
| 1035. | (structure with cyclopentyl group) |
| 1036. | (structure with cyclohexyl group) |

TABLE H-continued
| No. | Structure |
|---|---|
| 1037. | 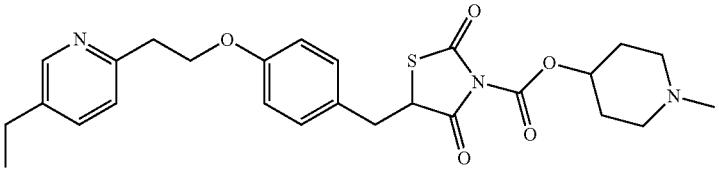 [SMILES: CCc1ccc(CCOc2ccc(CC3SC(=O)N(C(=O)OC4CCN(C)CC4)C3=O)cc2)nc1] |
| 1038. | 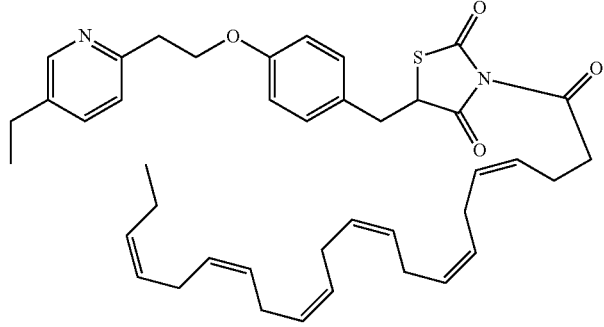 [SMILES: CC/C=C\C/C=C\C/C=C\C/C=C\C/C=C\C/C=C\CCC(=O)N1C(=O)SC(Cc2ccc(OCCc3ccc(CC)cn3)cc2)C1=O] |
| 1039. | 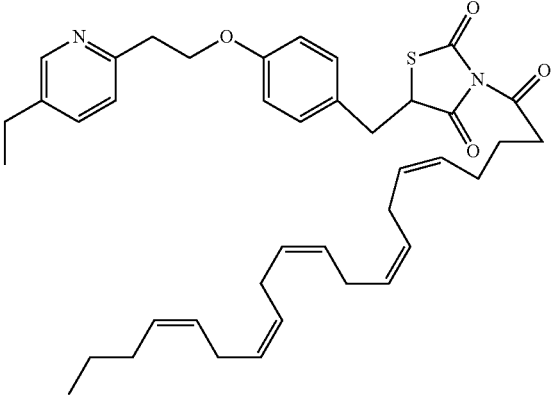 [SMILES: CCC/C=C\C/C=C\C/C=C\C/C=C\C/C=C\CCCC(=O)N1C(=O)SC(Cc2ccc(OCCc3ccc(CC)cn3)cc2)C1=O] |
| 1040. | 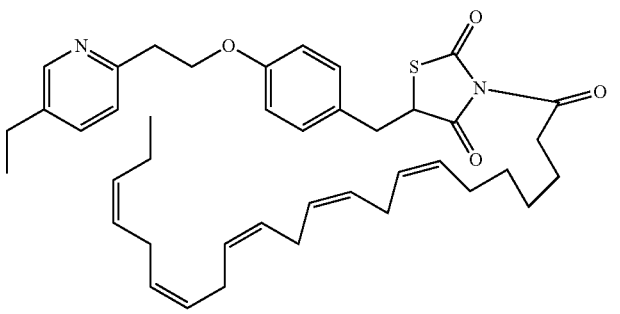 [SMILES: CC/C=C\C/C=C\C/C=C\C/C=C\C/C=C\CCCCCC(=O)N1C(=O)SC(Cc2ccc(OCCc3ccc(CC)cn3)cc2)C1=O] |
| 1041. | 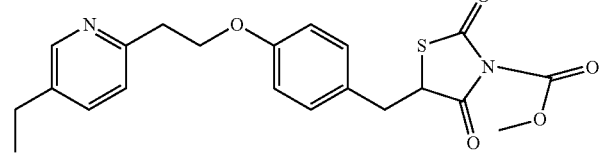 |

Barbiturates

In another embodiment, compounds of the present invention are represented by Formula XXXIII-XXXVII as illustrated below, or its geometric isomers, enantiomers, diastereomers, racemates, pharmaceutically acceptable salts and solvates thereof:

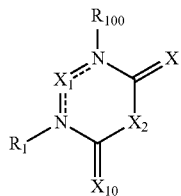

Formula XXXIII

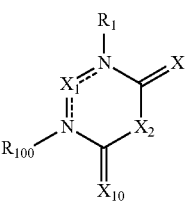

Formula XXXIV

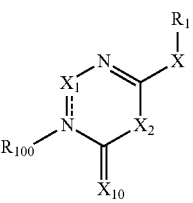

Formula XXXV

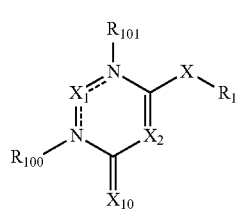

Formula XXXVI

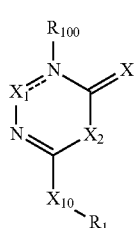

Formula XXXVII wherein, X, $X_1$, $X_2$, $R_{100}$, $R_{101}$, and $R_1$ are as defined above; $X_{10}$ is —S or —O.

In a preferred embodiment a compound from Table XXXIII-XXXVII is provided. A more preferred embodiment is a compound of table XXXIII-XXXVII wherein $R_1$ is selected from tables 1-4.

TABLE XXXIII-XXXIV

| | |
|---|---|
| 1 | 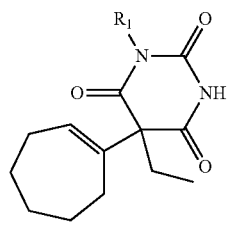 |
| 2 | 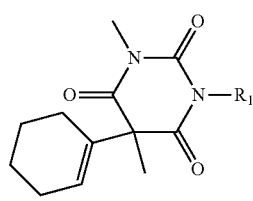 |
| 3 | 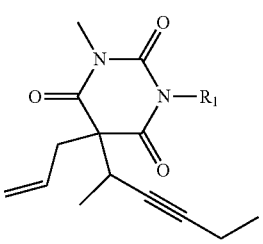 |
| 4 | 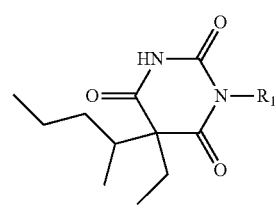 |
| 5 | 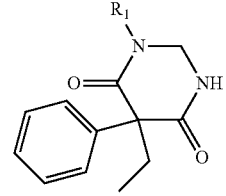 |
| 6 | 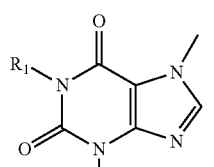 |
| 7 | 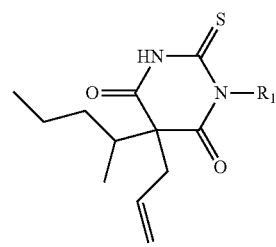 |

TABLE XXXIII-XXXIV-continued

| 8 | 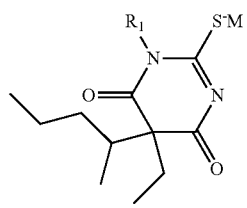 |
| --- | --- |
| 9 | 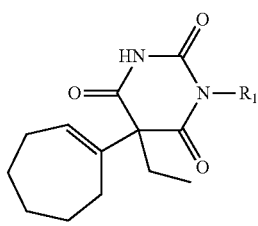 |
| 10 | 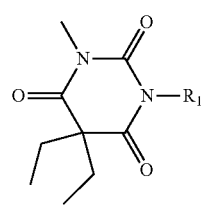 |
| 11 | 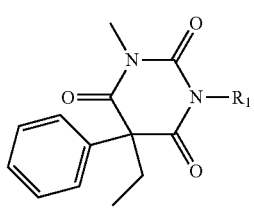 |
| 12 | 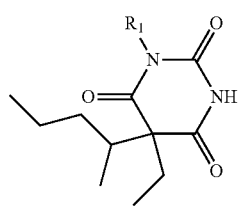 |
| 13 | 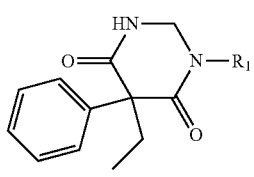 |
| 14 | 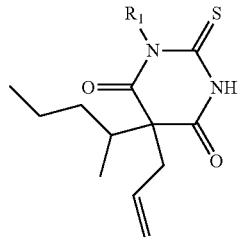 |

TABLE XXXIII-XXXIV-continued

| 15 | 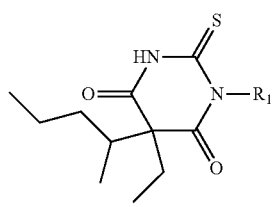 |
| --- | --- |
| 16 | 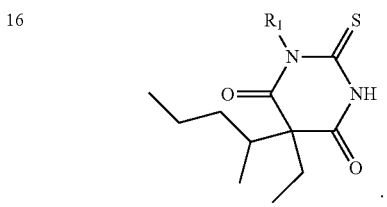 |

Pyridone Pyrimidone and Pyrimidione Prodrugs

In another embodiment, compounds of the present invention are represented by Formula XXXVIII or XXXIX as illustrated below, or its geometric isomers, enantiomers, diastereomers, racemates, pharmaceutically acceptable salts and solvates thereof:

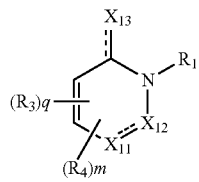

Formula XXXVIII

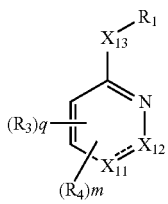

Formula XXXIX wherein X, $R_1$, $R_3$, $R_4$, m and q are as defined above;

$X_{11}$ is —N— or —C($R_{10}$)—;

$X_{12}$ is —C(O)—, —C(S)—, —C($R_{10}$)($R_{11}$)— or —C($R_{10}$)(O$R_{11}$)—; and $X_{13}$ is —O, —S, —N($R_{10}$)($R_{11}$), —O$R_{10}$.

A preferred embodiment is a compound selected from table XXXVIII-XXXIX. A more preferred embodiment is a compound from table XXXVIII-XXXIX wherein $R_1$ is selected from Tables 1-4.

TABLE XXXVIII
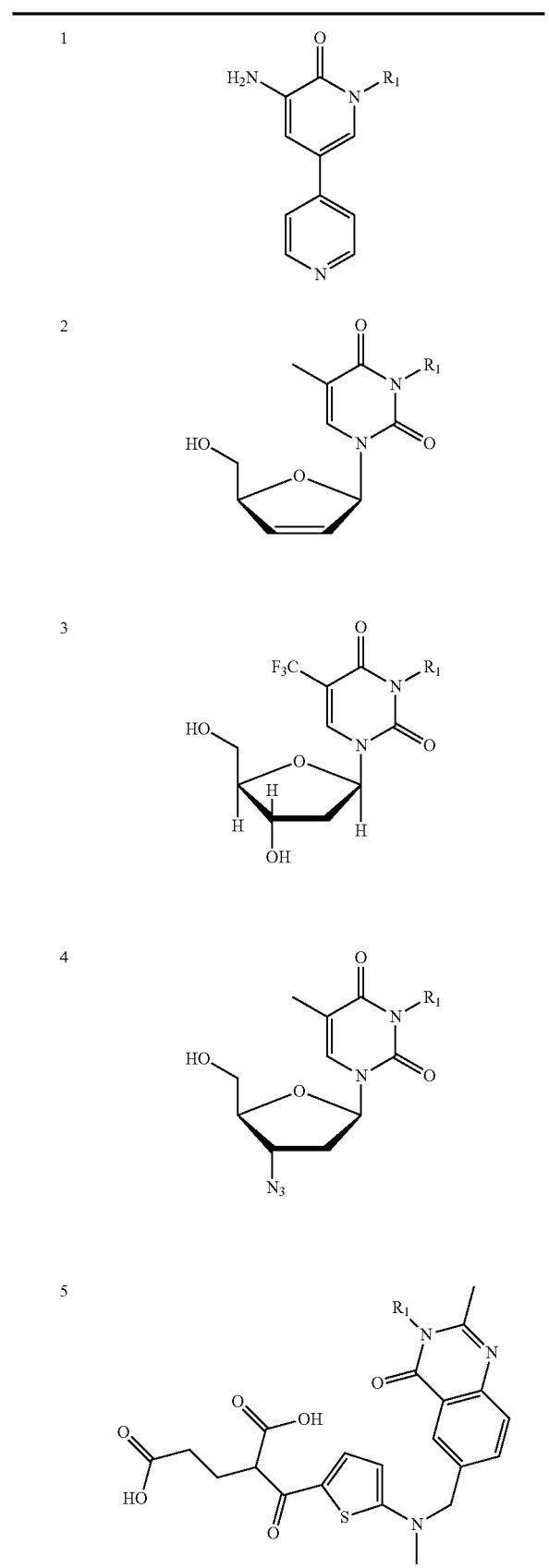
TABLE XXXVIII-continued
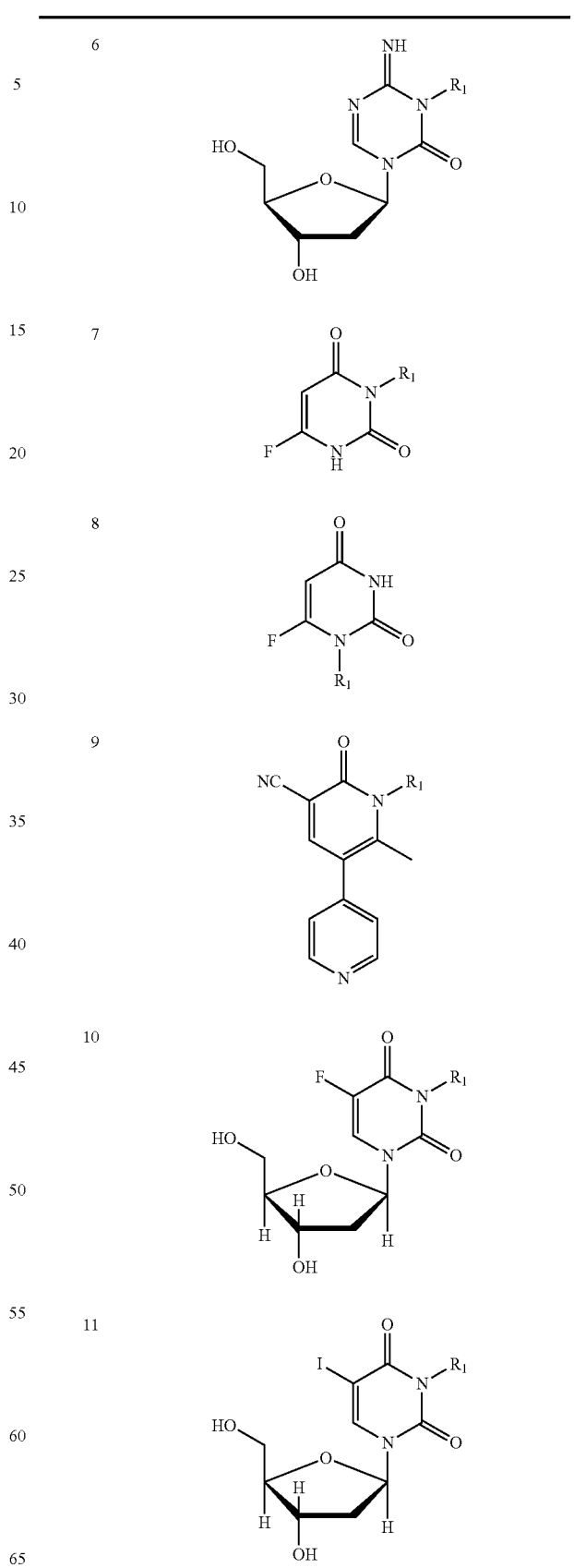

TABLE XXXVIII-continued

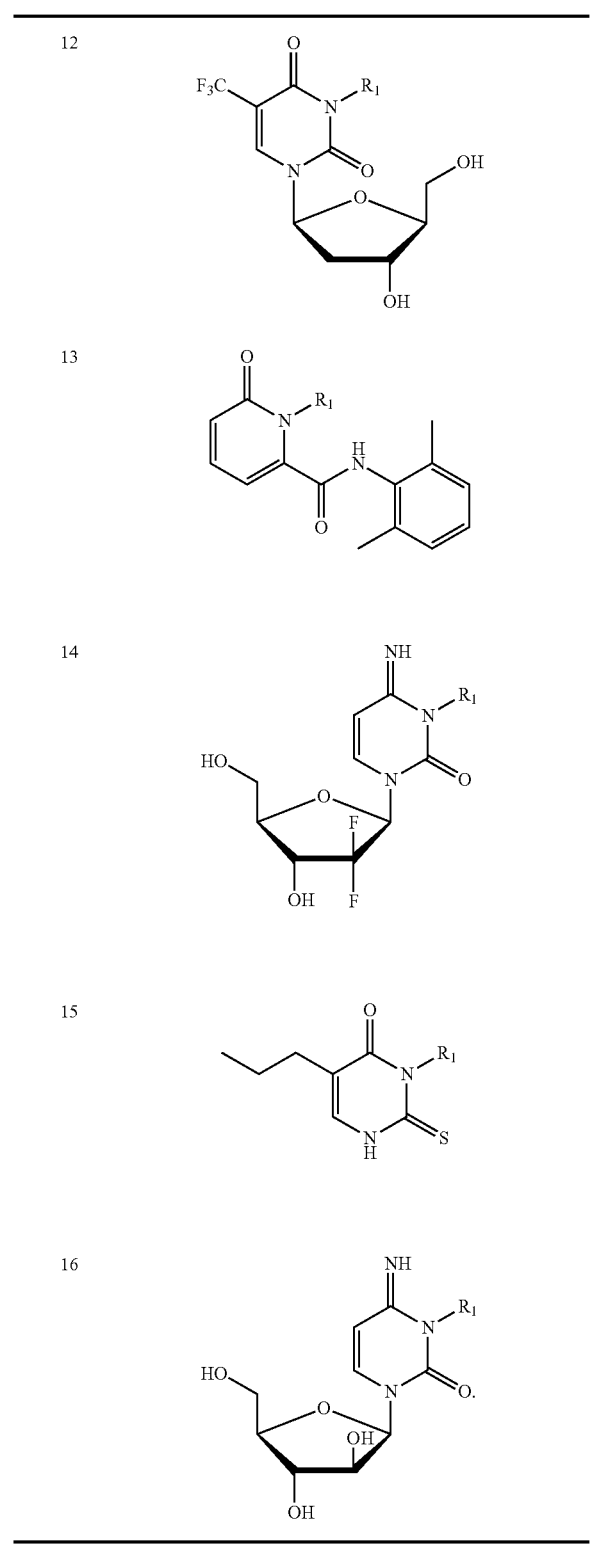

Prodrugs of Benzamide Pharmacophores

In another embodiment, compounds of the present invention are represented by Formula XL or XLI as illustrated below, or its geometric isomers, enantiomers, diastereomers, racemates, pharmaceutically acceptable salts and solvates thereof:

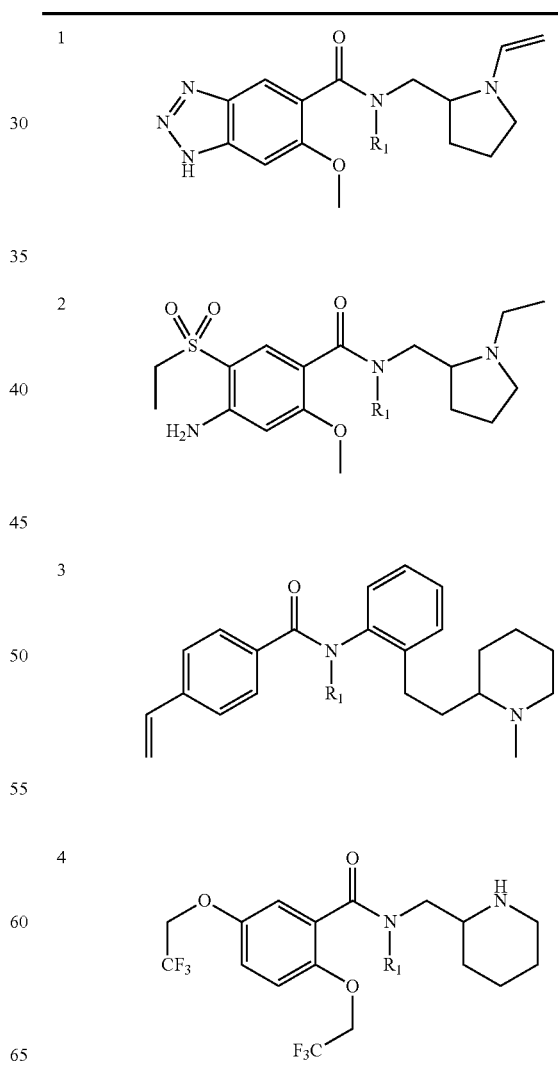

wherein $R_1$, $R_{50}$, $R_{51}$, $R_{52}$, $R_{53}$, $R_{54}$ and $R_{55}$ are as defined above.

TABLE XL-XLI

TABLE XL-XLI-continued
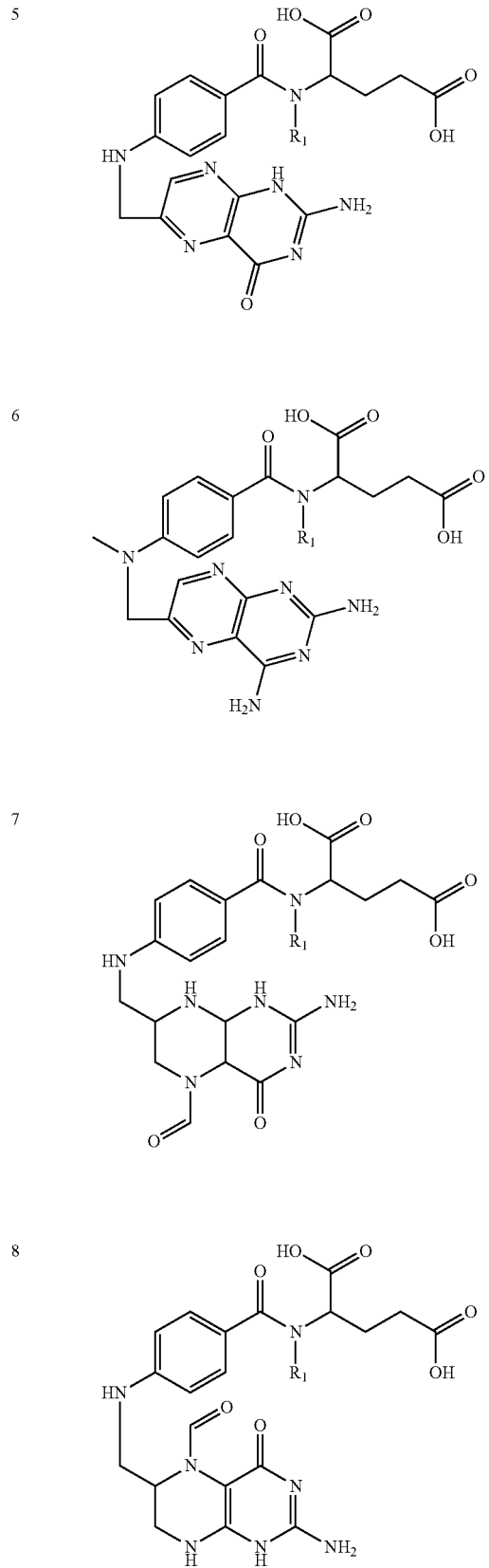
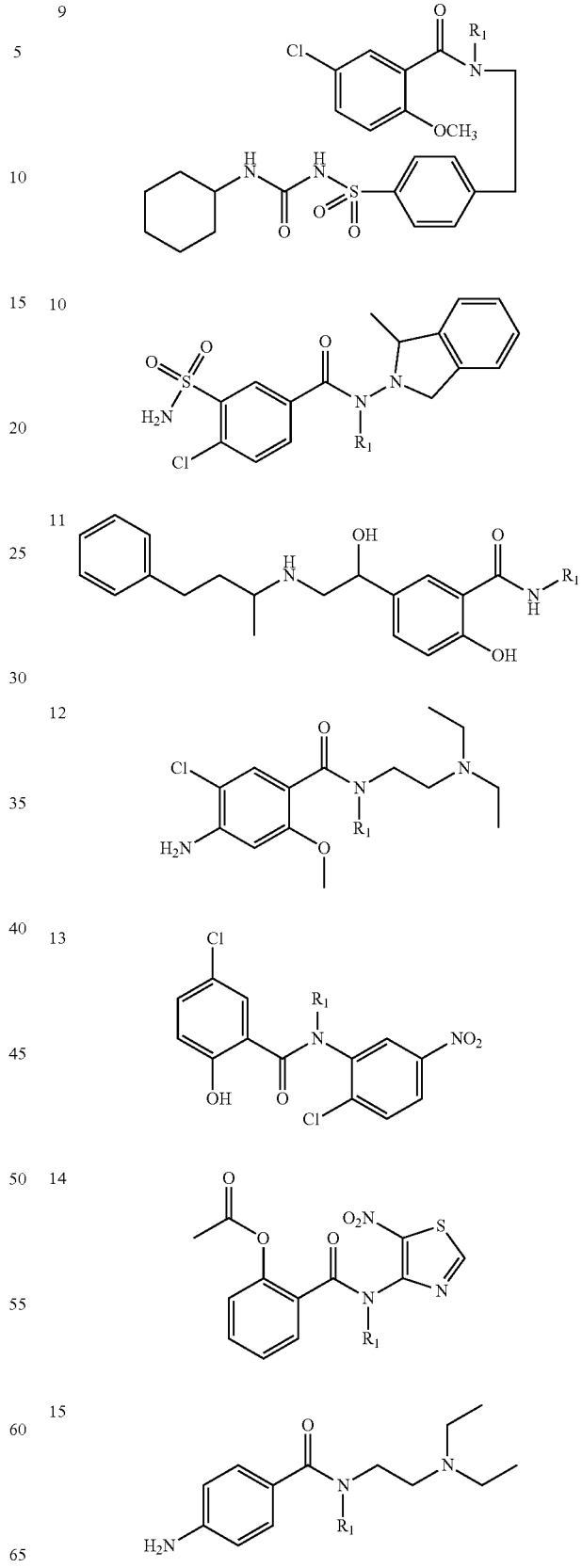

TABLE XL-XLI-continued
| | | | |
|---|---|---|---|
| 16 | 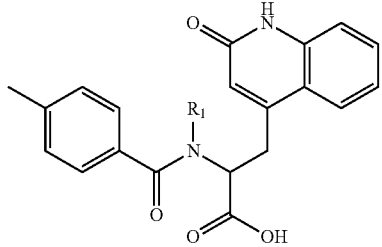 | 22 | 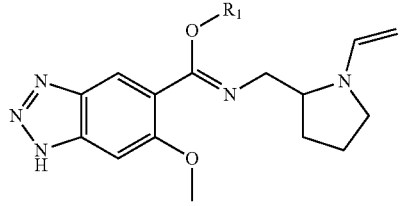 |
| 17 | 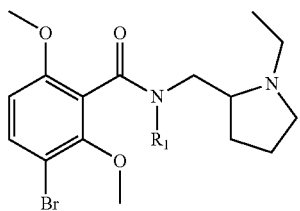 | 23 | 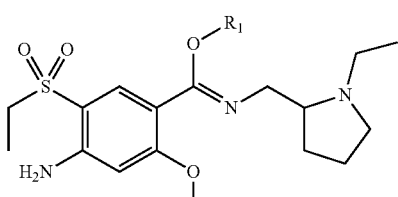 |
| 18 | 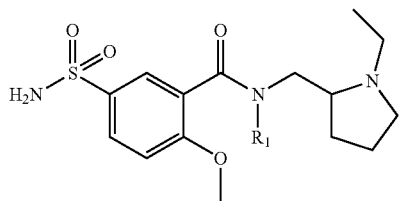 | 24 | 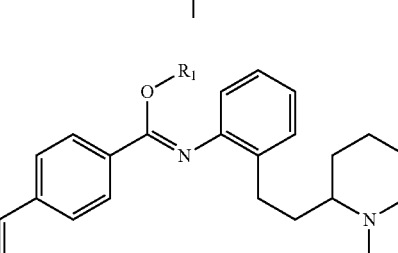 |
| 19 | 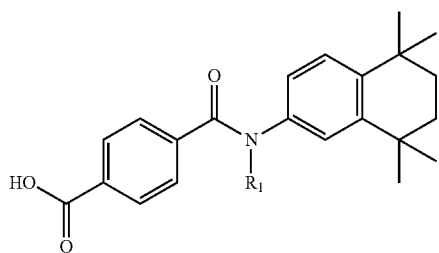 | 25 | 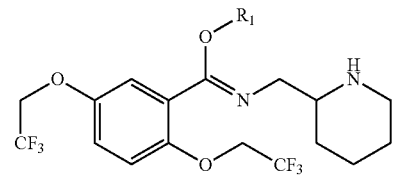 |
| 20 | 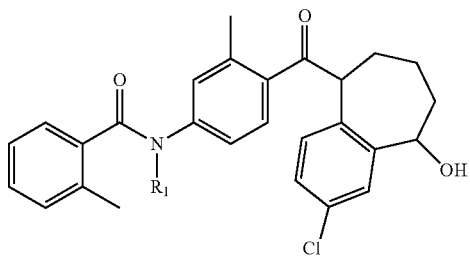 | 26 | 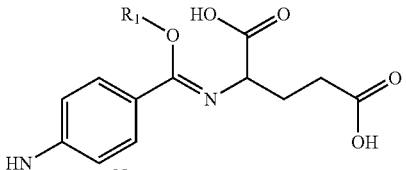 |
| 21 | 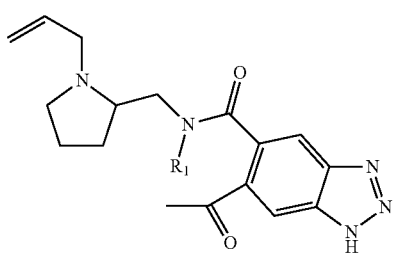 | 27 | 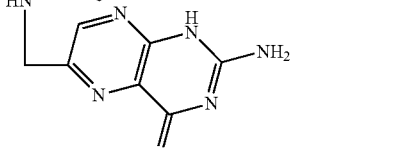 |

TABLE XL-XLI-continued
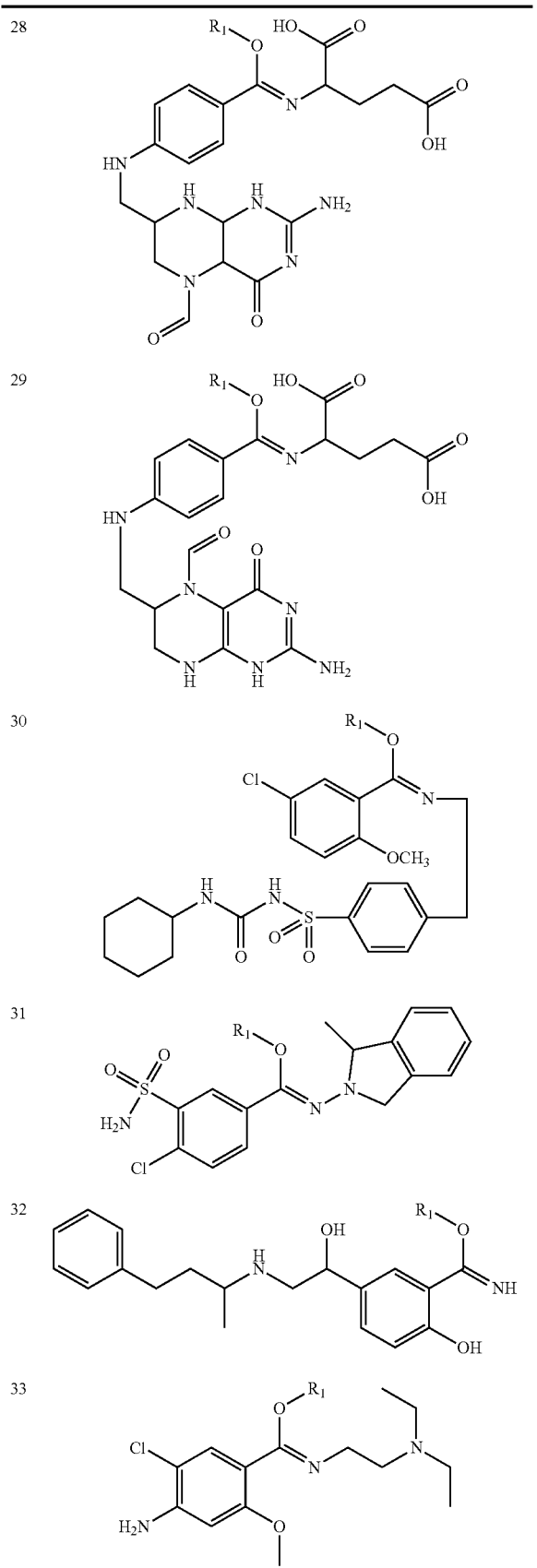
TABLE XL-XLI-continued
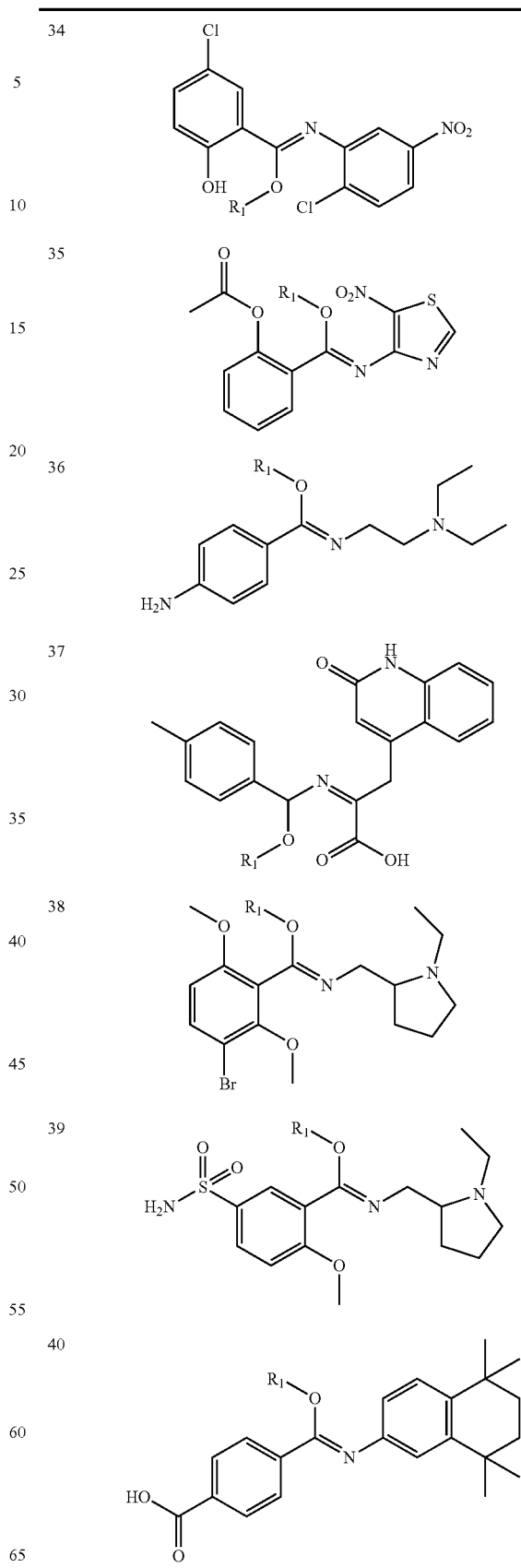

TABLE XL-XLI-continued

41 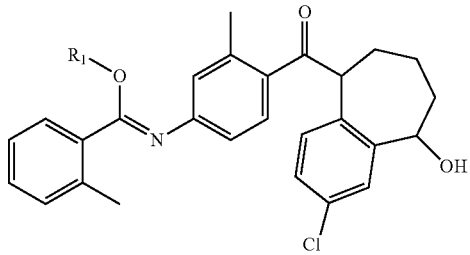

42 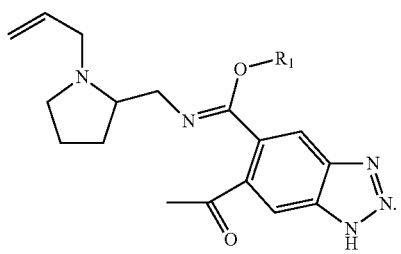

Prodrugs of Imide Pharmacophores

In another embodiment, compounds of the present invention are represented by Formula XLII, XLIII or XLIV as illustrated below, or its geometric isomers, enantiomers, diastereomers, racemates, pharmaceutically acceptable salts and solvates thereof:

Formula XLII

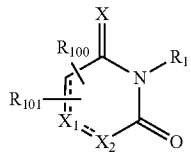

Formula XLIII

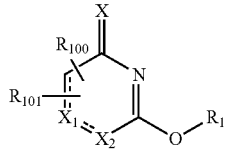

Formula XLIV

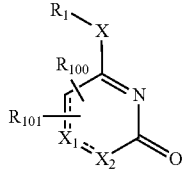

wherein $R_1$ $R_{100}$, $R_{101}$, X, $X_1$ and $X_2$ are as defined above; alternatively $R_{100}$ and $R_{101}$ together with the atoms to which they are attached form an optionally substituted 3, 4, 5, 6, or 7 membered ring.

A preferred embodiment is a compound selected from table XLII-XLIV. A more preferred embodiment is a compound from table XLII-XLIV wherein $R_1$ is selected from Tables 1-4.

TABLE XLII-XLIV

| XLII- |
|---|
| 1 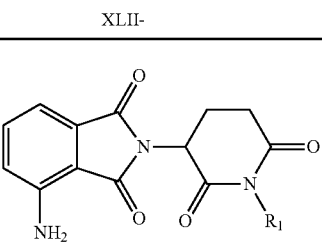 |
| 2 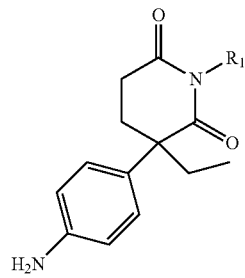 |
| 3 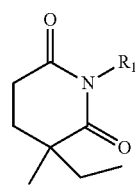 |
| 4 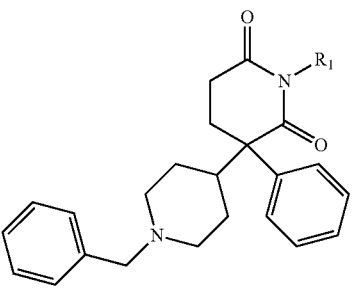 |
| 5 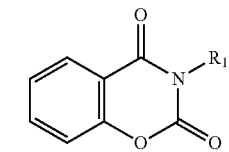 |
| 6 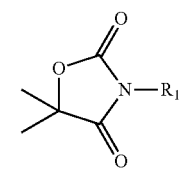 |
| 7 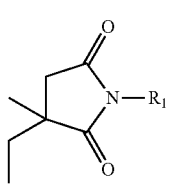 |

TABLE XLII-XLIV-continued
| 8 | 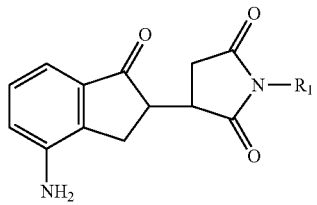 |
| --- | --- |
| 9 | 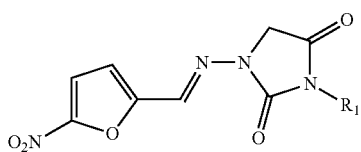 |
| 10 | 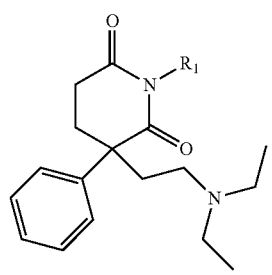 |
| 11 | 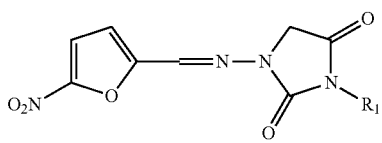 |
| 12 | 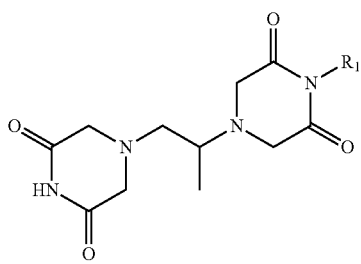 |
| 13 | 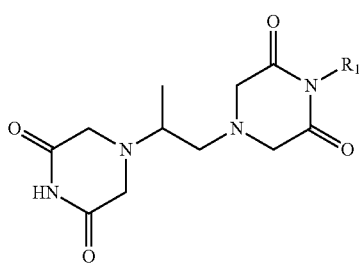 |
TABLE XLII-XLIV-continued
| 14 | 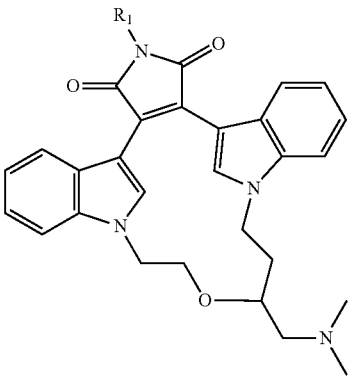 |
| --- | --- |
| 15 | 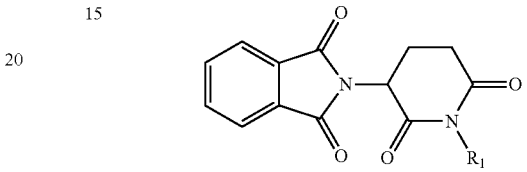 |
| 16 | 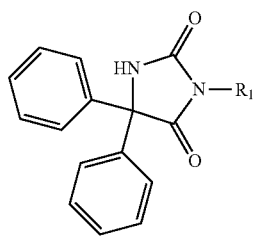 |
XLIII-
| 1 | 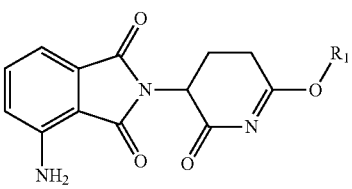 |
| --- | --- |
| 2 | 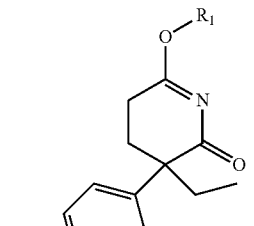 |
| 3 | 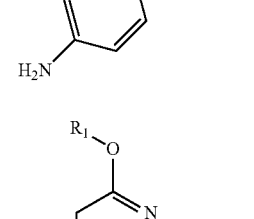 |

TABLE XLII-XLIV-continued
| | |
|---|---|
| 4 | 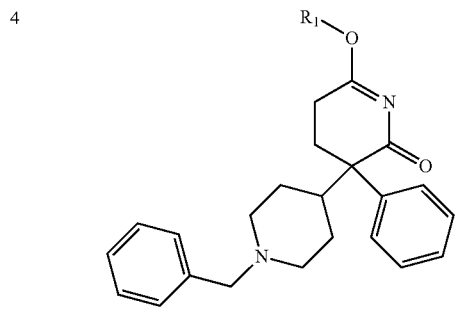 |
| 5 | 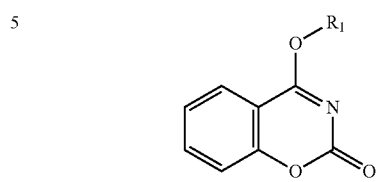 |
| 6 | 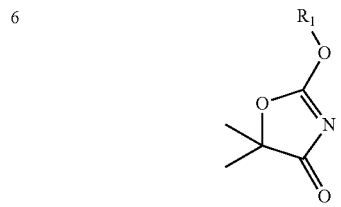 |
| 7 | 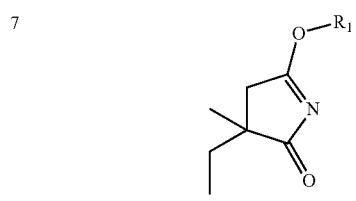 |
| 8 | 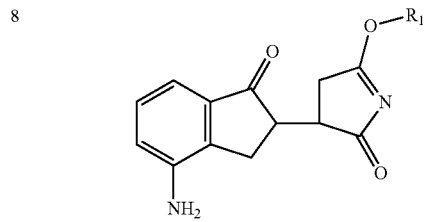 |
| 9 | 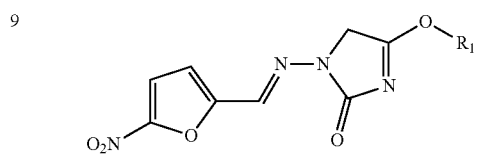 |
| 10 | 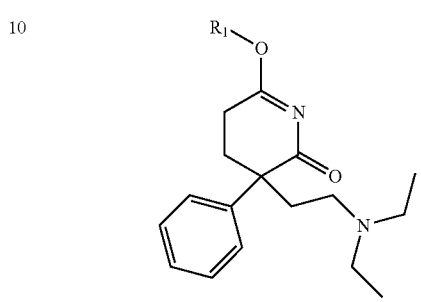 |
TABLE XLII-XLIV-continued
| | |
|---|---|
| 11 | 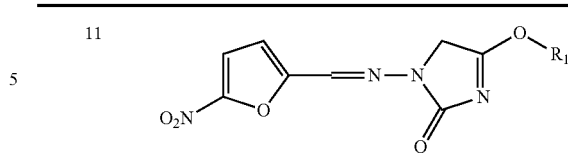 |
| 12 | 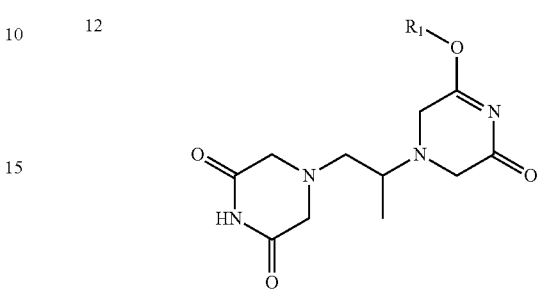 |
| 13 | 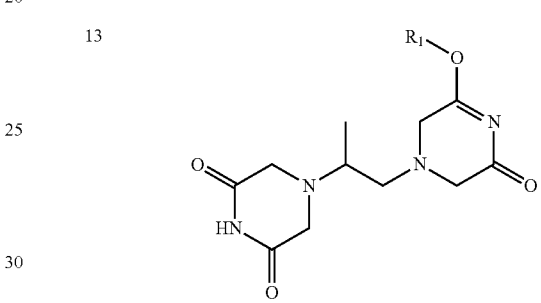 |
| 14 | 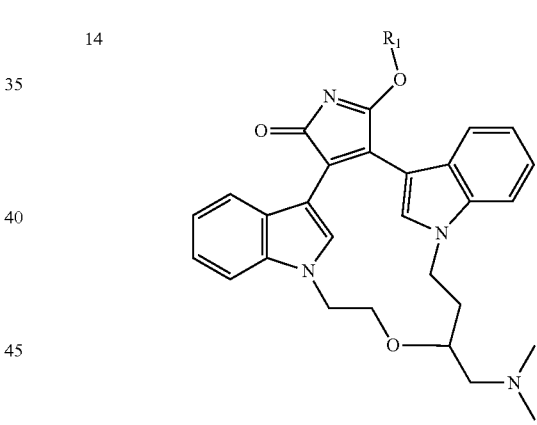 |
| 15 | 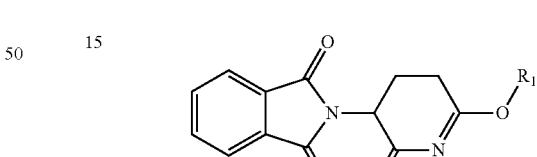 |
| 16 | 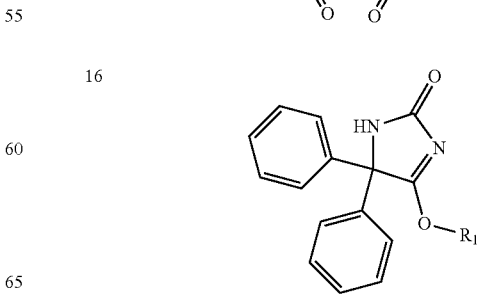 |

TABLE XLII-XLIV-continued

XLIV-

TABLE XLII-XLIV-continued
14 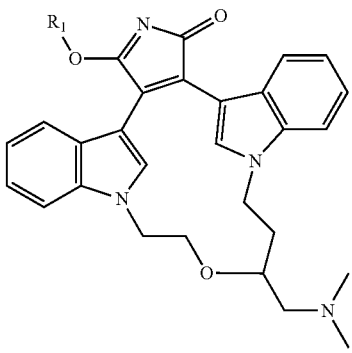
15 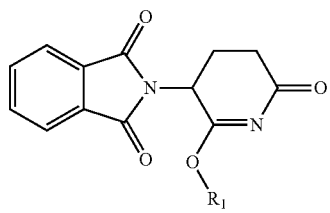
16 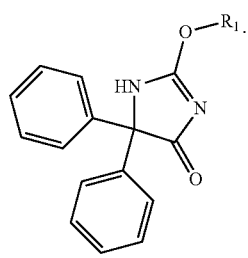
In another embodiment, compounds of the present invention having the Formula VI or VII is selected from Table VI-VII.
TABLE VI-VII
1 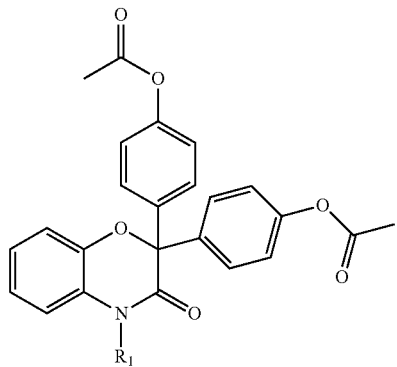
2 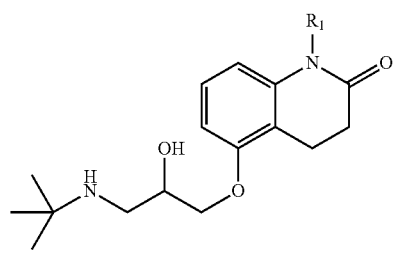
TABLE VI-VII-continued
3 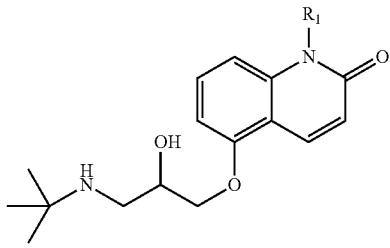
4 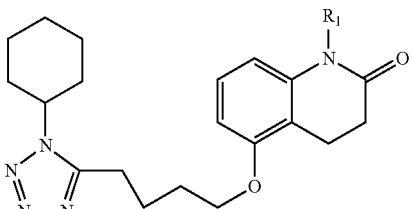
5 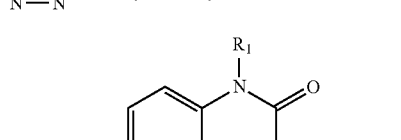
6 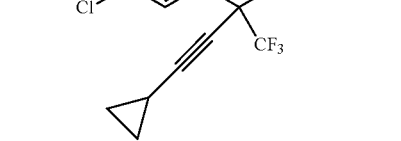
7 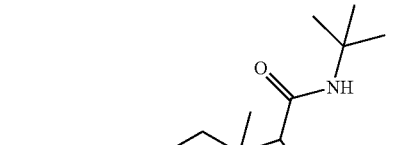
8 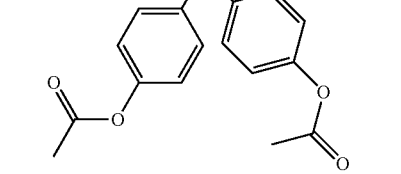

TABLE VI-VII-continued
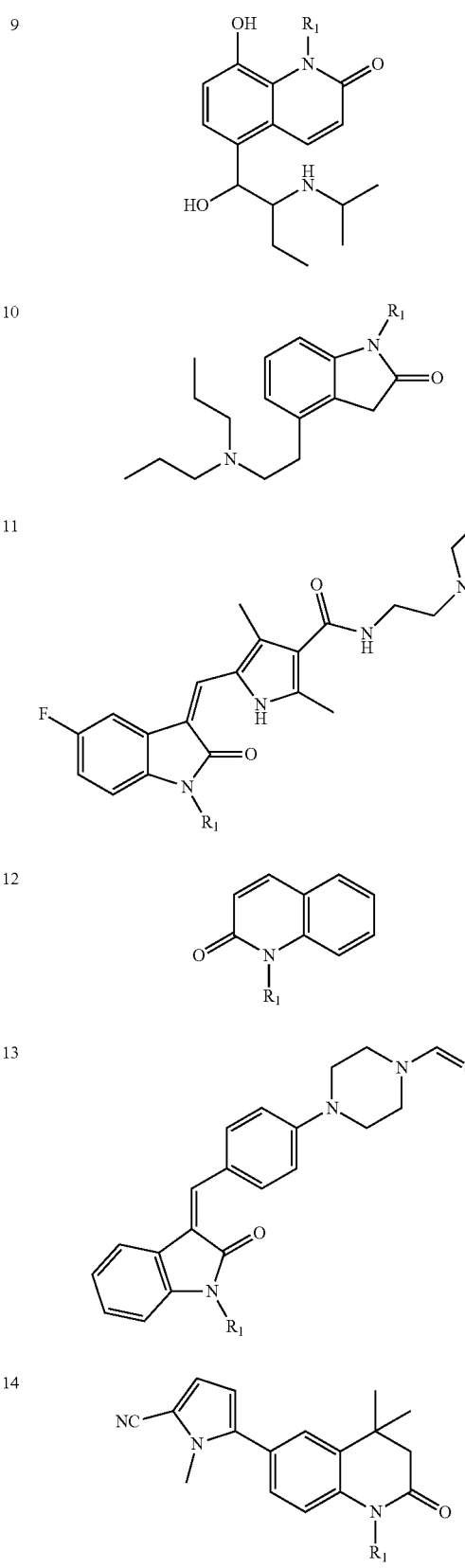
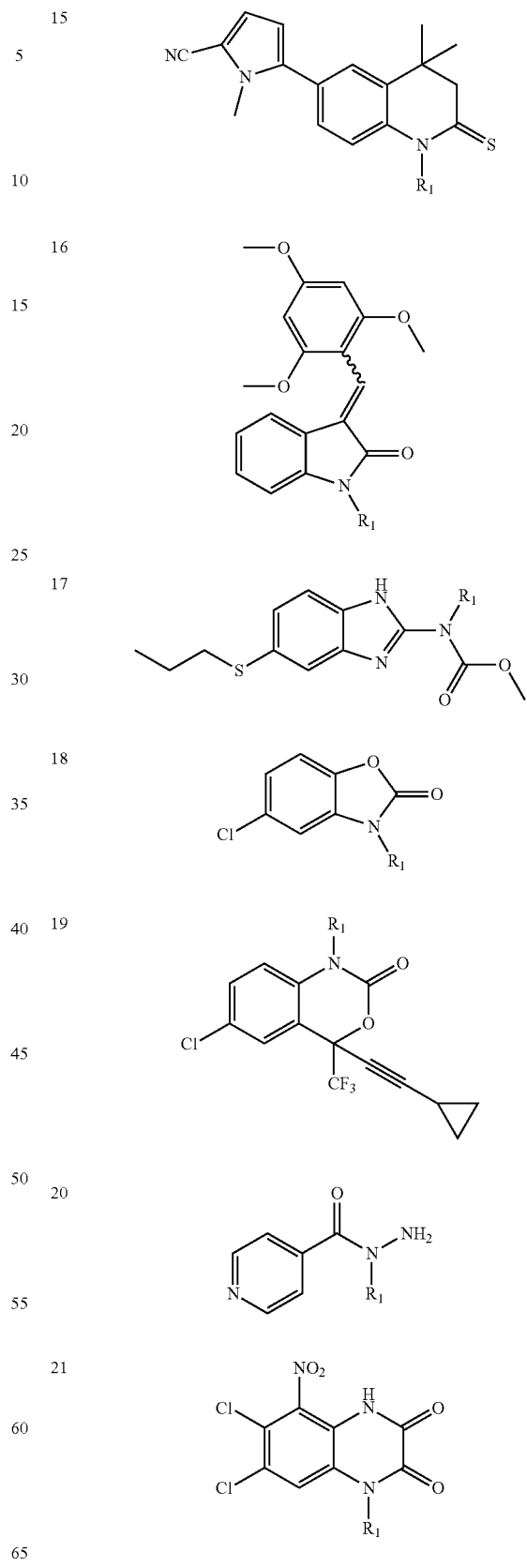

TABLE VI-VII-continued
| 22 | 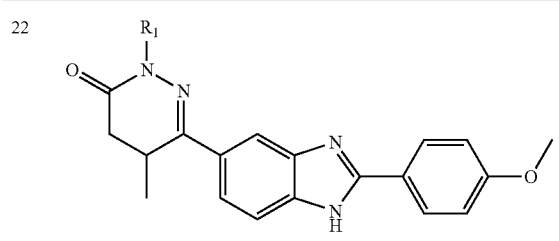 |
| --- | --- |
| 23 | 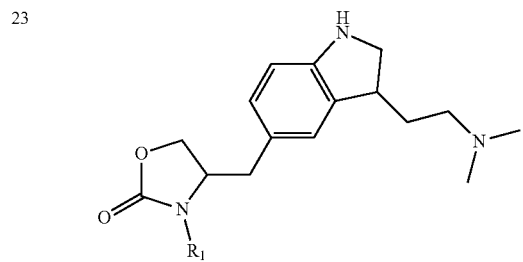 |
| 24 | 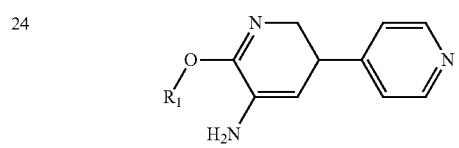 |
| 25 | 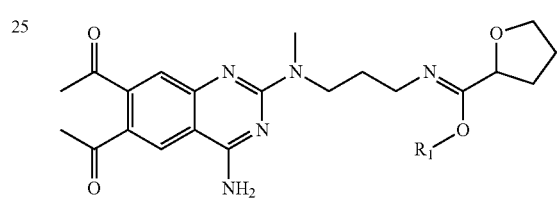 |
| 26 | 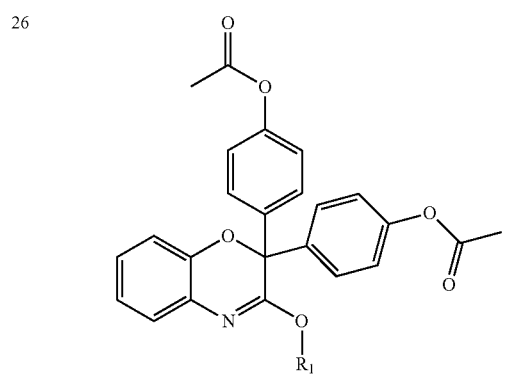 |
| 27 | 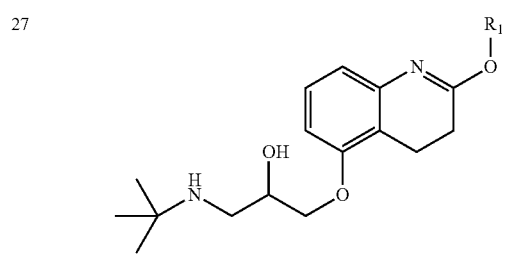 |
TABLE VI-VII-continued
| 28 | 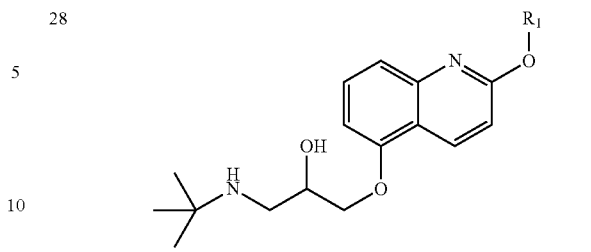 |
| --- | --- |
| 29 | 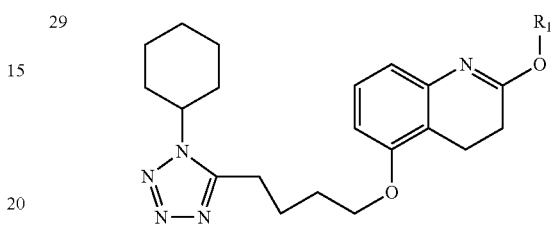 |
| 30 | 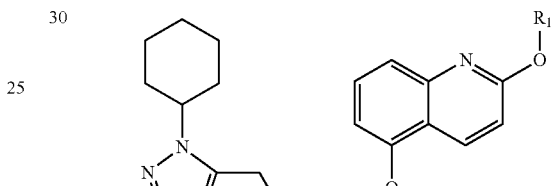 |
| 31 | 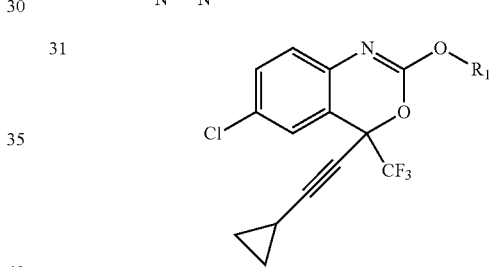 |
| 32 | 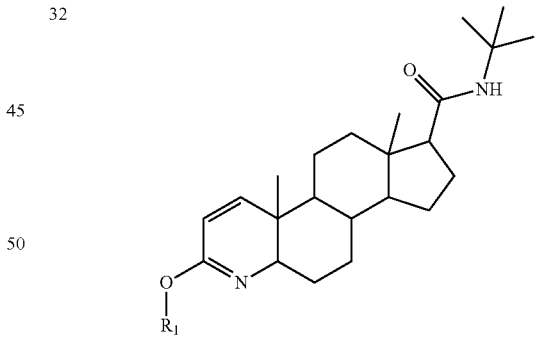 |
| 33 | 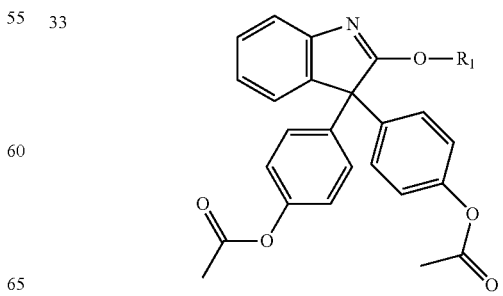 |

TABLE VI-VII-continued
| 34 | 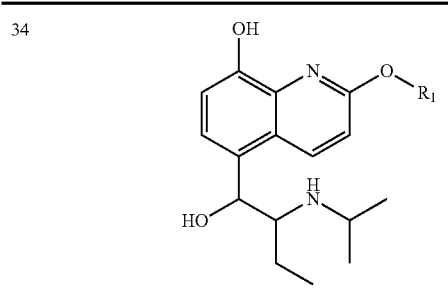 |
| --- | --- |
| 35 | 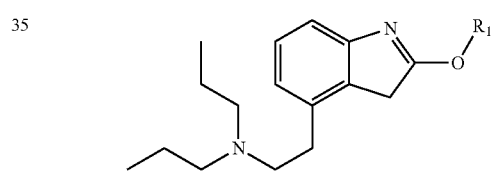 |
| 36 | 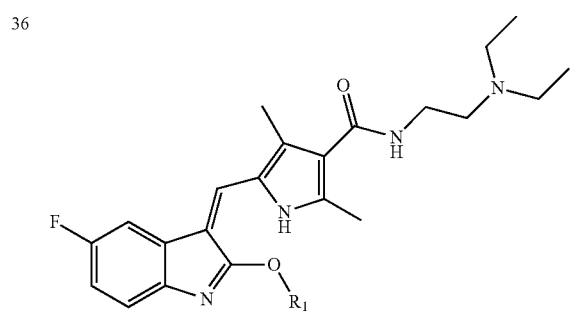 |
| 37 | 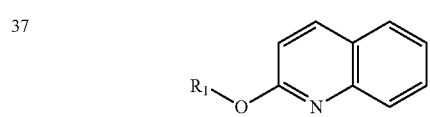 |
| 38 | 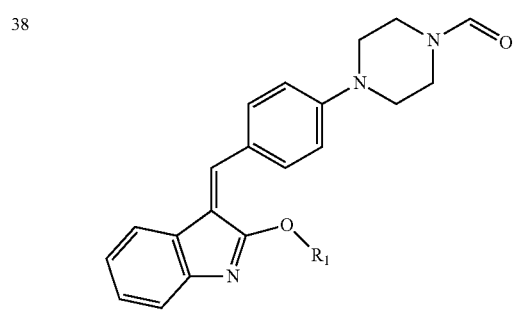 |
| 39 | 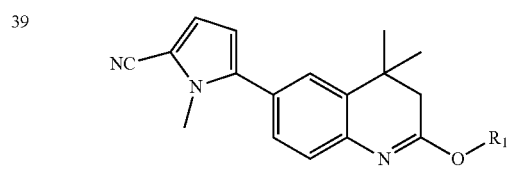 |
| 40 | 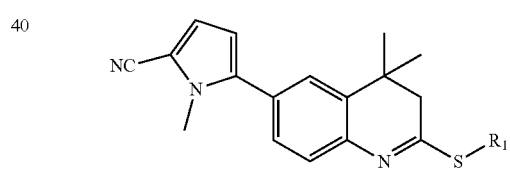 |
TABLE VI-VII-continued
| 41 | 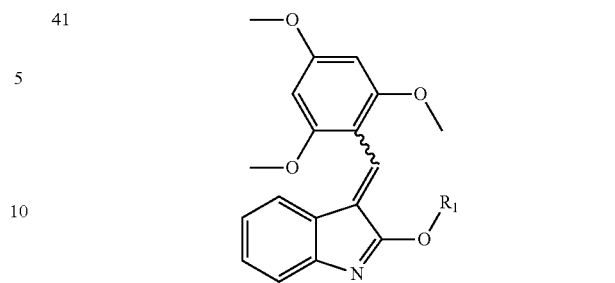 |
| --- | --- |
| 42 | 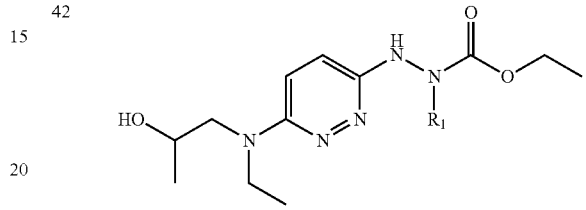 |
| 43 | 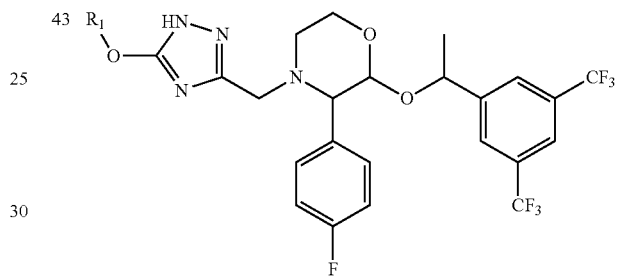 |
| 44 | 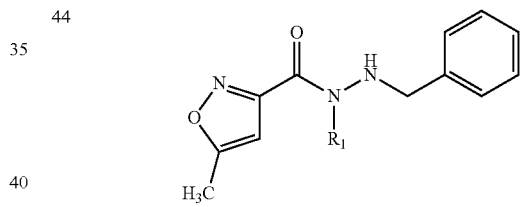 |
| 45 | 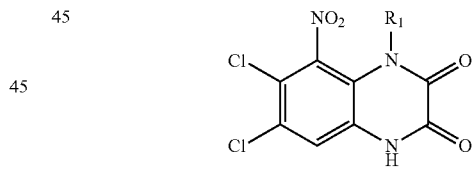 |
| 46 | 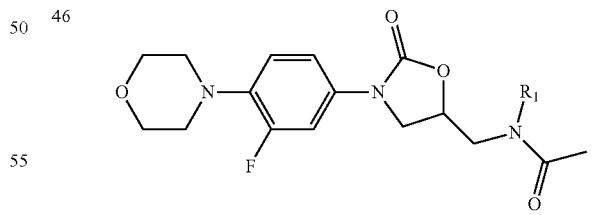 |
| 47 | 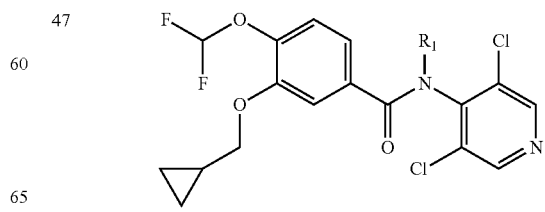 |

TABLE VI-VII-continued

| | |
|---|---|
| 48 | 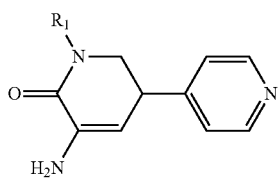 |
| 49 | 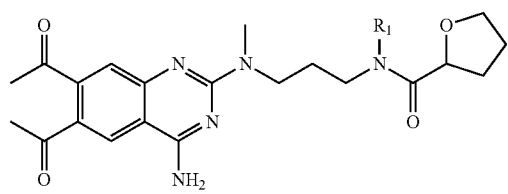 |
| 50 | 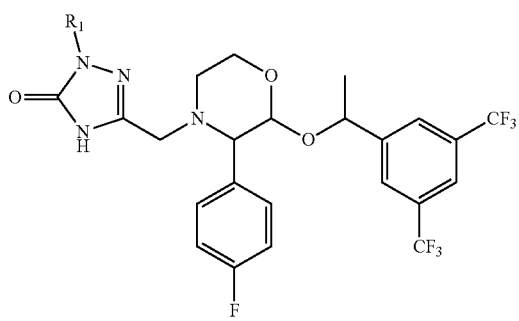 |
| 51 | 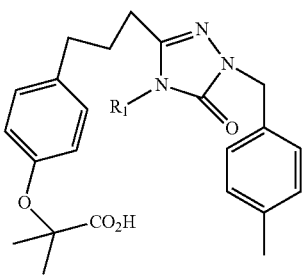 |
| 52 | 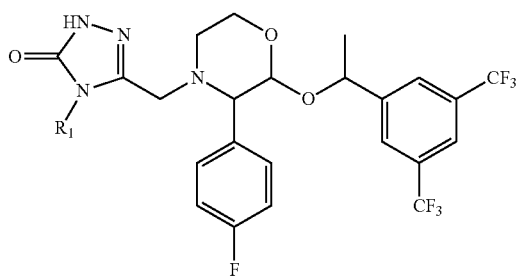 |
| 53 | 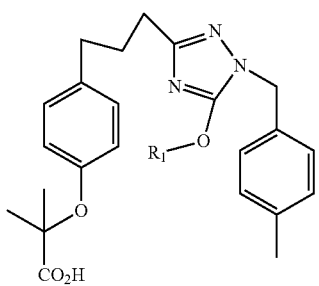 |

TABLE VI-VII-continued

| | |
|---|---|
| 53 | 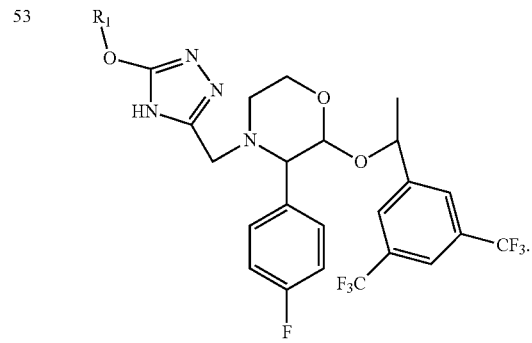 |

Prodrugs of Sulfonamide Pharmacophores

In another embodiment, compounds of the present invention are represented by Formula III as illustrated below, or its geometric isomers, enantiomers, diastereomers, racemates, pharmaceutically acceptable salts and solvates thereof:

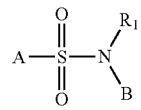

Formula III

A preferred embodiment is a compound selected from Table III. A more preferred embodiment is a compound from Table III wherein $R_1$ is selected from Tables 1-4.

TABLE III

| | |
|---|---|
| 1 | 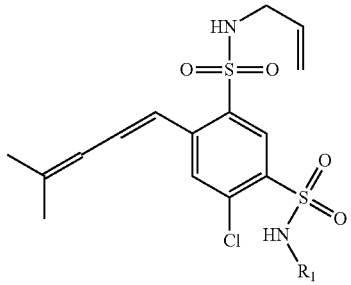 |
| 2 | 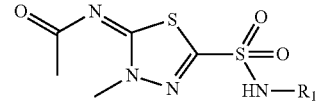 |
| 3 | 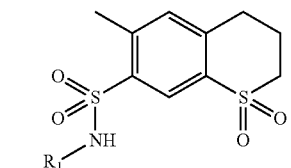 |
| 4 | 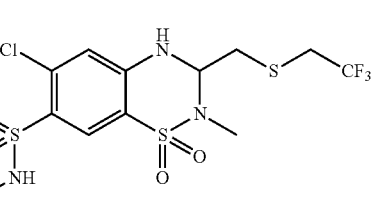 |

TABLE III-continued
| | |
|---|---|
| 5 | 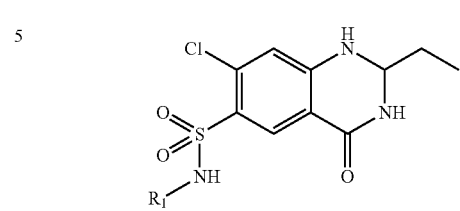 |
| 6 | 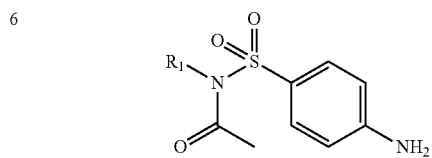 |
| 7 | 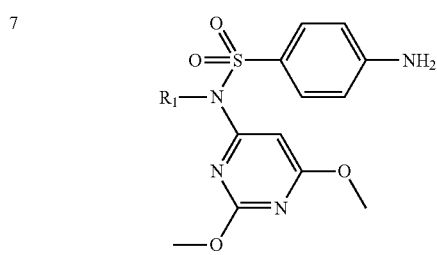 |
| 8 | 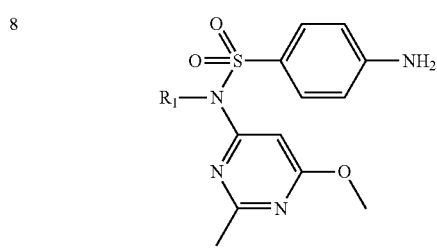 |
| 9 | 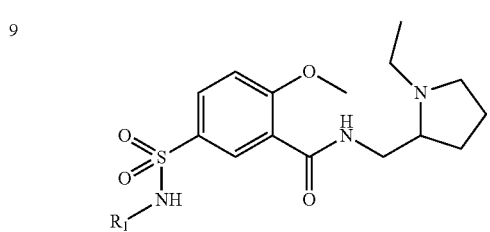 |
| 10 | 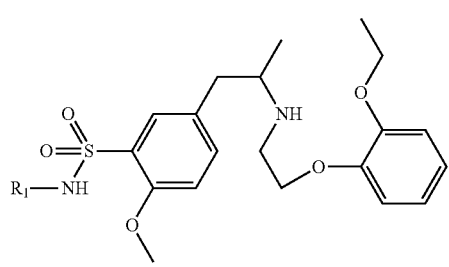 |
| 11 | 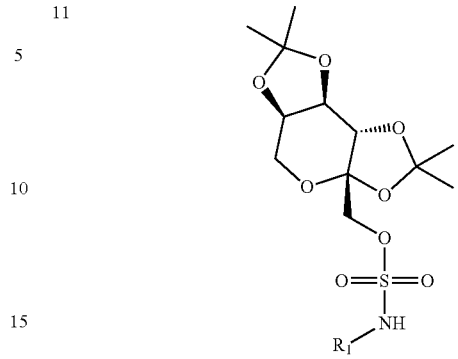 |
| 12 | 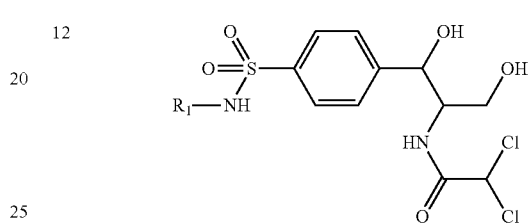 |
| 13 | 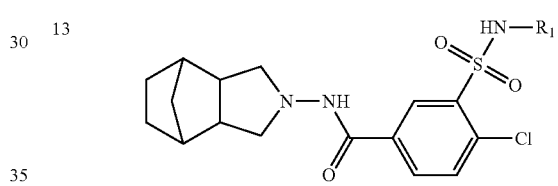 |
| 14 | 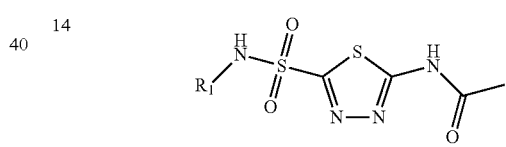 |
| 15 | 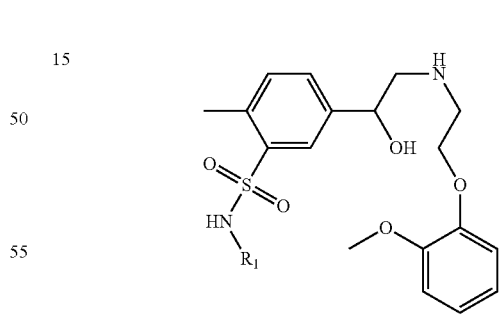 |
| 16 | 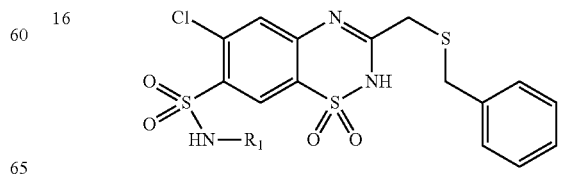 |

TABLE III-continued
17 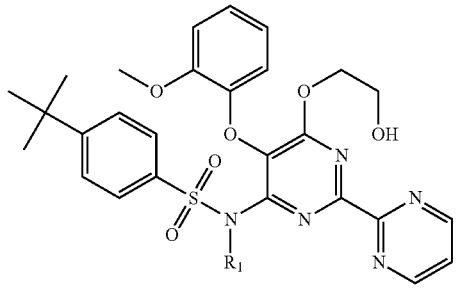
18 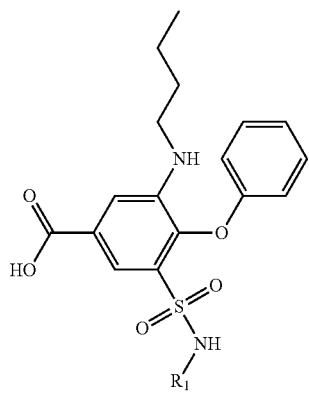
19 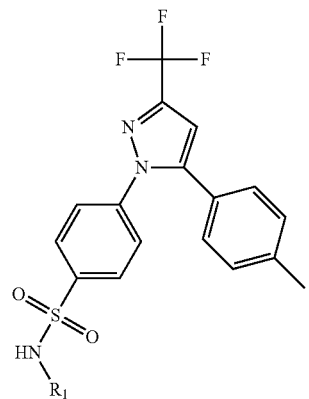
20 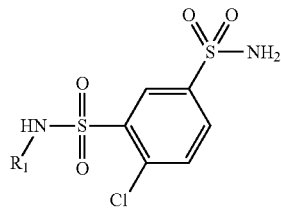
21 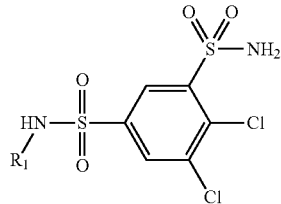
22 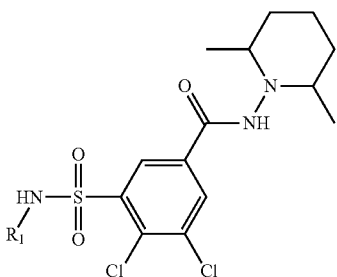
23 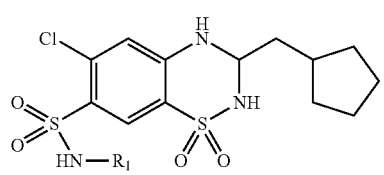
24 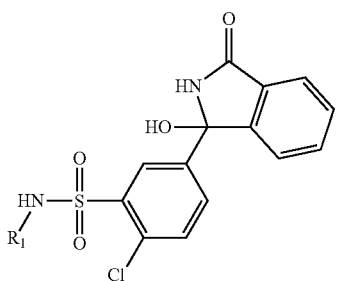
25 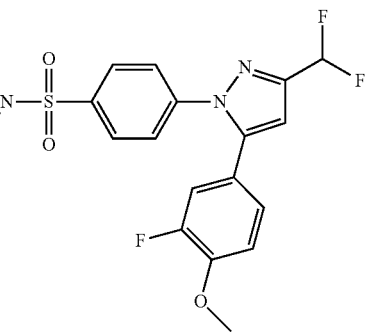
26 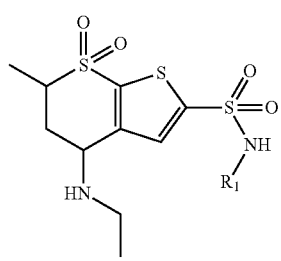
27 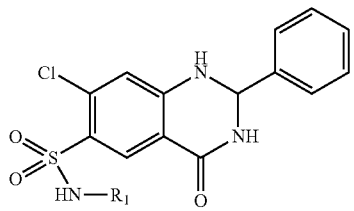

TABLE III-continued
28 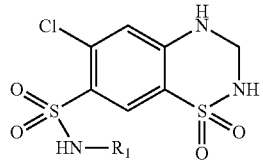
29 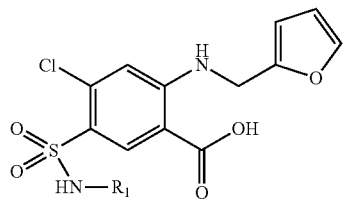
30 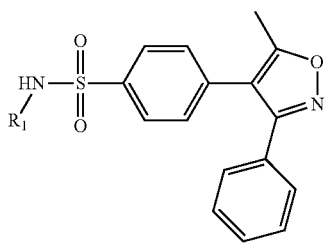
31 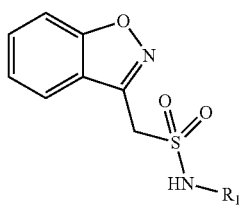
32 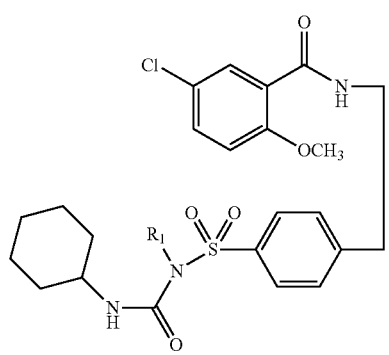
33 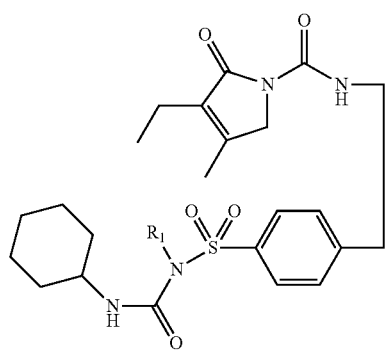
TABLE III-continued
34 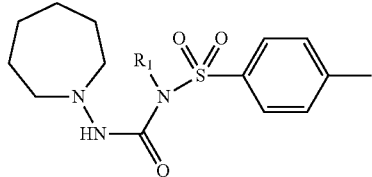
35 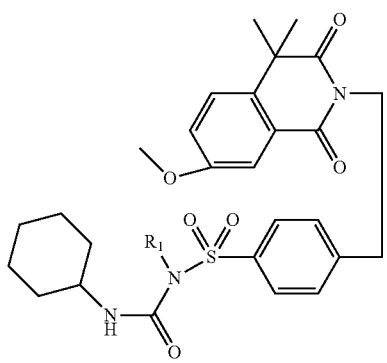
36 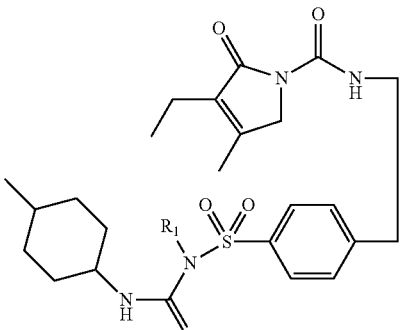
37 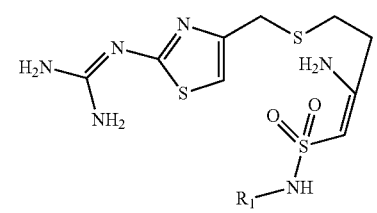
38 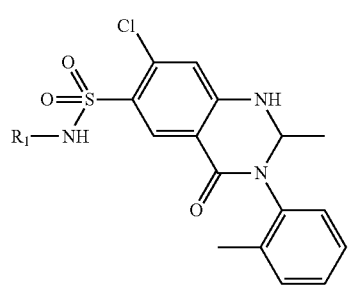

TABLE III-continued
| | | |
|---|---|---|
| 39 | 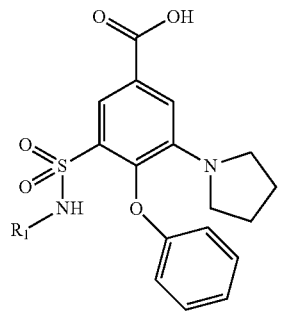 | |
| 40 | 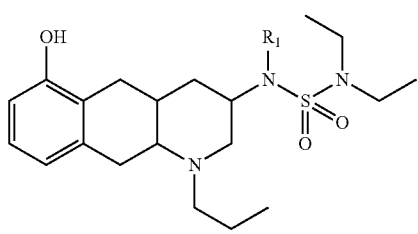 | |
| 41 | 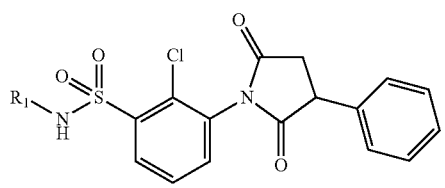 | |
| 42 | 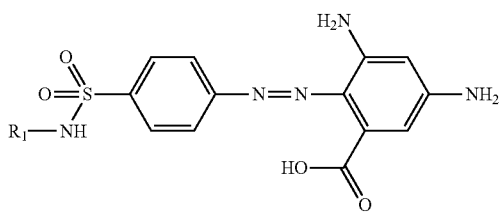 | |
| 43 | 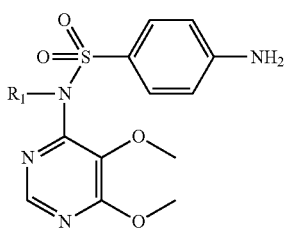 | |
| 44 | 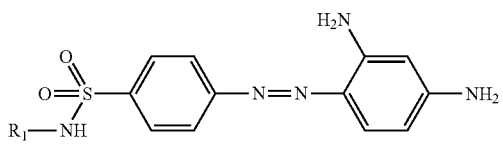 | |
| 45 | 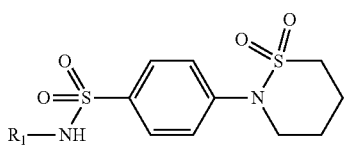 | |
TABLE III-continued
| | | |
|---|---|---|
| 46 | 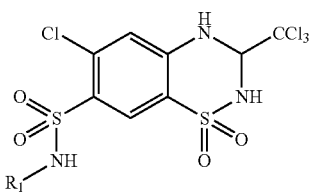 | |
| 47 | 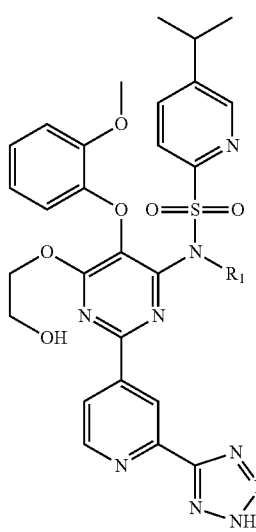 | |
| 48 | 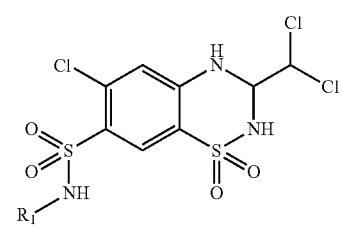 | |
| 49 | 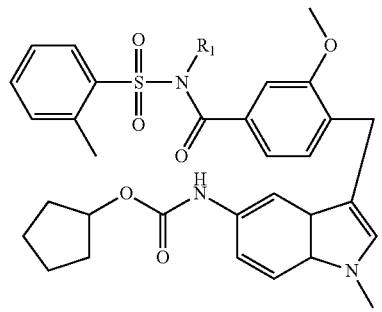 | |
| 50 | 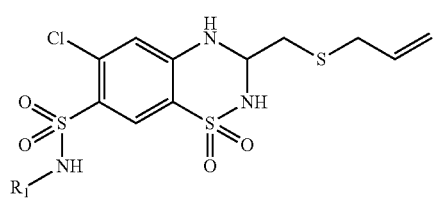 | |

TABLE III-continued
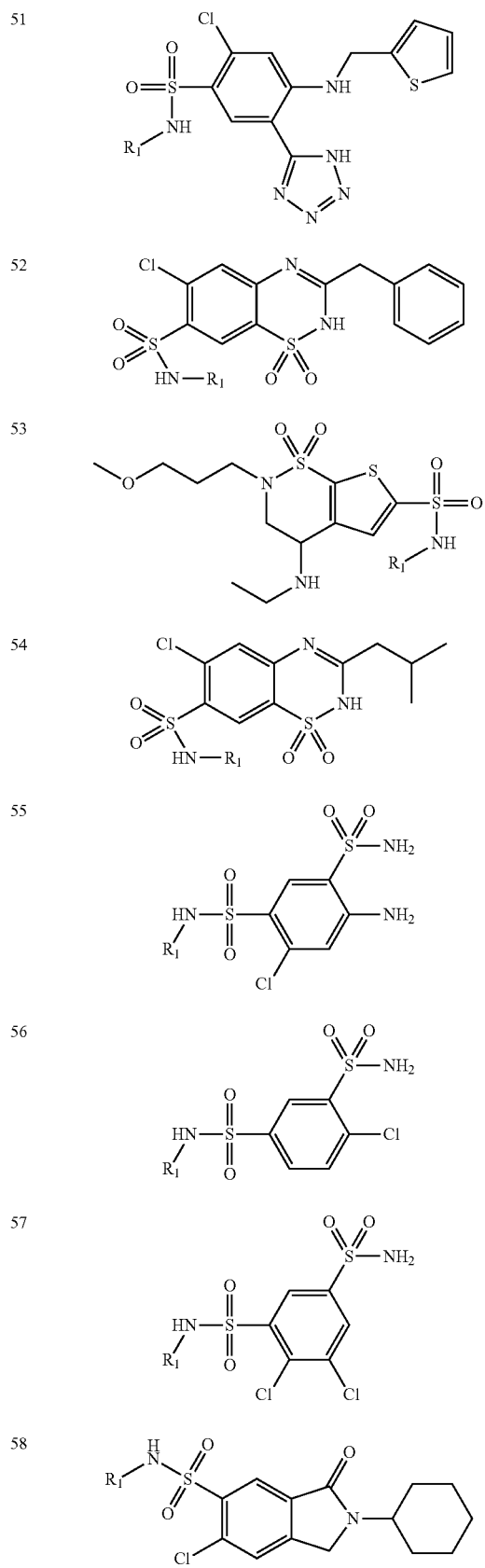
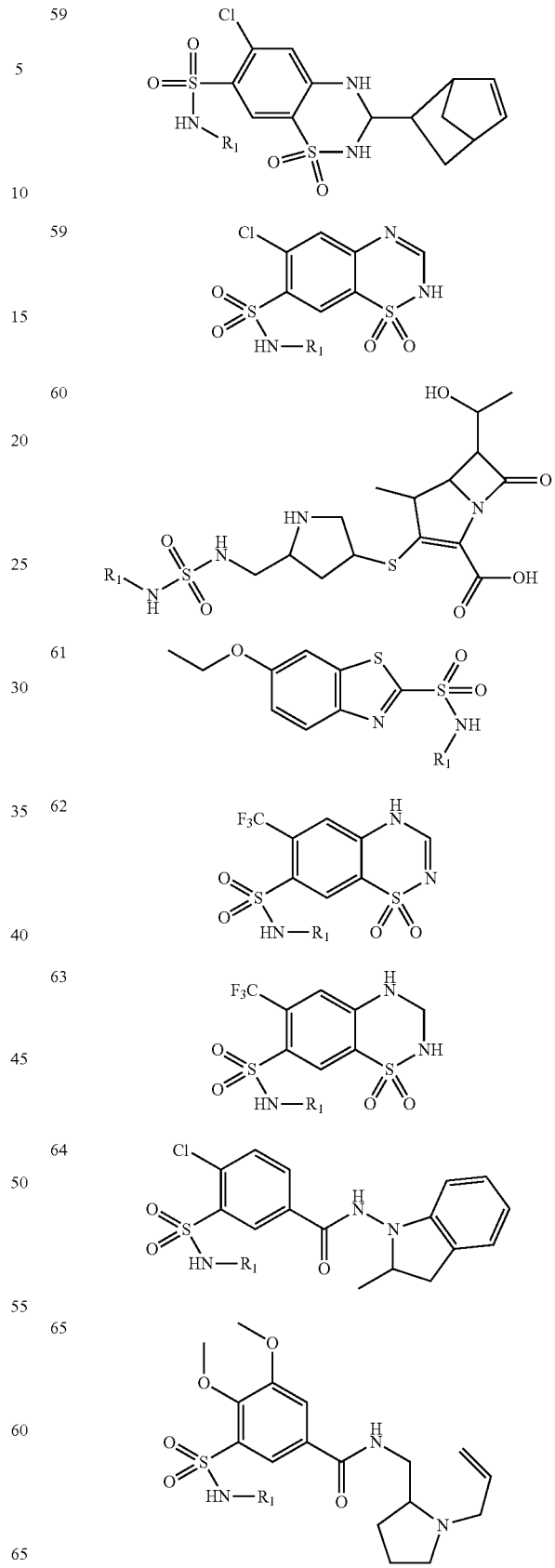

TABLE III-continued

| | |
|---|---|
| 66 | 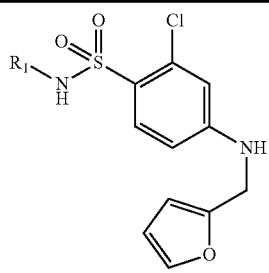 |
| 67 | 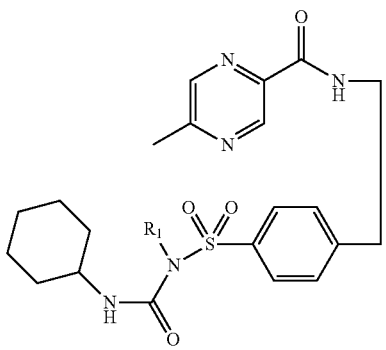 |
| 68 | 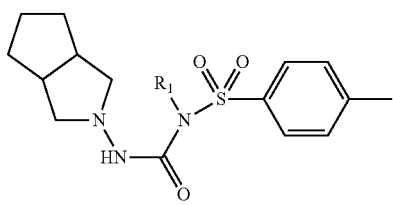 |
| 69 | 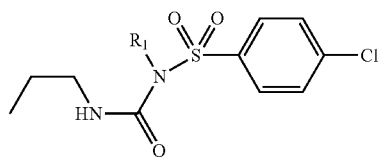 |
| 70 | 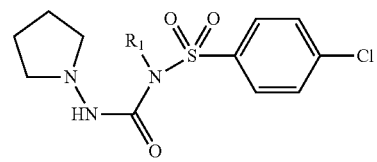 |
| 71 | 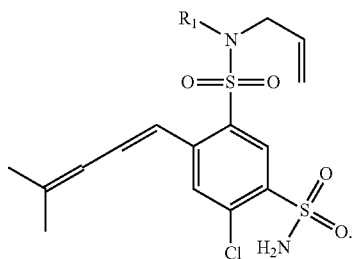 |

Chlorothiazide and hydrochlorothiazide compounds of Formula III and in particular Table III are useful for the treatment of hypertension, congestive heart failure, osteoporosis, symptomatic edema peripheral edema, kidney stones, diabetes, nephrogenic diabetes insipidus, hypercalcaemia, Dent's disease and Meniere's disease. Compounds of Formula III and Table III provide sustained release of parent drugs by cleavage of the labile $R_1$ moiety. Compounds of Formula III, for example III-63 to III-71 are useful as prodrugs for the treatment of diabetes.

Scheme 1:

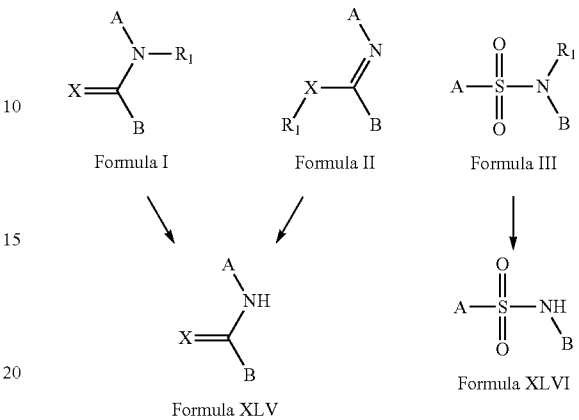

The invention further relates the sustained delivery of a compound of Formula XLV or XLVI by the administration of a compound of Formula I-III as shown in Scheme I. Upon administration of a compound of Formula I-III, the labile $R_1$ moiety may be cleaved off enzymatically, chemically or through first phase metabolism giving a compound of Formula XLV or XLVI. Without being bound to any theory, it is postulated that for some of the compounds of Formula I-III, the release of a compound of Formula XLV or XLVI upon cleavage of the $R_1$ moiety results in a therapeutically active agent. For example such active ingredient can be aripiprazole, ziprasidone or bifeprunox. In one embodiment, the sustained release comprises a therapeutically effective amount of a compound of Formula XLV or XLVI in the blood stream of the patient for a period of at least about 8, preferably at least about 12, more preferably at least about 24 and even more preferably at least about 36 hours after administration of a compound of Formula I-III. In one embodiment, the compound of Formula XLV or XLVI is present in the blood stream of the patient for a period selected from: at least 48 hours, at least 4 days, at least one week, and at least one month. In one embodiment, a compound of Formula I-III is administered by injection.

Compounds of Formula IX, X, XI, XII, XIII, XIV, XXXIII, XXXIV, XXXV, XXXVI, and XXXVII are useful for the treatment of neurological and psychological disorders. Neurological and psychiatric disorders include, but are not limited to, disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, eating disorders and conduct disorder.

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$") preferably about 7 to about 24 carbon atoms ("$C_7$-$C_{24}$"), preferably about 8 to about 24 carbon atoms ("$C_8$-$C_{24}$"), preferably about 9 to about 24 carbon atoms ("$C_9$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug", and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

The term "labile" as used herein refers to the capacity of the prodrug of the invention to undergo enzymatic and/or chemical cleavage in vivo thereby forming the parent drug. As used herein the term "prodrug" means a compounds as disclosed herein which is a labile derivative compound of a heteroaromatic NH-containing parent drug which when administered to a patient in vivo becomes cleaved by chemical and/or enzymatic hydrolysis thereby forming the parent drug such that a sufficient amount of the compound intended to be delivered to the patient is available for its intended therapeutic use in a sustained release manner.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-($\beta$) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® OR OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Additional sustained release in accordance with the invention may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

In one preferred embodiment, the formulation provides a sustained release delivery system that is capable of minimizing the exposure of the prodrug to water. This can be accomplished by formulating the prodrug with a sustained release delivery system that is a polymeric matrix capable of minimizing the diffusion of water into the matrix. Suitable polymers comprising the matrix include polylactide (PLA) polymers and the lactide/glycolide (PLGA) co-polymers.

Alternatively, the sustained release delivery system may comprise poly-anionic molecules or resins that are suitable for injection or oral delivery. Suitable polyanionic molecules include cyclodextrins and polysulfonates formulated to form a poorly soluble mass that minimizes exposure of the prodrug to water and from which the prodrug slowly leaves.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a prodrug compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect).

In accordance with the invention, the therapeutically effective amount of a prodrug of the invention is typically based on the target therapeutic amount of the parent drug. Information regarding dosing and frequency of dosing is readily available for many parent drugs from which the prodrugs of the invention are derived and the target therapeutic amount can be calculated for each prodrug of the invention. In accordance with the invention, the same dose of a prodrug of the invention provides a longer duration of therapeutic effect as compared to the parent drug. Thus if a single dose of the parent drug provides 12 hours of therapeutic effectiveness, a prodrug of that same parent drug in accordance with the invention that provides therapeutic effectiveness for greater than 12 hours will be considered to achieve a "sustained release".

The precise dose of a prodrug of the invention depends upon several factors including the nature and dose of the parent drug and the chemical characteristics of the prodrug moiety linked to the parent drug. Ultimately, the effective dose and dose frequency of a prodrug of the invention will be decided by the attending physician within the scope of sound medical judgment. The specific therapeutically effective dose level and dose frequency for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. General methodology for the preparation of lactam compounds can be found in the following publications: U.S. Pat. Nos. 7,160,888; 5,462,934; 4,914,094; 4,234,584; 4,514,401; 5,462,934; 4,468,402; WO 2006/090273 A2; WO 2008/150848 A1; WO 2006/112464 A1; WO 2008/132600 A1.

Hexyl 7-(4-(4-(2,3-dichlorophenyl)piperazin-1-yl)butoxy)-2-oxo-3,4-dihydroquinoline-1(2H)-carboxylate (Example 1, Compound 59)

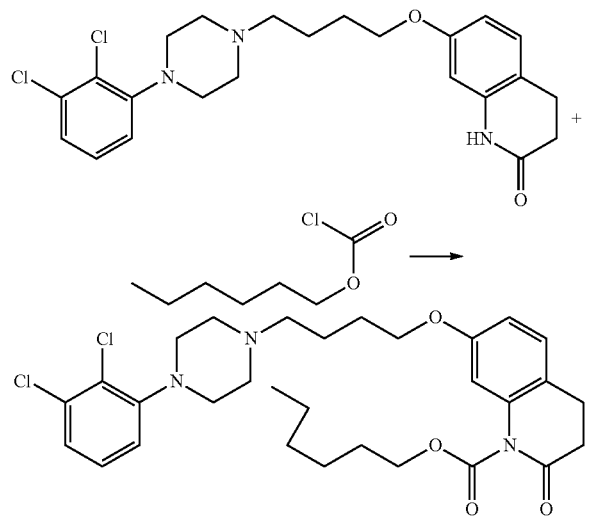

To a solution of diisopropylamine (1.11 mL, 7.87 mmol) in 2-methyltetrahydrofuran (37 mL) at −5° C. was added n-BuLi (3.0 mL, 2.5 M in hexanes, 7.49 mmol) slowly. After 20 minutes, the reaction was cooled to −78° C. and Aripiprazole (1.68 g, 3.74 mmol) was added. After a further 10 minutes, hexylchloroformate (1.53 mL, 9.37 mmol) was added. The reaction was held at −78° C. for 2 hours before allowing to warm to room temperature overnight. The reaction was quenched with saturated aqueous ammonium chloride solution (30 mL) and extracted with ethyl acetate (2×30 mL). The organics were combined, washed with saturated aqueous sodium hydrogen carbonate solution (30 mL), brine (30 mL), dried over MgSO$_4$ and concentrated. The crude product was purified by column chromatography on silica eluting with 0 to 3% tetrahydrofuran in ethyl acetate. The product was triturated in heptane to remove aliphatic impurities and then filtered and dried to afford Compound-59 (0.487 g) as a colorless solid.

$^1$H-NMR (300 MHz, CDCl$_3$) δ 7.14 (2H, m), 7.07 (1H, d), 6.95 (1H, m), 6.62 (1H, dd), 6.54 (1H, d), 4.38 (2H, t), 3.95 (2H, t), 3.06 (4H, m), 2.89 (2H, t), 2.66 (6H, m), 2.47 (2H, t), 1.90-1.65 (6H, m), 1.49-1.30 (6H, m), 0.88 (3H, t). [M+H]$^+$=576.2.

Isopropyl 7-(4-(4-(2,3-dichlorophenyl)piperazin-1-yl)butoxy)-2-oxo-3,4-dihydroquinoline-1(2H)-carboxylate (Example 2, Compound 75)

To a solution of diisopropylamine (1.11 mL, 7.87 mmol) in 2-methyltetrahydrofuran (37 mL) at −5° C. was added n-BuLi (3.0 mL, 2.5 M in hexanes, 7.49 mmol) slowly. After 20 minutes, the reaction was cooled to −78° C. and Aripiprazole (1.68 g, 3.74 mmol) was added. After a further 10 minutes, isopropylchloroformate (9.37 mL, 1.0 mol in toluene, 9.37 mmol) was added. The reaction was held at −78° C. for 2 hours before allowing to warm to room temperature overnight. The reaction was quenched with saturated aqueous ammonium chloride solution (30 mL) and extracted with ethyl acetate (2×30 mL). The organics were combined, washed with saturated aqueous sodium hydrogen carbonate solution (30 mL), brine (30 mL), dried over MgSO$_4$ and concentrated. The crude product was purified by column chromatography on silica eluting with 1:1 ethyl acetate to dichloromethane to 2% methanol in 1:1 ethyl acetate to dichloromethane to give the product. The product was recrystallized from isopropanol to remove aliphatic impurities. The product was not sufficiently pure so was purified by column chromatography eluting with 0 to 10% tetrahydrofuran in ethyl acetate. The product was triturated in heptane and filtered to afford Compound-75 (0.593 g) as a colorless solid.

$^1$H-NMR (300 MHz, CDCl$_3$) δ 7.16 (2H, m), 7.05 (1H, d), 6.95 (1H, m), 6.60 (1H, dd), 6.52 (1H, d), 5.22 (1H, quintet), 3.95 (2H, t), 3.07 (4H, m), 2.89 (2H, t), 2.66 (6H, m), 2.47 (2H, t), 1.81 (2H, m), 1.74 (2H, m), 1.42 (3H, s), 1.40 (3H, s). [M+H]$^+$=534.2.

7-(4-(4-(2,3-dichlorophenyl)piperazin-1-yl)butoxy)-N-ethyl-3,4-dihydro-2-oxoquinoline-1(2H)-carboxamide (Example 3, Compound 72)

To a solution of aripiprazole (1.5 g, 3.35 mmol) in dichloromethane (33 mL) was added triethylamine (0.56 mL, 4.01 mmol) and ethyl isocyanate (0.53 mL, 6.69 mmol). The reaction was stirred at room temperature for 5 days. The reaction was quenched with water and extracted with dichloromethane (3×20 mL). The organics were combined, washed with saturated aqueous sodium hydrogen carbonate (20 mL) and brine (20 mL), dried over MgSO$_4$ and concentrated. The product was purified by column chromatography on silica eluting with 0-3% methanol in 1:1 ethyl acetate to dichloromethane. The product was triturated in heptane to remove aliphatic impurities and then filtered and dried. The material was dissolved in ethyl acetate and washed with saturated aqueous sodium hydrogen carbonate (6×15 mL) to afford Compound-72 (0.482 g) as a pink solid.

$^1$H-NMR (300 MHz, CDCl$_3$) δ 8.44 (1H, t), 7.14 (2H, m), 7.05 (1H, d), 6.94 (2H, m), 6.65 (1H, dd), 3.96 (2H, t), 3.43 (2H, quintet), 3.07 (4H, m), 2.79 (2H, m), 2.67 (6H, m), 2.47 (2H, t), 1.80 (2H, m), 1.69 (2H, m), 1.26 (3H, t). [M+H]$^+$ =519.2.

N-benzyl-7-(4-(4-(2,3-dichlorophenyl)piperazin-1-yl)butoxy)-2-oxo-3,4-dihydroquinoline-1(2H)-carboxamide (Example 4, Compound 79)

To a solution of aripiprazole (1.5 g, 3.35 mmol) in dichloromethane (33 mL) was added triethylamine (0.56 mL, 4.01 mmol) and benzyl isocyanate (0.82 mL, 6.69 mmol). The reaction was stirred at room temperature for 48 hours. The reaction was quenched with water and extracted with dichloromethane (3×20 mL). The organics were combined, washed with brine (20 mL), dried over MgSO$_4$ and concentrated. The residue was purified by column chromatography on silica eluting with 0-10% tetrahydrofuran in ethyl acetate. The product was triturated in heptane to remove aliphatic impurities and then filtered and dried to afford Compound-79 (0.575 g) as a colorless solid.

$^1$H-NMR (300 MHz, CDCl$_3$) δ 8.90 (1H, t), 7.44-7.28 (5H, m), 7.15 (2H, m), 7.05 (1H, d), 6.97 (2H, m), 6.66 (1H, dd), 4.60 (2H, d), 3.96 (2H, t), 3.07 (4H, m), 2.81 (2H, m), 2.67 (6H, m), 2.48 (2H, t), 1.81 (2H, m), 1.69 (2H, m). [M+H]$^+$ =581.2.

7-(4-(4-(2,3-dichlorophenyl)piperazin-1-yl)butoxy)-3,4-dihydroquinolin-2-yl dibenzylcarbamate (Example 5, Compound 242)

A mixture of aripiprazole (1.5 g, 3.3 mmol), dibenzylcarbamoyl chloride (1.74 g, 6.7 mmol) silver carbonate (3.75 g, 13.4 mmol) and 2-methyltetrahydrofuran (30 mL) was heated at reflux for 4 days. The reaction mixture was cooled, diluted with ethyl acetate and water, and then filtered through celite. The organic phase was separated, dried over MgSO$_4$ and evaporated. The residue obtained was further purified on silica eluting with ethyl acetate/tetrahydrofuran to give after evaporation of the major product containing fractions, Compound-80 (1.02 g) was a yellow oil.

$^1$H-NMR (300 MHz, CDCl$_3$) δ 7.44-7.21 (m, 8H), 7.20-7.10 (m, 4H), 7.04 (d, 1H), 7.00-6.93 (m, 1H), 6.57 (dd, 1H), 6.40 (d, 1H), 4.80 (d, 1H), 4.54 (d, 1H), 4.35 (d, 1H), 4.26 (d, 1H), 3.90-3.81 (m, 1H), 3.74-3.67 (m, 1H), 3.15-3.03 (m, 4H), 2.92-2.80 (m, 2H), 2.75-2.60 (m, 6H), 2.65 (t, 2H), 2.84-2.63 (m, 4H). [M+H]$^+$=671.3.

7-(4-(4-(2,3-dichlorophenyl)piperazin-1-yl)butoxy)-3,4-dihydroquinolin-2-yl diethylcarbamate (Example 6, Compound 234)

Compound-51 was synthesized in a similar manner to Compound-80, (0.80 g) as a yellow oil.

$^1$H-NMR (300 MHz, CDCl$_3$) δ 7.17-7.12 (2H, m), 7.07 (d, 1H), 7.99-7.92 (m, 1H), 6.57 (dd, 1H), 6.39 (dd, 1H), 4.00-3.85 (m, 2H), 3.76-3.62 (m, 2H), 3.54-3.40 (m, 2H), 3.25-3.15 (m, 2H), 3.12-3.01 (m, 4H), 2.92 (t, 2H), 2.76-2.56 (m, 6H), 2.47 (t, 2H), 1.84-1.60 (m, 4H), 1.31 (t, 3H), 1.10 (t, 3H). [M+H]$^+$=547.2.

Methyl 7-(4-(4-(2,3-dichlorophenyl)piperazin-1-yl)butoxy)-2-oxo-3,4-dihydroquinoline-1(2H)-carboxylate (Example 7, Compound 74)

To a solution of diisopropylamine (0.99 mL, 7.02 mmol) in 2-methyltetrahydrfuran (33 mL) at –5° C. was added n-BuLi (2.67 mL, 2.5 M in hexanes, 6.69 mmol) slowly. After 20 minutes, the reaction was cooled to –78° C. and aripiprazole (1.50 g, 3.34 mmol) was added. After a further 10 minutes, methylchloroformate (0.65 mL, 8.36 mmol) was added. The reaction was held at –78° C. for 2 hours before allowing to warm to room temperature. After 2 hours the reaction was quenched with saturated aqueous ammonium chloride solution (30 mL) and extracted with ethyl acetate (2×30 mL). The organics were combined, washed with saturated aqueous sodium hydrogen carbonate solution (30 mL), brine (30 mL), dried over MgSO$_4$ and concentrated. The crude product was purified by column chromatography on silica eluting with 1:1 ethyl acetate to dichloromethane to 10% methanol in 1:1 ethyl acetate to dichloromethane to give the product. The product was triturated in heptane to remove aliphatic impurities and then filtered to afford Compound-74 (0.824 g) as a colorless solid.

$^1$H-NMR (300 MHz, CDCl$_3$) δ 7.15 (2H, m), 7.06 (1H, d), 6.95 (1H, m), 6.63 (1H, dd), 6.56 (1H, d), 3.99 (3H, s), 3.95 (2H, t), 3.07 (4H, m), 2.89 (2H, t), 2.67 (6H, m), 2.48 (2H, t), 1.81 (2H, m), 1.72 (2H, m). [M+H]$^+$=506.1.

7-(4-(4-(2,3-dichlorophenyl)piperazin-1-yl)butoxy)-1-isobutyryl-3,4-dihydroquinolin-2(1H)-one (Example 8, Compound-16)

To a solution of diisopropylamine (1.3 mL, 8.9 mmol) in tetrahydrofuran (25 mL) at 78° C. was added n-BuLi (2.2M in hexanes, 4.1 mL, 8.9 mmol). The reaction mixture was warmed to 0° C. and after 10 min was re-cooled to 78° C. and aripiprazole (2.0 g, 4.5 mmol) added. The reaction mixture was stirred for 30 min and then isobutyryl chloride (0.7 mL, 6.7 mmol) added. After 2 h the reaction mixture was warmed to room temperature and stirred for 1 h. A second reaction was carried out under exactly the same conditions and the two reactions were combined. This mixture was washed with water, dried over MgSO$_4$, filtered and evaporated. The residue was dissolved in diethyl ether and 4M HCl in diethyl ether added to form a precipitate. The mother liquor was decanted and the residual gum was washed with diethyl ether. The gum was then partitioned between ethyl acetate and saturated sodium bicarbonate, and the organic layer separated. After drying over MgSO$_4$ and evaporation, the residue was further purified on silica eluting with 1:1:0.1 dichloromethane/ethyl acetate/methanol to give Compound-16 (1.3 g) as a yellow solid.

$^1$H-NMR (300 MHz, CDCl$_3$) δ 7.16-7.13 (m, 2H), 7.08 (d, 1H), 6.98-6.92 (m, 1H), 6.65-6.59 (m, 2H), 3.93 (t, 2H), 3.48 (dt, 1H), 3.12-3.01 (m, 4H), 2.86 (dd, 1H), 2.72-2.59 (m, 6H), 2.47 (t, 2H), 1.84-1.64 (m, 4H), 1.25 (d, 6H). [M+H]$^+$=518.2.

7-(4-(4-(2,3-dichlorophenyl)piperazin-1-yl)butoxy)-3,4-dihydroquinolin-2-yl pivalate (Example 9, Compound-216)

To a stirred solution of aripiprazole (0.1 g, 0.223 mmol) in pyridine (1 mL) at 0° C. was added pivaloyl chloride (0.055 mL, 0.446 mmol). After stirring at 0° C. for 5 minutes the reaction was allowed to warm to room temperature. After a further 5 minutes the temperature was increased to 50° C. for approximately 19 hours. The reaction was allowed to cool to room temperature. The reaction was repeated in a similar manner using of aripiprazole (1.75 g, 3.90 mmol). The two reaction mixtures were combined and quenched with approximately methanol (5 mL). The majority of the pyridine was removed in vacuo and the residue partitioned between dichloromethane (30 mL) and saturated NaHCO$_3$ solution (30 mL). The aqueous phase was extracted with dichloromethane (2×30 mL) and the combined organic extracts washed with brine (20 mL) and dried over MgSO$_4$. After filtration, the volatiles were removed (toluene and methanol/dichloromethane azeotrope) and the residue purified by silica chromatography eluting first with dichloromethane followed by ethyl acetate/dichloromethane/methanol (1:1:0.04) to give the title compound (1.19 g, 54%).

$^1$H NMR (CDCl$_3$, 300 MHz) δ 7.13-7.17 (m, 2H), 7.09 (d, 1H), 6.99-6.92 (m, 1H), 6.57 (dd, 1H), 6.24 (d, 1H), 3.90 (t, 2H), 3.2-3.0 (m, 4H), 2.94-2.83 (m, 2H), 2.78-2.4 (m, 8H), 1.85-1.45 (m, 4H), 1.3 (s, 9H); m/z (M$^+$H) 532.26.

7-(4-(4-(2,3-dichlorophenyl)piperazin-1-yl)butoxy)-1-hexanoyl-3,4-dihydroquinolin-2(1H)-one (Example 10, Compound-4)

To a stirred solution of diisopropylamine (1.26 mL, 8.92 mmol) in 2-methyltetrahydrofuran (40 mL) at −7° C. was added 1.47 M butyl lithium in hexanes (6.07 mL, 8.92 mmol) dropwise keeping the temperature between 0° C. and 5° C. After stirring at −7° C. for 20 minutes the reaction was cooled to −78° C. A suspension of aripiprazole (2 g, 4.46 mmol) in 2-methyltetrahydrofuran (40 mL) was added to the lithium diisopropylamide (LDA) solution keeping the temperature below −65° C. After 10 minutes hexanoic anhydride (2.58 mL, 11.15 mmol) was added dropwise and the reaction stirred at −78° C. under argon gas. After 2.5 hours the reaction was allowed to warm to room temperature (removal of bath). After a further 40 minutes the reaction was quenched with saturated aqueous NH$_4$Cl (50 mL) and diluted with ethyl acetate (100 mL). The aqueous layer was extracted with ethyl acetate (2×50 mL) and the combined organics washed with water (50 mL), saturated aqueous NaHCO$_3$ (3×50 mL), brine (50 mL) and dried over MgSO$_4$. After filtration, the volatiles were removed. The crude mixture was purified by silica chromatography eluting with 1% methanol (1:1 ethyl acetate/dichloromethane). This material was further purified by partitioning between ethyl acetate (50 mL) and sat. aqueous NaHCO$_3$ (50 mL). The organic layer was washed with sat. aqueous NaHCO$_3$ (2×50 mL), brine (50 mL) and dried over MgSO$_4$. After filtration, the volatiles were removed to give Compound-4, 0.95 g.

$^1$H-NMR (300 MHz, CDCl$_3$) δ 7.18-7.12 (2H, m), 7.12-7.05 (1H, m), 6.99-6.92 (1H, m), 6.81 (1H, d), 6.66 (1H, dd), 3.95 (2H, t), 3.13-3.01 (4H, bs), 2.97 (2H, t), 2.87-2.78 (2H, m), 2.74-2.57 (6H, m), 2.48 (2H, t), 1.87-1.64 (6H, m), 1.43-1.29 (4H, m), 0.90 (3H, m). m/z [M+H] 546.1.

7-(4-(4-(2,3-dichlorophenyl)piperazin-1-yl)butoxy)-1-dodecanoyl-3,4-dihydroquinolin-2(1H)-one (Example 11, Compound-7)

Compound-7 was synthesized in a similar manner to Compound-4 in Example 10. $^1$H-NMR (300 MHz, CDCl$_3$) δ 7.18-7.12 (2H, m), 7.12-7.05 (1H, m), 6.99-6.92 (1H, m), 6.81 (1H, d), 6.65 (1H, dd), 3.95 (2H, t), 3.17-3.01 (4H, bs), 2.97 (2H, t), 2.88-2.78 (2H, m), 2.75-2.56 (6H, m), 2.49 (2H, bt), 1.87-1.56 (6H, m), 1.45-1.17 (16H, m), 0.87 (3H, t) m/z [M+H] 629.9.

7-(4-(4-(2,3-dichlorophenyl)piperazin-1-yl)butoxy) quinolin-2-yl hexyl carbonate (Example 12, Compound-328)

To a mixture of dehydro-aripiprazole (1.5 g, 3.4 mmol), potassium tert-butoxide (0.75 g, 6.7 mmol) and 2-methyltetrahydrofuran (30 mL) at 0° C. was added hexyl chloroformate (1.32 mL, 8.1 mmol). The reaction mixture was stirred for 2 h, allowed to self warm to room temperature and stirred for a further 4 h. The reaction mixture was then diluted with water and extracted with ethyl acetate. The organic phase was dried over MgSO$_4$, filtered and evaporated. The residue was further purified on silica eluting with ethyl acetate/tetrahydrofuran and the major product containing fractions evaporated to give a yellow solid. This was triturated in heptane (30 mL) for 2.5 h, filtered and dried to give Compound-328 (1.55 g) as a white solid.

$^1$H-NMR (300 MHz, CDCl$_3$) δ 8.15 (d, 1H), 7.71 (d, 1H), 7.32 (d, 1H), 7.21-7.12 (m, 3H), 7.09 (d, 1H), 6.97-6.91 (m, 1H), 4.29 (t, 1H), 4.13 (t, 1H), 3.12-3.01 (m, 4H), 2.73-2.55 (m, 4H), 2.50 (t, 2H), 1.95-1.85 (m, 2H), 1.82-1.70 (m, 4H), 1.50-1.28 (m, 6H), 0.94-0.86 (m, 3H). [M+H]$^+$=574.2.

7-(4-(4-(2,3-dichlorophenyl)piperazin-1-yl)butoxy) quinolin-2-yl isopropyl carbonate (Example 13, Compound-323)

Compound-323 was synthesized in a similar manner as Compound-328 in Example 12.

$^1$H-NMR (300 MHz, CDCl$_3$) δ 8.14 (d, 1H), 7.70 (d, 1H), 7.32 (d, 1H), 7.20-7.12 (m, 3H), 7.07 (d, 1H), 6.97-6.91 (m, 1H), 5.16-4.98 (m, 1H), 4.13 (t, 2H), 3.11-3.02 (m, 4H), 2.72-2.59 (m, 4H), 2.50 (t, 2H), 1.94-1.84 (m, 2H), 1.80-1.68 (m, 2H), 1.40 (d, 6H). [M+H]$^+$=532.1.

7-(4-(4-(2,3-dichlorophenyl)piperazin-1-yl)butoxy) quinolin-2-yl diethylcarbamate (Example 14, Compound-334)

A mixture of dehydro-aripiprazole (1.50 g, 3.36 mmol), triethylamine (1.03 mL, 7.39 mmol), diethyl carbamoyl chloride (1.02 mL) were combined in tetrahydrofuran (30 mL). This was then heated to 100° C. for 6 hours by microwave. The reaction was quenched with water (50 mL) and extracted with dichloromethane (2×100 mL). The combined organics were dried (MgSO$_4$) and concentrated. The crude product was purified by column chromatrography on silica eluting with ethyl acetate to 20% tetrahydrofuran/ethyl acetate to give the product. The product was then triturated with heptane to remove aliphatic impurities and then dried to give Compound-334 (1.54 g) as a light brown oil.

$^1$H-NMR (300 MHz, CDCl$_3$) δ 8.10 (1H, d), 7.69 (1H, d), 7.31 (1H, d), 7.16-7.07 (4H, m), 6.99-6.92 (1H, m), 4.12 (2H, t), 3.54-3.39 (4H, 2×q), 3.12-2.96 (4H, br s), 2.78-2.54 (4H, br s), 2.50 (2H, t), 1.97-1.62 (4H, m), 1.32-1.16 (6H, 2×t). [M+H]$^+$=545.2.

N,N-diethyl-7-(4-(4-(2,3-dichlorophenyl)piperazin-1-yl)butoxy)-2-oxoquinoline-1(2H)-carboxamide (Example 15, Compound-150)

Compound-334 was synthesized as described above. Compound-334 (2.17 g, 3.99 mmol) was dissolved in pyridine (10 mL) and heated in the microwave to 175° C. for 5 hours. The reaction was diluted with ethyl acetate (10 mL) and concentrated, co-evaporating with toluene (3×5 mL). The product was purified by column chromatography on silica eluting with 10 to 30% tetrahydrofuran in ethyl acetate to provide Compound-150 (0.81 g) as a yellow oil.

$^1$H-NMR (300 MHz, CDCl$_3$) δ 7.64 (1H, d), 7.45 (1H, d), 7.16 (2H, m), 6.96 (1H, m), 6.89 (1H, dd), 6.54 (1H, d), 6.47 (1H, d), 4.04 (2H, m), 3.78 (1H, m), 3.57 (1H, m), 3.28-3.00

(6H, m), 2.66 (4H, m), 2.49 (2H, m), 1.85 (2H, m), 1.72 (2H, m), 1.39 (3H, t), 1.08 (3H, t). [M+H]⁺=545.2.

7-(4-(4-(2,3-dichlorophenyl)piperazin-1-yl)butoxy) quinolin-2-yl dibenzylcarbamate (Example 16, Compound-342)

To a solution of dibenzylcarbamoyl chloride (1.7 g, 6.7 mmol) in pyridine (15 mL) was added dehydro-aripiprazole (1.5 g, 3.4 mmol) and the reaction mixture heated at reflux for 4 h. The reaction mixture was concentrated and the residue co-evaporated with toluene (×3). The residue was dissolved in ethyl acetate (ethyl acetate), washed with water and dried over MgSO₄. After evaporation the residue was further purified on silica eluting with ethyl acetate and after drying gave Compound-342 (0.71 g) as a white solid.
¹H-NMR (300 MHz, CDCl₃) δ 8.13 (d, 1H), 7.70 (d, 1H), 7.42-7.29 (m, 11H), 7.20-7.08 (m, 4H), 7.00-6.92 (m, 1H), 4.64 (s, 2H), 4.56 (s, 2H), 4.14 (t, 2H), 3.15-3.02 (m, 4H), 2.74-2.60 (m, 4H), 2.58-2.48 (m, 2H), 1.98-1.88 (m, 2H), 1.83-1.70 (m, 2H). [M+H]⁺=669.1.

N,N-dibenzyl-7-(4-(4-(2,3-dichlorophenyl)piperazin-1-yl)butoxy)-2-oxoquinoline-1(2H)-carboxamide (Example 17, Compound-179)

A solution of Compound-342 (0.94 g, 1.4 mmol) in pyridine (10 mL) was heated in a microwave at 175° C. for 10 h. The reaction mixture was evaporated and then co-evaporated with toluene. The residue was further purified on silica eluting with ethyl acetate to give after evaporation of the product containing fractions, Compound-179 (0.36 g) as a yellow oil.
¹H-NMR (300 MHz, CDCl₃) δ 7.65 (1H, d), 7.51 (2H, d), 7.39 (5H, m), 7.23 (2H, m), 7.16 (4H, m), 6.96 (1H, m), 6.77 (1H, dd), 6.50 (1H, d), 6.39 (1H, s), 4.89 (1H, d), 4.64 (1H, d), 4.27 (2H, d), 3.85 (1H, m), 3.65 (1H, m), 3.10 (4H, m), 2.68 (4H, m), 2.52 (2H, m), 1.79 (2H, m), 1.72 (2H, m). [M+H]⁺=669.1.

7-(4-(4-(2,3-dichlorophenyl)piperazin-1-yl)butoxy) quinolin-2-yl diethyl phosphate (Example 18, Compound-331)

To a solution of dibenzyl phosphate (2.48 g, 8.91 mmol) in dichloromethane (25 ml) was added N,N-dimethyl formamide (1 drop) followed by oxalyl chloride (0.75 mL, 8.91 mmol). After 2 hours the reaction mixture was concentrated in vacuo. The residue was dissolved in 2-methyltetrahydrfuran (5 mL) and added to a suspension of dehydro-aripiprazole (1.66 g, 3.71 mmol) and potassium t-butoxide (0.92 g, 8.17 mmol) in 2-methyltetrahydrfuran (35 mL) at 0° C. under argon gas, then allowed to gradually warm to room temperature. After stirring overnight the reaction was quenched with water (25 mL) and 28% aq NH₃ (15 mL) and stirred for 10 minutes. The reaction mixture was then extracted with ethyl acetate (2×40 mL). The combined organics were washed with water (50 mL) and brine (50 mL) then dried (MgSO₄) and concentrated in vacuo. The crude mixture was purified by column chromatography eluting with 5% methanol (1:1 ethyl acetate/dichloromethane) to give the product. The 1H-NMR showed minor impurities still present (impurities not observed by LCMS). Various further purifications were attempted but failed to remove these impurities.
¹H-NMR (300 MHz, CDCl₃) δ 8.04 (1H, d), 7.65 (1H, d), 7.44-7.10 (14H, m), 6.95 (2H, m), 5.33 (4H, m), 4.09 (2H, t), 3.06 (4H, m), 2.65 (4H, m), 2.50 (2H, t), 1.90 (2H, m), 1.74 (2H, m). [M+H]⁺ 707.8.

7-(4-(4-(2,3-dichlorophenyl)piperazin-1-yl)butoxy) quinolin-2-yl dibenzyl phosphate (Example 19, Compound-322)

To a solution of dibenzyl phosphate (2.48 g, 8.91 mmol) in dichloromethane (25 ml) was added dimethyl formamide (1 drop) followed by oxalyl chloride (0.75 mL, 8.91 mmol). After 2 hours the reaction mixture was concentrated in vacuo. The residue was dissolved in 2-methyltetrahydrfuran (5 mL) and added to a suspension of dehydro-aripiprazole (1.66 g, 3.71 mmol) and potassium t-butoxide (0.92 g, 8.17 mmol) in 2-methyltetrahydrfuran (35 mL) at 0° C. under Ar (g) then allowed to gradually warm to room temperature. After stirring overnight the reaction was quenched with water (25 mL) and 28% aq NH₃ (15 mL) and stirred for 10 minutes. The reaction mixture was then extracted with ethyl acetate (2×40 mL). The combined organics were washed with water (50 mL) and brine (50 mL) then dried (MgSO₄) and concentrated in vacuo. The crude mixture was purified by column chromatography eluting with 5% methanol (1:1 ethyl acetate/dichloromethane) to give the product. The 1H-NMR showed minor impurities still present (impurities not observed by LCMS). Various further purifications were attempted but failed to remove these impurities.
1H-NMR (300 MHz, CDCl3) δ 8.04 (1H, d), 7.65 (1H, d), 7.44-7.10 (14H, m), 6.95 (2H, m), 5.33 (4H, m), 4.09 (2H, t), 3.06 (4H, m), 2.65 (4H, m), 2.50 (2H, t), 1.90 (2H, m), 1.74 (2H, m). [M+H]+707.8.

7-(4-(4-(2,3-dichlorophenyl)piperazin-1-yl)butoxy) quinolin-2-yl pivalate (Example 20, Compound-316)

To a solution of dehydro-aripiprazole (1.2 g, 2.7 mmol) in dichloromethane (30 mL) was added pyridine (1 mL), followed by pivaloyl chloride (0.66 mL, 5.4 mmol). The reaction mixture was stirred for 20 hours, then washed with water and dried over MgSO₄. After evaporation the residue was co-evaporated with toluene and then further purified on silica eluting with ethyl acetate. After evaporation of the product containing fraction, Compound-316 (0.53 g) was obtained as a colourless oil.
¹H-NMR (300 MHz, CDCl₃) δ 8.12 (d, 1H), 7.70 (d, 1H), 7.34 (d, 1H), 7.20-7.11 (m, 3H), 7.00-6.92 (m, 2H), 4.12 (t, 2H), 3.18-3.02 (m, 4H), 2.77-2.45 (m, 6H), 1.95-1.85 (m, 2H), 1.83-1.72 (m, 2H), 1.42 (s, 9H). [M+H]⁺ 530.1.

Acetoxymethyl 7-(4-(4-(2,3-dichlorophenyl)piperazin-1-yl)butoxy)-2-oxo-3,4-dihydroquinoline-1 (2H)-carboxylate (Example 21, Compound-87)

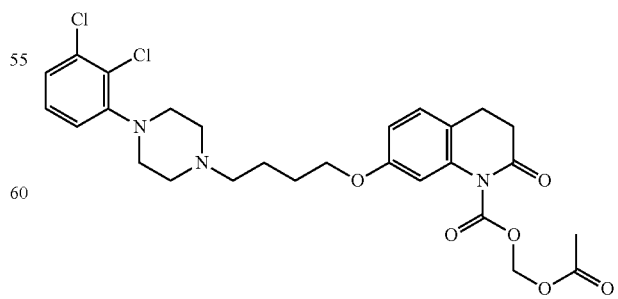

The reactions were carried out in 2×1 g batches side by side.

To a suspension of aripiprazole (2 g, 4.46 mmol) in 2-methyltetrahydrofuran (40 mL) was added NaH (357 mg, 8.92 mmol). After 20 minutes, further 2-methyltetrahydrofuran (20 mL) was added to aid stirring. Chloromethyl chloroformate (1.19 mL, 13.38 mmol) was then added and the reaction stirred for 2 days. The reactions were combined for work up. The reaction was cooled to 0° C., diluted with ethyl acetate (50 mL) and quenched with aqueous saturated NaHCO$_3$ solution (50 mL). The reaction was extracted with ethyl acetate (3×50 mL) and the combined organics washed with brine (100 mL), then dried (MgSO$_4$) and concentrated to give chloromethyl 7-(4-(4-(2,3-dichlorophenyl)piperazin-1-yl)butoxy)-2-oxo-3,4-dihydroquinoline-1(2H)-carboxylate (crude yield 2.59 g) as 3:2 mixture of product/aripiprazole. The product was not purified due to instability during silica chromatography and so taken onto the next step crude.

Synthesis of Compound 87

To a solution of chloromethyl 7-(4-(4-(2,3-dichlorophenyl)piperazin-1-yl)butoxy)-2-oxo-3,4-dihydroquinoline-1(2H)-carboxylate (1.20 g, 2.22 mmol) in dimethyl formamide (20 mL) was added cesium acetate (639 mg, 3.33 mmol). The reaction was then stirred at ambient temperature overnight. The reaction was diluted with ethyl acetate (50 mL) and quenched with water/brine (1:1, 50 mL). The reaction was extracted with ethyl acetate (3×50 mL). The combined organics were washed with water (50 mL) then brine (50 mL) and dried (MgSO$_4$) and concentrated. The crude product was purified by column chromatography on silica eluting with 0-10% tetrahydrofuran/dichloromethane with 1% Et$_3$N to give the product which required further purification. The product was purified by column chromatography on silica eluting with 0.5% Et$_3$N/ethyl acetate to give acetoxymethyl 7-(4-(4-(2,3-dichlorophenyl)piperazin-1-yl)butoxy)-2-oxo-3,4-dihydroquinoline-1(2H)-carboxylate, Compound-87 (243 mg, 19% over 2 steps).

$^1$H-NMR (300 MHz, CDCl$_3$) δ 7.17-7.08 (3H, m), 6.99-6.89 (1H, m), 6.66-6.58 (2H, m), 5.95 (2H, s), 3.96 (2H, t), 3.12-3.01 (4H, m), 2.89-2.85 (2H, m), 2.69-2.65 (6H, m), 2.50-2.45 (2H, m), 2.17 (3H, s), 1.86-1.59 (4H, m). [M+H]$^+$ =564.17.

Butyryloxymethyl 7-(4-(4-(2,3-dichlorophenyl)piperazin-1-yl)butoxy)-2-oxo-3,4-dihydroquinoline-1(2H)-carboxylate (Example 22, Compound-88)

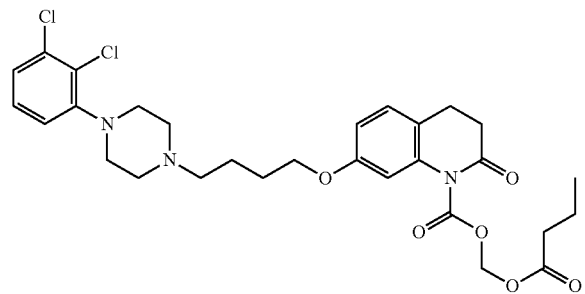 [SMILES: CCCC(=O)OCOC(=O)N1C(=O)CCc2ccc(OCCCCN3CCN(c4cccc(Cl)c4Cl)CC3)cc21]

To a solution of chloromethyl 7-(4-(4-(2,3-dichlorophenyl)piperazin-1-yl)butoxy)-2-oxo-3,4-dihydroquinoline-1(2H)-carboxylate (1.20 g, 2.22 mmol) in dimethyl formamide (20 mL) was added butyric acid (0.30 mL, 3.33 mmol) followed by cesium carbonate (542 mg, 1.67 mmol). The reaction was then stirred at ambient temperature overnight. The reaction was diluted with ethyl acetate (50 mL) and quenched with water/brine (1:1, 50 mL). The reaction was extracted with ethyl acetate (3×50 mL). The combined organics were washed with water (50 mL) then brine (50 mL) and dried (MgSO$_4$) and concentrated. The crude product was purified by column chromatography on silica eluting with 010% tetrahydrofuran/dichloromethane with 1% Et$_3$N to give the product which required further purification. The product was purified by column chromatography on silica eluting with 0.51.5% Et$_3$N/ethyl acetate to give butyryloxymethyl 7-(4-(4-(2,3-dichlorophenyl)piperazin-1-yl)butoxy)-2-oxo-3,4-dihydroquinoline-1(2H)-carboxylate, Compound-88 (348 mg, 26% over 2 steps).

$^1$H-NMR (300 MHz, CDCl$_3$) δ 7.17-7.07 (3H, m), 7.01-6.89 (1H, m), 6.66-6.58 (2H, m), 5.97-5.92 (2H, m), 3.96 (2H, t), 3.07-2.99 (4H, m), 2.89-2.84 (2H, m), 2.70-2.58 (6H, m), 2.51-2.37 (4H, m), 1.86-1.61 (6H, m), 0.96 (3H, m). [M+H]$^+$ =592.28.

Palmitoyloxymethyl 7-(4-(4-(2,3-dichlorophenyl)piperazin-1-yl)butoxy)-2-oxo-3,4-dihydroquinoline-1(2H)-carboxylate (Example 23, Compound-89)

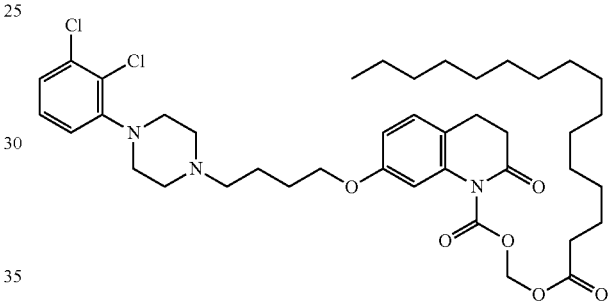

Synthesis of chloromethyl 7-(4-(4-(2,3-dichlorophenyl)piperazin-1-yl)butoxy)-2-oxo-3,4-dihydroquinoline-1(2H)-carboxylate To a suspension of aripiprazole (1 g, 2.23 mmol) in 2-methyltetrahydrofuran (20 mL) was added NaH (178 mg, 4.46 mmol). After 1 hour, a further of NaH (178 mg) was added. The reaction was stirred at ambient temperature overnight then heated to reflux for 3 hours. The reaction was cooled to room temperature and chloromethyl chloroformate (0.60 mL, 6.69 mmol) was then added and the reaction stirred for 2 hours. The reaction was cooled to 0° C., diluted with ethyl acetate (20 mL) and quenched with aqueous saturated NaHCO$_3$ solution (20 mL). The reaction was extracted with ethyl acetate (3×20 mL) and the combined organics washed with brine (50 mL), then dried (MgSO$_4$) and concentrated to give chloromethyl 7-(4-(4-(2,3-dichlorophenyl)piperazin-1-yl)butoxy)-2-oxo-3,4-dihydroquinoline-1(2H)-carboxylate (crude yield 1.54 g) as a 2:1 mixture of product/aripiprazole. The product was taken onto the next step crude.

Synthesis of Compound-89

To a solution of chloromethyl 7-(4-(4-(2,3-dichlorophenyl)piperazin-1-yl)butoxy)-2-oxo-3,4-dihydroquinoline-1(2H)-carboxylate (1.16 g, 2.14 mmol) in dimethyl formamide (20 mL) was added palmitic acid (825 mg, 3.22 mmol) and cesium carbonate (524 mg, 1.61 mmol). The reaction was heated to 60° C. for 5 hours then allowed to cool to room temperature. The reaction was diluted with ethyl acetate (20 mL) and washed with 1:1 water/brine (3×40 mL). The organics were filtered to remove a white precipitate then dried (MgSO$_4$) and concentrated. The crude product was purified by column chromatography on silica eluting with 0.5% Et$_3$N/ethyl acetate to give palmitoyloxymethyl 7-(4-(4-(2,3-dichlorophenyl)piperazin-1-yl)butoxy)-2-oxo-3,4-dihydroquinoline-1(2H)-carboxylate, Compound-89 (548 mg, 32% over 2 steps). The material was determined to be 83% pure by LCMS.

$^1$H-NMR (300 MHz, CDCl$_3$) δ 7.17-7.07 (3H, m), 6.99-6.93 (1H, m), 6.67-6.59 (2H, m), 5.96-5.91 (2H, m), 3.96 (2H, t), 3.11-3.03 (4H, m), 2.92-2.83 (2H, m), 2.70-2.65 (6H, m), 2.52-2.38 (4H, m), 1.83-1.57 (6H, m), 1.35-1.15 (24H, m), 0.87 (3H, t). [M+H]$^+$=760.48.

1-(butyryloxy)ethyl 7-(4-(4-(2,3-dichlorophenyl)piperazin-1-yl)butoxy)-2-oxo-3,4-dihydroquinoline-1(2H)-carboxylate) (Example 24, Compound-90)

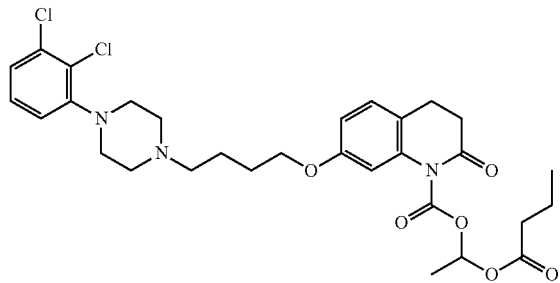 [SMILES: CCCC(=O)OC(C)OC(=O)N1C(=O)CCc2ccc(OCCCCN3CCN(c4cccc(Cl)c4Cl)CC3)cc21]

Synthesis of 1-chloroethyl 7-(4-(4-(2,3-dichlorophenyl)piperazin-1-yl)butoxy)-2-oxo-3,4-dihydroquinoline-1(2H)-carboxylate To a suspension of aripiprazole (2.0 g, 4.46 mmol) in 2-methyltetrahydrofuran (50 mL) was added NaH (357 mg, 8.92 mmol). The reaction was stirred overnight at room temperature then chloroethyl chloroformate (1.46 mL, 13.38 mmol) was added. Further 2-methyltetrahydrofuran (10 mL) was added to aid stirring. The reaction was stirred overnight at room temperature. The reaction was cooled to 0° C., diluted with ethyl acetate (50 mL) and quenched with aqueous saturated NaHCO$_3$ (50 mL). The reaction was extracted with ethyl acetate (3×50 mL). The combined organics were dried (MgSO$_4$) and concentrated to give 1-chloroethyl 7-(4-(4-(2,3-dichlorophenyl)piperazin-1-yl)butoxy)-2-oxo-3,4-dihydroquinoline-1(2H)-carboxylate (crude yield 2.22 g) as a 3:2 mixture of aripiprazole/product. The product was taken onto the next step without purification.

Synthesis of Compound-90

1-chloroethyl 7-(4-(4-(2,3-dichlorophenyl)piperazin-1-yl)butoxy)-2-oxo-3,4-dihydroquinoline-1(2H)-carboxylate (2.0 g, 3.60 mmol) was stirred with butyric acid (1.0 mL, 10.81 mmol) and ethyldiisopropylamine (0.94 mL, 5.41 mmol) at 50° C. for 48 hours. The reaction was diluted with diethyl ether (20 mL) and quenched with aqueous saturated NaHCO$_3$ (40 mL). The reaction was extracted with ethyl acetate (2×50 mL) and the combined organics were washed with water (50 mL), brine (50 mL) then dried (MgSO$_4$). The crude product was purified by column chromatography on silica eluting with 0.5% Et$_3$N/ethyl acetate to give 1-(butyryloxy)ethyl 7-(4-(4-(2,3-dichlorophenyl)piperazin-1-yl)butoxy)-2-oxo-3,4-dihydroquinoline-1(2H)-carboxylate, Compound-90 (628 mg, 23% over 2 steps).

$^1$H-NMR (300 MHz, CDCl$_3$) δ 7.18-6.89 (5H, m), 6.67-6.58 (2H, m), 4.01-3.93 (2H, m), 3.11-2.99 (4H, m), 2.94-2.83 (2H, m), 2.69-2.57 (6H, m), 2.53-2.47 (2H, m), 2.38-2.27 (3H, m), 1.91-1.60 (9H, m). [M+H]$^+$=606.5.

1-(butyryloxy)ethyl 7-(4-(4-(2,3-dichlorophenyl)piperazin-1-yl)butoxy)-2-oxo-3,4-dihydroquinoline-1(2H)-carboxylate (Example 25, Compound-91)

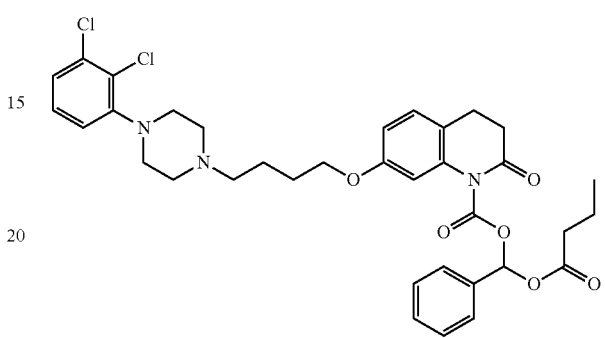

Synthesis of chloro(phenyl)methyl carbonochloridate

To a solution of benzaldehyde (2.67 mL, 26.29 mmol) in diethyl ether (40 mL) at −20° C. under argon was added triphosgene (8.61 g, 28.92 mmol) followed by pyridine (90.21 mL, 2.63 mmol). The reaction was allowed to gradually warm to room temperature and stirred for 2 hours. The reaction was filtered through celite and concentrated. The residue was co-evaporated with diethylether (3×20 mL) to give chloro(phenyl)methyl carbonochloridate (5.44 g). This was used without further purification (contains ~11% benzaldehyde).

Synthesis of chloro(phenyl)methyl 7-(4-(4-(2,3-dichlorophenyl)piperazin-1-yl)butoxy)-2-oxo-3,4-dihydroquinoline-1(2H)-carboxylate To a suspension of aripiprazole (1 g, 2.23 mmol) in 2-methyltetrahydrofuran (20 mL) was added NaH (178 mg, 4.46 mmol). The reaction was heated to reflux for 1.5 hours then cooled to room temperature. Chloro(phenyl)methyl carbonochloridate (1.37 g, 6.69 mmol) was then added and the reaction stirred overnight at room temperature. The reaction was cooled to 0° C., diluted with ethyl acetate (20 mL) and quenched with aqueous saturated NaHCO$_3$ (20 mL) solution. The reaction was extracted with ethyl acetate (3×20 mL) and the combined organics washed with brine (50 mL), then dried (MgSO$_4$) and concentrated to give chloro(phenyl)methyl 7-(4-(4-(2,3-dichlorophenyl)piperazin-1-yl)butoxy)-2-oxo-3,4-dihydroquinoline-1(2H)-carboxylate (crude yield 2.10 g) as a 1:3 mixture of product/aripiprazole. The product was taken onto the next step crude.

Synthesis of Compound-91

To a solution of chloro(phenyl)methyl 7-(4-(4-(2,3-dichlorophenyl)piperazin-1-yl)butoxy)-2-oxo-3,4-dihydroquinoline-1(2H)-carboxylate (4.11 g, 6.66 mmol) in dimethyl formamide (40 mL) was added butyric acid (0.91 mL, 9.99 mmol) and cesium carbonate (1.63 g, 4.99 mmol). The reaction was stirred at room temperature for 20 hours then diluted with ethyl acetate (40 mL) and washed with 1:1 water/brine (3×50 mL). The organics were dried (MgSO$_4$) and concentrated. The crude product was purified by column chromatography on silica eluting with 0.5% Et₃N/ethyl acetate to give butyryloxy(phenyl)methyl 7-(4-(4-(2,3-dichlorophenyl)piperazin-1-yl)butoxy)-2-oxo-3,4-dihydroquinoline-1(2H)-carboxylate, Compound-91 (1.12 g). The material was determined to be 67% pure by LCMS.

¹H-NMR (300 MHz, CDCl₃) δ 7.66-7.57 (2H, m), 7.49-7.38 (3H, m), 7.18-7.13 (2H, m), 7.07-7.04 (1H, m), 6.98-6.92 (1H, m), 6.73-6.61 (2H, m), 3.96-3.83 (2H, m), 3.11-3.00 (4H, m), 2.89-2.85 (2H, m), 2.74-2.63 (6H, m), 2.57-2.51 (2H, m), 2.48-2.41 (2H, m), 1.81-1.60 (6H, m), 0.96 (3H, dt). [M+H]⁺=668.48.

Pharmacokinetic Evaluation in Rats

Pharmacokinetic Evaluation of Prodrugs in Rats Following Oral Administration (PO)

Animals: Male Sprague—Dawley rats (Charles River Laboratories, Wilmington, Mass.) were obtained. Approximately 24 rats were used in each study. Rats were approximately 350-375 g at time of arrival. Rats were housed 2 per cage with ad libitum chow and water. Environmental conditions in the housing room: 64-67° F., 30% to 70% relative humidity, and 12:12-h light:dark cycle. All experiments were approved by the institutional animal care and use committee.

Pharmacokinetics study: Rats were dosed 10 mg/kg (3.3 mL suspension) of the test compound (see Table E). Blood samples were collected from the jugular vein after brief anesthesia with Isoflurane. A 27½G needle and 1 cc syringe without an anticoagulant was used for the blood collection. Approximately 250ℓ of whole blood was collected at each sampling time-point of 15 and 30 minutes, and 1, 2, 4, 7 and 24 hours after administration. Once collected, whole blood was immediately transferred prechilled tubes containing EDTA, inverted 10-15 times and immediately placed on ice. The tubes were centrifuged for 2 minutes at >14,000 g's (11500 RPMs using Eppendorf Centrifuge) at room temperature to separate plasma. Plasma samples were transferred to labeled plain tubes (MICROTAINER®) and stored frozen at <−70° C.

Data Analysis: Drug concentrations in plasma samples were analyzed by liquid chromatography—mass spectroscopy using appropriate parameters for each compound. Half-life, volume of distribution, clearance, maximal concentration, and AUC were calculated by using WinNonlin Version 5.2_software (Pharsight, St. Louis, Mo.). Results are shown in The FIGURE.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of Formula XVII, XVIII or XIX:

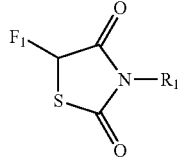

Formula XVII

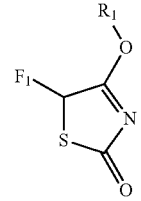

Formula XVIII

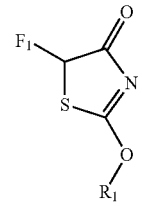

Formula XIX or a pharmaceutically acceptable salt thereof;

wherein $R_1$ is selected from —C(O)O—CH₂—OC(O)$R_{21}$ or —C(O)NH-CH₂—OC(O)$R_{21}$, —C(O)O—CH₂—OC(O)N($R_{21}$)₂, —PO₃MY, —P(O)₂(O$R_{20}$)M and —P(O)(O$R_{20}$)(O$R_{21}$);

wherein each $R_{20}$ and $R_{21}$ is independently selected from hydrogen, aliphatic, substituted aliphatic, aryl or substituted aryl;

Y and M are the same or different and each is a monovalent cation; or M and Y together is a divalent cation;

$F_1$ is $R_5$-A-$Cy_1$—B-D-;

wherein, A is selected from absent, optionally substituted alkyl, optionally substituted alkenyl, optionally substituted alkynyl, —S—, —O—, —S(O)—, —S(O)₂—, —S[C($R_{30}$)($R_{31}$)]$_u$—, —S(O)[C($R_{30}$)($R_{31}$)]$_u$—, —(O)[C($R_{30}$)($R_{31}$)]$_u$—, —N($R_{30}$)—, —N($R_{30}$)[C($R_{31}$)($R_{32}$)]$_u$—, —[C($R_{30}$)($R_{31}$)]$_u$—C(O)[C($R_{30}$)($R_{31}$)]$_u$—;

wherein each u is independently 1, 2, 3, 4, 5, 6 or 7;

$Cy_1$ is absent or an optionally substituted cycloalkyl, optionally substituted cycloalkenyl, optionally substituted heterocyclyl, optionally substituted aryl or optionally substituted heteroaryl;

B is absent, or a linker;

D is selected from absent, —O—, —N$R_{33}$, —C($R_{34}$)($R_{35}$)—, —S—S(O)—S(O)₂—, —C(O)—;

each $R_5$, $R_{30}$, $R_{31}$, $R_{32}$ $R_{33}$, $R_{34}$, and $R_{35}$ is independently selected from absent, hydrogen, halogen, —O$R_{10}$, —S$R_{10}$, —N$R_{10}R_{11}$—, —C(O)$R_{10}$, optionally substituted aliphatic, optionally substituted aryl or optionally substituted heterocyclyl;

wherein each $R_{10}$ and $R_{11}$ is independently absent, hydrogen, halogen, aliphatic, substituted aliphatic, aryl or substituted aryl; alternatively two $R_{10}$ and $R_{11}$ together with the atoms to which they are attached may form an additional optionally substituted, 3, 4, 5, 6 or 7 membered ring; and, each u is independently 1, 2, 3, 4, 5, 6 or 7.

2. A compound having the formula XX, XXI or XXII, or a pharmaceutically acceptable salt thereof:

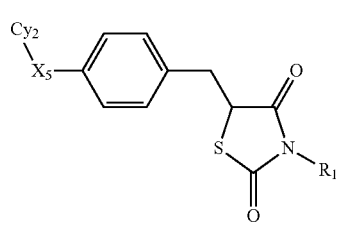

Formula XX

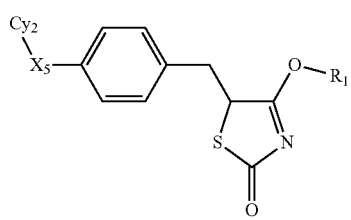

Formula XXI

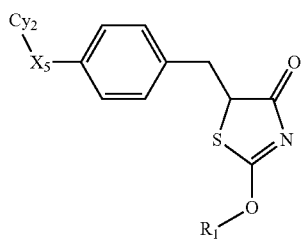

Formula XXII

Wherein $R_1$ is selected from —C(O)OR$_{20}$, —C(O)R$_{20}$, —C(O)NR$_{20}$R$_{21}$, —PO$_3$MY, —P(O)$_2$(OR$_{20}$)M and —P(O)(OR$_{20}$)(OR$_{21}$);
  wherein each $R_{20}$ and $R_{21}$ is independently selected from hydrogen, aliphatic, substituted aliphatic, aryl or substituted aryl;
  Y and M are the same or different and each is a monovalent cation; or M and Y together is a divalent cation;
  Cy$_2$ is an optionally substituted heterocyclic ring; and
  X$_5$ is selected from absent, —S—, —O—, —S(O)—, —S(O)$_2$—, —N(R$_{10}$)—, —C(O)—, —C(OR$_{10}$)(R$_{11}$)—, —[C(R$_{10}$)(R$_{11}$)]$_v$—, —O[C(R$_{10}$)(R$_{11}$)]$_v$—, —O[C(R$_{10}$)(R$_{11}$)]$_v$O—, —NR$_{12}$[C(R$_{10}$)(R$_{11}$)]$_v$O—, —NR$_{12}$[C(R$_{10}$)(R$_{11}$)]$_v$ S—, —S[C(R$_{10}$)(R$_{11}$)]$_v$—, —C(O)[C(R$_{10}$)(R$_{11}$)]$_v$—, and —C(R$_{10}$)(R$_{11}$)=C(R$_{10}$)(R$_{11}$)—; wherein v is 0, 1, 2, 3, 4, 5, 6, 7, 8, 9 or 10; and,
  wherein each $R_{10}$ and $R_{11}$ is independently absent, hydrogen, halogen, aliphatic, substituted aliphatic, aryl or substituted aryl; alternatively two $R_{10}$ and $R_{11}$ together with the atoms to which they are attached may form an additional optionally substituted, 3, 4, 5, 6 or 7 membered ring.

3. A compound having the Formula XXIV, XXV or XXVI, or a pharmaceutically acceptable salt thereof:

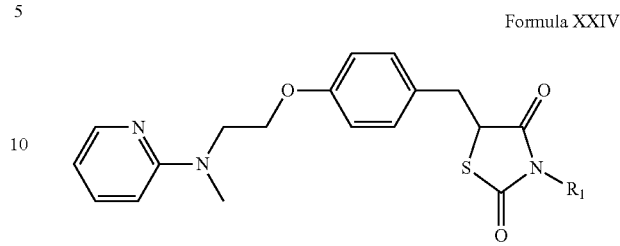

Formula XXIV

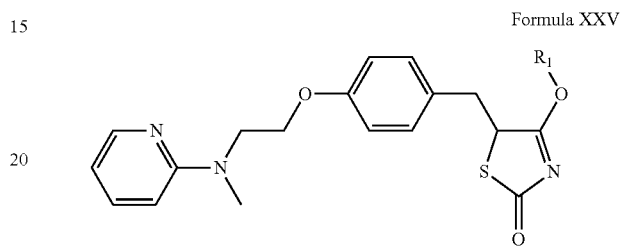

Formula XXV

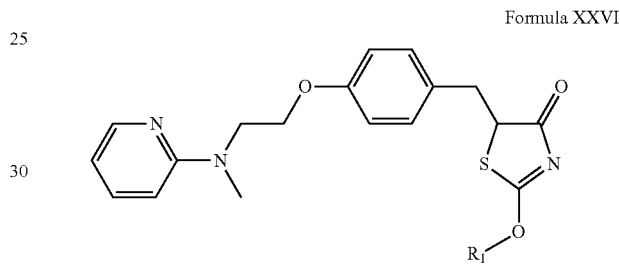

Formula XXVI wherein $R_1$ is selected from —C(O)RO$_{20}$, —C(O)R$_{20}$, —C(O)NR$_{20}$R$_{21}$, —PO$_3$MY, —P(O)$_2$(OR$_{20}$)M and —P(O)(OR$_{20}$)(OR$_{21}$);

wherein each $R_{20}$ and $R_{21}$ is independently selected from hydrogen, aliphatic, substituted aliphatic, aryl or substituted aryl;

Y and M are the same or different and each is a monovalent cation; or M and Y together is a divalent cation.

4. A compound of claim 3, wherein $R_1$ is selected from Table 1, or a pharmaceutically acceptable salt thereof;

TABLE 1

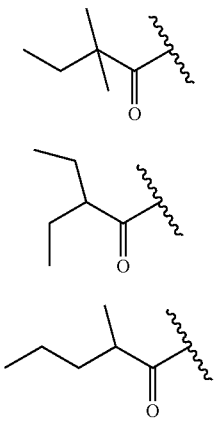

TABLE 1-continued
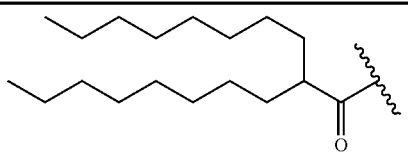
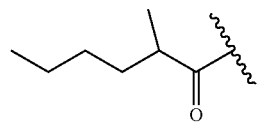 [SMILES: *C(=O)C(C)CCCC]
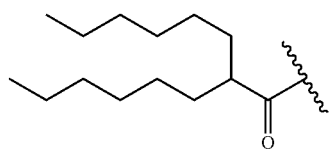 [SMILES: *C(=O)C(CCCCCC)CCCCCC]
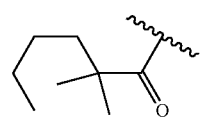 [SMILES: *C(=O)C(C)(C)CCCC]
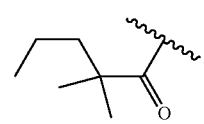 [SMILES: *C(=O)C(C)(C)CCC]
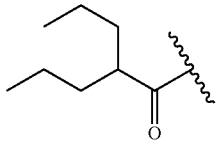 [SMILES: *C(=O)C(CCC)CCC]
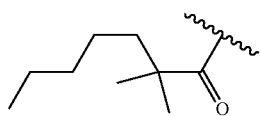 [SMILES: *C(=O)C(C)(C)CCCCC]
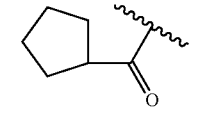 [SMILES: *C(=O)C1CCCC1]
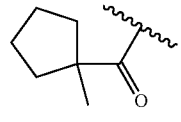 [SMILES: *C(=O)C1(C)CCCC1]
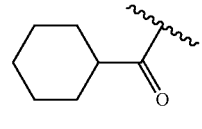 [SMILES: *C(=O)C1CCCCC1]
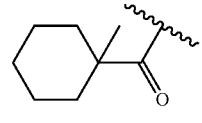 [SMILES: *C(=O)C1(C)CCCCC1]
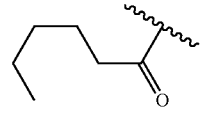 [SMILES: *C(=O)CCCCC]
TABLE 1-continued
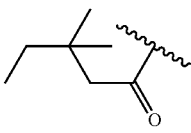 [SMILES: *C(=O)CC(C)(C)CC]
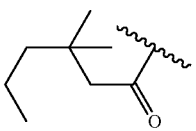 [SMILES: *C(=O)CC(C)(C)CCC]
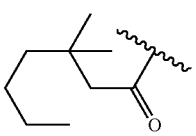 [SMILES: *C(=O)CC(C)(C)CCCC]
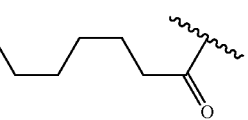
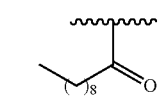
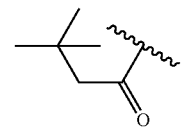 [SMILES: *C(=O)CC(C)(C)C]
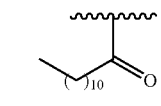
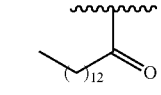
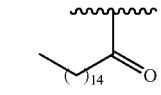
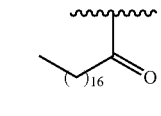
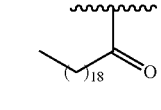
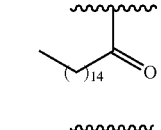
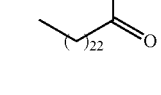

TABLE 1-continued
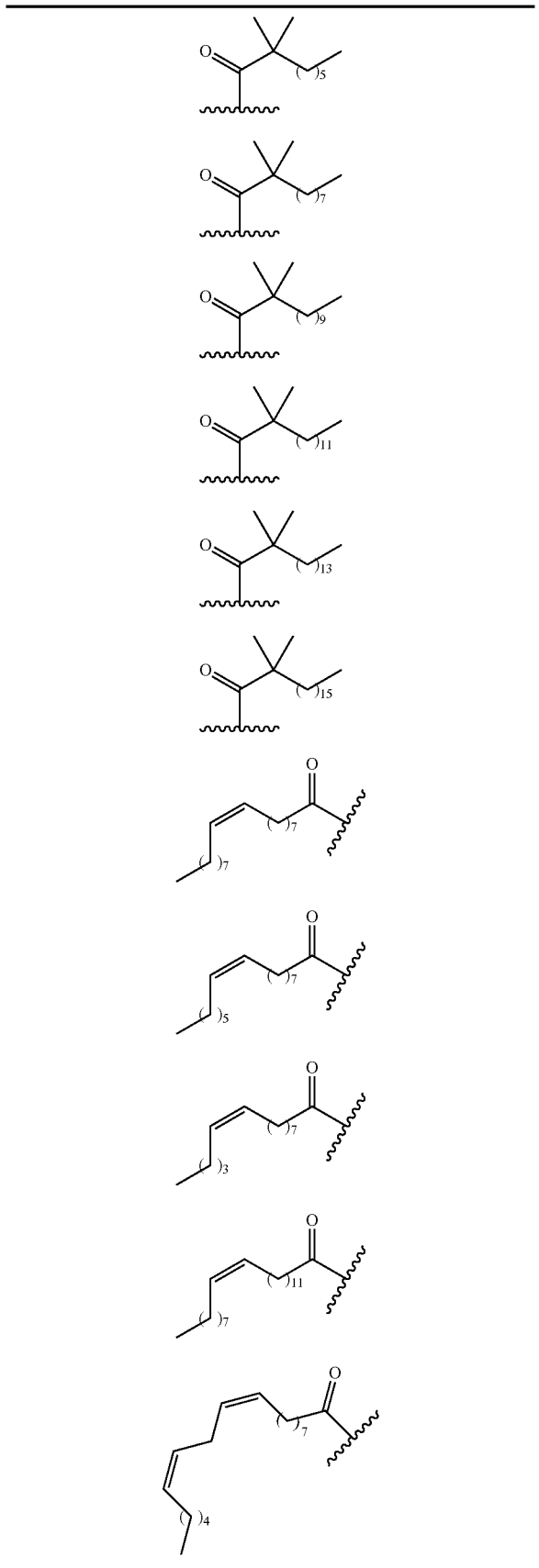
TABLE 1-continued
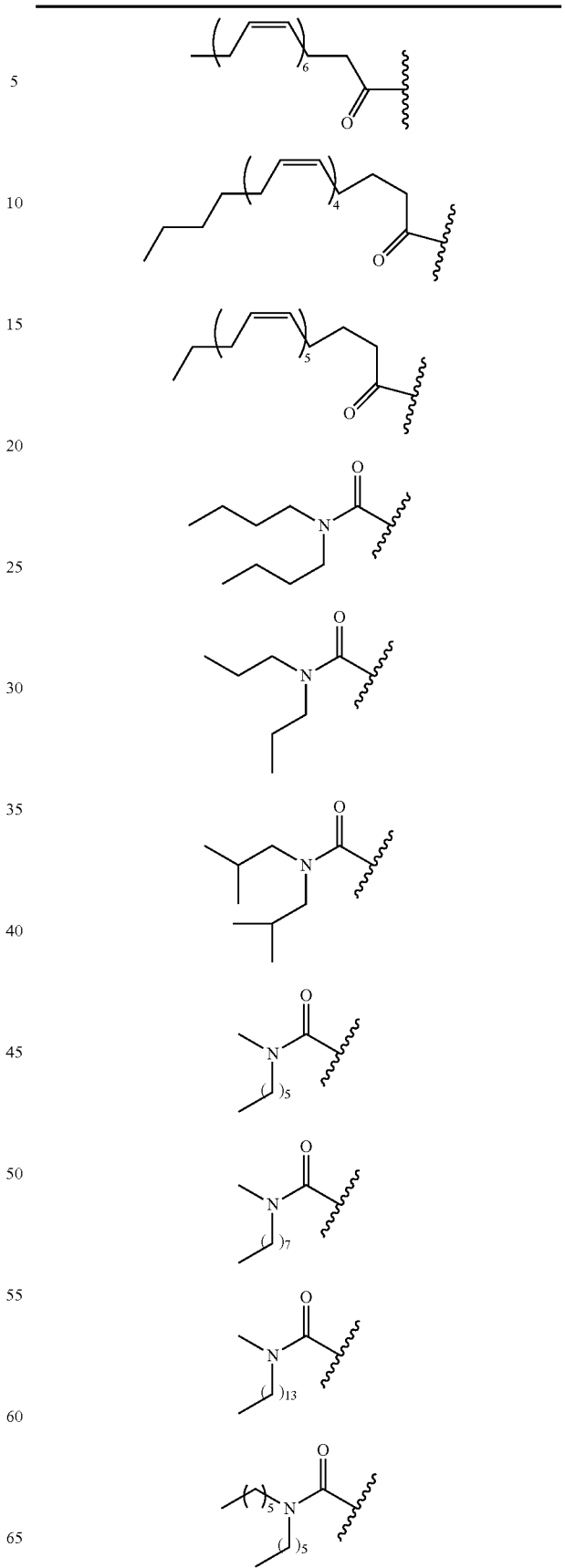

TABLE 1-continued
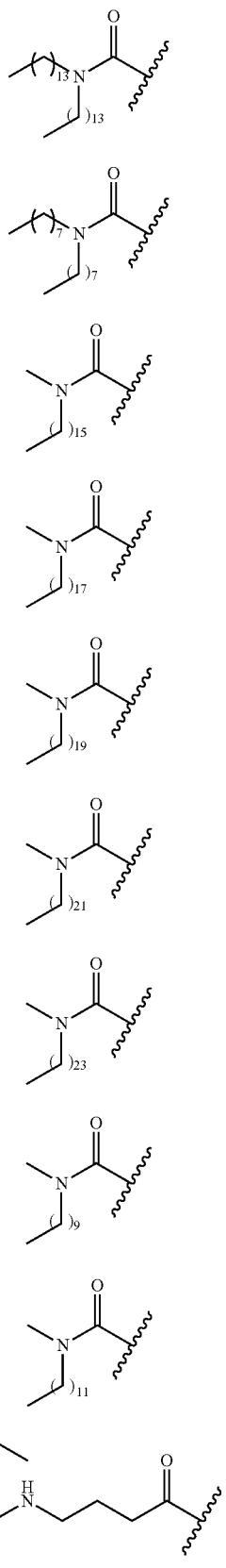
TABLE 1-continued
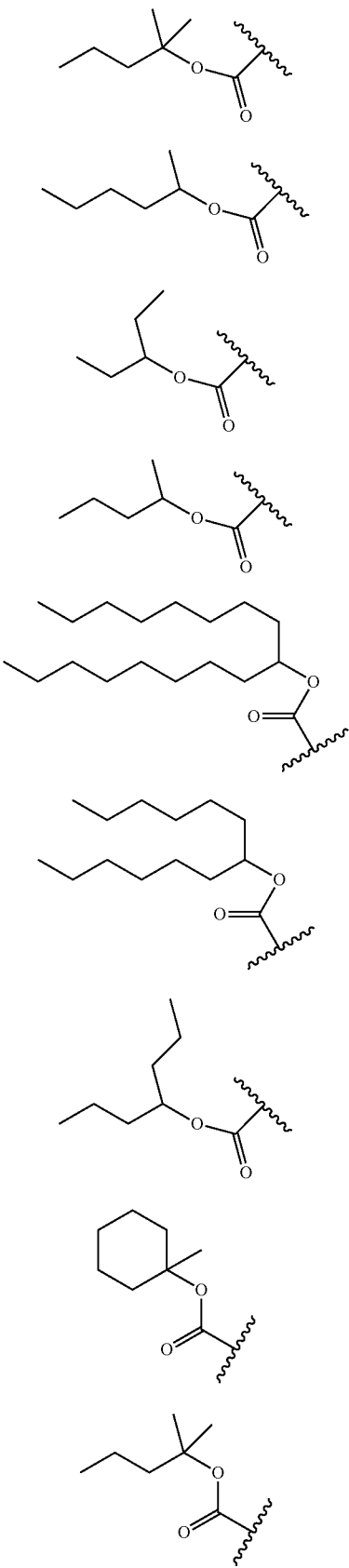

TABLE 1-continued
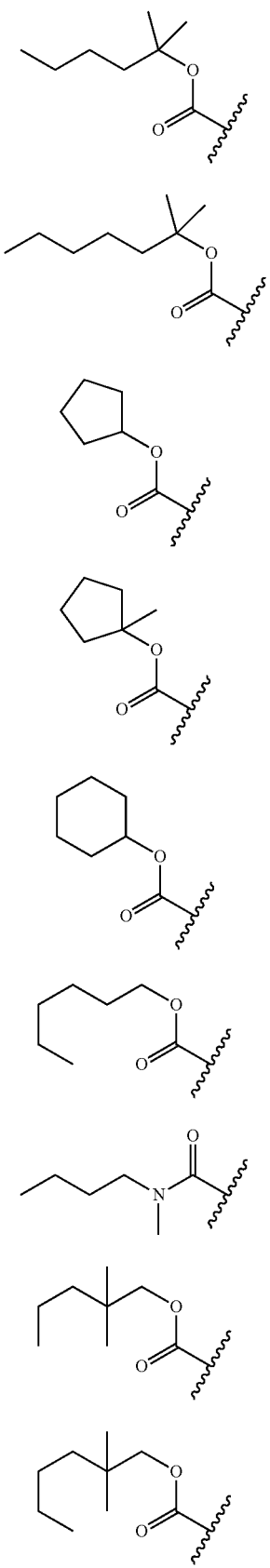
TABLE 1-continued
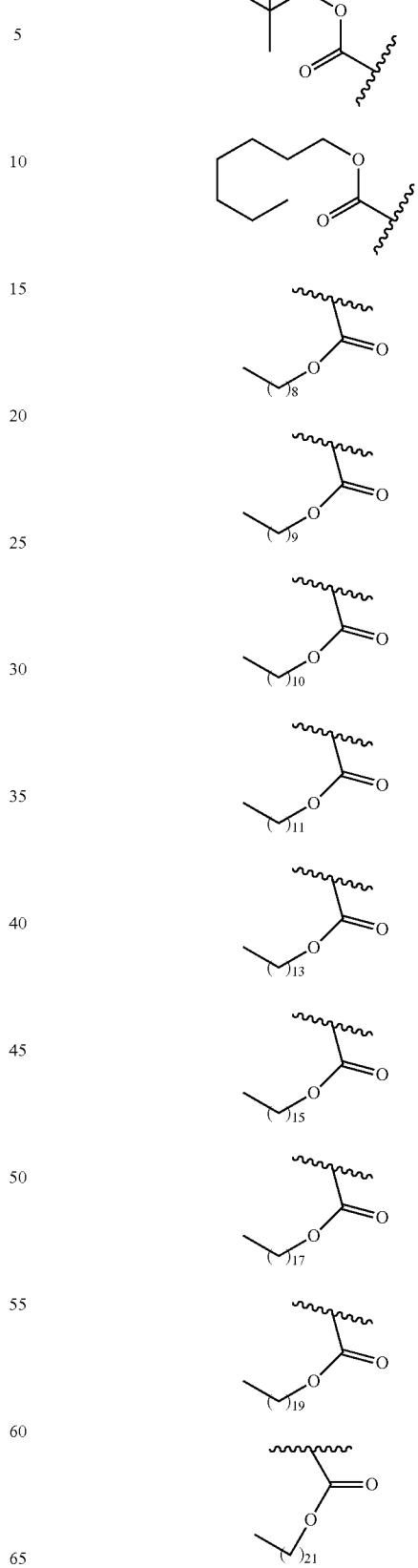

TABLE 1-continued
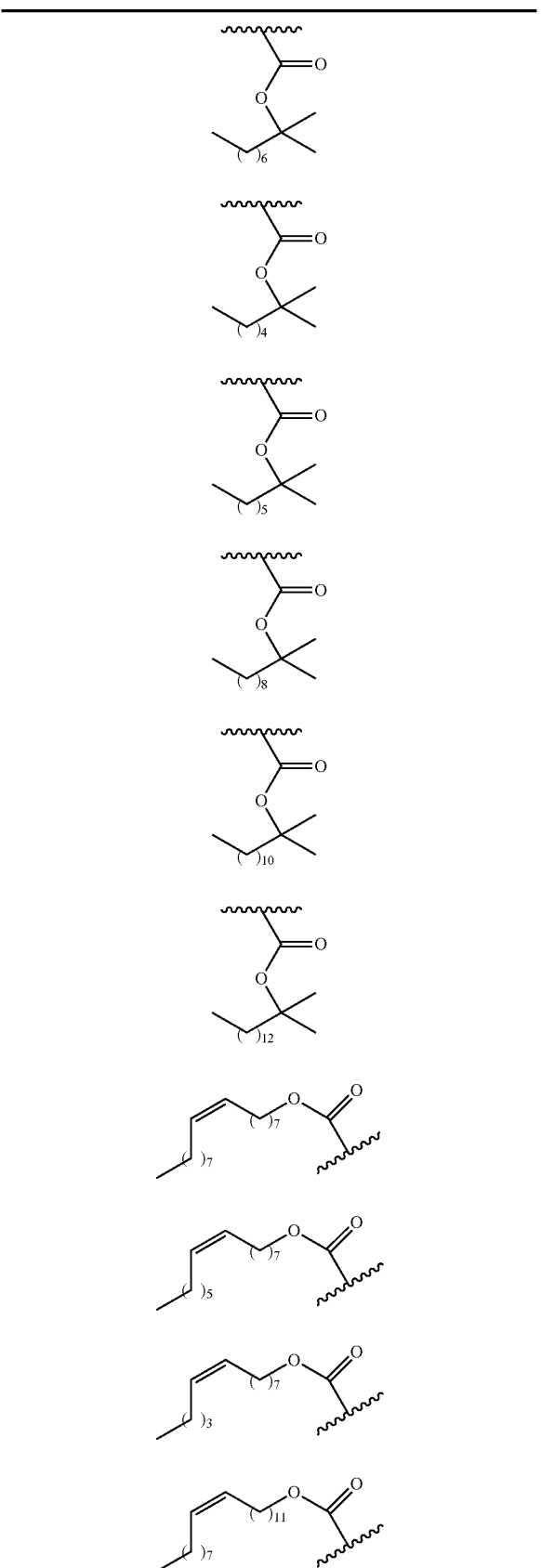
TABLE 1-continued
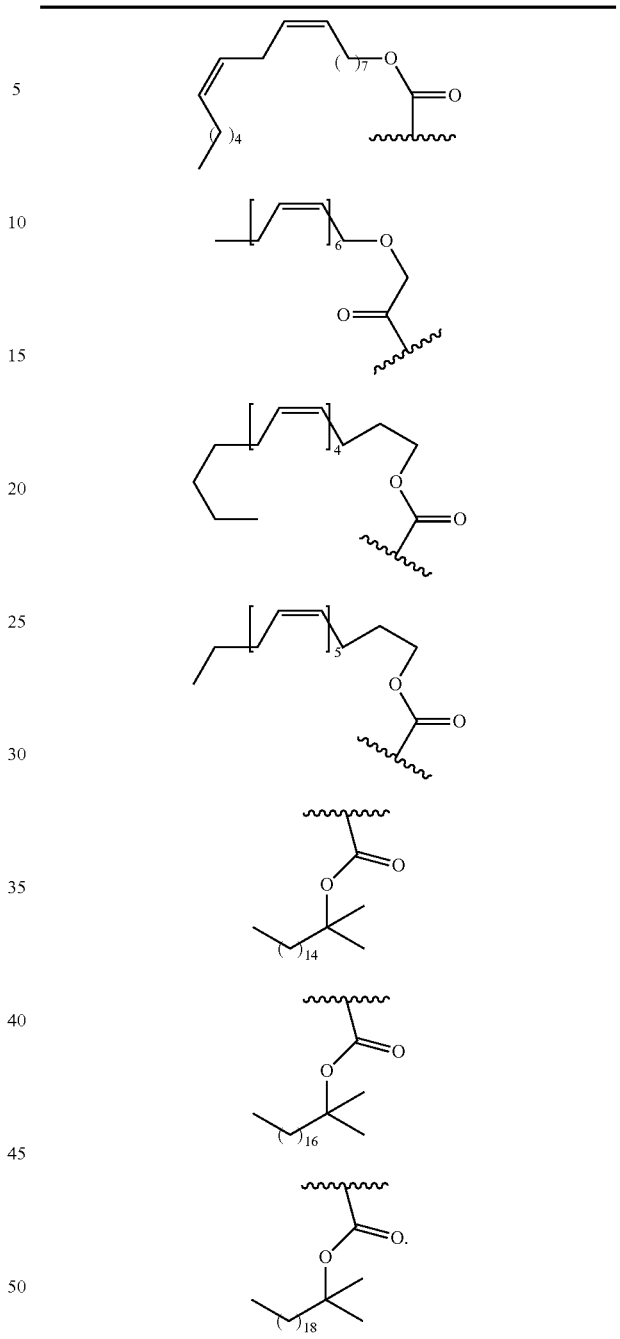
5. A compound having the Formula XXVII, XXVIII or XXIX:
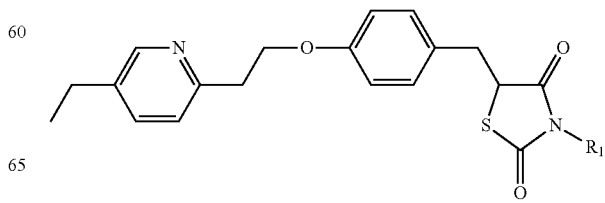
Formula XXVII Formula XXVIII
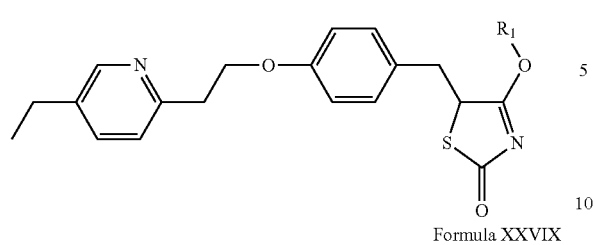
Formula XXVIX
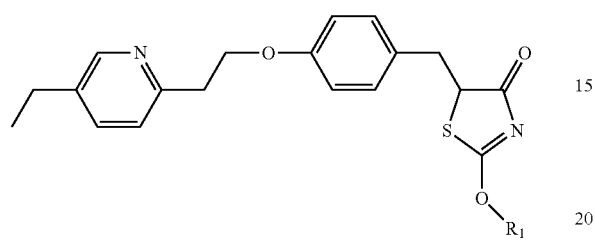
wherein R₁ is selected from —C(O)OR$_{20}$, —C(O)R$_{20}$, —C(O)NR$_{20}$R$_{21}$, —PO$_3$MY, —P(O)$_2$(OR$_{20}$)M and —P(O)(OR$_{20}$)(OR$_{21}$), or a pharmaceutically acceptable salt thereof.
6. A compound of claim 5, wherein R₁ is selected from Table 1, or a pharmaceutically acceptable salt thereof;
TABLE 1
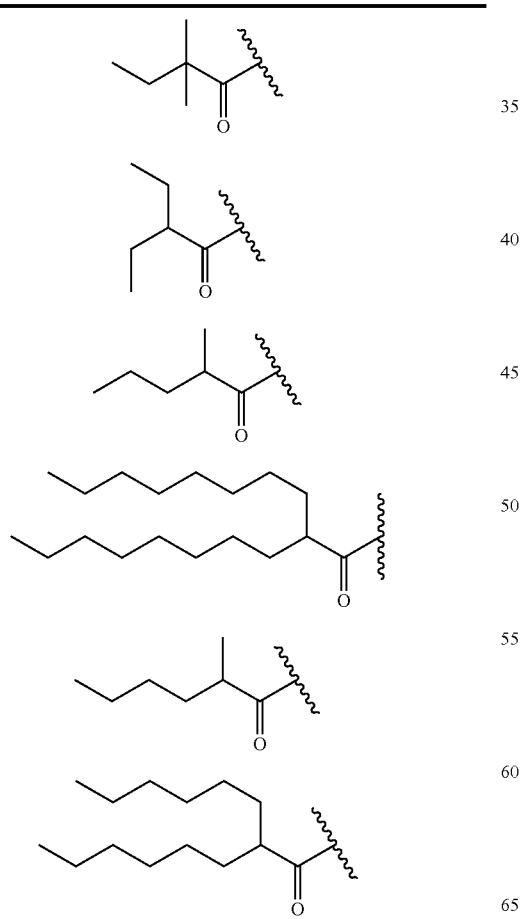
TABLE 1-continued
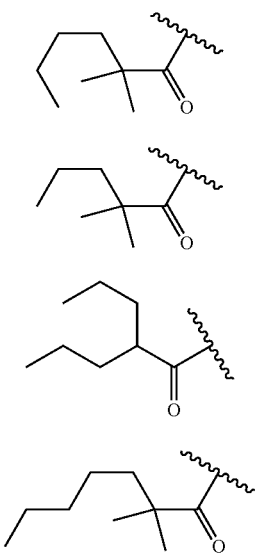
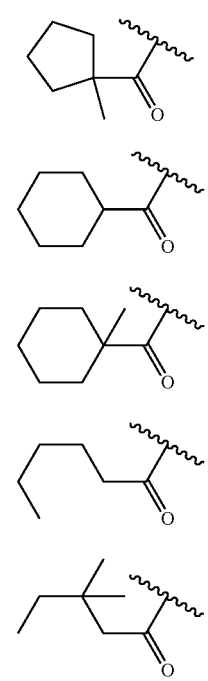
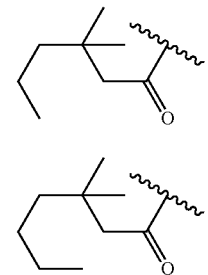

TABLE 1-continued
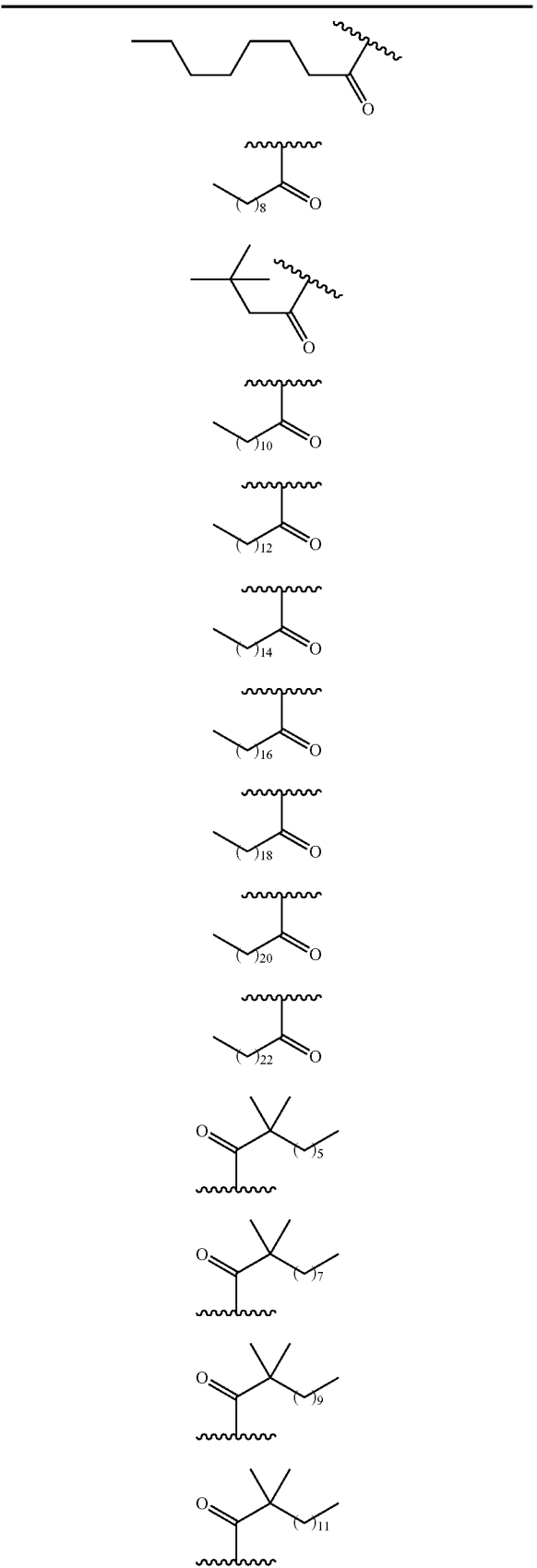
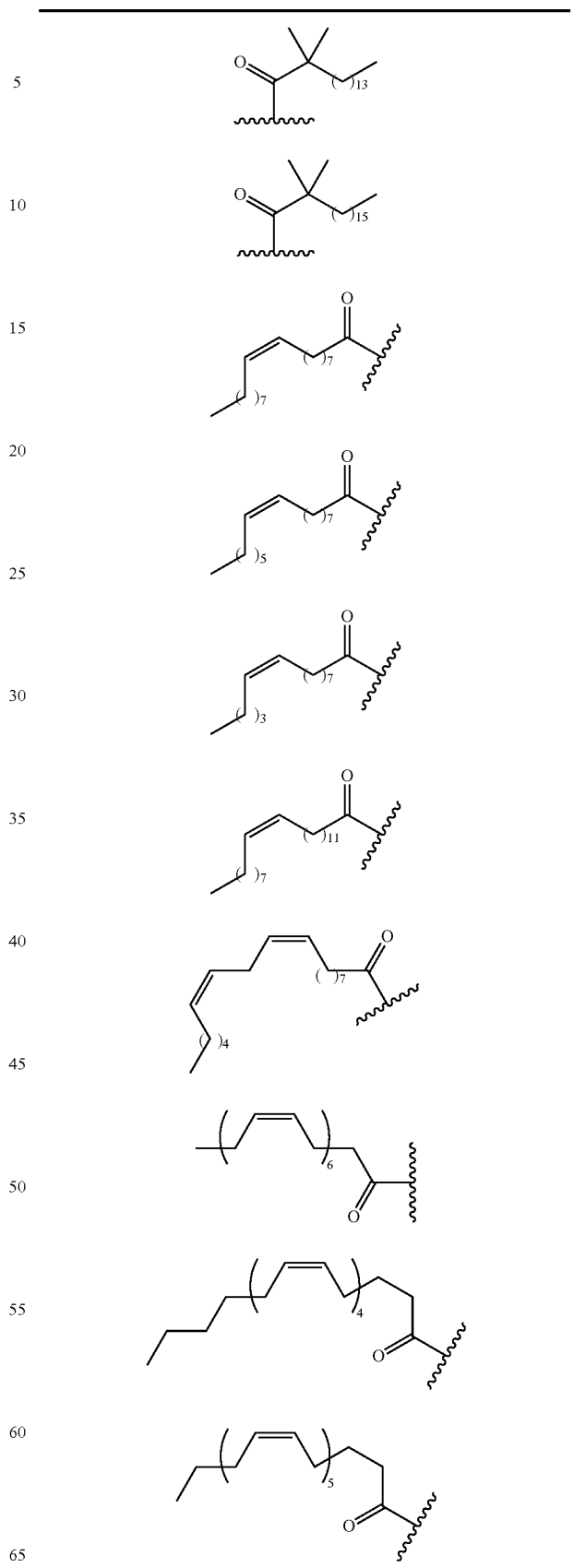

TABLE 1-continued
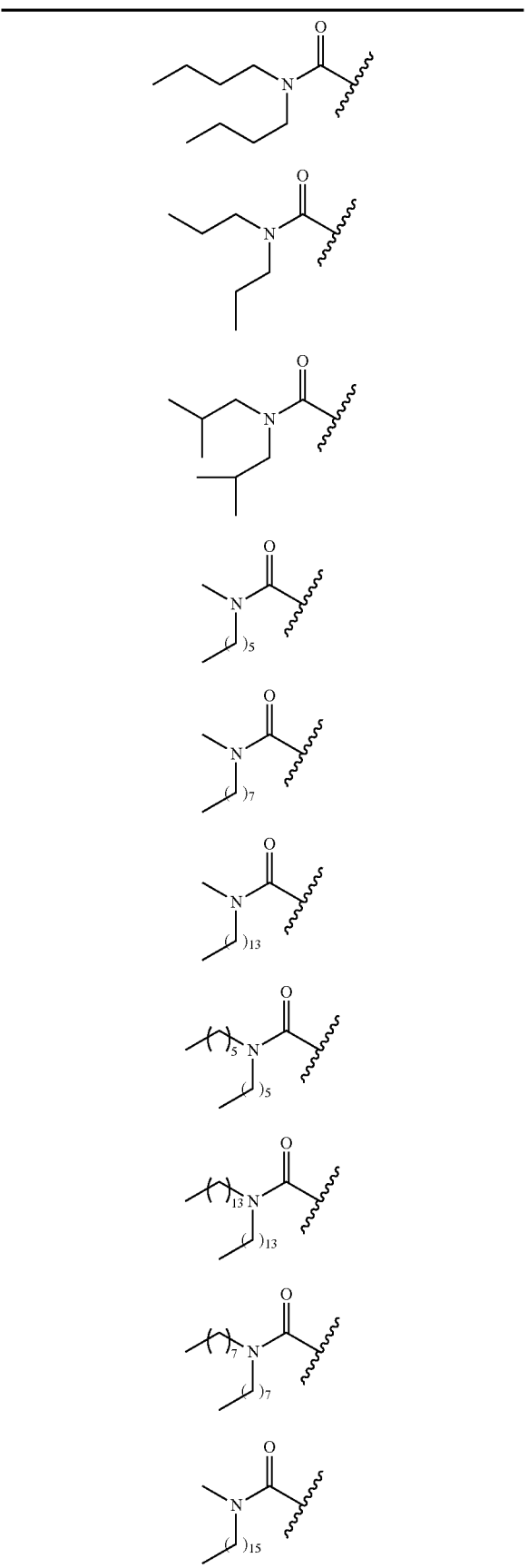
TABLE 1-continued
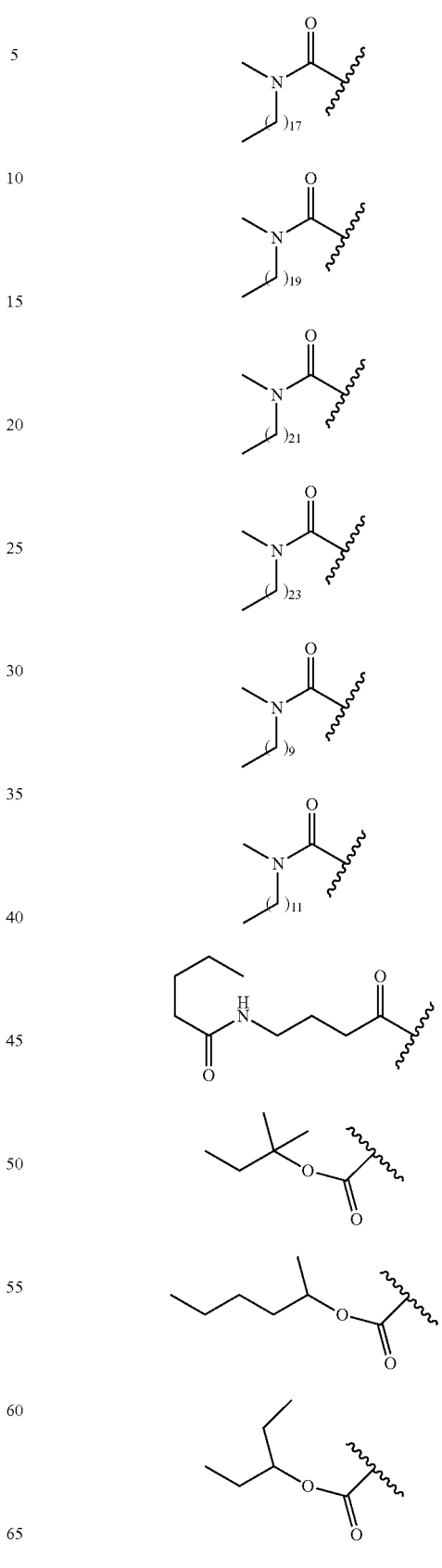

TABLE 1-continued
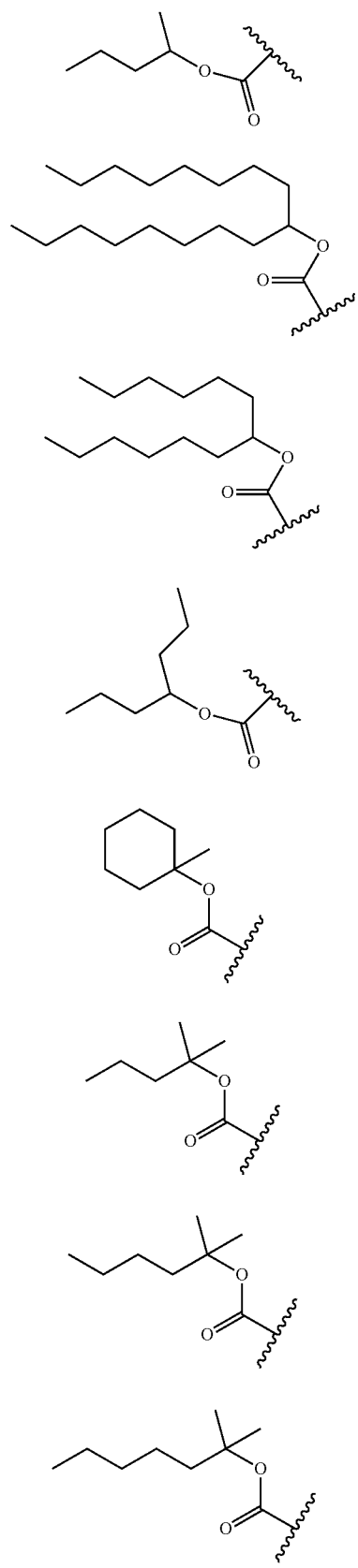
TABLE 1-continued
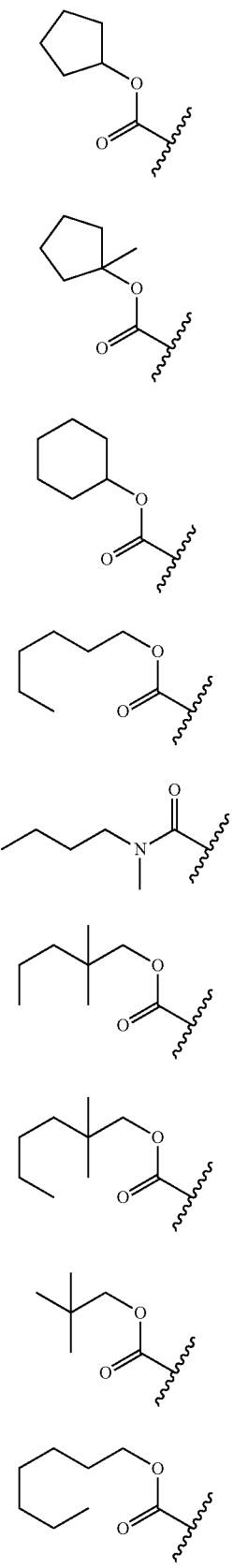

TABLE 1-continued
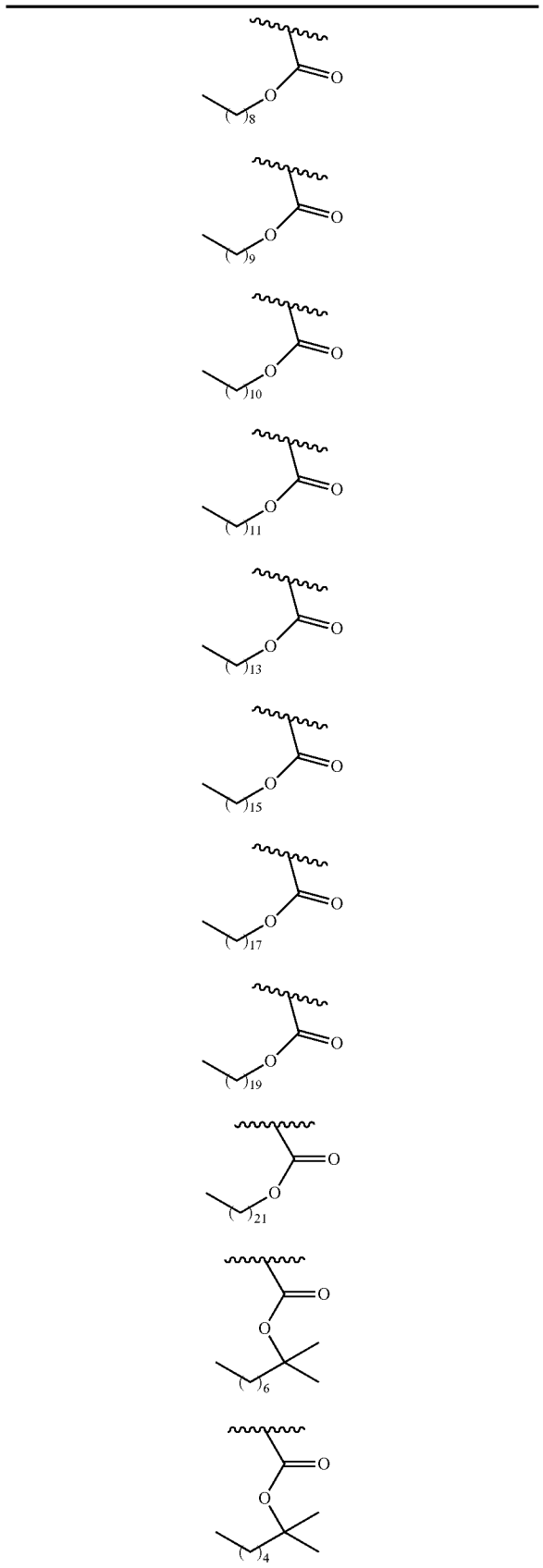
TABLE 1-continued
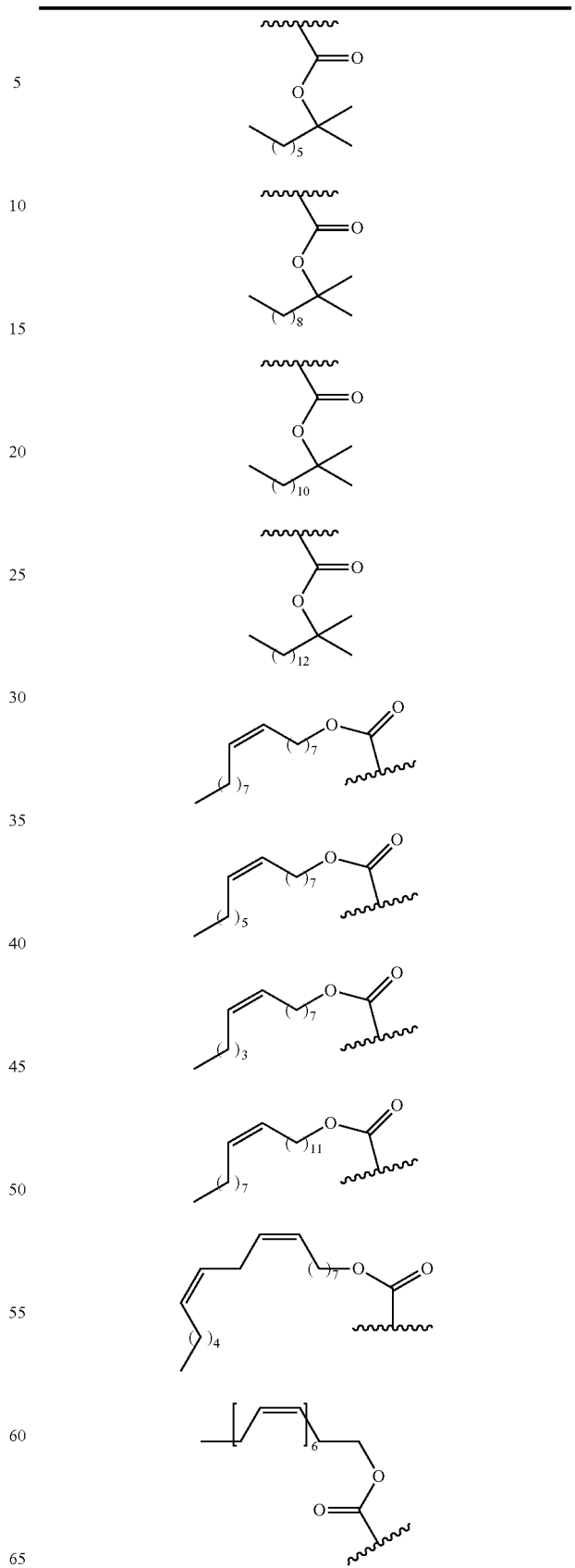

TABLE 1-continued
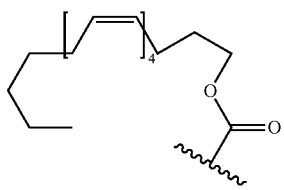
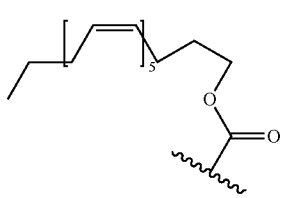
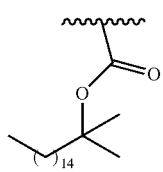
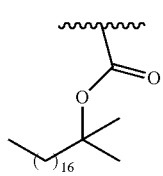
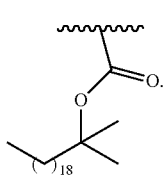
7. A compound of claim 1 having the Formula XXX, XXXI or XXXII:
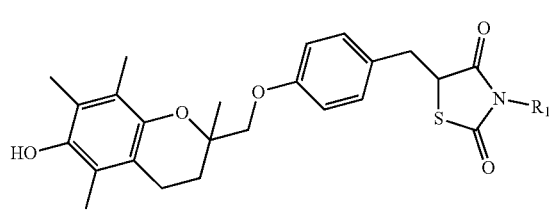
Formula XXX
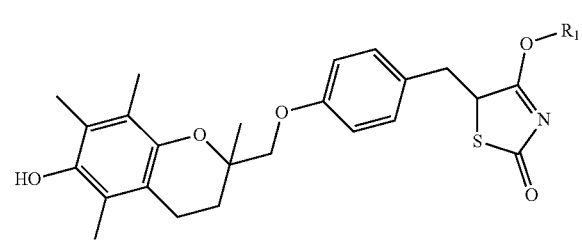
Formula XXXI
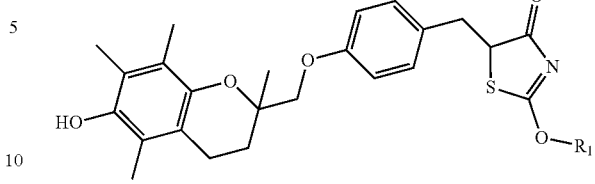
Formula XXXII
wherein $R_1$ is selected from —C(O)OR$_{20}$, —C(O)R$_{20}$, —C(O)NR$_{20}$R$_{21}$, —Po$_3$MY, —P(O)$_2$(OR$_{20}$)M and —P(O)(OR$_{20}$)(OR$_{21}$), or a pharmaceutically acceptable salt thereof.
8. A compound of claim 7, wherein $R_1$ is selected from Table 1, or a pharmaceutically acceptable salt thereof;
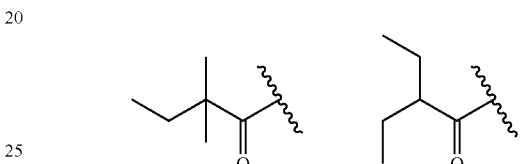
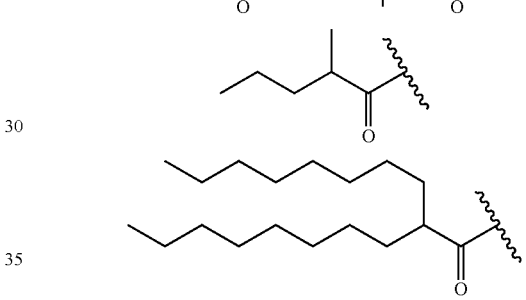
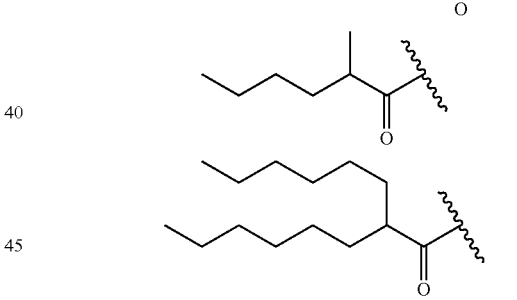
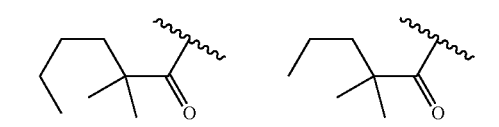
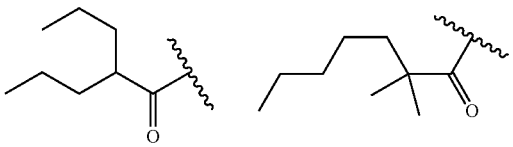
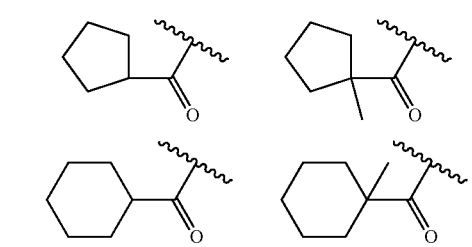

331
-continued
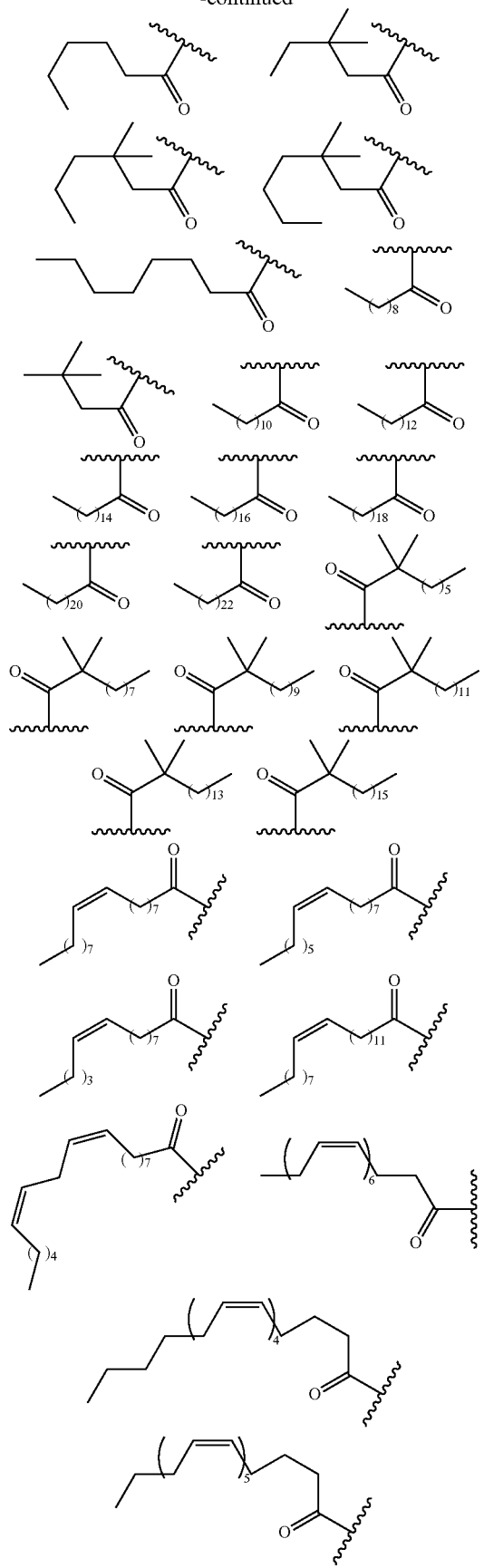
332
-continued
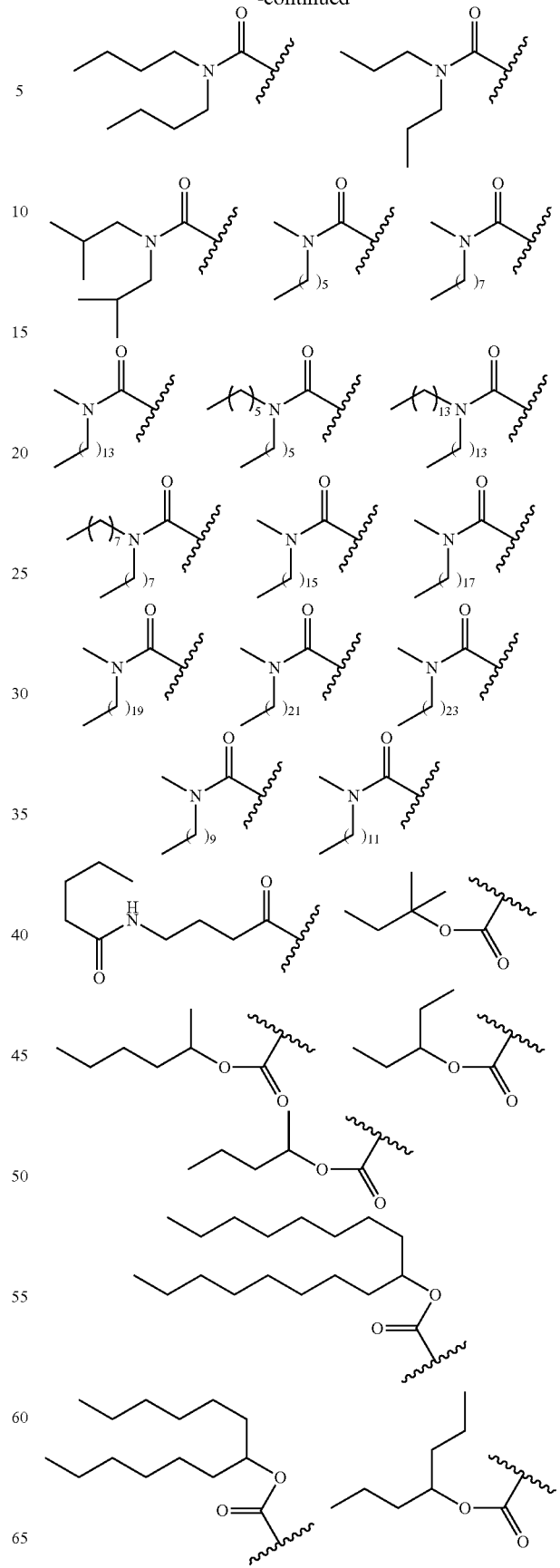

333
-continued

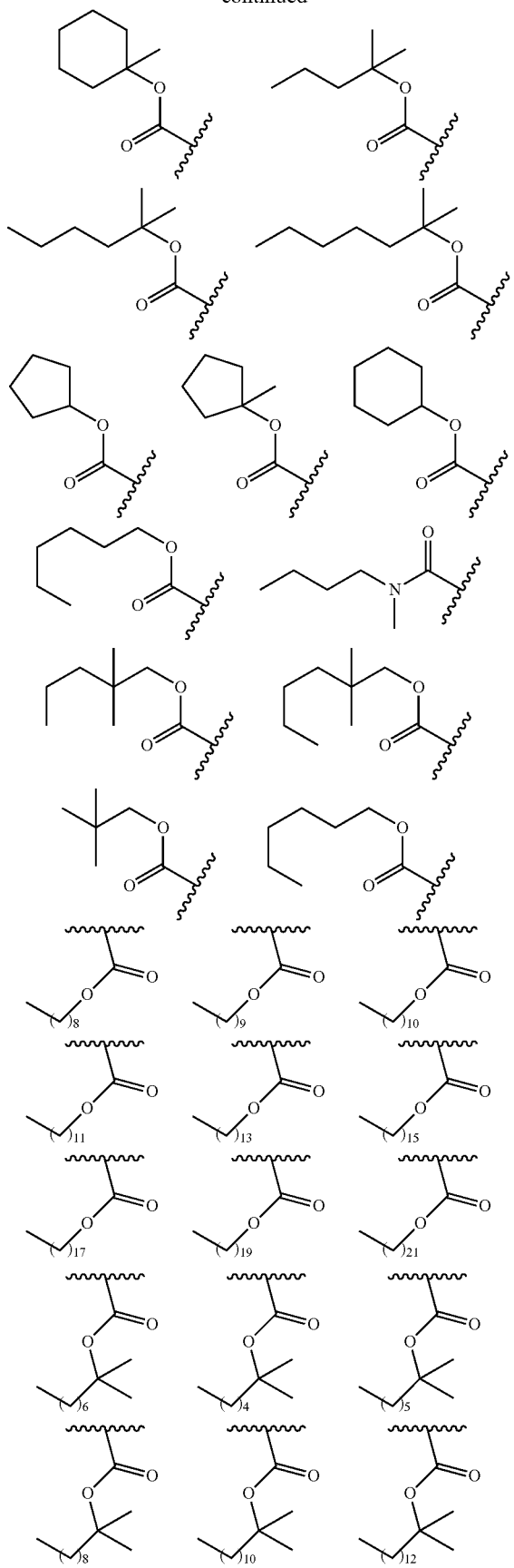

334
-continued

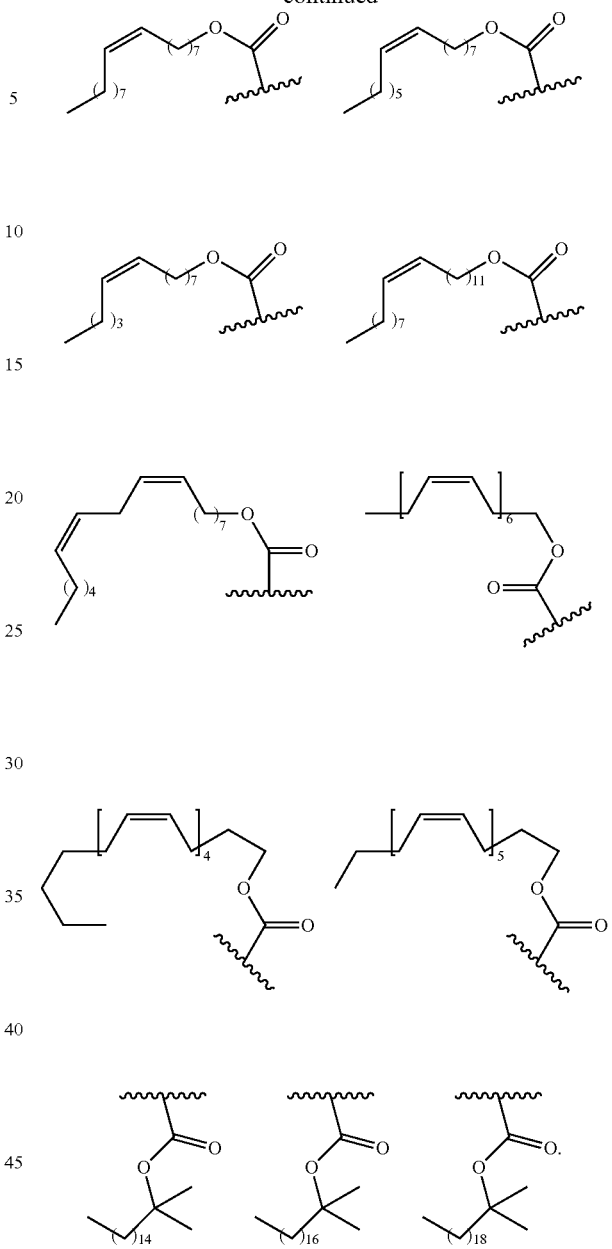

9. A compound of claim 1, wherein said $R_1$ is —C(O)O—$CH_2$—OC(O)$R_{21}$;

wherein each $R_{20}$ and $R_{21}$ is independently selected from hydrogen, aliphatic, substituted aliphatic, aryl and substituted aryl.

10. A compound of claim 1, wherein said $R_1$ is —C(O)NH—$CH_2$—OC(O)$R_{21}$;

wherein each $R_{20}$ and $R_{21}$ is independently selected from hydrogen, aliphatic, substituted aliphatic, aryl and substituted aryl.

11. A compound of claim 1, wherein said $R_1$ is —C(O)O—$CH_2$—OC(O)N($R_{21}$)$_2$;

wherein each $R_{20}$ and $R_{21}$ is independently selected from hydrogen, aliphatic, substituted aliphatic, aryl and substituted aryl.

12. A compound of Table H or a pharmaceutically acceptable salt thereof:

TABLE H

| No. | Structure |
|---|---|
| 1000. | 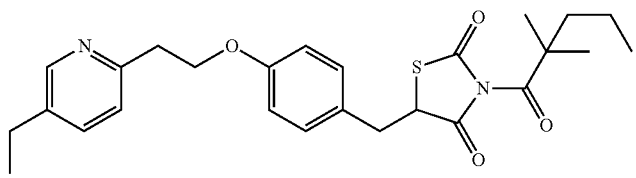 [SMILES: CCCC(C)(C)C(=O)N1C(=O)SC(Cc2ccc(OCCc3ccc(CC)cn3)cc2)C1=O] |
| 1001. | 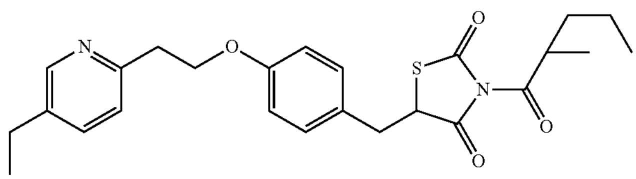 [SMILES: CCCC(C)C(=O)N1C(=O)SC(Cc2ccc(OCCc3ccc(CC)cn3)cc2)C1=O] |
| 1002. | 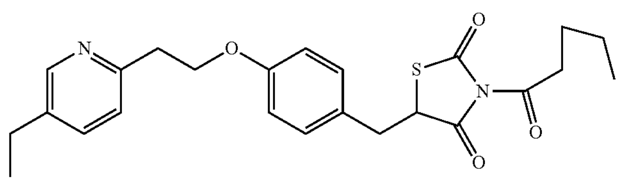 [SMILES: CCCCC(=O)N1C(=O)SC(Cc2ccc(OCCc3ccc(CC)cn3)cc2)C1=O] |
| 1003. | 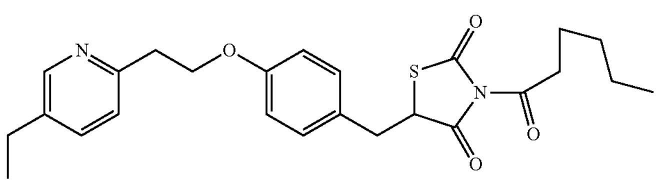 [SMILES: CCCCCC(=O)N1C(=O)SC(Cc2ccc(OCCc3ccc(CC)cn3)cc2)C1=O] |
| 1004. | 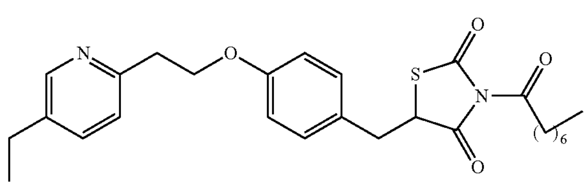 |
| 1005. | 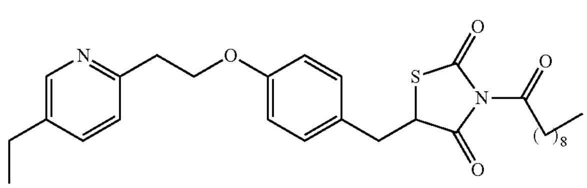 |
| 1006. | 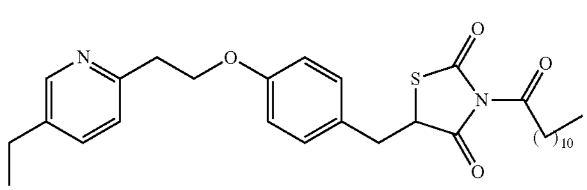 |
| 1007. | 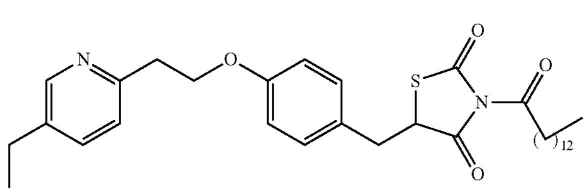 |

TABLE H-continued
| No. | Structure |
|---|---|
| 1008. | 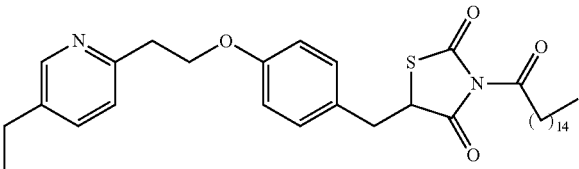 |
| 1009. | 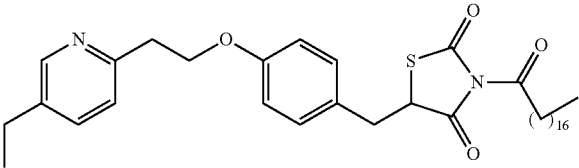 |
| 1010. | 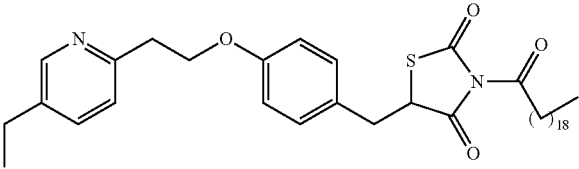 |
| 1011. | 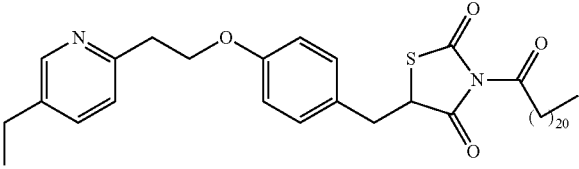 |
| 1012. | 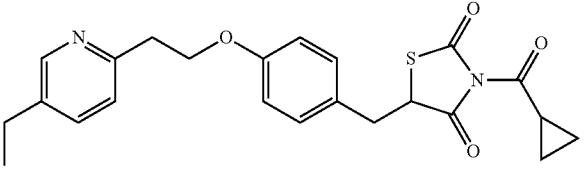 [SMILES: CCc1ccc(CCOc2ccc(CC3SC(=O)N(C(=O)C4CC4)C3=O)cc2)nc1] |
| 1013. | 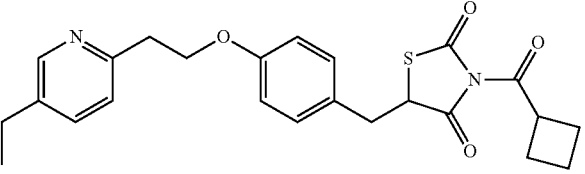 [SMILES: CCc1ccc(CCOc2ccc(CC3SC(=O)N(C(=O)C4CCC4)C3=O)cc2)nc1] |
| 1014. | 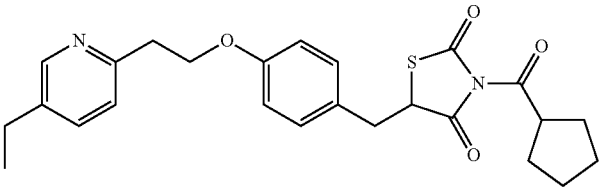 [SMILES: CCc1ccc(CCOc2ccc(CC3SC(=O)N(C(=O)C4CCCC4)C3=O)cc2)nc1] |
| 1015. | 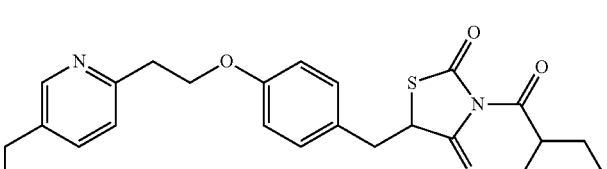 |

TABLE H-continued

| No. | Structure |
|---|---|
| 1016. | 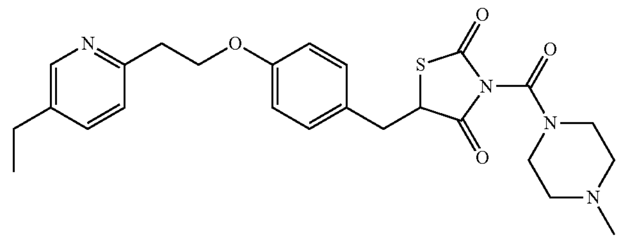 [SMILES: CCc1ccc(CCOc2ccc(CC3SC(=O)N(C(=O)N4CCN(C)CC4)C3=O)cc2)nc1] |
| 1017. | 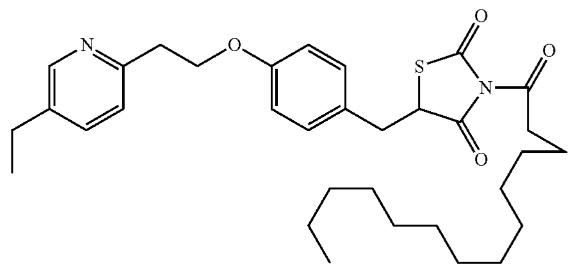 [SMILES: CCCCCCCCCCCCCC(=O)N1C(=O)SC(Cc2ccc(OCCc3ccc(CC)cn3)cc2)C1=O] |
| 1018. | 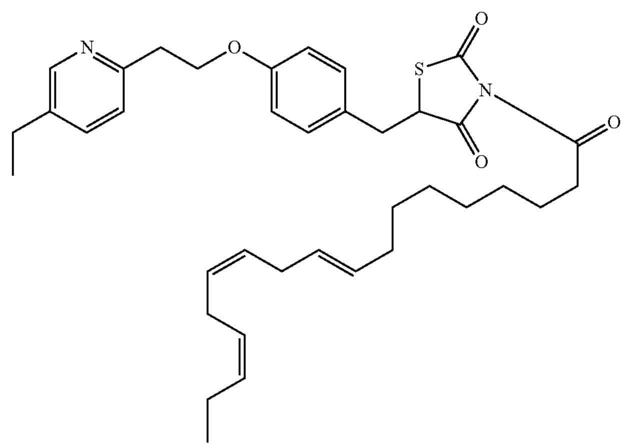 [SMILES: CC/C=C\C/C=C\C/C=C/CCCCCCCC(=O)N1C(=O)SC(Cc2ccc(OCCc3ccc(CC)cn3)cc2)C1=O] |
| 1019. | 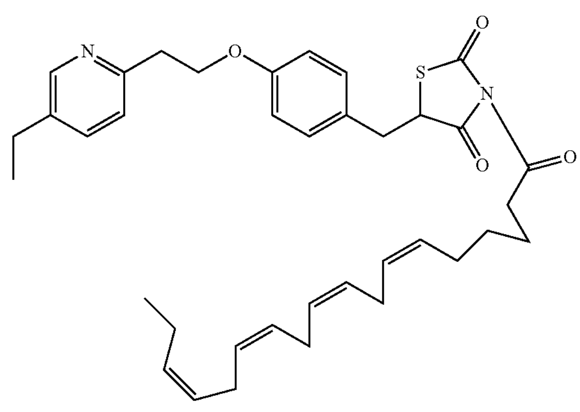 [SMILES: CC/C=C\C/C=C\C/C=C\C/C=C\CCCCC(=O)N1C(=O)SC(Cc2ccc(OCCc3ccc(CC)cn3)cc2)C1=O] |
| 1020. | 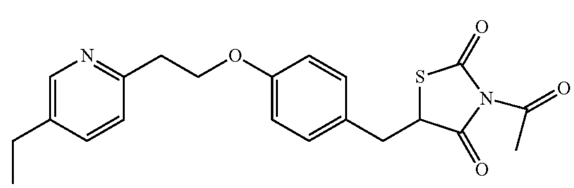 [SMILES: CCc1ccc(CCOc2ccc(CC3SC(=O)N(C(C)=O)C3=O)cc2)nc1] |

TABLE H-continued
| No. | Structure |
|---|---|
| 1021. | 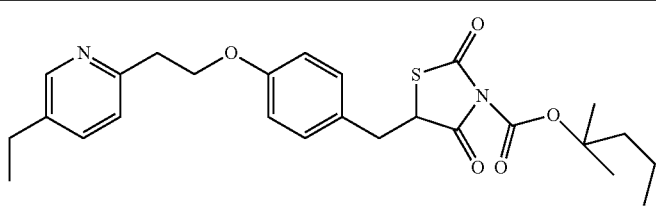 |
| 1022. | 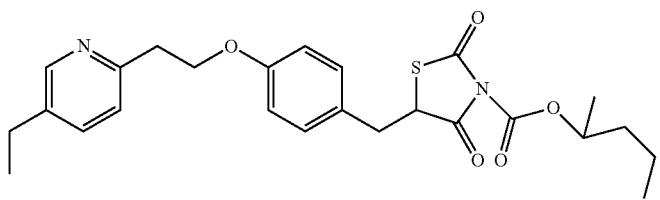 [SMILES: CCCC(C)OC(=O)N1C(=O)SC(Cc2ccc(OCCc3ccc(CC)cn3)cc2)C1=O] |
| 1023. | 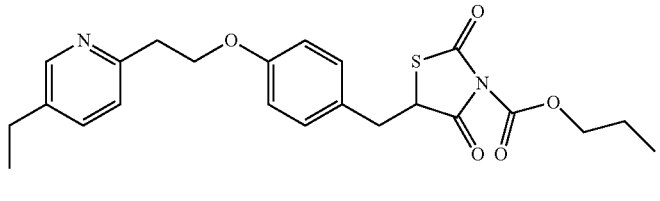 [SMILES: CCCOC(=O)N1C(=O)SC(Cc2ccc(OCCc3ccc(CC)cn3)cc2)C1=O] |
| 1024. | 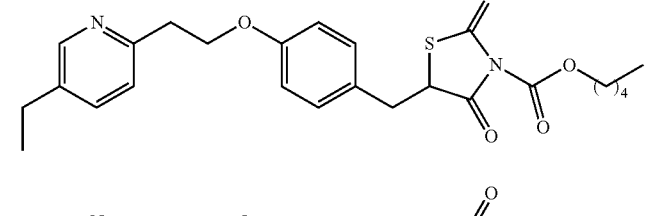 |
| 1025. | 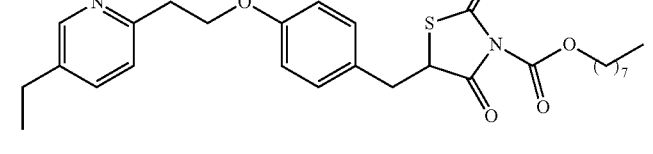 |
| 1026. | 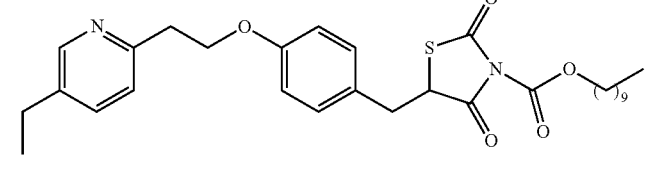 |
| 1027. | 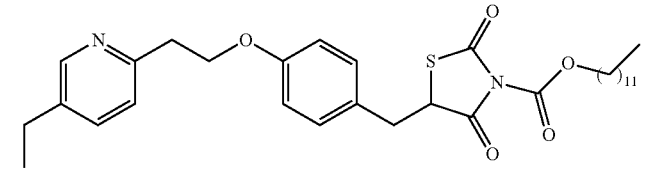 |
| 1028. | 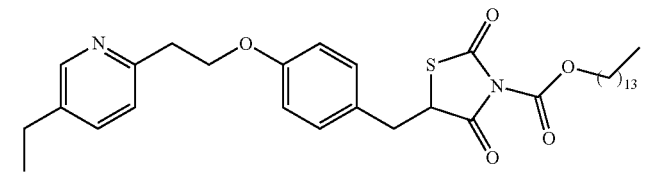 |

TABLE H-continued

| No. | Structure |
|---|---|
| 1029. | 5-ethylpyridin-2-yl-ethoxy-phenyl-methyl-thiazolidine-2,4-dione N-C(O)O-(CH₂)₁₅-CH₃ |
| 1030. | 5-ethylpyridin-2-yl-ethoxy-phenyl-methyl-thiazolidine-2,4-dione N-C(O)O-(CH₂)₁₇-CH₃ |
| 1031. | 5-ethylpyridin-2-yl-ethoxy-phenyl-methyl-thiazolidine-2,4-dione N-C(O)O-(CH₂)₁₉-CH₃ |
| 1032. | 5-ethylpyridin-2-yl-ethoxy-phenyl-methyl-thiazolidine-2,4-dione N-C(O)O-(CH₂)₂₁-CH₃ |
| 1033. | 5-ethylpyridin-2-yl-ethoxy-phenyl-methyl-thiazolidine-2,4-dione N-C(O)O-cyclopropyl |
| 1034. | 5-ethylpyridin-2-yl-ethoxy-phenyl-methyl-thiazolidine-2,4-dione N-C(O)O-cyclobutyl |
| 1035. | 5-ethylpyridin-2-yl-ethoxy-phenyl-methyl-thiazolidine-2,4-dione N-C(O)O-cyclopentyl |
| 1036. | 5-ethylpyridin-2-yl-ethoxy-phenyl-methyl-thiazolidine-2,4-dione N-C(O)O-cyclohexyl |

TABLE H-continued
| No. | Structure |
|---|---|
| 1037. | 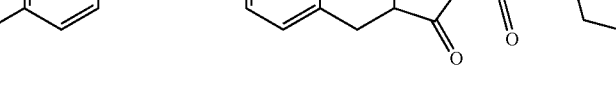 |
| 1038. | 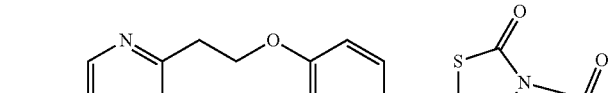 |
| 1039. | 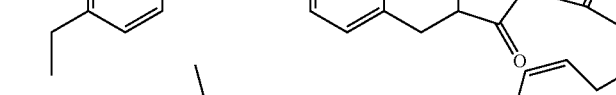 |
| 1040. | 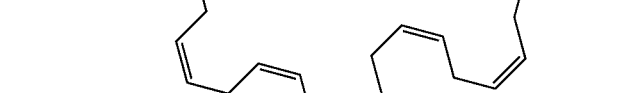 |
| 1041. | 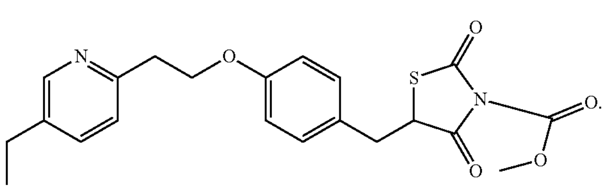 [SMILES: CCc1ccc(CCOc2ccc(CC3SC(=O)N(C(=O)OC)C3=O)cc2)nc1] |
\* \* \* \* \*